(12) United States Patent
Setoi et al.

(10) Patent No.: US 6,316,482 B1
(45) Date of Patent: Nov. 13, 2001

(54) BENZAMIDE DERIVATIVES HAVING A VASOPRESSIN ANTAGONISTIC ACTIVITY

(75) Inventors: Hiroyuki Setoi, Tsukuba; Takehiko Ohkawa, Yuki-gun; Tatsuya Zenkoh, Kitasouma-gun; Hitoshi Sawada, Tsukuba; Yuki Sawada, Ushiku; Teruo Oku, Takatsuki, all of (JP)

(73) Assignee: Fujisawa Pharmaceutical Co., Ltd., Osaka (JP)

(*) Notice: Subject to any disclaimer, the term of this patent is extended or adjusted under 35 U.S.C. 154(b) by 0 days.

(21) Appl. No.: 09/614,132

(22) Filed: Jul. 11, 2000

Related U.S. Application Data

(62) Division of application No. 09/308,662, filed as application No. PCT/JP97/04192 on Nov. 18, 1997.

(30) Foreign Application Priority Data

Dec. 2, 1996 (AU) .................................................. P03953

(51) Int. Cl.[7] ...................... A61K 31/415; A61K 31/495; C07D 403/06; C07D 401/04; C07D 235/04
(52) U.S. Cl. .................. 514/394; 514/338; 514/252.16; 544/370; 546/273.4; 546/273.7; 548/304.7; 548/306.4; 548/309.7
(58) Field of Search ............... 548/304.7, 306.4, 548/309.7; 546/273.4, 273.7; 544/370; 514/394, 252.16, 338

(56) References Cited

U.S. PATENT DOCUMENTS

| | | |
|---|---|---|
| 5,521,170 | 5/1996 | Setoi et al. . |
| 6,054,457 | 4/2000 | Setoi et al. . |

Primary Examiner—Floyd D. Higel
Assistant Examiner—Ebenezer Sackey
(74) Attorney, Agent, or Firm—Oblon, Spivak, McClelland, Maier & Neustadt, P.C.

(57) ABSTRACT

This invention relates to new benzamide derivatives having a vasopressin antagonistic activity, etc. and represented by general formula (I):

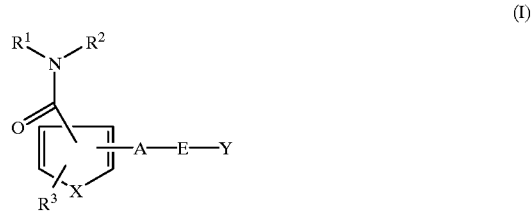

wherein
$R^1$ is aryl optionally substituted with lower alkoxy, etc.,
$R^2$ is lower alkyl, etc.,
$R^3$ is hydrogen, etc.,
A is NH, etc.,
E is

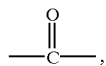

etc.,
X is —CH=CH—, —CH=N—, or S, and
Y is a condensed heterocyclic group, etc.,
and pharmaceutically acceptable salts thereof, to processes for preparation thereof and to a pharmaceutical composition comprising the same.

16 Claims, No Drawings

BENZAMIDE DERIVATIVES HAVING A VASOPRESSIN ANTAGONISTIC ACTIVITY

This application is a Division of No. 09/308,662 filed Jun. 2, 1999 which is a 371 of PCT/JP97/04192 filed Nov. 18, 1997.

TECHNICAL FIELD

This invention relates to new benzamide derivatives and pharmaceutically acceptable salts thereof which are useful as a medicament.

BACKGROUND ART

Some benzamide derivatives have been known as vasopressin antagonist, for example, in PCT International Publication Nos. WO 91/05549, WO 95/29152 and WO 96/41795, and EP Application Publication No. 0620216.

DISCLOSURE OF INVENTION

This invention relates to new banzamide derivatives and pharmaceutically acceptable salts thereof.

More particularly, it relates to new benzamide derivatives and pharmaceutically acceptable salts thereof which possess activities as vasopressin antagonistic activity, vasodilating activity, hypotensive activity, activity for inhibiting saccharide release in liver, activity for inhibiting growth of mesangium cells, water diuretic activity, platelet agglutination inhibitory activity, oxytocin antagonistic activity and the like, to a pharmaceutical composition comprising the salt and to a method for the treatment and/or prevention of hypertension, heart failure, renal insufficiency, edema, ascites, vasopressin parasecretion syndrome, hepatocirrhosis, hyponatremia, hypokalemia, diabetic, circulation disorder, cerebrovascular disease (e.g. cerebral edema, cerebral infarction, etc.), Meniere's syndrome (e.g. Meniere's disease, etc.), motion sickness and the like in human beings or animals.

One object of this invention is to provide new and useful benzamide derivatives which possess aforesaid activities.

Another object of this invention is to provide processes for the preparation of said benzamide derivatives and salts thereof.

A further object of this invention is to provide a pharmaceutical composition comprising, as an active ingredient, said benzamide derivatives and pharmaceutically acceptable salts thereof.

Still further object of this invention is to provide a therapeutical method for the treatment and/or prevention of aforesaid diseases in human beings or animals, using said benzamide derivatives and pharmaceutically acceptable salts thereof.

The object benzamide derivatives of this invention are new and can be represented by the following general formula (I):

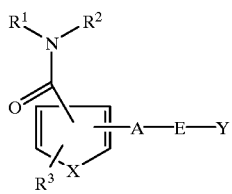

wherein $R^1$ is aryl, cyclo(lower)alkyl or a heterocyclic group, each of which may be substituted with substituent(s) selected from the group consisting of halogen; hydroxy; nitro; protected amino; amino; acyl; substituted acyl; acyl(lower)alkylsulfinyl; acyl(lower)alkylsulfonyl; acyloxy; lower alkylamino(lower)alkylcarbamoyloxy; aryl; cyano; a heterocyclic group; lower alkenyl optionally substituted with acyl, substituted acyl, aryl or acyl-substituted aryl; lower alkynyl optionally substituted with amino, acylamino or substituted acylamino; lower alkyl optionally substituted with halogen, amino, lower alkylamino, acylamino, substituted acylamino, hydroxy, acyloxy, acyl(lower)alkanoyloxy, acyl, substituted acyl, acyl(lower)alkoxyimino, aryl or acyl-substituted aryl; lower alkylthio optionally substituted with acyl or substituted aryl; alkoxy optionally substituted with aryl, substituted aryl, hydroxy, acyloxyl amino, lower alkylamino, protected amino, a heterocyclic group, acyl-substituted pyridyl, substituted acyl-substituted pyridyl, halogen, acyl(lower)alkylamino, N-protected-acyl(lower)alkylamino, N-acyl(lower)alkyl-N-lower alkylamino, acyl, substituted acyl, acylamino, substituted acylamino, lower alkylhydrazinocarbonylamino, hydroxyimino, acyl(lower)alkoxyimino, substituted acyl(lower)alkoxyimino, acyl(lower)alkoxy, guanidino or N-protected guanidino; and lower alkenyloxy optionally substituted with acyl or substituted acyl;

$R^2$ is hydrogen; lower alkyl optionally substituted with hydroxy, aryl or acyl; or cyclo(lower)alkyl;

$R^3$ is hydrogen; halogen; hydroxy; acyloxy; substituted acyloxy; lower alkyl optionally substituted with hydroxy or lower alkoxy; lower alkoxy optionally substituted with aryl, amino, protected amino, acyl, hydroxy, cyano or lower alkylthio; nitro; amino; acyl; substituted acyl; or cyclo(lower)alkyloxy;

A is a single bond, O or NH;

E is lower alkylene, lower alkenylene,

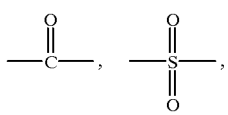

or a group of the formula:

—G—J— in which G is lower alkylene or

and

J is O or

(wherein R⁴ is hydrogen or N-protective group);

X is —CH=CH—, —CH=N— or S; and

Y is aryl which may be substituted with acyl, protected amino(lower)alkanoyl, protected amino and nitro, amino and nitro or diamino; or a condensed heterocyclic group which may be substituted with substituent(s) selected from the group consisting of halogen, acyl, lower alkoxy, hydroxy, guanidino, mercapto, acylamino, amino, a heterocyclic group, cyanoamino, amino(lower)alkyl(lower)alkylamino, lower alkylamino, lower alkylamino(lower)alkylamino, substituted-heterocyclic group, lower alkylhydrazino, aryloxy, lower alkylthio, aryl, protected amino, N-protected lower alkylamino(lower)alkylamino, N-protected amino(lower)alkyl(N'-lower alkyl)amino, amino(lower)alkyl (N-lower alkyl)amino, lower alkylamino(lower)alkyl (N-lower alkyl)amino, lower alkoxy(lower)alkylamino and lower alkyl optionally substituted with aryl, ar(lower)alkoxy, cyano, hydroxyimino, mercapto, lower alkylamino, acyloxy, halogen, lower alkoxy, protected hydroxy, hydroxy, lower alkoxyaryl, protected amino, amino, a heterocyclic group or substituted heterocyclic group;

provided that when Y is phenyl which may be substituted with lower alkyl or acyl, then A is a single bond and E is

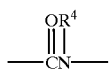

(wherein R⁴ is as defined above);

and pharmaceutically acceptable salt thereof.

The object compound (I) or its salt can be prepared by the processes as illustrated in the following reaction schemes.

Process 1

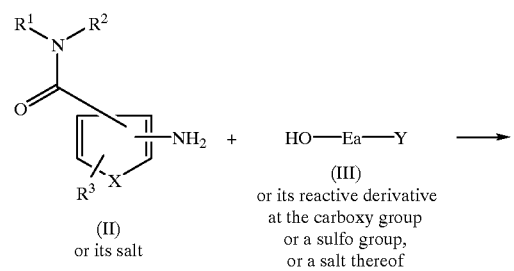

(II)
or its salt (III)
or its reactive derivative
at the carboxy group
or a sulfo group,
or a salt thereof

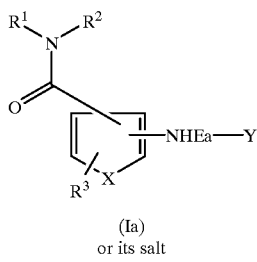

(Ia)
or its salt

Process 2

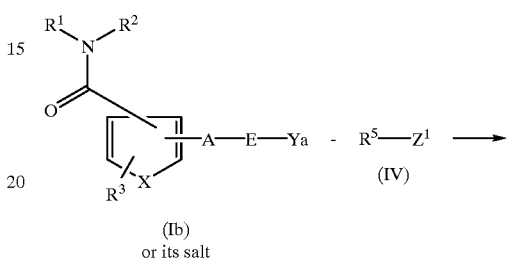

(Ib)
or its salt

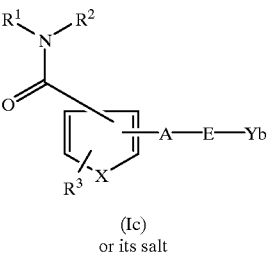

(Ic)
or its salt

Process 3

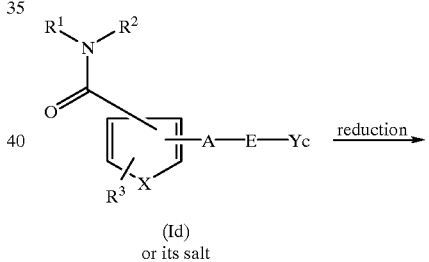

(Id)
or its salt reduction

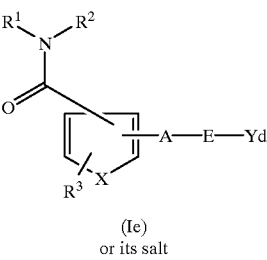

(Ie)
or its salt

Process 4

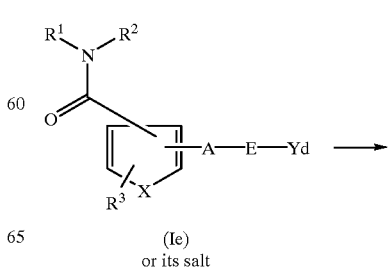

(Ie)
or its salt

-continued

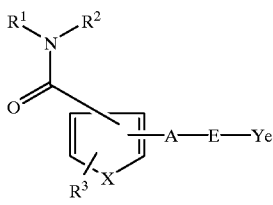

(If) or its salt

Process 5

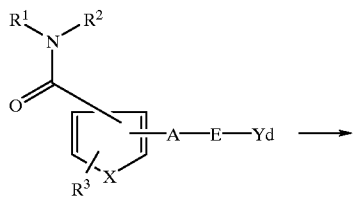

(Ie) or its salt

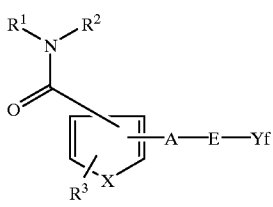

(Ig) or its salt

Process 6

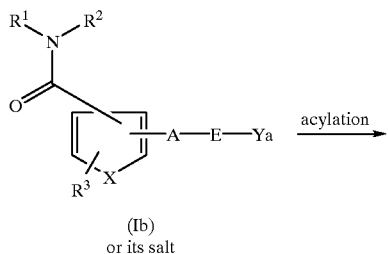 acylation 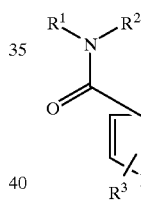

(Ib) or its salt (Ih) or its salt

Process 7

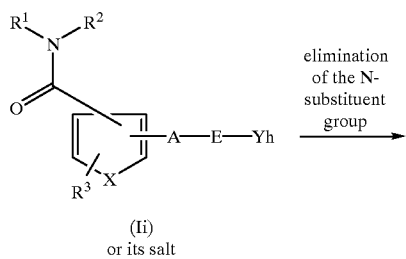 elimination of the N-substituent group (Ii) or its salt

-continued

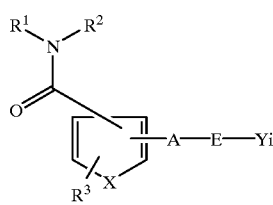

(Ij) or its salt

Process 8

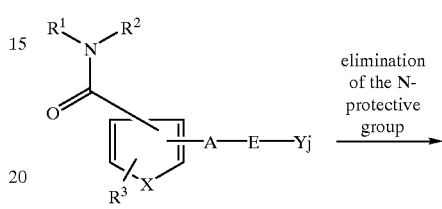 elimination of the N-protective group (Ik) or its salt

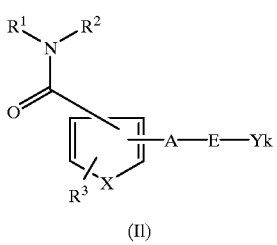

(Il) or its salt

Process 9

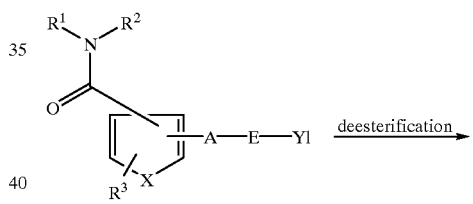 deesterification (Im) or its salt

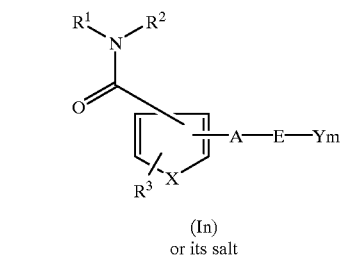

(In) or its salt

Process 10

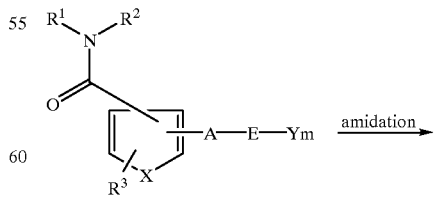 amidation (In) or its reactive derivative at the carboxy group or a salt thereof

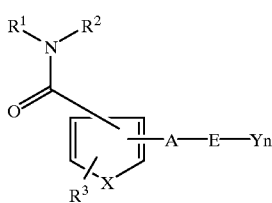
(Io) or its salt
Process 11
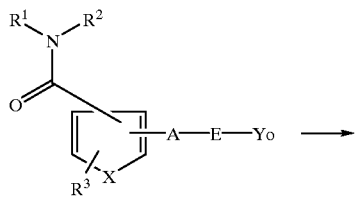
(Ip) or its salt
(Iq) or its salt
Process 12
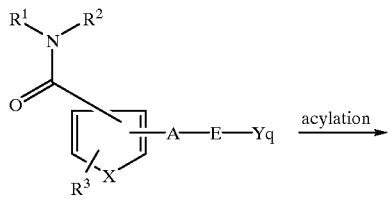
(Ir) or its salt
acylation →
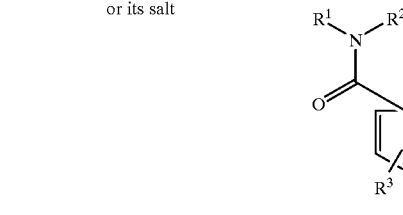
(Is) or its salt
Process 13
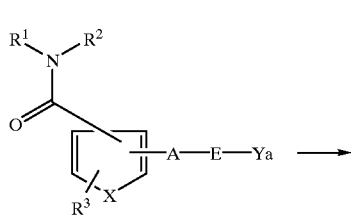
(Ib) or its salt →
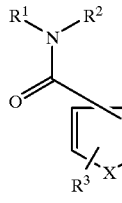
(It) or its salt
Process 14
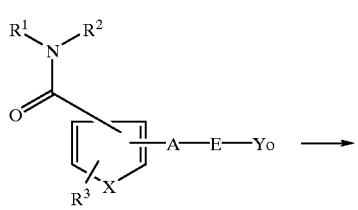
(Iu) or its salt
oxidation →
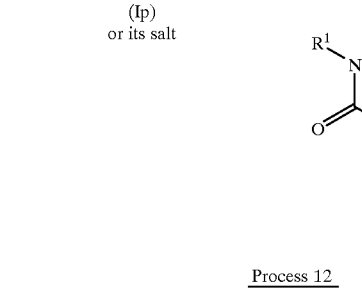
(Iv) or its salt
Process 15
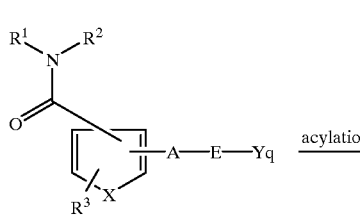
(Iw) or its salt
deesterfication →
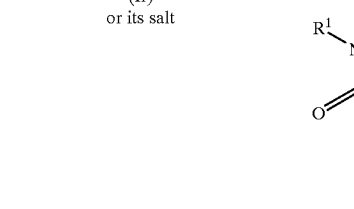
(Ix) or its salt
Process 16
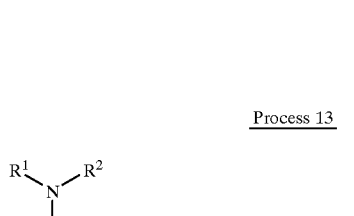
(Iy) or its salt →

-continued
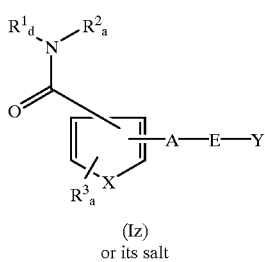
(Iz)
or its salt
Process 17
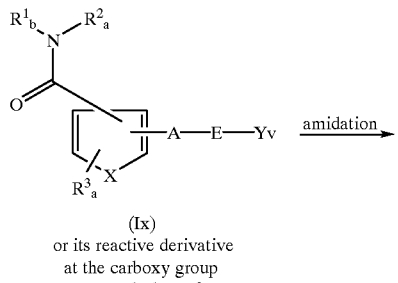
(Ix)
or its reactive derivative
at the carboxy group
or a salt thereof
amidation →
(I-1)
or its salt
Process 18
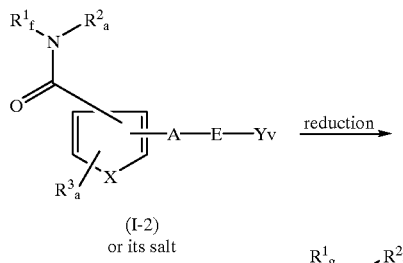
reduction →
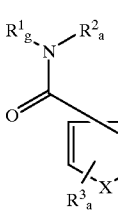
(I-3)
or its salt
Process 19
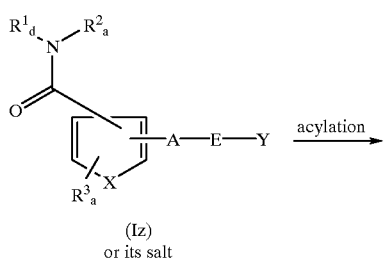
(Iz)
or its salt
acylation →
-continued
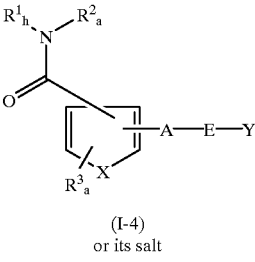
(I-4)
or its salt
Process 20
$Z^2$—$R^6$
(V)
→
(Iz)
or its salt
(I-5)
or its salt
Process 21
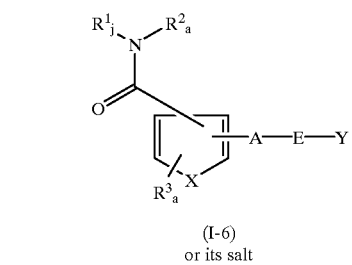
(I-5)
or its salt
→
(I-6)
or its salt
Process 22
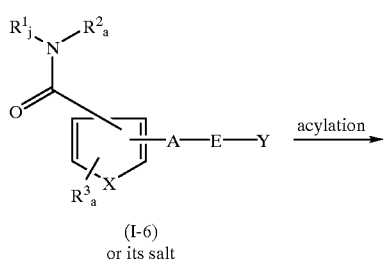
(I-6)
or its salt
acylation →

-continued
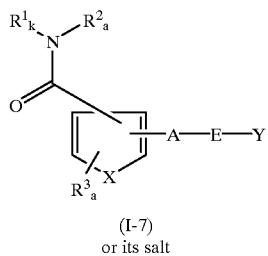
(I-7) or its salt
Process 23
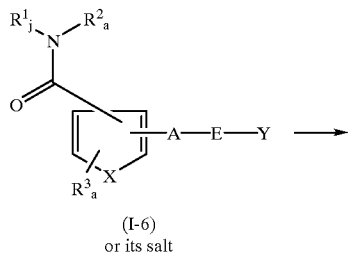
(I-6) or its salt
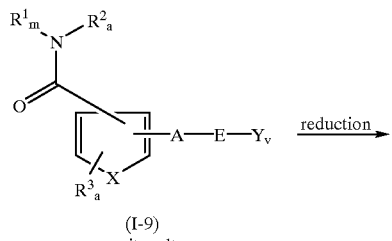
(I-8) or its salt
Process 24
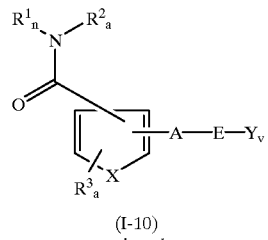
(I-9) or its salt
reduction
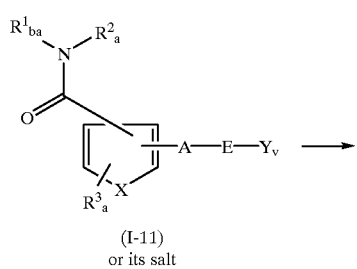
(I-10) or its salt
Process 25
-continued
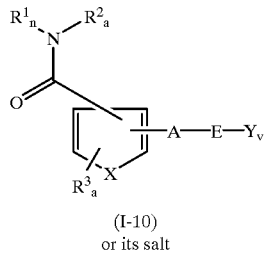
(I-10) or its salt
Process 26
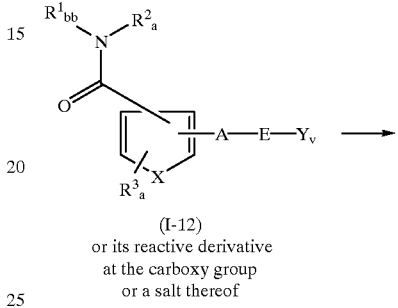
(I-12) or its reactive derivative at the carboxy group or a salt thereof
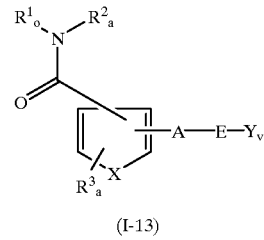
(I-13) or its salt
Process 27
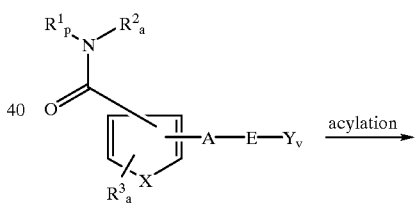
(I-14) or its salt
acylation
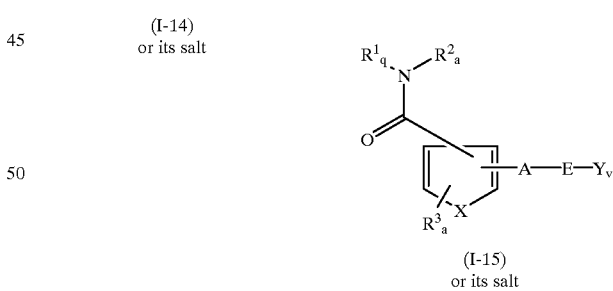
(I-15) or its salt
Process 28
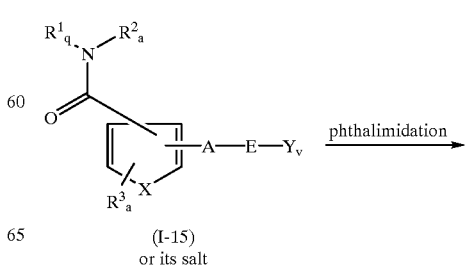
(I-15) or its salt
phthalimidation -continued

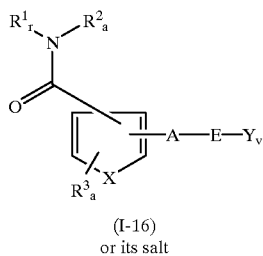

(I-16) or its salt

Process 29

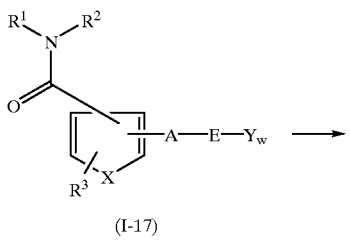

(I-17) or its salt

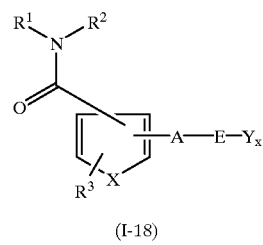

(I-18) or its salt

Process 30

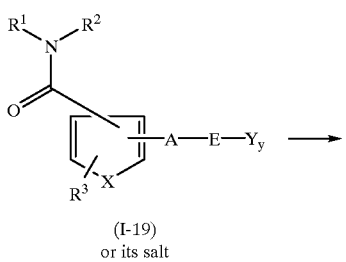

(I-19) or its salt

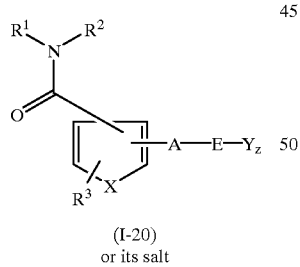

(I-20) or its salt

Process 31

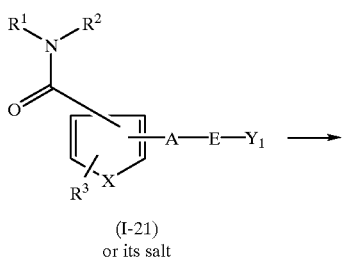

(I-21) or its salt

-continued

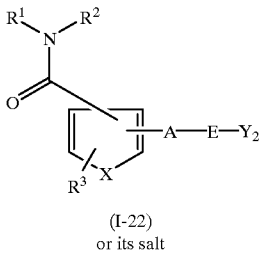

(I-22) or its salt

Process 32

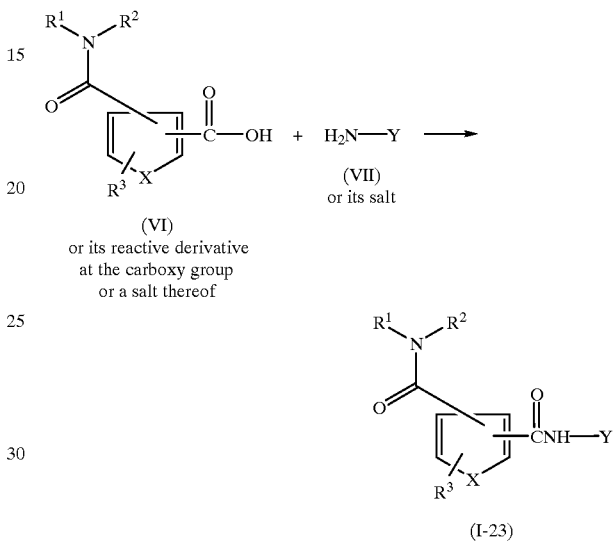

(I-23) or its salt wherein
R¹, R², R³, A, E, X and Y are each as defined above,

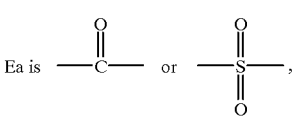

Ya is indolyl,
R⁵ is lower alkyl,
Z¹ is an acid residue,
Yb is N-(lower alkyl)indolyl,
Yc is phenyl substituted with amino and nitro,
Yd is phenyl substituted with diamino,
Ye is benzimidazolyl optionally 2-position substituted with aryl, phenoxy, sulfamoylamino, cyanoamino, guanidino, mercapto, amino, lower alkoxycarbonylamino, lower alkoxy or lower alkyl optionally substituted with cyano, mercapto, hydroxy, halogen, protected amino or a heterocyclic group;
Yf is quinoxalinyl or benzotriazolyl,
Yg is N-acylindolyl,
Yh is (N-acyl)acylindolinyl, N-acylindolinyl, (N-acyl)hydroxy(lower)alkylindolinyl, lower alkylamino(lower)alkylamino(N-acyl)indolinyl, (N-lower alkoxyarylmethyl)acylbenzimidazolyl, (N-lower alkoxycarbonyl)phthalimido(lower)alkylindolyl, N-protected lower alkylamino(lower)alkylamino(N-acyl)benzimidazolyl, (N-acyl)benzimidazolyl, (N-acyl)

(lower)alkylbenzimidazolyl, N-protected amino(lower) alkyl(N-lower alkyl; amino(N-acyl)benzimidazolyl, N-acylindolyl, (N-acyloxymethyl)indolyl, (N-acyl) acylindolyl, (N-arylmethyl)lower alkoxy(lower) alkylbenzimidazolyl or (N-lower alkoxyarylmethyl) acylbenzimidazolyl;

Yi is acylindolinyl, indolinyl, hydroxy(lower) alkylindolinyl, lower alkylamino(lower) alkylaminoindolinyl, acylbenzimidazolyl, phthalimido (lower)alkylindolyl, amino(lower)alkylindolyl, lower alkylamino(lower)alkylaminobenzimidazolyl, benzimidazolyl, lower alkylbenzimidazolyl, amino (lower)alkyl (N-lower alkyl)aminobenzimidazolyl, indolyl, acylindolyl, lower alkoxy(lower) alkylbenzimidazolyl or acylbenzimidazolyl;

yj is aryl which is substituted with protected amino and nitro; or a condensed heterocyclic group which is substituted with protected amino or lower alkyl substituted with protected amino;

Yk is aryl which is substituted with amino and nitro; or a condensed heterocyclic group which is substituted with amino or lower alkyl substituted with amino;

Yl is aryl substituted with esterified carboxy, or a condensed heterocyclic group substituted with esterified carboxy, Ym is aryl substituted with carboxy, or a condensed heterocyclic group substituted with carboxy, Yn is aryl or a condensed heterocyclic group, each of which is substituted with substituted or unsubstituted N-containing heterocycliccarbonyl, carbamoyl, heterocycliccarbamoyl, or substituted or unsubstituted lower alkylcarbamoyl;

Yo is a condensed (N-acyl)N-containing heterocyclic group or a condensed heterocyclic group, each of which is substituted with methoxy or lower alkyl substituted with protected hydroxy;

Yp is a condensed (N-acyl)N-containing heterocyclic group or a condensed heterocyclic group, each of which is substituted with hydroxy or lower alkyl substituted with hydroxy;

Yq is a condensed heterocyclic group which is substituted with amino or amino(lower)alkyl, Yr is a condensed heterocyclic group which is substituted with acylamino or acylamino(lower)alkyl, Ys is indolyl which is substituted with methyl substituted with lower alkylamino, Yt is a condensed heterocyclic group which is substituted with lower alkyl substituted with hydroxy, Yu is a condensed heterocyclic group which is substituted with lower alkyl substituted with formyl, $R_a^1$ is aryl substituted with esterified carboxy or lower alkoxy substituted with esterified carboxy, $R_b^1$ is aryl substituted with carboxy or lower alkoxy substituted with carboxy, $R_a^2$ is lower alkyl, $R_a^3$ is hydrogen or lower alkoxy, Yv is benzimidazolyl optionally substituted with lower alkyl or protected amino(lower)alkyl, $R_c^1$ is aryl substituted with methoxy which is substituted with substituted or unsubstituted aryl, $R_d^1$ is aryl substituted with hydroxy, $R_e^1$ is aryl substituted with N-protected piperazinylcarbonyl, oxopiperidinylcarbonyl, carbamoyl, lower alkylcarbamoyl, lower alkylaminocarbamoyl or lower alkylamino(lower)alkyl (N-lower)alkylcarbamoyl, or aryl which is substituted with lower alkoxy substituted with N-protected piperazinylcarbonyl, oxopiperidinylcarbonyl, carbamoyl, lower alkylcarbamoyl, lower alkylaminocarbamoyl or lower alkylamino(lower)alkyl(N-lower) alkylcarbamoyl, $R_f^1$ is aryl which is substituted with lower alkoxy substituted with oxopiperidinylcarbonyl, $R_g^1$ is aryl which is substituted with lower alkoxy substituted with hydroxypiperidinylcarbonyl, $R_h^1$ is aryl substituted with acyloxy, $R_i^1$ is aryl which is substituted with lower alkoxy substituted with protected amino, $R^6$ is lower alkyl substituted with protected amino, $Z^2$ is an acid residue, $R_j^1$ is aryl which is substituted with lower alkoxy substituted with amino, $R_k^1$ is aryl which is substituted with acylamino, $R_l^1$ is aryl which is substituted with lower alkylamino, $R_m^1$ is aryl substituted with nitro, $R_n^1$ is aryl substituted with amino, $R_{ba}^1$ is aryl substituted with carboxy, $R_{bb}^1$ is aryl which is substituted with lower alkoxy substituted with carboxy, $R_o^1$ is aryl which is substituted with lower alkoxy substituted with hydroxymethyl, $R_p^1$ is aryl which is substituted with lower alkoxy substituted with hydroxy, $R_q^1$ is aryl which is substituted with lower alkoxy substituted with acyloxy, $R_r^1$ is aryl which is substituted with lower alkoxy substituted with phthalimido, Yw is benzimidazolyl substituted with halogen, Yx is benzimidazolyl substituted with N-lower alkylpiperidyl, morpholino, lower alkylamino, di(lower)alkylamino-piperidino, di(lower) alkylhydrazino, amino(lower)alkyl(N-lower alkyl) amino or di(lower)alkylamino(lower)alkylamino, Yy is benzimidazolyl substituted with N-protected piperidyl, Yz is benzimidazolyl substituted with piperidyl, $Y_1$ is benzimidazolyl or indolyl, each of which is substituted with formyl or cyano(lower)alkyl, and $Y_2$ is benzimidazolyl or indolyl, each of which is substituted with hydroxyiminomethyl or amino (hydroxyimino) (lower)alkyl.

In the above and subsequent description of the present specification, suitable examples of the various definitions to be included within the scope of the invention are explained in detail in the following.

The term "lower" is intended to mean a group having 1 to 6 carbon atom(s), unless otherwise provided.

The "higher" is intended to mean 7 to 20 carbon atoms, unless otherwise provided.

The lower moiety in the terms "cyclo(lower)alkyl" and "cyclo(lower)alkyloxy" is intended to mean a group having 3 to 6 carbon atoms.

The lower moiety in the terms "lower alkenyl", "lower alkenyloxy" and "lower alkynyl" is intended to mean a group having 2 to 6 carbon atoms.

The term "alkoxy" may include lower alkoxy and higher alkoxy.

Suitable "lower alkoxy" and lower alkoxy moiety in the terms "ar(lower)alkoxy", "lower alkoxy(lower)alkylamino", "acyl(lower)alkoxy", "acyl(lower)alkoxyimino", "esterified carboxy(lower)alkoxyimino", "carboxy(lower)alkoxyimino", "N-containing heterocycliccarbonyl(lower)alkoxyimino", "carbamoyl(lower)alkoxyimino", "lower alkylcarbamoyl(lower)alkoxyimino" and "lower alkoxycarbonyl" may be straight or branched $C_1$–$C_6$ alkoxy such as methoxy, ethoxy, propoxy, isopropoxy, methylpropoxy, butoxy, isobutoxy, tert-butoxy, pentyloxy, hexyloxy or the like.

Suitable "higher alkoxy" may be straight or branched $C_7$–$C_{20}$ alkoxy such as heptyloxy, octyloxy, nonyloxy, decyloxy, undecyloxy, dodecyloxy, tridecyloxy, tetradecyloxy, pentadecyloxy, hexadecyloxy, heptadecyloxy, octadecyloxy, nonadecyloxy, eicosyloxy, methylheptyloxy, methyloctyloxy, methylnonyloxy, methyldecyloxy, ethylheptyloxy, ethyloctyloxy, ethylnonyloxy, ethyldecyloxy or the like, in which preferable one is heptyloxy.

Suitable "lower alkyl" an lower alkyl moiety in the terms "amino(lower)alkyl(lower)alkylamino", "lower alkylamino(lower)alkylamino", "mercapto(lower)alkyl", "lower alkylhydrazino", "lower alkylthio", "N-protected lower alkylamino(lower)alkylamino", "N-protected amino(lower)alkyl(N'-lower alkyl)amino", "amino(lower)alkyl(N-lower alkyl)amino", "lower alkylamino(lower)alkyl(N-lower alkyl)amino, "lower alkoxy(lower)alkylamino", "acyl(lower)alkylsulfinyl", "acyl(lower)alkylsulfonyl", "lower alkylamino(lower)alkylcarbamoyloxy", "acyl(lower)alkylamino", "N-protected-acyl(lower)alkylamino", "N-acyl(lower)alkyl-N-lower alkylamino", "lower alkylhydrazinocarbonylamino", "esterified carboxy(lower)alkylamino", "N-protected-esterified carboxy(lower)alkylamino", "N-esterified carboxy(lower)alkyl-N-lower alkylamino", "carboxy(lower)alkylamino", "N-protected-carboxy(lower)alkylamino", "N-carboxy(lower)alkyl-N-lower alkylamino", "lower alkylcarbamoyl", "lower alkylcarbamoyl(lower)alkanoyloxy", "lower alkylcarbamoyl(lower)alkoxyimino", "N-protected-(substituted or unsubstituted N-containing heterocyclic)-carbonyl(lower)alkylamino", "N-protected-carbamoyl(lower)-alkylamino", "N-protected-substituted or unsubstituted lower alkylcarbamoyl(lower)alkylamino:, "N-(substituted or unsubstituted N-containing heterocyclic)carbonyl(lower)alkyl-N-lower alkylamino", "N-carbamoyl(lower)alkyl-N-lower alkylamino", "N-lower alkylcarbamoyl-N-lower alkylamino", "lower alkylcarbamoyl(lower)alkoxyimino", "1-=hydroxy(lower)alkyl", "1-(lower alkyl)amino(lower)alkyl", "mono(lower)alkylamino", "lower alkylamino(lower)alkyl", "acyloxy(lower)alkyl", "halo(lower)alkyl", "lower alkoxy(lower)alkyl", "protected hydroxy(lower)alkyl", "hydroxy(lower)alkyl", "ar(lower)alkyl", "protected amino(lower)alkyl", "amino(lower)alkyl", "a heterocyclic(lower)alkyl", "acyl(lower)alkyl", "di(lower)alkylamino", "lower alkylsulfonyl" and "lower alkylamino" may be straight or branched $C_1$–$C_6$ alkyl such as methyl, ethyl, propyl, isopropyl, butyl, isobutyl, tert-butyl, pentyl, ethylpropyl, hexyl or the like.

Suitable "cyclo(lower)alkyl" and the cyclo(lower)alkyl moiety in the term "cyclo(lower)alkyloxy" may be cyclo-($C_3$–$C_6$) alkyl such as cyclopropyl, cyclobutyl, cyclopentyl or cyclohexyl.

Suitable "aryl", aryl moiety in the terms "aryloxy", "haloaryl", "alkylsulfonyl", "acyl-substituted aryl", "(N-arylmethyl)lower alkoxy(lower)alkylbenzimidazolyl" and "N-lower alkoxyarylmethyl)acylbenzimidazolyl" and ar moiety in the terms "ar(lower)alkyl" and "ar(lower)alkoxy" may be phenyl, naphthyl, phenyl substituted with lower alkyl [e.g. tolyl, xylyl, mesityl, cumenyl, di(tert-butyl)phenyl, etc.] and the like, in which preferable one is phenyl, tolyl or xylyl.

Suitable "substituted aryl" may be aryl substituted with suitable substituent(s) such as acyl, substituted acyl, N-protected piperazinylsulfonyl, piperazinylsulfonyl, N-lower alkylpiperazinylsulfonyl, hydroxy(lower)alkyl, a heterocyclic(lower)alkyl, halogen, nitro, amino, lower alkylamino, a heterocyclic group [e.g. thiazolyl, oxazolyl, tetrazolyl, oxazolinyl, pyridyl, pyrimidinyl, pyrrolyl optionally substituted with lower alkyl and cyano, etc.], cyano, lower alkoxy or the like, in which preferable one for the substituent of alkoxy for $R^1$ is aryl substituted with N-lower alkylpiperazinylcarbonyl.

Suitable "halogen" and halo moiety in the terms "halo(lower)alkyl" and "haloaryl" may be fluorine, chlorine, bromine and iodine, in which preferable one is chlorine or bromine.

Suitable "lower alkylamino" and lower alkylamino moiety in the terms "amino(lower)alkyl(lower)alkylamino", "lower alkylamino(lower)alkylamino", "N-protected lower alkylamino(lower)alkylamino", "N-protected amino(lower)(N'-lower alkyl)amino", "amino(lower)alkyl(N-lower alkyl)amino", "lower alkylamino(lower)alkyl(N-lower alkyl)amino", "lower alkoxy(lower)alkylamino", "lower alkylamino(lower)alkylcarbamoyloxy", "acyl(lower)alkylamino", "esterified carboxy(lower)alkylamino", "carboxy(lower)alkylamino", "N-containing heterocycliccarbonyl(lower)alkylamino", "carbamoyl(lower)alkylamino", "lower alkylcarbamoyl(lower)alkylamino", "lower alkylamino(lower)alkyl" and "lower alkylaminopiperidylcarbonyl" may be mono or di(lower alkyl)amino such as methylamino, ethylamino, propylamino, isopropylamino, butylamino, tert-butylamino, isobutylamino, pentylamino, hexylamino, dimethylamino, diethylamino, dipropylamino, dibutylamino, diisopropylamino, dipentylamino, dihexylamino, N-methylethylamino or the like, in which preferable one is methylamino, dimethylamino or diethylamino.

Suitable "lower alkylhydrazino" may be 2-mono or 2,2-di(lower alkyl)hydrazino such as 2-methylhydrazino, 2,2-dimethylhydrazino, 2-ethylhydrazino, 2,2-diethylhydrazino or the like, in which preferable one 2,2-dimethylhydrazino.

Suitable "1-hydroxy(lower)alkyl" may be 1-hydroxy-($C_1$–$C_6$)alkyl such as hydroxymethyl, 1-hydroxyethyl, 1-hydroxypropyl, 1-hydroxybutyl, 1-hydroxy-3-methylpropyl or the like, in which preferable one is hydroxymethyl or 1-hydroxyethyl.

Suitable "1-(lower alkyl)amino(lower)alkyl" may be 1-mono or di($C_1$–$C_6$ alkyl)amino($C_1$–$C_6$)alkyl such as methylaminomethyl, dimethylaminomethyl, 1-methylaminoethyl, 1-dimethylaminoethyl, ethylaminomethyl, 1-ethylaminoethyl or the like, in which preferable one is methylaminomethyl, dimethylaminomethyl, 1-methylaminoethyl or 1-dimethylaminoethyl.

Suitable "lower alkylamino(lower)alkyl" may be mono or di(lower alkyl)amino(lower)alkyl such as methylaminomethyl, dimethylaminomethyl, dimethylaminoethyl or the like.

Suitable "amino(lower)alkyl(lower)alkylamino" may be aminomethylmethylamino, aminomethylethylamino, aminoethylmethylamino, aminoethylethylamino and the like, in which preferable one is aminoethylmethylamino.

Suitable "lower alkylamino(lower)alkylamino" may be mono or di(lower alkyl)amino(lower)alkylamino such as methylethylamino, dimethylethylamino and the like.

Suitable "N-protected lower alkylamino)lower)alkylamino" may be N-tert-butoxycarbonyl(lower)alkylamino(lower)alkylamino such as N-tert-butoxycarbonylmethylaminoethylamino or the like.

Suitable "N-protected amino(lower)alkyl (N'-lower alkyl) amino" may be N-tert-butoxycarbonylamino(lower)alkyl (N'-lower alkyl)amino such as N-tert-butoxycarbonylaminoethyl(N-methyl) amino or the like.

Suitable "amino(lower)alkyl(N-lower alkyl)amino" may be aminoethyl(N-methyl)amino or the like.

Suitable "lower alkylamino(lower)alkyl(N-lower alkyl) amino" may be mono or di(lower alkyl)amino(lower)alkyl (N-lower alkyl)amino such as dimethylaminoethyl(N-methyl)amino or the like.

Suitable "lower alkoxy(lower)alkylamino" may be methoxyethylamino and the like.

Suitable "acyloxy(lower)alkyl" may be pivaloyloxymethyl and the like.

Suitable "lower alkoxy(lower)alkyl" may be methoxymethyl and the like.

"hydroxy-protective group" in protected hydroxy moiety in the term "protected hydroxy(lower)alkyl" may be common hydroxy-protective group such as substituted or unsubstituted arylmethyl (e.g. benzyl, lower alkoxybenzyl, etc., acyl, substituted silyl (e.g. tert-butyldiphenylsilyl, etc.) or the like.

Suitable "heterocyclic group" may be one containing at least one hetero atom selected from nitrogen, sulfur and oxygen atom, and may include saturated or unsaturated, monocyclic or condensed heterocyclic group, and preferable heterocyclic group may be N-containing heterocyclic group such as unsaturated 3 to 6-membered heteromonocyclic group containing 1 to 4 nitrogen atoms, for example, pyrrolyl, pyrrolinyl, imidazolyl, pyrazolyl, pyridyl, pyrimidinyl, pyrazinyl, pyridazinyl, triazolyl [e.g. 4H-1,2,4-triazolyl, 1H-1,2,3-triazolyl, 2H-1,2,3-triazolyl, etc.], tetrazolyl [e.g. 1H-tetrazolyl, 2H-tetrazolyl, etc.], etc.; saturated 3 to 7-membered heteromonocyclic group containing 1 to 4 nitrogen atoms (e.g. pyrrolidinyl, imidazolidinyl, piperidyl, piperazinyl, homopiperazinyl, etc.); saturated condensed heterocyclic group containing 1 to 5 nitrogen atoms, for example, quinuclidinyl, etc. unsaturated condensed heterocyclic group containing 1 to 5 nitrogen atoms, for example, indolyl, isoindolyl, indolizinyl, benzimidazolyl, quinolyl, isoquinolyl, imidazopyridyl [e.g. imidazo [4,5-bipyridyl, imidazo [1,2-a]-pyridyl, imidazo [3,4-a]pyridyl, etc.], purinyl, indazolyl, benzotriazolyl, tetrazolopyridazinyl [e.g. tetrazolo[1,5-b]-pyridazinyl, etc.], indolinyl, tetrahydroquinolyl, quinoxalinyl, 1H-indazolyl, 1H-pyrazolo [1,5-b][1,2,4]-triazolyl, quinazolinyl, etc.; unsaturated 3 to 6-membered heteromonocyclic group containing an oxygen atom, for example, pyranyl, furyl, etc.;

saturated 3 to 6-membered heteromonocyclic group containing an oxygen atom, for example, 1H-tetrahydropyranyl, tetrahydrofuranyl, etc.; unsaturated, 3 to 6-membered heteromonocyclic group containing 1 to 2 sulfur atoms, for example, thienyl, etc.; unsaturated 3 to 6-membered heteromonocyclic group containing 1 to 2 oxygen atoms and 1 to 3 nitrogen atoms, for example, oxazolyl, isoxazolyl, oxadiazolyl [e.g. 1,2,4-oxadiazolyl, 1,3,4-oxadiazolyl, 1,2,5-oxadiazolyl, etc.], oxazolinyl [e.g. 2,5-oxazolinyl, etc.], oxazinyl [e.g. 3H, 4H, 5H-2,6-oxazinyl, etc.], etc.; saturated 3 to 6-membered heteromonocyclic group containing 1 to 2 oxygen atoms and 1 to 3 nitrogen atoms [e.g. morpholinyl, etc.]; unsaturated condensed heterocyclic group containing 1 to 2 oxygen atoms and 1 to 3 nitrogen atoms [e.g. benzofurazanyl, benzoxazolyl, benzoxadiazolyl, benzoxazinyl, etc.]; unsaturated 3 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.], etc.; saturated 3 to 6-membered heteromonocyclic group containing 1 to 2 sulfur atoms and 1 to 3 nitrogen atoms [e.g., thiazolidinyl, etc.]; unsaturated condensed heterocyclic group containing 1 to 2 sulfur atoms and 1 to 3 nitrogen atoms [e.g., benzothiazolyl, benzothiadiazolyl, etc.]; unsaturated condensed heterocyclic group containing 1 to 2 oxygen atoms [e.g. benzofuranyl, benzodioxolyl, etc.] and the like.

Said "heterocyclic group" includes one substituted with lower alkyl as exemplified above or oxo, and spiro-typed one substituted with $C_2$–$C_6$ alkylene, in which preferable one is N-methylpiperazinyl, tetrazolyl, morpholinyl, pyrrolidinyl, N-methylpiperidyl, N-methylhomopiperazinyl, 1H-tetrahydropyranyl, thienyl, pyridyl, piperidyl, oxopiperidyl, pyrrolyl, oxazolyl, 2,5-oxazolinyl, 4,4-dimethyl (2,5-oxazolinyl), 1-aza-3-oxaspiro [4.4]non-1-en-2-yl, 3H, 4H, 5H-2,6-oxazinyl.

Suitable "condensed heterocyclic group" may be saturated or unsaturated one above-mentioned, in which preferable one is indolyl, benzimidazolyl, benzoxazolyl, benzotriazolyl, imidazopyridyl (e.g. imidazo [4,5-b]pyridyl, imidazo [1,2-a]-pyridyl, imidazo [3,4-a]pyridyl, etc., purinyl, indolinyl, tetrahydroquinolyl, quinoxalinyl, 1H-indazolyl, 1H-pyrazolo [1,5-b][1,2,4]triazolyl, quinazolinyl, 2H-1,4-benzoxazin-3-oxo-8-yl.

Suitable acyl and acyl moiety in the terms "acyl (lower) alkylsulfinyl", "acyl (lower) alkylsulfonyl", "acyloxy", "acyloxy (lower) alkyl", "acylamino", "acyl (lower) aklanoyloxy", "acyl (lower) alkoxyimino", "acyl (lower) alkylamino", "N-protected-acyl (lower) alkylamino", "N-acyl (lower) alkyl-N-lower alkylamino" and "acyl (lower (alkoxy" may be carboxy, esterified carboxy, carbamoyl, lower alkylcarbamoyl, lower alkanoyl, aroyl, a heterocycliccarbonyl, lower alkylsulfonyl, arylsulfonyl, sulfamoyl, lower alkylsulfamoyl and the like.

The esterified carboxy may be substituted or unsubstituted lower alkoxycarbonyl [e.g. methoxycarbonyl, ethoxycarbonyl, propoxycarbonyl, butoxycarbonyl, tert-butoxycarbonyl, hexyloxycarbonyl, 2-iodoethoxycarbonyl, 2,2,2-trichloroethoxycarbonyl, dimethylaminopropoxycarbonyl, dimethylaminoethoxycarbonyl, etc.], substituted or unsubstituted aryloxycarbonyl [e.g. phenoxycarbonyl, 4-nitrophenoxycarbonyl, 2-naphthyloxycarbonyl, etc.], substituted or unsubstituted ar (lower) alkoxycarbonyl [e.g. benzyloxycarbonyl, phenethyloxycarbonyl, benzhydryloxycarbonyl, 4-nitrobenzyloxycarbonyl, 3-methoxy-4-nitrobenzyloxycarbonyl, etc.], N-containing heterocyclicoxycarbonyl [e.g. N-methylpiperidyloxycarbonyl, etc.] and the like.

The lower alkylcarbamoyl may be mono or di (lower alkyl)-carbamoyl such as methylcarbamoyl, ethylcarbamoyl, propylcarbamoyl, dimethylcarbamoyl, diethylcarbamoyl, N-methyl-N-ethylcarbamoyl or the like.

The lower alkanoyl may be substituted or unsubstituted $C_1$–$C_6$ alkanoyl such as formyl, acetyl, propionyl, butyryl, isobutyryl, valeryl, isovaleryl, pivaloyl, hexanoyl, trifluoroacetyl or the like, in which preferable one is formyl or acetyl.

The aroyl may be benzoyl, naphthoyl, toluoyl, di(tertbutyl) benzoyl and the like, in which preferable one is benzoyl.

The heterocyclic moiety in the terms "a heterocycliccarbonyl", "heterocyclicoxycarbonylamino", "heterocycliccarbamoyl" and "heterocyclicsulfonyl" may be one mentioned above as a heterocyclic group.

Preferred "a heterocycliccarbonyl" may be N-containing heterocycliccarbonyl.

The "N-containing heterocycliccarbonyl" may be one containing at least one nitrogen atom in heterocyclic group mentioned above, in which preferable one is N-(lower alkyl)-piperazinylcarbonyl (e.g. N-methylpiperazinylcarbonyl, etc.), N-(lower alkyl) homopiperazinylcarbonyl (e.g. N-methylhomopiperazinylcarbonyl, etc.), piperazinylcarbonyl, pyrrodinylcarbonyl, piperidylcarbonyl, morpholinocarbonyl, lower alkylpiperidylcarbonyl (e.g. methylpiperidylcarbonyl, etc.) or oxopiperidylcarbonyl.

Suitable "substituted acyl" may be carbamoyl substituted with amino, a heterocyclic group [e.g. N-(lower alkyl) piperazinyl, pyridyl, etc.], lower alkylsulfonyl or arylsulfonyl, substituted lower alkylcarbamoyl [e.g. N-lower alkylamino-N-lower alkylcarbamoyl, pyridyl (lower) alkylcarbamoyl, morpholino (lower) alkylcarbamoyl, bis [hydroxy (lower) alkyl] carbamoyl, hydroxy (lower) alkylcarbamoyl, carbamoyl (lower) alkylcarbamoyl, lower alkylamino (lower) alkylcarbamoyl, N-lower alkyl-N-lower alkylcarbamoyl, etc.], substituted N-containing heterocycliccarbonyl [e.g. trifluoroacetylpiperazinylcarbonyl, pyridylpiperazinylcarbonyl, hydroxypiperidylcarbonyl, dimethylaminopiperidylcarbonyl, diethylaminopiperidylcarbonyl, carbamoylpyrrolidinylcarbonyl, dimethylaminopiperazinylcarbonyl, hydroxyethoxyethylpiperazinylcarbonyl, pyrrolidinylcarbonylmethylpiperazinylcarbonyl, etc.], N-protected-N-containing heterocycliccarbonyl [e.g. N-t-butoxycarbonylpiperidylcarbonyl, N-t-butoxycarbonylpiperazinylcarbonyl, etc.], N-protected amino (lower) alkanoyl, amino (lower) alkanoyl, benzyloxybenzoyl, and the like.

"N-Protective group" in "protected amino" may be common N-protective group such as substituted or unsubstituted lower alkanoyl [e.g. formyl, acetyl, propionyl, trifluoroacetyl, etc.], phthaloyl, lower alkoxycarbonyl [e.g. tert-butoxycarbonyl, tert-amyloxycarbonyl, etc.], substituted or unsubstituted aralkyloxycarbonyl [e.g. benzyloxycarbonyl, p-nitrobenzyloxycarbonyl, etc.], 9-fluorenylmethoxycarbonyl, substituted or unsubstituted arenesulfonyl [e.g. benzenesulfonyl, tosyl, etc.], nitrophenylsulfenyl, aralkyl [e.g. trityl, benzyl, etc.]or the like, in which preferable one is phthaloyl, tert-butoxycarbonyl or 9-fluorenylmethoxycarbonyl.

"N-protective group" in "N-protected guanidino" may be common N-protective group such as lower alkoxycarbonyl [e.g. tert-butoxycarbonyl, etc.] or the like.

Suitable "acid residue" may be halogen [e.g. fluoro, chloro, bromo, iodo], arenesulfonyloxy [e.g. benzenesulfonyloxy, tosyloxy, etc.], alkanesulfonyloxy [e.g. mesyloxy, ethanesulfonyloxy, etc.], and the like, in which preferable one is halogen.

Suitable "lower alkylsulfonyl" may be $(C_1-C_8)$-alkylsulfonyl such as methylsulfonyl, ethylsulfonyl, propylsulfonyl or the like; in which preferable one is methylsulfonyl.

Suitable "arylsulfonyl" may be phenylsulfonyl, tolylsulfonyl and the like.

The substituent(s) on aryl for $R^1$ or a condensed heterocyclic group for Y, and the substituent(s) on lower alkyl as substituent of a condensed heterocyclic group for Y may be plural and in such case the substituents may be the same or different.

Preferred "aryl" for $R^1$ may be phenyl or phenyl substituted with lower alkyl.

Preferred "a heterocyclic group" as substituent of aryl for $R^1$ may be piperidino, N-lower alkylpiperazinyl [e.g. N-methylpiperazinyl, etc.], morpholino, 4,4-dimethyl (2,5-oxazolinyl), pyrrolyl, 2,5-oxazolyl, 2,5-oxazolinyl, 3H, 4H, 5H-2,6-oxazinyl or 1-aza-3-oxaspiro [4.4 non-1-en-2-yl.

Preferred "a heterocyclic group" in a heterocyclic-(lower) alkyl as substituent of a condensed heterocyclic group for Y may be pyridyl, N-lower alkylpiperazinyl [e.g. N-methylpiperazinyl, etc.], morpholino, imidazolyl, pyrrolidinyl.

Preferred "substituted-heterocyclic group" in substituted heterocyclic (lower) alkyl as substituent of a condensed heterocyclic group for Y may be substituted-piperidyl such as lower alkylaminopiperidyl including mono or di (lower alkyl) aminopiperidyl [e.g. dimethylaminopiperidyl, etc.] or the like.

Preferred compound (I) is one having tolyl which is substituted with lower alkoxy substituted with N-(lower alkyl)piperazinylcarbonyl for $R^1$, lower alkyl for $R^2$, lower alkoxy for $R^3$, NH for A and

for E, or a single bond for A

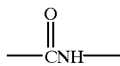

for E, —CH=CH— for X and benzimidazolyl which is substituted with lower alkyl optionally substituted with hydroxy, amino or N-lower alkyl piperazinyl for Y.

Suitable pharmaceutically acceptable salts of the object compound (I) are conventional non-toxic salts and include an acid addition salt such as an inorganic acid addition salt [e.g. hydrochloride, hydrobromide, sulfate, phosphate, etc.], an organic acid addition salt [e.g. formate, acetate, trifluoroacetate, maleate, tartrate, methanesulfonate, benzenesulfonate, toluenesulfonate, etc.], a metal salt such as an alkali metal salt [e.g. sodium salt, potassium salt, etc.] and an alkaline earth metal salt [e.g. calcium salt, magnesium salt, etc.] and the like.

The processes for preparing the object compound (I) are explained in details in the following.

Process 1

The object compound (Ia) or its salt can be prepared by reacting a compound (II) or its salt with a compound (III) or its reactive derivative at the carboxy group or the sulfo group, or a salt thereof.

Suitable salts of the compounds (Ia) and (II) may be the same as those exemplified for the compound (I).

Suitable salts of the compound (III) and its reactive derivative at the carboxy group or the sulfo group may be base salts as exemplified for the compound (I).

Suitable reactive derivative at the carboxy group or the sulfo group of the compound (III) may include an acid halide, an acid anhydride containing intramolecular, intermolecular and a mixed ones, an activated amide, an activated ester, and the like. Suitable examples of the reactive derivatives may be an acid chloride; an acid azide; a mixed acid anhydride with an acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole or tetrazole; or an activated ester [e.g. ethyl ester, cyanomethyl ester, methoxymethyl ester, dimethyliminomethyl $[(CH_3)_2N^+=CH—]$ ester, intramolecular trifluoromethyl-substituted iminomethyl ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.] or an ester with an N-hydroxy compound [e.g. N,N-dimethylhydroxylamine, 1-hydroxy-2-(1H)-pyridone, N-hydroxysuccinimide, n-hydroxyphthalimide, 1-hydroxy-1H-benzotriazole, etc.], and the like. These reactive derivatives can optionally be selected from them according to the kind of the compound (III) to be used.

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvents may also be used in a mixture with water.

In this reaction, when the compound (III) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl) carbodiimide; N,N'-diethylcarbodiimide, N,N'-diisopropylcarbodiimide; N-ethyl-N'-(3-dimethylaminopropyl) carbodiimide; N,N'-carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; diphenylphosphoryl azide; diphenyl chlorophosphate; diphenylphosphinic chloride; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl) isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as an alkali metal bicarbonate, tri (lower) alkylamine, pyridine, N,4-dimethylaminopyridine, N-(lower) alkylmorpholine, N,N-di (lower) alkylbenzylamine, or the like.

The reaction temperature is not critical, and the reaction is usually carried out under cooling to heating.

In this reaction, in case that the compound (II) having aryl substituted with phthalimido for $R^1$, the compound (Ia) having aryl substituted with amino may be obtained according to reaction condition.

This case is included within the scope of this reaction.
Process 2

The object compound (Ic) or its salt can be prepared by reacting a compound (Ib) or its salt with a compound (IV) in the presence of a base.

Suitable salts of the compounds (Ib) and (Ic) may be the same as those exemplified for the compound (I).

Suitable base may be an alkali metal (e.g. sodium, potassium, etc.), an alkali metal hydride (e.g. sodium hydride), an alkali metal alkoxide (e.g. potassium tert-butoxide, etc.) and the like.

The reaction is carried out in a solvent such as N,N-dimethylformamide, tetrahydrofuran, dioxane, a mixture thereof or any other solvent which does not adversely influence the reaction.

The reaction temperature is not critical and the reaction is usually carried out under cooling to warming.
Process 3

The object compound (Ie) or its salt can be prepared by subjecting a compound (Id) or its salt to reduction.

Suitable salts of the compounds (Id) and (Ie) may be the same as those exemplified for the compound (I).

The reduction may include chemical reduction and catalytic reduction, which are carried out in a conventional manner.

Suitable reducing agents to be used in chemical reduction are a metal [e.g. tin, zinc, iron, nickel, etc.], a combination of such metal and/or metallic compound [e.g. nickel chloride, chromium chloride, chromium acetate, etc.] and an organic or inorganic acid [e.g. formic acid, acetic acid, propionic acid, tifuluoroacetic acid, p-toluenesulfonic acid, hydrochloric acid, hydrobromic acid, etc.], a combination of such metal and/or metallic compound and base [e.g. ammonia, ammonium chloride, sodium hydroxide, etc.], a metal hydride compound such as aluminum hydride compound [e.g. lithium aluminum hydride, sodium aluminum hydride, aluminum hydride, lithium trimethoxyaluminum hydride, lithium tri-t-butoxyaluminum hydride, etc.], borohydride compound [e.g. sodium borohydride, lithium borohydride, sodium cyanoborohydride, tetramethylammonium borohydride, borane, diborane, etc.], a phosphorus compound [e.g. phosphorus trichloride, phosphorus tribromide, triphenylphosphine, triethylphosphine, etc.] and the like.

Suitable catalysts to be used in catalytic reduction are conventional ones such as platinum catalysts [e.g. platinum plate, spongy platinum, platinum black, colloidal platinum, platinum oxide, platinum wire, etc.], palladium catalyst [e.g. spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.], or the like.

The reduction is usually carried out in a solvent. A suitable solvent to be used may be water, an alcohol [e.g. methanol, ethanol, propanol, etc.], acetonitrile or any other conventional organic solvent such as diethyl ether, dioxane, tetrahydrofuran, etc. or a mixture thereof.

The reaction temperature is not critical, and the reaction is preferably carried out under cooling to heating.
Process 4

The object compound (If) or its salt can be prepared by reacting a compound (Ie) or its salt with aroyl halide, cyano (lower) alkylcarboxylic acid, mercapto (lower) alkylcarboxylic acid, lower alkyllactone, 1,1-dihalo-1,1-diphenoxymethane, diphenyl N-sulfamoylcarbonimidate, diphenyl N-cyanocarbonimidate, dicyandiamide, 1,1'-thiocarbonyl-diimidazole, cyanogen bromide, lower alkoxycarbonyl isothiocyanate, tri (lower) alkyl orthoformate, tetra (lower) alkyl orthocarbonate, lower alkylcarboxylic acid, halo (lower) alkylcarboxylic acid, protected amino (lower)-alkylcarbonyl halide or a heterocyclic (lower) alkylcarbonyl halide.

Suitable salts of the compounds (Ie) and (If) may be the same as those exemplified for the compound (I).

The reaction is carried out in no solvent or a solvent such as water, hydrochloric acid, tetrahydrofuran, ethyl acetate, acetonitrile, benzene, acetic acid, dichloromethane, pyridine, an alcohol (e.g. methanol, ethanol, isopropanol, etc.), a mixture thereof or any other solvent which does no adversely influence the reaction.

The reaction is also preferably carried out in the presence of base (e.g. sodium carbonate, etc.) or a conventional condensing agent such as N,N'-dicyclohexyl-carbodiimide, p-toluenesulfonic acid, or the like.

The reaction temperature of this reaction is not critical and the reaction is usually carried out under cooling to heating.

Process 5

The object compound (Ig) or its salt can be prepared by reacting a compound (Ie) or its salt with glyoxal and sodium hydrogen sulfite, or sodium nitrite.

Suitable salts of the compounds (Ie) and (Ig) may be the same as those exemplified for the compound (I).

The reaction is usually carried out in a solvent such as water, acetic acid, an alcohol (e.g. methanol, ethanol, etc.), a mixture thereof or any other solvent which does not adversely influence the reaction.

The reaction temperature of this reaction is not critical and the reaction is usually carried out under cooling to heating.

Process 6

The object compound (Ih) or its salt can be prepared by reacting a compound (Ib) or its salt with an acylating agent.

Suitable salts of the compounds (Ib) and (Ih) may be the same as those exemplified for the compound (I).

The acylating agent may include an organic acid represented by the formula: $R^7$—OH, in which $R^7$ is acyl as illustrated above, or its reactive derivative.

The suitable reactive derivative of organic acid may be a conventional one such as an acid halide [e.g. acid chloride, acid bromide, etc.], an acid azide, an acid anhydride containing intramolecular and intermolecular ones, an activated amide, an activated ester or the like.

When free acid is used as an acylating agent, the acylation reaction may preferably be conducted in the presence of a conventional condensing agent such as N,N'-dicyclohexylcarbodiimide or the like.

The reaction is usually carried out in a conventional solvent such as water, pyridine, acetone, dioxane, chloroform, methylene chloride, acetonitrile, ethylene chloride, tetrahydrofuran, ethyl acetate, N,N-dimethylformamide, pyridine or any other organic solvent which does not adversely influence the reaction, or a mixture thereof.

The reaction is also preferably carried out in the presence of a conventional base such as triethylamine, pyridine, N,N-dimethylaminopyridine, sodium hydroxide or the like.

The reaction temperature is not critical, and the reaction can be carried out under cooling to heating.

Process 7

The object compound (Ij) or its salt can be prepared by subjecting a compound (Ii) or its salt to elimination reaction of the N-substituent group.

Suitable salts of the compounds (Ii) and (Ij) may be the same as those exemplified for the compound (I).

The reaction is carried out in accordance with a conventional method such as hydrolysis, reduction or the like.

In case that the N-substituent group is acyl, acyloxymethyl or lower alkoxyarylmethyl, the reaction is preferably carried out in accordance with hydrolysis, and in case that the N-substituent is arylmethyl, the reaction is preferably carried out in accordance with reduction.

The hydrolysis is preferably carried out in the presence of a base or an acid including Lewis acid.

Suitable base may include an inorganic base and an organic base such as an alkali metal [e.g. sodium, potassium, etc.], an alkaline earth metal [e.g. magnesium, calcium, etc.], the hydroxide or carbonate or bicarbonate or lower alkoxide thereof, hydrazine, alkylamine [e.g. methylamine, trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, or the like.

Suitable acid may include an organic acid [e.g. formic acid, acetic acid, propionic acid, trichloroacetic acid, trifuloroacetic acid, etc.], an inorganic acid [e.g. hydrochloric acid, hydrobromic acid, sulfuric acid, hydrogen chloride, hydrogen bromide, hydrogen fluoride, etc.] and an acid addition salt compound [e.g. pyridine hydrochloride, etc.].

The elimination using trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, chloroform, tetrachloromethane, tetrahydrofuran, a mixture thereof or any other solvent which does not adversely influence the reaction. A liquid base or acid can be also used as the solvent. The reaction temperature is not critical and the reaction is usually carried out under cooling to heating.

The reduction method applicable for the elimination reaction may include chemical reduction and catalytic reduction.

Suitable reducing agents to be used in chemical reduction are a combination of metal [e.g. tin, zinc, iron, etc.] of metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalyst [e.g. reduced iron, Raney iron, etc.], copper catalysts [e.g. reduced copper, Raney copper, Ullman copper, etc.] and the like.

In case that the N-substituent group is benzyl, the reduction is preferably carried out in the presence of a combination of palladium catalysts [e.g. palladium black, palladium on carbon, etc.] and formic acid or its salt [e.g. ammonium formate, etc.].

The reduction is usually carried out in a conventional solvent which does not adversely influence the reaction such as water, methanol, ethanol, propanol, N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc. or a mixture thereof.

The reaction temperature of this reduction is not critical and the reaction is usually carried out under cooling to heating.

In this reaction, in case that the compound (Ii) having (N-lower alkoxycarbonyl)phthalimido(lower)alkylindolyl, (N-lower alkoxycarbonyl)lower alkylamino(lower)alkylamino(N-lower alkoxycarbonyl)benzimidazolyl or N-lower alkoxycarbonylamino(lower)alkyl(N-lower alkyl)amino(N-lower alkoxycarbonyl)benzimidazolyl for Yh, the compound (Ij) having amino(lower)alkylindolyl, lower alkylamino(lower)alkylaminobenzimidazolyl or amino(lower)alkyl(N-lower)alkylaminobenzimidazolyl for Yi may be obtained according to reaction condition. This case is included within the scope of this reaction.

Process 8

The object compound (Il) or its salt can be prepared by subjecting a compound (Ik) or its salt to elimination reaction of the N-protective group.

Suitable salts of the compounds (Ik) and (Il) may be the same as those exemplified for the compound (I).

This reaction can be carried out in substantially the same manner as Process 7, and therefore the reaction mode and reaction condition (e.g. solvent, reaction temperature, etc.) of this reaction are to be referred to those as explained in Process 7.

Process 9

The object compound (In) or its salt can be prepared by subjecting a compound (Im) or its salt to deesterification reaction.

Suitable salts of the compounds (Im) and (In) may be the same as those exemplified for the compound (I).

The reaction is carried out in accordance with a conventional method such as hydrolysis, reduction or the like.

The hydrolysis is preferably carried out in the presence of a base or an acid including Lewis acid. Suitable base may include an inorganic base and an organic base such as an alkali metal [e.g. lithium, sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4.3.0]non-5-one, 1,4-diazabicyclo[2.2.2]octane, 1,8-diazabicyclo[5.4.0]undec-7-ene, or the like. Suitable acid may include an organic acid [e.g. formic acid, acetic acid, propionic acid, trichloroacetic acid, trifluoroacetic acid, etc.], an inorganic acid [e.g. hydrochloric acid, hydrobromic acid, hydroiodic acid, sulfuric acid, etc.] and Lewis acid [e.g. boron tribromide, etc.].

The reaction is usually carried out in a solvent such as water, an alcohol [e.g. methanol, ethanol, etc.], xylene, diethylene, glycol monomethyl ether, methylene chloride, tetrahydrofuran, a mixture thereof or any other solvent which does not adversely influence the reaction. A liquid base or acid can be also used as the solvent.

The reaction temperature is not critical and the reaction is usually carried out under cooling to warming.

The reduction can be applied preferably for elimination of the ester moiety such as 4-nitrobenzyl, 2-iodoethyl, 2,2,2-trichloroethyl, or the like. The reduction method applicable for the elimination reaction may include chemical reduction and catalitic reduction.

Suitable reducing agents to be used in chemical reduction are a combination of metal [e.g. tin, zinc, iron, palladium back, etc.] or metallic compound [e.g. chromium chloride, chromium acetate, etc.] and an organic or inorganic acid [e.g. formic acid, acetic acid, propionic acid, trifluoroacetic acid, carbamic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalyst [e.g. spongy palladium, palladium black, palladium oxide, palladium hydroxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.] or the like.

The reduction is usually carried out in a conventional solvent which does not adversely influence the reaction such as water, an alcohol [e.g. methanol, ethanol, propanol, etc.], N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to warming.

Process 10

The object compound (Io) or its salt can be prepared by reacting a compound (In) or its reactive derivative at the carboxy group or a salt thereof with an amine or its salt.

Suitable salt of amine may be an acid addition salt as exemplified for the compound (I).

Suitable salts of the compounds (In) and (Io) and its reactive derivative at the carboxy group may be the same as those exemplified for the compound (I).

Suitable "amine" may be ammonia, substituted or unsubstituted lower alkylamine, substituted or unsubstituted N-containing heterocyclic compound and the like.

The substituted or unsubstituted lower alkylamine may be mono or di(lower)alkylamine (e.g. methylamine, ethylamine, propylamine, isopropylamine, butylamine, isobutylamine, pentylamine, hexylamine, dimethylamine, diethylamine, dipropylamine, dibutylamine, di-isopropylamine, dipentylamine, dihexylamine, etc.), pyridyl(lower)alkylamine, (e.g. pyridylmethylamine, etc.), lower alkylamino(lower)alkylamine (e.g. N-dimethylaminoethylamine, N-dimethylaminopropylamine, N-diethylaminoethyl-N-methylamine, etc.), morpholino(lower)alkylamine (e.g. morpholinoethylamine, etc.) or the like.

The substituted or unsubstituted N-containing heterocyclic compound may be a heterocyclic group substituted with amino (e.g. aminopyridine, N-methyl-N'-aminopiperazine, etc.), saturated 5 or 6-membered N-, or N- and S-, or N- and O-containing heterocyclic compound such as pyrrolidine, imidazolidine, piperidine, piperidone, piperazine, lower alkylaminopiperidine (e.g. dimethylaminopiperidine, etc.), N-(lower)alkylhomopiperazine (e.g.

N-methylhomopiperazine, etc.), N-(lower)alkylpiperazine (e.g. N-methylpiperazine, N-ethylpiperazine, etc.), morpholine, thiomorpholine, N-pyridylpiperazine, N-hydroxy(lower)alkoxy(lower)alkylpiperazine (e.g. N-hydroxyethoxyethylpiperazine, etc.), N-pyrrolidinylcarbonyl(lower)alkylpiperazine (e.g. N-pyrrolidinylcarbonylmethylpiperazine, etc.), or the like, in which preferable one is N-methylpiperazine.

This reaction an be carried out in substantially the same manner as Process 1, and therefore the reaction mode and reaction condition (e.g. solvent, reaction temperature, etc.) of this reaction are to be referred to those as explained in Process 1.

Process 11

The object compound (Iq) or its salt can be prepared by subjecting a compound (Ip) or its salt to elimination reaction of methyl or the hydroxy-protective group.

Suitable salts of the compounds (Ip) can (Iq) may be the same as those exemplified for the compound (I).

This reaction can be carried out in substantially the same manner as Process 7, and therefore the reaction mode and reaction condition (e.g. solvent, reaction temperature, etc.) of this reaction are to be referred to those as explained in Process 7.

In case that the hydroxy-protective group is tert-butyldiphenylsilyl, the reaction is preferably carried out in the presence of tetrabutylammonium fluoride.

Process 12

The object compound (Is) or its salt can be prepared by reacting a compound (Ir) or its salt with an acylating agent.

Suitable salts of the compounds (Ir) and (Is) may be the same as those exemplified for the compound (I).

This reaction can be carried out in substantially the same manner as Process 6, and therefore the reaction mode and reaction condition (e.g. solvent, reaction temperature, etc.) of this reaction are to be referred to those as explained in Process 6.

Process 13

The object compound (It) or its salt can be prepared by reacting a compound (Ib) or its salt with N-lower alkylmethyleneammonium halide.

Suitable salts of the compounds (Ib) and (It) may be the same as those exemplified for the compound (I).

Suitable N-lower alkylmethyleneammonium halide may be N-mono or di(lower alkyl)methyleneammonium halide such as N-methylmethyleneammonium chloride, N,N-dimethylmethyleneammonium chloride or the like, in which preferable one is N,N-dimethylmethyleneammonium chloride.

The reaction is usually carried out in a conventional solvent which does not adversely influence the reaction such as chloroform, methylene chloride or the like.

The reaction temperature of this reaction is not critical and the reaction is usually carried out under cooling to heating.

Process 14

The object compound (Iv) or its salt can be prepared by subjecting a compound (Iu) or its salt to oxidation reaction.

Suitable salts of the compounds (Iu) and (Iv) may be the same as those exemplified for the compound (I).

Suitable oxidizing agent used in this reaction may be manganese doixide, dimethyl sulfoxide, a mixture of dimethyl sulfoxide and oxalyl chloride or dimethyl sulfoxide and sulfur trioxide pyridine complex, and the like.

The reaction is usually carried out in a conventional solvent such as pentane, hexane, benzene, diethyl ether, dimethoxyethane, acetone, chloroform, dichloromethane or any other solvent which does not adversely influence the reaction.

Additionally in case that the above-mentioned oxidizing agent is liquid, it can be used as a solvent.

In this reaction, in case that dimethyl sulfoxide or a mixture of dimethyl sulfoxide and oxalyl chloride or dimethyl sulfoxide and sulfur trioxide pyridine complex is used as an oxidizing agent, the reaction is preferably carried out in the presence of alkali metal iodide (e.g. sodium iodide, etc.) and alkali metal carbonate (e.g. sodium carbonate) or tri(lower)alkylamine (e.g. triethylamine, etc.).

The reaction temperature is not critical, and the reaction is usually carried out under cooling to heating.

Process 15

The object compound (Ix) or its salt can be prepared by subjecting a compound (Iw) or its salt to deesterification reaction.

Suitable salts of the compounds (Iw) and (Ix) may be the same as those exemplified for the compound (I).

This reaction can be carried out in substantially the same manner as Process 9, and therefore the reaction mode and reaction condition (e.g. solvent, reaction temperature, etc.) of the reaction are to be referred to those as explained in Process 9.

Process 16

The object compound (Iz) or its salt can be prepared by subjecting a compound (Iy) or its salt to elimination reaction of methyl substituted with aryl or substituted aryl.

Suitable salts of the compounds (Iy) and (Iz) may be the same as those exemplified for the compound (I).

This reaction can be carried out in substantially the same manner as Process 11, and therefore the reaction mode and reaction condition (e.g. solvent, reaction temperature, etc.) of this reaction are to be referred to those as explained in Process 11.

Process 17

The object compound (I-1) or its salt can be prepared by reacting a compound (Ix) or its reactive derivative at the carboxy group or a salt thereof with an amine or its salt.

Suitable salts of the compounds (Ix) and (I-1) may be the same as those exemplified for the compound (I).

Suitable salts of amine may be an acid addition salt as exemplified for the compound (I).

Suitable "amine" may be N-protected piperazine, oxopiperidine, lower alkylamine (e.g. dimethylamine, etc.), ammonia, lower alkylaminoamine (e.g. N,N-dimethylhydrazine, etc.), lower alkyhlamino(lower)alkyl(N-lower alkyl)amine (e.g. dimethylaminoethyl(N-methyl) amine and the like.

This reaction can be carried out in substantially the same manner as Process 1, and therefore the reaction mode and reaction condition (e.g. solvent, reaction temperature, etc.) of this reaction are to be referred to those explained in Process 1.

Process 18

The object compound (I-3) or its salt can be prepared by reacting a compound (I-2) or its salt with a reducing agent.

Suitable salts of the compound (I-2) and (I-3) may be the same as those exemplified for the compound (I).

Suitable reducing agent may be alkali metal borohydride (e.g. sodium borohydride, etc.), and the like.

The reaction is carried out in a solvent such as an alcohol (e.g. methanol, ethanol, etc.), tetrahydrofuran, or the like.

The reaction temperature is not critical and the reaction is usually carried out under cooling to warming.

Process 19

The object compound (I-4) or its salt can be prepared by reacting a compound (Iz) or its salt with an acrylating agent.

Suitable salts of the compounds (Iz) and (I-4) may be the same as those exemplified for the compound (I).

This reaction can be carried out in substantially the same manner as Process 6, and therefore the reaction mode and reaction condition (e.g. solvent, reaction temperature, etc.) of this reaction are to be referred to those as explained in Process 6.

Process 20

The object compound (I-5) or its salt can be prepared by reacting a compound (Iz) or its salt with a compound (V).

Suitable salts of the compounds (Iz) and (I-5) may be the same as those exemplified for the compound (I).

When the compound (V) having halogen for $Z^2$ is used in this reaction, the reaction is preferably carried out in the presence of a base such as an alkali metal (e.g. sodium, potassium, etc.), an alkaline earth metal (e.g. magnesium, calcium, etc.), the hydride or hydroxide or carbonate or bicarbonate thereof.

The reaction is usually carried out in a conventional solvent which does not adversely influence the reaction such as water, dioxane, alcohol (e.g. methanol, ethanol, etc.), acetonitrile, tetrahydrofuran, acetic acid, N,N-dimethylformamide, or a mixture thereof.

The reaction temperature is not critical and the reaction can be carried out under cooling to heating.

Process 21

The object compound (I-6) or its salt can be prepared by subjecting a compound (I-5) or its salt or elimination reaction of the N-protective group.

Suitable salts of the compounds (I-5) and (I-6) may be the same as those exemplified for the compound (I).

This reaction can be carried out in substantially the same manner as Process 8, and therefore the reaction mode and reaction condition (e.g. solvent, reaction temperature, etc.) of this reaction are to be referred to those as explained in Process 8.

Process 22

The object compound (I-7) or its salt can be prepared by reacting a compound (I-6) or its salt with an acylating agent.

Suitable salts of the compounds (I-6) and (I-7) may be the same as those exemplified for the compound (I).

This reaction can be carried out in substantially the same manner as Process 6, and therefore the reaction mode and reaction condition (e.g. solvent, reaction temperature, etc.) of this reaction are to be referred to those as explained in Process 6.

Process 23

The object compound (I-8) or its salt can be prepared by reacting a compound (I-6) or its salt with lower alkanal in the presence of a reducing agent.

Suitable salts of the compounds (I-6) and (I-8) may be the same as those exemplified for the compound (I).

Suitable lower alkanal may be $C_1$–$C_6$ alkanal such as formaldehyde, ethanal, propanal or the like, in which preferable one is formaldehyde.

Suitable reducing agent may be diborane, borane-organic amine complex [e.g. borane-pyridine complex, etc.], alkali metal cyanoborohydride [e.g. sodium cyanoborohydride, lithium cyanoborohydride, etc.], sodium borohydride and the like.

The reaction is preferably carried out in the presence of molecular sieves.

The reaction is usually carried out in a conventional solvent such as water, an alcohol [e.g. methanol, ethanol, etc.], dioxane, tetrahydrofuran, a mixture therefore or any other organic solvent which does not adversely influence the reaction.

The reaction may also be carried out in an acidic condition [e.g. presence of acetic acid, sulfuric acid, etc.] and the reaction temperature is not critical, and the reaction is usually carried out under cooling to warming.

Process 24

The object compound (I-10) or its salt can be prepared by subjecting a compound (I-9) or its salt to reduction.

Suitable salts of the compounds (I-9) and (I-10) may be the same as those exemplified for the compound (I).

The reduction may include chemical reduction and catalytic reduction, which are carried out in a conventional manner.

Suitable reducing agents to be used in chemical reduction are a metal [e.g. tin, zinc, iron, nickel, etc.], a combination of such metal and/or metallic compound [e.g. nickel chloride, chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.], a combination of such metal and/or metallic compound and base [e.g. ammonia, ammonium chloride, sodium hydroxide, etc.], a metal hydride compound such as aluminum hydride compound [e.g. lithium aluminum hydride, sodium aluminum hydride, aluminum hydride, lithium trimethoxyaluminum hydride, lithium tri-t-butyoxyaluminum hydride, etc.], borohydride compound [e.g. sodium borohydride, lithium borohydride, sodium cyanoborohydride, tetramethylammonium borohydride, borane, diborane, etc.], a phosphorus compound [e.g. phosphorus trichloride, phosphorus tribromide, triphenylphosphine, triethylphosphine, etc.] or the like.

Suitable catalysts to be used in catalytic reduction are conventional ones such as platinum catalysts [e.g. platinum plate, spongy platinum, platinum black, colloidal platinum, platinum oxide, platinum wire, etc.], palladium catalyst [e.g. spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.], or the like.

The reduction is usually carried out in a solvent. A suitable solvent to be used may be water, an alcohol [e.g. methanol, ethanol, propanol, etc.], acetonitrile or any other conventional organic solvent such as dimethyl ether, dioxane, tetrahydrofuran, etc. or a mixture thereof.

The reaction temperature is not critical, and the reaction is preferably carried out under cooling to heating.

Process 25

The object compound (I-10) or its salt can be prepared by reacting a compound (I-11) or its salt with an azide compound.

Suitable salts of the components (I-10) and (I-11) may be the same as those exemplified for the compound (I).

Suitable azide compound may be sodium azide, diphenylphosporylazide and the like.

The reaction is usually carried out in a conventional solvent such as water, tetrahydrofuran, dioxane or any other organic solvent which does not adversely influence the reaction, or a mixture thereof.

The reaction is also preferably carried out in the presence of a conventional base such as triethylamine, pyridine or the like.

The reaction temperature is not critical, and the reaction is preferably carried out under warming to heating.

Process 26

The object compound (I-13) or its salt can be prepared by reacting a compound (I-12) or its reactive derivative at the carboxy group or a salt thereof with a reducing agent.

Suitable salts of the compound (I-13), (I-12) and its reactive derivative at the carboxy group may be the same as those exemplified for the compound (I).

Suitable reactive derivative at the carboxy group of the compound (I-12) may include an activated imide (e.g. phthalimido, etc.), an activated amide, an activated ester and the like.

Suitable reducing agent may be aluminum hydride compound [e.g. lithium aluminum hydride, lithium tri-t-butoxyaluminum hydride. etc.], borohydride compound [e.g. lithium borohydride, etc.], aluminum alkoxide [e.g. aluminum isopropoxide, etc.] and the like.

The reaction is usually carried out in a conventional solvent, such as diethyl ether, dioxane, or any other organic solvent which does not adversely influence the reaction, or a mixture thereof.

The reaction temperature is not critical, and the reaction is usually carried out under cooling to heating.

Process 27

The object compound (I-15) or its salt can be prepared by reacting a compound (I-14) or its salt with an acylating agent.

Suitable salts of the compounds (I-14) and (I-15) may be the same as those exemplified for the compound (I).

This reaction can be carried out in substantially the same manner as Process 6, and therefore the reaction mode and reaction condition (e.g. solvent, reaction temperature, etc.) of this reaction are to be referred to those as explained in Process 6.

Process 28

The object (I-16) or its salt can be prepared by reacting a compound (I-15) or its salt with an alkali metal salt of phthalimide.

Suitable salts of the compounds (I-15) and (I-16) may be the same as those exemplified for the compound (I).

Suitable alkali metal salt of phthalimide may be potassium phthalimide and the like.

The reaction is usually carried out in a conventional solvent such as dimethyl sulfoxide, tetrahydrofuran or any other solvent which does not adversely influence the reaction.

The reaction temperature is not critical, and the reaction can be carried out under cooling to heating.

Process 29

The object compound (I-18) or its salt can be prepared by reacting a compound (I-17) or its salt with an amine.

Suitable salts of the compounds (I-17) and (I-18) may be the same as those exemplified for the compound (I).

Suitable amine may be N-lower alkylpiperazine, morpholine, dimethylamine, di(lower) alkylaminopiperidine, di(lower)alkylhydrazine, amino (lower)alkyl(N-lower alkyl)amine, di(lower)alkylamino (lower)alkylamine and the like.

The reaction is carried out in no solvent or a solvent such as tetrahydrofuran, dioxane or any other solvent which does not adversely influence the reaction.

The reaction temperature is not critical, and the reaction is preferably carried out under warming to heating.

Process 30

The object compound (I-20) or its salt can be prepared by subjecting a compound (I-19) or its salt to elimination reaction of N-protective group.

Suitable salts of the compounds (I-19) and (I-20) may be the same as those exemplified for the compound (I).

This reaction can be carried out in substantially the same manner as Process 8, and therefore the reaction mode and reaction condition (e.g. solvent, reaction temperature, etc.) of this reaction are to be referred to those as explained in Process 8.

Process 31

The object compound (I-22) or its salt can be prepared by reacting a compound (I-21) with hydroxylamine or its salt.

Suitable salts of the compounds (I-21) and (I-22) may be the same as those exemplified for the compound (I).

Suitable salt of hydroxylamine may be an acid addition salt as exemplified for the compound (I).

The reaction is preferably carried out in the presence of a conventional base such as sodium acetate, sodium hydrogen carbonate or the like.

The reaction is usually carried out in a solvent which does not influence the reaction such as water, an alcohol (e.g. methanol, ethanol, etc.), pyridine or a mixture thereof.

The reaction temperature is not critical and the reaction is preferably carried out warming to heating.

Process 32

The object compound (I-23) or its salt can be prepared by reacting a compound (VI) or its reactive derivative at the carboxy group or a salt thereof with a compound (VII) or its salt.

Suitable salts of the compounds (I-23), (VII), (VI) and its reactive derivative at the carboxy group may be the same as those exemplified for the compound (I).

This reaction can be carried out in substantially the same manner as Process 1, and therefore the reaction mode and reaction condition (e.g. solvent, reaction temperature, etc.) of this reaction are to be referred to those as explained in Process 1.

The compounds obtained by the above processes can be isolated and purified by a conventional method such as pulverization, recrystallization, column chromatography, reprecipitation, or the like.

It is to be noted that the compound (I) and the other compounds may include one or more stereoisomer(s) such as optical isomer(s) or geometrical isomer(s) due to asymmetric carbon atom(s) and double bond(s), and all of such isomers and mixture thereof are included within the scope of this invention.

Additionally, it is to be noted that any hydrate of the compound (I) is also included within the scope of this invention.

The object compound (I) and pharmaceutically acceptable salts thereof possess activities as vasopressin antagonistic activity, vasodilating activity, hypotensive activity, activity for inhibiting saccharide release in liver, activity for inhibiting growth of mesangium cells, water diuretic activity, platelet agglutination inhibitory activity, oxytocin antagonistic activity and the like, and are useful for the treatment and/or prevention of hypertension, heart failure, renal insufficiency, edema, ascites, vasopressin parasecretion syndrome, hepatocirrhosis, hyponatremia, hypokalemia, diabetic, circulation disorder, cerebrovascular disease (e.g. cerebral edema, cerebral infarction, etc.), Meniere's syndrome (e.g. Meniere's disease, etc.), motion sickness and the like in human being and animals.

In order to illustrate the usefulness of the object compound (I), the pharmacological data of the compound (I) are shown in the following.

Test 1

Vasopressin 1 (V1) receptor binding (i) Test Method:

Blood was obtained by venipuncture from normal subjects. Platelet-rich plasma (PRP) was prepared by centrifugation of whole blood at 200×g for 10 minutes. PRP was centrifuged at 45,000×g for 30 minutes. The remaining pellet was resuspended in 10 volume of ice cold 100 mM Tris-HCl (pH 7.4) buffer (containing 5 mM $MgCl_2$, 0.1% bovine serum albumin and 1 mM EDTA), and centrifuged at 45,000×g for 30 minutes again. The final pellet was resuspended in 100 mM Tris-HCl buffer. The resulting membrane preparation was used immediately for the binding assay.

Competition assays were conducted at equilibrium (15 minutes at 30° C.) by using 1.5 nM $^3$H-vasopressin (40–87 Ci/mmol; New England Nuclear) in 100 mM Tric-HCl (pH 7.4) buffer. Nonspecific binding was determined by using 1 µM vasopressin. After incubation, reaction was terminated by adding 5 ml of ice-cold 100 mM Tris-HCl (pH 7.4) buffer, and then filtered rapidly through Whatman glass filter (GF/C). The filter was washed twice with the same buffer. The glass filter was mixed with liquid scintillation cocktail, and radioactivity was counted in a liquid scintillation counter. Competition activity of the test compound was represented by $IC_{50}$ values.

(ii) Test Result:

| Test Compound (Example No.) | $IC_{50}$ (nM) |
|---|---|
| 39-27) | 1.5 |
| 39-35) | <1.0 |
| 115-71) | 0.7 |
| 115-81) | 4.5 |

Test 2

Vasopressin 2 (V2) receptor binding (i) Test Method:

For binding assays, the receptor cDNA was permanently expressed in Chinese hamster ovary (CHO) cells. CHO cells were transfected with a vector directing expression of the cDNA for the human V2 receptor and the clonal cell lines expressing human V2 receptor was established essentially as described previously (Nakajina, Y., et al. J. Biol. Chem., 1992, 267, 2437).

DNA-transfected cells were harvested and homogenized in ice cold 250 mM sucrose buffer containing 25 mM Tris-HCl (pH 7.4), 10 mM $MgCl_2$, 1 mM EDTA and 5 µg/ml p-amidinophenylmethylsulfonyl fluoride (A-PMSF). The homogenate was centrifuged at 500×g for 10 minutes. The supernatant was centrifuged at 100,000×g for 1 hour. The final pellet was suspended in 25 mM Tris-HCl (pH 7.4) buffer (containing 10 mM $MgCl_2$, 1 mM EDTA and 5 µg/ml A-PMSF), and stored in small aliquots at −80° C.

Competition assays were conducted at equilibrium (2 hours at 22° C.) by using 0.5 nM $^3$H-vasopressin (40–87 Ci/mmol, New England Nuclear) in 100 mM Tris-HCl (pH 7.4) buffer (containing 5 mM $MgCl_2$, 5 µg/ml A-PMSF, 4 µg/ml leupeptin, 40 µg/ml bacitracin, 20 µg/ml chymostatin and 0.1% bovine serum albumin). Nonspecific binding was determined by using 1 µM vasopressin. After incubation, reaction mixture was rapidly filtered through Whatman glass filter (GF/C). The filter was washed twice with the same buffer. The radioactivity was counted in a liquid scintillation counter. Competition activity of the test compound was represented by $IC_{50}$ values.

(ii) Test Result:

| Test Compound (Example No.) | $IC_{50}$ (nM) |
|---|---|
| 39-27) | 460 |
| 39-35) | 380 |

For therapeutic purpose, the compound (I) of the present invention can be used in a form of pharmaceutical preparation containing one of said compounds, as an active ingredient, in admixture with a pharmaceutically acceptable carrier such as an organic or inorganic solid, semi-solid or liquid excipient suitable for oral, parenteral or external (topical) administration. The pharmaceutical preparations may be capsules, tablets, dragees, granules, suppositories, solution, lotion, suspension, emulsion, ointment, gel, or the like. If desires, there may be included in these preparations, auxiliary substances, stabilizing agents, wetting or emulisifying agents, buffers and other commonly used additives.

While the dosage of the compound (I) will vary depending upon the age and condition of the patient, an average single dose of about 0.1 mg, 1 mg, 10 mg, 50 mg, 100 mg, 250 mg, 500 mg and 1000 mg of the compound (I) may be effective for treating the above-mentioned diseases. In general, amounts between 0.1 mg/body and about 1,000 mg/body may be administered per day.

The following Preparations and Examples are given for the purpose of illustrating this invention.

Preparation 1

To a suspension of sodium hydride (133 mg) in tetrahydrofuran (5.0 ml) was added dropwise a solution of benzyl indole-4-carboxylate (580 mg) in tetrahydrofuran (5.0 ml) at 0° C. and the mixture was stirred at 0° C. for 1 hour. 4-Toluenesulfonyl chloride (440 mg) was added to the mixture and the solution was stirred at ambient temperature for 1 hour. The reaction was quenched with 1N hydrochloric acid and then the aqueous solution was extracted with ethyl acetate. Drying, filtering and removal of solvents afforded a crude product. The crude product was purified by column chromatography (eluent; n-hexane:ethyl acetate=15:1) to give benzyl 1-(4-toluenesulfonyl)indole-4-carboxylate (560 mg) as a colorless syrup.

NMR ($CDCl_3$, δ): 2.32 (3H, s), 5.39 (2H, s), 7.19–7.23 (2H, m), 7.31–7.48 (7H, m), 7.67 (1H, d, J=4 Hz), 7.72 (2H, d, J=9 Hz), 8.00 (1H, d, J=8 Hz), 8.20 (1H, d, J=8 Hz)

Preparation 2

To a suspension of sodium hydride (174 mg) in tetrahydrofuran (8.0 ml) was added dropwise a solution of benzyl indole-7-carboxylate (700 mg) in tetrahydrofuran (7.0 ml) at 0° C. and the mixture was stirred at 0° C. for 1 hour. Chloromethyl pivalate (461 mg) was added to the mixture and the solution was stirred at ambient temperature for 3 hours. The reaction was quenched with 1N hydrochloric acid and then the aqueous solution was extracted with ethyl acetate. Drying, filtering and removal of solvents afforded benzyl 1-pivaloyloxymethylindole-7-carboxylate (1.08 g) as a yellow oil.

NMR ($CDCl_3$, δ): 1.01 (9H, s), 5.42 (2H, s), 6.40 (2H, s), 6.58 (1H, d, J=4 Hz), 7.17 (1H, t, J=8 Hz), 7.28 (1H, d, J=4 Hz), 7.33–7.42 (3H, m), 7.47–7.51 (2H, m), 7.73–7.80 (2H, m)

Preparation 3

To a solution of 2,2,6,6-tetramethylpiperidine (322 mg) in tetrahydrofuran (5.0 ml) was added dropwise a solution of n-butyllithium (1.6M n-hexane solution 1.3 ml) at −70∼−60° C. and the solution was stirred at 0° C. for 30 minutes. A solution of benzyl 1-tert-butoxycarbonylindole-4-carboxylate (500 mg) in tetrahydrofuran (2.5 ml) was added dropwise to the above solution at −70∼−60° C. and the mixture was stirred at −70° C. for 30 minutes. To the mixture was added a solution of ethyl chloroformate (185 mg) in tetrahydrofuran (2.5 ml) at such a rate as to maintain the temperature below −60° C. The solution was stirred at −70°

C. for 2 hours and the reaction was quenched with aqueous saturated ammonium chloride solution at −20° C. The aqueous solution was extracted with ethyl acetate. Drying, filtering and removal of solvents afforded a crude product. The crude product was chromatographed on silica gel (eluent; n-hexane:ethyl acetate=15:1) to give benzyl 1-tert-butoxycarbonyl-2-ethoxycarbonylindole-4-carboxylate (100 mg) as a colorless oil.

NMR (CDCl$_3$, δ): 1.39 (3H, t, J=7 Hz), 1.62 (9H, s), 4.38 (2H, q, J=7 Hz), 5.43 (2H, s), 7.31–7.50 (6H, m), 7.78 (1H, s), 8.04 (1H, d, J=8 Hz), 8.32 (1H, d, J=9 Hz)

Preparation 4

To a solution of 2-amino-3-nitrobenzoic acid (4.47 g) in 1,2-dichloroethane (50 ml) was added trifluoroacetic anhydride (10.3 g) at 5° C. and the mixture was stirred at ambient temperature for 5 hours. To the mixture was added trifluoroacetic anhydride (5.15 g) and it was stirred at ambient temperature for additional 1 hour. The solution was concentrated in vacuo to give 8-nitro-2-trifluoromethyl-3,1-benzoxazin-4-one as a slight yellow powder (6.35 g).

NMR (CDCl$_3$, δ): 7.86 (1H, t, J=7 Hz), 8.29 (1H, d, J=7 Hz), 8.51 (1H, d, J=7 Hz)

Preparation 5

To a solution of ethyl 2-(N-benzylamino)-3-nitrobenzoate (400 mg) in N,N-dimethylaniline (3 ml) was added methoxyacetyl chloride (318 mg) at ambient temperature and the mixture was stirred at 90° C. for 4 hours. The reaction mixture was poured into water and the aqueous solution was extracted with ethyl acetate. The organic layer was washed successively with 1N hydrochloric acid, water and brine and the solution was dried over magnesium sulfate. The solvent was evaporated in vacuo and the residue was chromatographed on silica gel eluting with a mixture of n-hexane and ethyl acetate (3:1) to give ethyl 2-(N-benzyl-N-methoxyacetyl)-amino-3-nitrobenzoate (480 mg) as an oil.

NMR (CDCl$_3$, δ): 1.29 (3H, t, J=7 Hz), 3.37 (3H, s), 3.92 (2H, s), 4.09 (2H, q, J=7 Hz), 4.74 (1H, d, J=13 Hz), 4.83 (1H, d, J=13 Hz), 7.00–7.11 (2H, m), 7.11–7.31 (3H, m), 7.59 (1H, t, J=8 Hz), 7.96 (1H, d, J=8 Hz), 8.08 (1H, d, J=8 Hz)

Preparation 6

A mixture of 2,3-diaminotoluene (2.0 g) and ethyl N-methyloxamate (2.36 g) in N,N-dimethylformamide (10 ml) was stirred at 175° C. for 8 hours. After being cooled to ambient temperature, the mixture as poured into a mixture of saturated aqueous sodium bicarbonate solution and ethyl acetate and the organic layer was separated. The organic layer was washed with brine and the solution was dried over magnesium sulfate. The solvent was evaporated in vacuo and the residue was chromatographed on silica gel eluting with a mixtue of chloroform and methanol (50:1) to give 4-methyl-2-(N-methylcarbamoyl)-1H-benzimidazole (1.17 g) as a powder.

NMR (CDCl$_3$, δ): 2.60 (3H×1/2, s), 2.66 (3H×1/2, s), 3.10 (3H×1/2, s), 3.12 (3H×1/2, s), 7.06–7.19 (1H, m), 7.19–7.29 (1H, m), 7.36 (1H×1/2, d, J=8 Hz), 7.61 (1H×1/2, d, J=8 Hz), 7.71 (1H, br peak)

Preparation 7

To a suspension of 4-methyl-2-(N-methylcarbamoyl)-1H-benzimidazole (1.0 g) in 1N-aqueous sodium hydroxide solution (15 ml) was added portionwise potassium permanganate (3.34 g) at 100° C. and the reaction mixture was stirred at the same temperature for 15 minutes. The reaction mixture was filtered through a bed of celite and the filtrate was washed with chloroform. The aqueous layer was adjusted to pH 3 with 4N hydrochloric acid. The precipitate was collected by vacuum filtration to give 2-(N-methylcarbamoyl)-1H-benzimidazole-4-carboxylic acid (647 mg) as a solids.

NMR (DMSO-d$_6$, δ): 2.85 (3H, d, J=5 Hz), 7.41 (1H, t, J=8 Hz), 7.90 (1H, d, J=8 Hz), 7.95 (1H, d, J=8 Hz), 9.06 (1H, q-like)

Preparation 8

To a solution of methyl 2-hydroxymethyl-1H-benzimidazole-4-carboxylate (1.0 g) in N,N-dimethylformamide (10 ml) were added tert-butylchlorodiphenylsilane (1.87 g) and imidazole (495 mg) at ambient temperature and the mixture was stirred at the same temperature for 28 hours. The reaction mixture was poured into water and the aqueous solution was extracted with ethyl acetate. The organic layer was washed with water and brine and dried over magnesium sulfate. The solvent was evaporated in vacuo and the residue was chromatographed on silica gel eluting with a mixture of n-hexane and ethyl acetate (10:1) to give methyl 2-tert-butyldiphenylsiloxymethyl-1H-benzimidazole-4-carboxylate (1.45 g) as an oil.

NMR (CDCl$_3$, δ): 1.18 (9H, s), 4.02 (3H, s), 5.06 (2H, s), 7.30 (1H, t, J=8 Hz), 7.35–7.50 (6H, m), 7.67–7.73 (4H, m), 7.89 (1H, d, J=8 Hz), 7.92 (1H, d, J=8 Hz)

Preparation 9

To a solution of methyl 2-tert-butyldiphenylsiloxymethyl-1H-benzimidazole-4-carboxylate (500 mg) in pyridine (3 ml) was added lithium iodide (602 mg) under nitrogen at ambient temperature and the mixture was heated to reflux for 3 hours. The reaction mixture was concentrated in vacuo and the residue was dissolved in chloroform. The solution was washed with water and brine and the organic layer was dried over magnesium sulfate. The solvent was evaporated in vacuo and the residue was chromatographed on silica gel eluting with a mixture of chloroform and methanol (chloroform only~50:1~25:1~10:1) to give 2-tert-butyldiphenylsiloxymethyl-1H-benzimidazole-4-carboxylic acid (425 mg) as a powder.

NMR (DMSO-d$_6$, δ): 1.03 (9H, s), 5.00 (2H, s), 7.28 (1H, t, J=8 Hz), 7.38–7.52 (6H, m), 7.70–7.75 (4H, m), 7.80 (1H, d, J=8 Hz), 7.91 (1H, d, J=8 Hz)

Preparation 10

The mixture of benzyl 1-(4-toluenesulfonyl)indole-4-carboxylate (550 mg) and 10% palladium on charcoal (200 mg) in methanol (20 ml) and water (2 ml) was hydrogenated at ambient temperature (an initial hydrogen pressure was set to 3.5 atm.). The theoretical amount of hydrogen was absorbed in 6 hours. The resulting mixture was filtered through a bed of celite and the filtrate was evaporated in vacuo. The residue was diluted with chloroform and the solution was dried over magnesium sulfate. Filtering and removal of solvents afforded a crude product. The crude product was triturated with diethyl ether-n-hexane (1:3) to give 1-(4-toluenesulfonyl)indole-4-carboxylic acid (330 mg) as a brown powder.

NMR (DMSO-d$_6$, δ): 2.32 (3H, s), 7.30 (1H, d, J=4 Hz), 7.37–7.43 (2H, m), 7.47 (1H, d, J=8 Hz), 7.89 (3H, d, J=8 Hz), 7.97 (1H, d, J=4 Hz), 8.20 (1H, d, J=8 Hz)

Preparation 11

The following compounds were obtained according to a similar manner to that of Preparation 10.

1) 1-Pivaloyloxymethylindole-7-carboxylic acid

NMR (DMSO-$d_6$, δ): 1.00 (9H, s), 6.40 (2H, s), 6.61 (1H, d, J=3 Hz), 7.16 (1H, t, J=8 Hz), 7.53 (1H, d, J=3 Hz), 7.60 (1H, d, J=8 Hz), 7.78 (1H, d, J=8 Hz)

2) 1-Methylindole-7-carboxylic acid

NMR (CDCl$_3$, δ): 3.88 (3H, s), 6.52 (1H, d, J=4 Hz), 7.00–7.12 (2H, m), 7.72–7.79 (2H, m)

Preparation 12

To a mixture of 10% palladium on charcoal (130 mg) in 5.0% formic acid-methanol (5.0 ml) was added a solution of benzyl 1-tert-butoxycarbonyl-2-ethoxycarbonylindole-4-carboxylate (130 mg) in 5.0% formic acid-methanol (5.0 ml). The mixture was stirred under nitrogen atmosphere at ambient temperature for 30 minutes. The resulting mixture was filtered through a bed of celite and the filtrate was evaporated in vacuo to give 1-tert-butoxycarbonyl-2-ethoxycarbonylindole-4-carboxylic acid (87 mg) as a white crystal.

NMR (CDCl$_3$, δ): 1.44 (3H, t, J=7 Hz), 1.66 (9H, s), 4.42 (2H, q, J=7 Hz), 7.50 (1H, t, J=9 Hz), 7.83 (1H, s), 8.12 (1H, d, J=9 Hz), 8.39 (1H, d, J=9 Hz)

Preparation 13

To an ice water bath cooled 4N hydrogen chloride solution in 1,4-dioxane (5 ml) was added 2-(N-tert-butoxycarbonyl-N-methyl)amino-3-nitrobenzoic acid (900 mg) and the solution was stirred at ambient temperature for 2 hours. The reaction mixture was concentrated in vacuo and the residue was washed with diethyl ether and collected by vacuum filtration to give 2-(N-methylamino)-3-nitrobenzoic acid hydrochloride (687 mg) as a powder.

NMR (DMSO-$d_6$, δ): 2.70 (3H, s), 6.73 (1H, t, J=8 Hz), 7.98 (1H, d, J=8 Hz), 8.04 (1H, d, J=8 Hz)

Preparation 14

The following compound was obtained according to a similar manner to that of Preparation 13.

Ethyl 2-(N-benzylamino)-3-nitrobenzoate

NMR (CDCl$_3$, δ): 1.38 (3H, t, J=7 Hz), 4.16 (2H, d, J=6 Hz), 4.35 (2H, q, J=7 Hz), 6.72 (1H, t, J=8 Hz), 7.22–7.46 (5H, m), 8.00 (1H, d, J=8 Hz), 8.11 (1H, d, J=8 Hz), 8.80 (1H, br s)

Preparation 15

To a suspension of sodium hydride (60% dispersion in mineral oil, 142 mg) in N,N-dimethylformamide (1 ml) was added dropwise a solution of ethyl 2-(N-tert-butoxycarbonyl)amino-3-nitrobenzoate (1.0 g) in N,N-dimethylformamide (5 ml) under nitrogen in ice water bath and stirred at the same temperature for 1 hour. To the mixture was added methyl iodide (526 mg) at 0° C. under nitrogen and the solution was stirred at the same temperature for 2 hours. The reaction mixture was poured into water and the aqueous solution was extracted with ethyl acetate. The organic layer was washed with water and brine, dried over magnesium sulfate and the solvent was evaporated to give ethyl 2-(N-tert-butoxycarbonyl-N-methyl)amino-3-nitrobenzoate (1.05 g) as an oil.

NMR (CDCl$_3$, δ): 1.28 (9H, s), 1.41 (3H, t, J=7.5 Hz), 3.10–3.20 (3H, m), 4.30–4.48 (2H, m), 7.52 (1H, t, J=8 Hz), 7.95 (1H, d, J=8 Hz), 8.10 (1H, d, J=8 Hz)

Preparation 16

The following compounds were obtained according to a similar manner to that of Preparation 15.

1) Ethyl 2-(N-benzyl-N-tert-butoxycarbonyl)amino-3-nitrobenzoate

NMR (CDCl$_3$, δ): 1.17–1.38 (12H, m), 4.08–4.23 (2H, m), 4.53 (1H, d, J=13 Hz), 4.81 (1H, d, J=13 Hz), 7.03–7.16 (2H, m), 7.16–7.29 (3H, m), 7.45 (1H, t, J=8 Hz), 7.88 (1H, d, J=8 Hz), 8.04 (1H, d, J=8 Hz)

2) 3-(N-Acetyl-N-methyl)amino-2-nitrobenzoic acid

NMR (CDCl$_3$, δ): 1.87 (3H, s), 3.20 (3H, s), 7.55 (1H, d, J=8 Hz), 7.69 (1H, t, J=8 Hz), 8.20 (1H, d, J=8 Hz)

3) 3-(N-Acetyl-N-ethyl)amino-2-nitrobenzoic acid

NMR (DMSO-$d_6$, δ): 1.00 (3H, t, J=7 Hz), 1.72 (3H, s), 3.08 (1H, m), 3.86 (1H, m), 7.78–7.91 (2H, m), 8.12 (1H, d, J=8 Hz)

Preparation 17

To a solution of ethyl 2-(N-tert-butoxycarbonyl-N-methyl)amino-3-nitrobenzoate (1.0 g) in ethanol (10 ml) was added 1N aqueous sodium hydroxide solution (3.5 ml) and the solution was stirred at ambient temperature for 1 day. The reaction mixture was concentrated and the residue was dissolved in water. The aqueous layer was washed with diethyl ether and the aqueous solution was adjusted to pH 4 with 1N hydrochloric acid. The solution was extracted with chloroform and the organic layer was separated. The solution was washed with water and brine and the solution was dried over magnesium sulfate. The solvent was evaporated in vacuo to give 2-(N-tert-butoxycarbonyl-N-methyl)amino-3-nitrobenzoic acid (910 mg) as a powder.

NMR (CDCl$_3$, δ): 1.26 (9H, s), 3.20 (3H, s), 7.55 (1H, t, J=8 Hz), 8.00 (1H, d, J=8 Hz), 8.22 (1H, d, J=8 Hz)

Preparation 18

The following compounds were obtained according to a similar manner to that of Preparation 17.

1) 3-Benzyl-2-methoxymethyl-3H-benzimidazole-4-carboxylic acid

NMR (DMSO-$d_6$, δ): 3.40 (3H, s), 4.75 (2H, s), 5.95 (2H, s), 6.83–6.91 (2H, m), 7.16–7.26 (3H, m), 7.33 (1H, t, J=8 Hz), 7.72 (1H, d, J=8 Hz), 7.89 (1H, d, J=8 Hz)

2) 1,2-Dimethyl-1H-benzimidazole-4-carboxylic acid

NMR (DMSO-$d_6$, δ): 2.64 (3H, s), 3.82 (3H, s), 7.37 (1H, t, J=8 Hz), 7.76 (1H, d, J=8 Hz), 7.86 (1H, d, J=8 Hz)

3) 1-Ethyl-2-methyl-1H-benzimidazole-4-carboxylic acid

NMR (DMSO-$d_6$, δ): 1.33 (3H, t, J=7 Hz), 2.68 (3H, s), 4.33 (2H, q, J=7 Hz), 7.37 (1H, t, J=8 Hz), 7.78 (1H, d, J=8 Hz), 7.90 (1H, d, J=8 Hz)

4) 2-Methyl-1-propyl-1H-benzimidazole-4-carboxylic acid

NMR (DMSO-$d_6$, δ): 0.94 (3H, t, J=7 Hz), 1.82 (2H, m), 2.88 (3H, s), 4.41 (2H, t, J=7 Hz), 7.65 (1H, t, J=8 Hz), 8.05 (1H, d, J=8 Hz), 8.24 (1H, d, J=8 Hz)

5) 1-(4-Methoxybenzyl)-2-(N-methylcarbamoyl)-1H-benzimidazole-4-carboxylic acid

NMR (CD$_3$OD, δ): 2.96 (3H, s), 3.72 (3H, s), 6.00 (2H, s), 6.83 (2H, d, J=8 Hz), 7.20 (2H, d, J=8 Hz), 7.45 (1H, t, J=8 Hz), 7.84 (1H, d, J=8 Hz), 8.03 (1H, d, J=8 Hz)

Preparation 19

To a solution of ethyl 2-(N-benzyl-N-methoxyacetyl)amino-3-nitrobenzoate (478 mg) in ethanol (5 ml) were added iron powder (358 mg) and acetic acid (771 mg) and the mixture was refluxed for 2 hours. The reaction mixture was filtered through a bed of celite and the filtrate was concentrated in vacuo. The residue was diluted with a mixture of ethyl acetate and saturated aqueous sodium bicarbonate solution and the mixture was filtered through a bed of celite again. The organic layer was separated and washed with water and brine. The solution was dried over magnesium sulfate and the solvent was evaporated in vacuo to give ethyl 3-benzyl-2-methoxymethyl-3H-benzimidazole-4-carboxylate (364 mg) as an oil.

NMR (CDCl$_3$, δ): 1.20 (3H, t, J=7 Hz), 3.40 (3H, s), 4.15 (2H, q, J=7 Hz), 4.75 (2H, s), 5.91 (2H, s), 6.78–6.89 (2H, m), 7.14–7.41 (4H, m), 7.68 (1H, d, J=8 Hz), 7.98 (1H, d, J=8 Hz)

Preparation 20

The following compound was obtained according to a similar manner to that of Preparation 19.

Methyl 2-methyl-1H-benzimidazole-4-carboxylate

NMR (CDCl$_3$, δ): 2.67 (3H, s), 4.00 (3H, s), 7.25 (1H, t, J=8 Hz), 7.85 (1H, d, J=8 Hz), 7.89 (1H, d, J=8 Hz)

Preparation 21

The following compounds were obtained by using methyl 3-(N-acetyl-N-methyl)amino-2-nitrobenzoate as a starting compound according to a similar manner to that of Preparation 19.

A mixture of methyl 1,2-dimethyl-1H-benzimidazole-4-carboxylate and ethyl 1,2-dimethyl-1H-benzimidazole-4-carboxylate Methyl 1,2-dimethyl-1H-benzimidazole-4-carboxylate NMR (CDCl$_3$, δ): 2.69 (3H, s), 3.75 (3H, s), 4.02 (3H, s), 7.28 (1H, t, J=8 Hz), 7.48 (1H, d, J=8 Hz), 7.95 (1H, d, J=8 Hz)

Ethyl 1,2-dimethyl-1H-benzimidazole-4-carboxylate

NMR (CDCl$_3$, δ): 1.44 (3H, t, J=7 Hz), 2.67 (3H, s), 3.72 (3H, s), 4.48 (2H, q, J=7 Hz), 7.26 (1H, t, J=8 Hz), 7.45 (1H, d, J=8 Hz), 7.90 (1H, d, J=8 Hz)

Preparation 22

The following compound was obtained by using methyl 2-(N-acetyl-N-ethyl)amino-3-nitrobenzoate as a starting compound according to a similar manner to that of Preparation 19.

Ethyl 1-ethyl-2-methyl-1H-benzimidazole-4-carboxylate

NMR (CDCl$_3$, δ): 1.37 (3H, t, J=7 Hz), 1.43 (3H, t, J=7 Hz), 2.66 (3H, s), 4.19 (2H, q, J=7 Hz), 4.48 (2H, q, J=7 Hz), 7.25 (1H, t, J=8 Hz), 7.47 (1H, d, J=8 Hz), 7.89 (1H, d, J=8 Hz)

Preparation 23

To a solution of 3-(N-acetyl-N-methyl)amino-2-nitrobenzoic acid (700 mg) in 20% methanol in benzene solution (5 ml) was added dropwise 2N-trimethylsilyldiazomethane in n-hexane solution (5 ml) in ice water bath and the mixture was allowed to stand at ambient temperature for 1 hour. The reaction mixture was concentrated in vacuo and the residue was dissolved in ethyl acetate. The solution was washed successively with saturated aqueous sodium bicarbonate solution, water and brine and the organic layer was dried over magnesium sulfate. The solvent was evaporated in vacuo and the residue was chromatographed on silica gel eluting with a mixture of n-hexane—ethyl acetate (10:1) to give methyl 3-(N-acetyl-N-methyl)amino-2-nitrobenzoate (547 mg) as an oil.

NMR (CDCl$_3$, δ): 1.85 (3H, s), 3.19 (3H, s), 3.94 (3H, s), 7.54 (1H, d, J=8 Hz), 7.68 (1H, t, J=8 Hz), 8.13 (1H, d, J=8 Hz)

Preparation 24

The following compounds were obtained according to a similar manner to that of Preparation 23.

1) Methyl 3-(N-acetyl-N-ethyl)amino-2-nitrobenzoate

NMR (CDCl$_3$, δ): 1.11 (3H, t, J=7 Hz), 1.83 (3H, s), 3.20 (1H, m), 3.93 (3H, s), 4.10 (1H, m), 7.49 (1H, d, J=8 Hz), 7.67 (1H, t, J=8 Hz), 8.13 (1H, d, J=8 Hz)

2) Methyl 2-(N-methylcarbamoyl)-1H-benzimidazole-4-carboxylate

NMR (CDCl$_3$, δ): 3.08 (3H, d, J=5 Hz), 4.03 (3H, s), 7.40 (1H, t, J=8 Hz), 7.47 (1H, br s), 7.98 (1H, d, J=8 Hz), 8.04 (1H, d, J=8 Hz)

Preparation 25

2-(N-Methylamino)-3-nitrobenzoic acid hydrochloride (250 mg) in methanol (5 ml) was hydrogenated under medium pressure (3 atm.) at ambient temperature for 3 hours. The reaction mixture was filtered through a bed of celite and the filtrate was concentrated in vacuo. The crude 3-amino-2-(N-methylamino)benzoic acid hydrochloride was used without further purification.

NMR (CD$_3$OD, δ): 3.06 (3H, s), 7.23 (1H, d, J=8 Hz), 7.32 (1H, t, J=8 Hz), 7.59 (1H, d, J=8 Hz)

Preparation 26

The following compound was obtained according to a similar manner to that of Example 13.

3-Methyl-3H-benzimidazole-4-carboxylic acid hydrochloride

NMR (DMSO-d$_6$, δ): 4.07 (3H, s), 7.50 (1H, t, J=8 Hz), 7.88 (1H, d, J=8 Hz), 8.00 (1H, d, J=8 Hz), 9.02 (1H, s)

Preparation 27

The following compound was obtained by using 2-amino-3-hydroxybenzoic acid as a starting compound according to a similar manner to that of Example 13.

4-Benzoxazolecarboxylic acid

NMR (DMSO-d$_6$, δ): 7.55 (1H, t, J=8 Hz), 7.92 (1H, d, J=8 Hz), 8.03 (1H, d, J=8 Hz), 8.85 (1H, s)

Preparation 28

The following compound was obtained by using 3-amino-2-hydroxybenzoic acid as a starting compound according to a similar manner to that of Example 13.

7-Benzoxazolecarboxylic acid

NMR (DMSO-d$_6$, δ): 7.51 (1H, t, J=8 Hz), 7.96 (1H, d, J=8 Hz), 8.07 (1H, d, J=8 Hz), 8.88 (1H, s)

Preparation 29

The following compound was obtained according to a similar manner to that of Example 5.

Benzyl 1-methylindole-7-carboxylate

NMR (CDCl$_3$, δ): 3.83 (3H, s), 5.41 (2H, s), 6.53 (1H, d, J=3 Hz), 7.01–7.11 (2H, m), 7.31–7.42 (3H, m), 7.47–7.50 (2H, m), 7.70 (1H, d, J=8 Hz), 7.77 (1H, d, J=8 Hz)

Preparation 30

To a solution of benzyl indole-4-carboxylate (1.85 g) and N,N-dimethylaminopyridine (180 mg) in acetonitrile (10 ml) was added portionwise di-tert-butyl dicarbonate (1.61 g), and then the mixture was stirred at ambient temperature for 2 hours and stand overnight. The resulting mixture was concentrated in vacuo and the residue was diluted with ethyl acetate (30 ml). The organic layer was washed successively with 1N hydrochloric acid, saturated sodium bicarbonate aqueous solution and brine. The solution was dried over magnesium sulfate and concentrated in vacuo. The residue was purified by silica gel column chromatography (eluent; n-hexane:ethyl acetate=10:1) to give benzyl 1-tert-butoxycarbonylindole-4-carboxylate (2.26 g).

NMR (CDCl$_3$, δ): 1.68 (9H, s), 5.42 (2H, s), 7.26 (1H, d, J=4 Hz), 7.31–7.43 (4H, m), 7.47–7.51 (2H, m), 7.69 (1H, d, J=4 Hz), 8.02 (1H, d, J=8 Hz), 8.40 (1H, d, J=9 Hz)

Preparation 31

To a solution of methyl 2-methyl-1H-benzimidazole-4-carboxylate (250 mg) in N,N-dimethylformamide (4 ml) were added potassium carbonate (363 mg) and n-propyl bromide at ambient temperature and the mixture was stirred at the same temperature for 2 days. The reaction mixture was poured into water and the aqueous solution was extracted with ethyl acetate. The organic layer was washed with water and brine and the solution was dried over magnesium sulfate. The solvent was evaporated in vacuo and the residue was chromatographed on silica gel eluting with a mixture of n-hexane and ethyl acetate (1:1~1:2~1:3~ethyl acetate only) to give methyl 2-methyl-1-propyl-1H-benzimidazole-4-carboxylate (173 mg) as an oil.

NMR (CDCl$_3$, δ): 0.97 (3H, t, J=7 Hz), 1.84 (2H, m), 2.69 (3H, s), 4.05 (3H, s), 4.11 (2H, t, J=7 Hz), 7.27 (1H, t, J=8 Hz), 7.49 (1H, d, J=8 Hz), 7.94 (1H, d, J=8 Hz)

Preparation 32

The following compound was obtained according to a similar manner to that of Preparation 31.

Methyl 1-(4-methoxybenzyl)-2-(N-methylcarbamoyl)-1H-benzimidazole-4-carboxylate

NMR (CDCl$_3$, δ): 3.04 (3H, d, J=5 Hz), 3.74 (3H, s), 4.04 (3H, s), 6.01 (2H, s), 6.80 (2H, d, J=8 Hz), 7.17 (2H, d, J=8 Hz), 7.38 (1H, t, J=8 Hz), 7.63 (1H, d, J=8 Hz), 8.01 (1H, d, J=8 Hz), 8.05 (1H, br peak)

EXAMPLE 1

To a mixture of 1H-imidazo[4,5-b]pyridine-7-carboxylic acid (203 mg) and oxalyl chloride (0.217 ml) in dichloromethane (25 ml) was added 1 drop of N,N-dimethylformamide and the mixture was stirred at ambient temperature for 2 hours. After being removed a solvent by evaporation, residual acid chloride in dichloromethane (5 ml) was added to a mixture of 4-amino-3-methoxy-N-methyl-N-[4-methyl-2-[5-(4-methylpiperazin-1-ylcarbonyl)pent-1-yloxy]phenyl]benzamide (400 mg) and triethylamine (210 mg) in dichloromethane (20 ml) and the mixture was stirred at ambient temperature for 2 hours. The mixture was washed successively with saturated aqueous sodium hydrogen carbonate and brine, and dried over sodium sulfate. The solvent was removed by rotary evaporation and the residue was purified by silica gel column chromatography (SiO$_2$ 30 g, 3% methanol in dichloromethane) to give 4-[1H-imidazo[4,5-b]pyridin-7-yl]carbonylamino-3-methoxy-N-methyl-N-[4-methyl-2-[5-(4-methylpiperazin-1-yl)carbonylpent-1-yloxy]phenyl]benzamide (393 mg).

NMR (CDCl$_3$, δ): 1.42–1.61 (2H, m), 1.63–1.92 (4H, m), 2.25 (3H, s), 2.29 (3H, s), 2.32–2.47 (6H, m), 3.34 (3H, s), 3.42–3.55 (2H, m), 3.60–3.70 (2H, m), 3.72–4.00 (5H, m), 6.50–6.66 (3H, m), 6.76–7.08 (3H, m), 8.03 (1H, m), 8.32 (1H, s), 8.44 (1H, m), 8.59 (1H, m)

EXAMPLE 2

The following compounds were obtained according to a similar manner to that of Example 1.

1) 4-[[1-(4-Toluenesulfonyl)indol-4-yl]carbonyl]amino-3-methoxy-N-methyl-N-[4-methyl-2-[5-(4-methylpiperazin-1-yl)carbonylpent-1-yloxy]phenyl]benzamide NMR (CDCl$_3$, δ): 1.48–1.58 (2H, m), 1.66–1.87 (4H, m), 2.27 (3H, s), 2.31–2.39 (8H, m), 2.42–2.53 (4H, m), 3.32 (3H, s), 3.52–3.58 (2H, m), 3.64–3.72 (2H, m), 3.77 (3H, s), 3.83–4.00 (2H, m), 6.59 (1H, d, J=8 Hz), 6.62 (1H, s), 6.85 (1H, d, J=8 Hz), 6.92 (1H, d, J=8 Hz), 7.01 (1H, s), 7.19–7.27 (3H, m), 7.38 (1H, t, J=8 Hz), 7.58 (1H, d, J=8 Hz), 7.69 (1H, d, J=4 Hz), 7.75 (2H, d, J=8 Hz), 8.17 (1H, d, J=8 Hz), 8.28 (1H, d, J=8 Hz), 8.47 (1H, s)

2) 4-[(1-Pivaloyloxymethylindole-7-yl)carbonyl]amino-3-methoxy-N-methyl-N-[4-methyl-2-[5-(4-methylpiperazin-1-yl)carbonylpent-1-yloxy]phenyl]benzamide NMR (CDCl$_3$, δ): 0.84 (9H, s), 1.48–1.61 (2H, m), 1.68–1.90 (4H, m), 2.28 (3H, s), 2.31 (3H, s), 2.33–2.46 (6H, m), 3.33 (3H, s), 3.48–3.54 (2H, m), 3.60–3.68 (2H, m), 3.70 (3H, s), 3.88–4.00 (2H, m), 6.28 (2H, s), 6.57 (1H, d, J=3 Hz), 6.59–6.66 (2H, m), 6.83 (1H, d, J=8 Hz), 6.97 (1H, d, J=8 Hz), 7.02 (1H, s), 7.19 (1H, t, J=8 Hz), 7.29 (1H, d, J=3 Hz), 7.42 (1 H, d, J=8 Hz), 7.74 (1 H, d, J=8 Hz), 8.28–8.37 (2 H, m).

3) 4-[(1-Methylindol-7-yl)carbonyl]amino-3-methoxy-N-methyl-N-[4-methyl-2-[5-(4-methylpiperazin-1-yl)carbonylpent-1-yloxy]phenyl]benzamide NMR (CDCl$_3$, δ): 1.48–1.89 (6 H, m), 2.29 (6 H, s), 2.31–2.42 (6 H, m), 3.33 (3 H, s), 3.46–3.51 (2 H, m), 3.59–3.67 (2 H, m), 3.72 (3 H, s), 3.80 (3 H, s), 3.88–4.00 (2 H, m), 6.55 (1 H, d, J=4 Hz), 6.61 (1 H, d, J=8 Hz), 6.67 (1 H, s), 6.81–7.12 (5 H, m), 7.33 (1 H, d, J=8 Hz), 7.72 (1 H, d, J=8 Hz), 8.28–8.36 (2 H, m).

4) 4-(1-tert-Butoxycarbonyl-2-ethoxycarbonylindol-4-yl)carbonyl]amino-3-methoxy-N-methyl-N-[4-methyl-2-[5-(4-methylpiperazin-1-yl)carbonylpent-1-yloxy]phenyl]benzamide NMR (CDCl$_3$, δ): 1.40 (3 H, t, J=8 Hz), 1.50–1.89 (6 H, m), 1.63 (9 H, s), 2.28 (3 H, s), 2.30 (3 H, s), 2.32–2.43 (6 H, m), 3.34 (3 H, s), 3.47–3.52 (2 H, m), 3.60–3.68 (2 H, m), 3.79 (3 H, s), 3.87–4.00 (2 H, m), 4.38 (2 H, q, J=8 Hz), 6.60 (1 H, d, J=8 Hz), 6.64 (1 H, s), 6.86 (1 H, d, J=8 Hz), 6.95 (1 H, d, J=8 Hz), 7.06 (1 H, s), 7.48 (1 H, t, J=8 Hz), 7.62 (1 H, d, J=8 Hz), 7.69 (1 H, s), 8.27–8.33 (2 H, m), 8.54 (1 H, s).

5) 4-[2-Chloro-1H-benzimidazol-4-yl]carbonylamino-3-methoxy-N-methyl-N-[4-methyl-2-[5-(4-methylpiperazin-1-yl)carbonylpent-1-yloxy]phenyl]benzamide NMR (CDCl$_3$, δ): 1.45–1.60 (2 H, m), 1.63–1.92 (4 H, m), 2.25 (3 H, s), 2.29 (3 H, s), 2.31–2.49 (6 H, m), 3.35 (3 H, s), 3.44–3.55 (2 H, m), 3.59–3.70 (2 H, m), 3.71–4.01 (5 H, m), 6.52–6.66 (2 H, m), 6.80–7.06 (3 H, m), 7.24–7.37 (1 H, m), 7.42–8.50 (3 H, m).

6) 3-Methoxy-N-methyl-N-[4-methyl-2-[5-(4-methylpiperazin-1-yl)carbonylpent-1-yloxy]phenyl]-4-(purin-6-yl)carbonylaminobenzamide NMR (DMSO-d$_6$, δ): 1.40–1.50 (2 H, m), 1.50–1.62 (2 H, m), 1.70–1.79 (2 H, m), 2.14 (3 H, s), 2.18–2.36 (9 H, m), 3.20 (3 H, s), 3.35–3.43 (6 H, m), 3.75 (3 H, s), 3.81–3.99 (2 H, m), 6.65 (1 H, d, J=7 Hz), 6.82 (1 H, s), 6.95–7.08 (3 H, m), 8.27 (1 H, d, J=6 Hz), 8.83 (1 H, s), 9.10 (1 H, s).

7) 4-(3-Benzyl-2-methoxymethyl-3H-benzimidazol-4-yl)carbonylamino-3-methoxy-N-methyl-N-[4-methyl-2-[5-(4-methylpiperazin-1-yl)carbonylpent-1-yloxy]phenyl]benzamide NMR (CDCl$_3$, δ): 1.49–1.64 (2 H, m), 1.64–1.81 (2 H, m), 1.81–1.95 (2 H, m), 2.21–2.31 (6 H, m), 2.31–2.44 (6 H, m), 3.34 (3 H, s), 3.43 (3 H, s), 3.46–3.54 (2 H, m), 3.58 (3 H, s), 3.60–3.70 (2 H, m), 3.90–4.04 (2 H, m), 4.82 (2 H, s), 5.63 (2 H, s), 6.60–6.75 (6 H, m), 6.75–6.83 (1 H, m), 6.83–6.93 (2 H, m), 6.99 (1 H, d, J=8 Hz), 7.19–7.31 (2 H, m), 7.55 (1 H, s), 7.90 (1 H, d, J=8 Hz), 8.20 (1 H, d, J=8 Hz).

8) 4-(1,2-Dimethyl-1H-benzimidazol-4-yl)carbonylamino-3-methoxy-N-methyl-N-[4-methyl-2-[5-(4-methylpiperazin-1-yl)carbonylpent-1-yloxy]phenyl]benzamide NMR (CDCl$_3$, δ): 1.45–1.76 (4 H, m), 1.76–1.91 (2 H, m), 2.25 (3 H, s), 2.30 (3 H, s), 2.32–2.42 (6 H, m), 2.69 (3 H, s), 3.33 (3 H, s), 3.45–3.52 (2 H, m), 3.59–3.68 (2 H, m), 3.78 (3 H, s), 3.81–3.90 (4 H, m), 3.90–4.01 (1 H, m), 6.54–6.64 (2 H, m), 6.86 (1 H, d, J=8 Hz), 6.96 (1 H, d, J=8 Hz), 7.01 (1 H, s), 7.34 (1 H, t, J=8 Hz), 7.44 (1 H, d, J=8 Hz), 8.14 (1 H, d, J=8 Hz), 8.53 (1 H, d, J=8 Hz).

9) 4-(1-Ethyl-2-methyl-1H-benzimidazol-4-yl)carbonylamino-3-methoxy-N-methyl-N-[4-methyl-2-[5-(4-methylpiperazin-1-yl)carbonylpent-1-yloxy]phenyl]benzamide NMR (CDCl$_3$, δ): 1.44 (3 H, t, J=7 Hz), 1.48–1.61 (2 H, m), 1.65–1.75 (2 H, m), 1.75–1.98 (2 H, m), 2.27 (3 H, s), 2.29 (3 H, s), 2.31–2.43 (6 H, m), 2.70 (3 H, s), 3.34 (3 H, s), 3.44–3.53 (2 H, m), 3.59–3.68 (2 H, m), 3.79–3.90 (4 H, m), 3.90–4.00 (1 H, m), 4.22 (2 H, q, J=7 Hz), 6.53–6.63 (2 H, m), 6.86 (1 H, d, J=8 Hz), 6.96 (1 H, d, J=8 Hz), 7.01 (1 H, s), 7.34 (1 H, t, J=8 Hz), 7.46 (1 H, d, J=8 Hz), 8.13 (1 H, d, J=8 Hz), 8.52 (1 H, d, J=8 Hz).

10) 3-Methoxy-N-methyl-N-[4-methyl-2-[5-(4-methylpiperazin-1-yl)carbonylpent-1-yloxy]phenyl]-4-(2-methyl-1-propyl-1H-benzimidazol-4-yl)carbonylaminobenzamide NMR (CDCl$_3$, δ): 0.97 (3 H, t, J=7 Hz), 1.44–1.74 (4 H, m), 1.74–1.92 (4 H, m), 2.24 (3 H, s), 2.27 (3 H, s), 2.31–2.42 (6 H, m), 2.67 (3 H, s), 3.32 (3 H, s), 3.43–3.53 (2 H, m), 3.58–3.66 (2 H, m), 3.76–3.90 (4 H, m), 3.90–4.00 (1 H, m), 4.13 (2 H, t, J=7 Hz), 6.52–6.62 (2 H, m), 6.86 (1 H, d, J=8 Hz), 6.96 (1 H, d, J=8 Hz), 7.00 (1 H, s-like), 7.33 (1 H, t, J=8 Hz), 7.45 (1 H, d, J=8 Hz), 8.13 (1 H, d, J=8 Hz), 8.53 (1 H, d, J=8 Hz).

11) 3-Methoxy-4-[1-(4-mehoxybenzyl)-2-(N-methylcarbamoyl)-1H-benzimidazol-4-yl]carbonylamino-N-methyl-N-[4-methyl-2-[5-(4-methylpiperazin-1-yl)carbonylpent-1-yloxy]phenyl]benzamide NMR (CDCl$_3$, δ): 1.46–1.63 (2 H, m), 1.63–1.77 (2 H, m), 1.77–1.91 (2 H, m), 2.25 (3 H, s), 2.28 (3 H, s), 2.31–2.41 (6 H, m), 3.13 (3 H, d, J=5 Hz), 3.34 (3 H, s), 3.44–3.51 (2 H, m), 3.56–3.65 (2 H, m), 3.74 (3 H, s), 3.82–4.01 (5 H, m), 6.00 (2 H, s), 6.58 (1 H, d, J=8 Hz), 6.64 (1 H, s), 6.82 (2 H, d, J=8 Hz), 6.87 (1 H, d, J=8 Hz), 6.97 (1 H, d, J=8 Hz), 7.10 (1 H, s), 7.21 (2 H, d, J=8 Hz), 7.46 (1 H, t, J=8 Hz), 7.60 (1 H, d, J=8 Hz), 7.95 (1 H, br peak), 8.24 (1 H, d, J=8 Hz), 8.50 (1 H, d, J=8 Hz).

12) 4-(2-tert-Butyldiphenylsiloxymethyl-1H-benzimidazol-4-yl)carbonylamino-3-methoxy-N-methyl-N-[4-methyl-2-[5-(4-methylpiperazin-1-yl)carbonylpent-1-yloxy]phenyl]benzamide NMR (DMSO-d$_6$, δ): 1.04 (9 H, s), 1.35–1.49 (2 H, m), 1.49–1.64 (2 H, m), 1.64–1.80 (2 H, m), 2.11 (3 H, s), 2.13–2.25 (7 H, m), 2.30 (2 H, t, J=7.5 Hz), 3.17 (3 H, s), 3.27–3.45 (7 H, m), 3.84 (3 H, br peak), 3.96 (1 H, br peak), 5.03 (2 H, s), 6.63 (1 H, d, J=8 Hz), 6.80 (2 H, s-like), 6.94 (1 H, d, J=8 Hz), 7.02 (1 H, d, J=8 Hz), 7.30–7.50 (7 H, m), 7.69 (4 H, d, J=8 Hz), 7.79 (1 H, d, J=8 Hz), 7.91 (1 H, d, J=8 Hz), 8.35 (1 H, d, J=8 Hz).

13) 4-(Benzoxazol-4-yl)carbonylamino-3-methoxy-N-methyl-N-[4-methyl-2-[5-(4-methylpiperazin-1-yl)carbonylpent-1-yloxy]phenyl]benzamide NMR (CDCl$_3$, δ): 1.47–1.65 (2 H, m), 1.65–1.78 (2 H, m), 1.78–1.92 (2 H, m), 2.26 (3 H, s), 2.30 (3 H, s), 2.32–2.43 (6 H, m), 3.35 (3 H, s), 3.44–3.54 (2 H, m), 3.58–3.68 (2 H, m), 3.79–4.02 (5 H, m), 6.54–6.66 (2 H, m), 6.87 (1 H, d, J=8 Hz), 6.98 (1 H, d, J=8 Hz), 7.04 (1 H, s-like), 7.55 (1 H, t, J=8 Hz), 7.77 (1 H, d, J=8 Hz), 8.23–8.31 (2 H, m), 8.44 (1 H, d, J=8 Hz).

14) 4-(Benzoxazol-7-yl)carbonylamino-3-methoxy-N-methyl-N-[4-methyl-2-[5-(4-methylpiperazin-1-yl)carbonylpent-1-yloxy]phenyl]benzamide NMR (CDCl$_3$, δ): 1.45–1.76 (4 H, m), 1.76–1.90 (2 H, m), 3.33 (3 H, s), 3.43–3.52 (2 H, m), 3.56–3.68 (2 H, m), 3.83 (3 H, s), 3.86–4.01 (2 H, m), 6.54–6.65 (2 H, m), 6.85 (1 H, d, J=8 Hz), 6.96 (1 H, d, J=8 Hz), 7.06 (1 H, s), 7.52 (1 H, t, J=8 Hz), 7.97 (1 H, d, J=8 Hz), 8.18 (1 H, d, J=8 Hz), 8.23 (1 H, s), 8.36 (1 H, d, J=8 Hz), 9.50 (1 H, s).

15) 4-(3-Bromo-2-methylimidazo[1,2-a]pyridin-8-yl)carbonylamino-3-methoxy-N-methyl-N-[4-methyl-2-[5-(4-methylpiperazin-1-yl)carbonylpent-1-yloxy]phenyl]benzamide NMR (CDCl$_3$, δ): 1.44–1.61 (2 H, m), 1.61–1.78 (2 H, m), 1.78–1.92 (2 H, m), 2.28 (3 H, s), 2.30 (3 H, s), 2.33–2.45 (3 H, m), 2.54 (3 H, s), 3.33 (3 H, s), 3.45–3.55 (2 H, m), 3.60–3.70 (2 H, m), 3.88 (3 H, s), 3.91–4.01 (2 H, m), 6.53–6.64 (2 H, m), 6.86 (1 H, d, J=8 Hz), 6.93–7.03 (2 H, m), 7.07 (1 H, t, J=8 Hz), 8.19 (1 H, d, J=8 Hz), 8.25 (1 H, d, J=8 Hz), 8.45 (1 H, d, J=8 Hz).

16) 3-Methoxy-N-methyl-4-(2-methylimidazo[1,2-a]pyridin-4-yl)carbonylamino-N-[4-methyl-2-[5-(4-methylpiperazin-1-yl)carbonylpent-1-yloxy]phenyl]benzamide NMR (CDCl$_3$, δ): 1.45–1.65 (2 H, m), 1.65–1.75 (2 H, m), 1.75–1.90 (2 H, m), 2.25 (3 H, s), 2.29 (3 H, s), 2.31–2.42 (6 H, m), 2.52 (3 H, s), 3.33 (3 H, s), 3.42–3.52 (2 H, m), 3.57–3.66 (2 H, m), 3.77–3.90 (4 H, m), 3.90–4.02 (1 H, m), 6.51–6.62 (2 H, m), 6.80–7.04 (4 H, m), 7.41 (1 H, s), 8.16 (2 H, d-like), 8.48 (1 H, d, J=8 Hz).

EXAMPLE 3

To a suspension of 3-methyl-3H-benzimidazole-4-carboxylic acid hydrochloride (112 mg) in dichrometha 3. (2 ml) was added oxalyl chloride (79 mg) in an ice water bath under nitrogen and then added 1 drop of N,N-dimethylformamide. After being stirred under the same condition for 2 hours, the reaction mixture was concentrated in vacuo. The residue was added to a solution of 4-amino-3-methoxy-N-methyl-N-[4-methyl-2-[5-(4-methylpiperazin-1-yl)carbonylpent-1-yloxy]phenyl]benzamide (150 mg) in pyridine (2 ml) under nitrogen at ambient temperature and the mixture was stirred for 2 hours and allowed to stand at same temperature overnight. The reaction mixture was concentrated in vacuo and the residue was dissolved in chloroform. The solution was washed with water and saturated aqueous sodium bicarbonate solution and the organic layer was dried over magnesium sulfate. The solvent was evaporated in vacuo and the residue was purified by preparative thin-layer chromatography (ethyl acetate-methanol=1:1) to give 3-methoxy-N-methyl-4-(3-methyl-3H-benzimidazol-4-yl)carbonylamino-N-[4-methyl-2-[5-(4-methylpiperazin-1-yl)carbonylpent-1-yloxy]phenyl]benzamide (52 mg) as a powder.

NMR (CDCl$_3$, δ): 1.45–1.63 (2 H, m), 1.63–1.79 (2 H, m), 1.79–1.91 (2 H, m), 2.30 (6 H, s), 2.32–2.43 (6 H, m), 3.33 (3 H, s), 3.43–3.52 (2 H, m), 3.52–3.68 (2 H, m), 3.75

(3 H, s), 3.83–4.03 (5 H, m), 6.55–6.72 (2 H, m), 6.88 (1 H, d, J=8 Hz), 6.97 (1 H, d, J=8 Hz), 7.04 (1 H, s), 7.22–7.35 (1 H, m), 7.50 (1 H, d, J=8 Hz), 7.88 (1 H, s), 7.95 (1 H, d, J=8 Hz), 8.30 (1 H, d, J=6 Hz), 8.38 (1 H, s).

EXAMPLE 4

To a solution of 4-amino-3-methoxy-N-methyl-N-[4-methyl-2-[5-(4-methylpiperazin-1-yl)carbonylpent-1-yloxy]phenyl]benzamide (6.0 g) in 1,4-dioxane (200 ml) was added 8-nitro-2-trifluoromethyl-3,1-benzoxazin-4-one (3.24 g) and the mixture was stirred at 100° C. for 4 hours. To the mixture was added 8-nitro-2-trifluoromethyl-3,1-benzoxazin-4-one (3.24 g). and the solution was stirred at 100° C. for additional 3 hours. To the mixture was added 1N sodium hydroxide solution (90 ml) and the resulting solution was stirred at 60° C. for 1 hour. After being concentrated in vacuo, the residue was diluted with chloroform and the organic solution was washed with saturated aqueous sodium bicarbonate solution and brine. The organic layer was dried over magnesium sulfate and the solvent was concentrated in vacuo to give 3-methoxy-N-methyl-N-[4-methyl-2-[5-(4-methylpiperazin-1-yl)carbonylpent-1-yloxy]phenyl]-4-(3-nitro-2-trifluoroacetylaminobenzoyl)aminobenzamide as a yellow powder (10.6 g). The crude product was used for next step without further purification.

EXAMPLE 5

To a solution of 4-[(indol-4-yl)carbonyl]amino-3-methoxy-N-methyl-N-[4-methyl-2-[5-(4-methylpiperazin-1-yl)carbonylpent-1-yloxy]phenyl]benzamide (160 mg) in N,N-dimethylformamide (3.0 ml) was added portionwise potassium tert-butoxide (37.3 mg) at 0° C. and the mixture was stirred at 0° C. for 1 hour. Methyl iodide (47.2 mg) was added to the mixture and the solution was stirred at 0° C. for 1 hour. The reaction was quenched with water and then the aqueous solution was extracted with ethyl acetate. Drying, filtering and removal of solvents afforded a crude product. The crude product was purified by column chromatography (eluent; 2% methanol in chloroform) to give 4-[(1-methylindol-4-yl)carbonyl]amino-3-methoxy-N-methyl-N-[4-methyl-2-[5-(4-methylpiperazin-1-yl)carbonylpent-1-yloxy]phenyl]benzamide (65 mg) as a white syrup.

NMR (CDCl$_3$, δ): 1.49–1.89 (6 H, m), 2.28 (3 H, s), 2.29 (3 H, s), 2.32–2.42 (6 H, m), 3.34 (3 H, s), 3.46–3.52 (2 H, m), 3.60–3.68 (2 H, m), 3.78 (3 H, s), 3.86 (3 H, s), 3.88–3.99 (2 H, m), 6.60 (1 H, d, J=8 Hz), 6.64 (1 H, s), 6.87 (1 H, d, J=8 Hz), 6.91–6.98 (2 H, m), 7.06 (1 H, s), 7.21 (1 H, d, J=3 Hz), 7.27–7.32 (1 H, m), 7.49 (1 H, d, J=8 Hz), 7.63 (1 H, d, J=8 Hz), 8.38 (1 H, d, J=8 Hz), 8.76 (1 H, s).

EXAMPLE 6

The following compound was obtained according to a similar manner to that of Example 5.

4-[(1-Isopropylindol-4-yl)carbonyl]amino-3-methoxy-N-methyl-N-[4-methyl-2-[5-(4-methylpiperazin-1-yl) carbonylpent-1-yloxy]phenyl]benzamide NMR (CDCl$_3$, δ): 1.48–1.59 (2 H, m), 1.57 (6 H, d, J=7 Hz), 1.66–1.88 (4 H, m), 2.29 (6 H, s), 2.32–2.40 (6 H, m), 3.33 (3 H, s), 3.46–3.51 (2 H, m), 3.60–3.67 (2 H, m), 3.79 (3 H, s), 3.88–4.00 (2 H, m), 4.68–4.78 (1 H, m), 6.60 (1 H, d, J=8 Hz), 6.65 (1 H, s), 6.87 (1 H, d, J=8 Hz), 6.93 (1 H, d, J=8 Hz), 6.97 (1 H, d, J=3 Hz), 7.07 (1 H, s), 7.27 (1 H, t, J=8 Hz), 7.38 (1 H, d, J=3 Hz), 7.54 (1 H, d, J=8 Hz), 7.62 (1 H, d, J=8 Hz), 8.38 (1 H, d, J=8 Hz), 8.76 (1 H, s).

EXAMPLE 7

To a solution of 4-(2-amino-3-nitrobenzoyl)amino-3-methoxy-N-methyl-N-[4-methyl-2-[5-(4-methylpiperazin-1-yl)carbonylpent-1-yloxy]phenyl]benzamide (3.88 g) in ethanol (40 ml) were added a solution of ammonium chloride (385 mg) in water (10 ml) and iron powder (2.01 g) and the mixture was stirred at 100° C. for 2 hours. The mixture was filtered through a bed of celite and the filtrate was concentrated in vacuo. The residue was diluted with ethyl acetate and the solution was washed with aqueous saturated sodium bicarbonate solution and brine. The organic layer was dried over magnesium sulfate and the solution was concentrated in vacuo to give 4-(2,3-diaminobenzoyl) amino-3-methoxy-N-methyl-N-[4-methyl-2-[5-(4-methylpiperazin-1-yl)carbonylpent-1-yloxy]phenyl] benzamide as a yellow powder (3.42 g).

NMR (CDCl$_3$, δ): 1.47–1.59 (2 H, m), 1.59–1.90 (4 H, m), 2.29 (3 H, s), 2.30 (3 H, s), 2.33–2.42 (6 H, m), 3.33 (3 H, s), 3.47–3.50 (2 H, m), 3.62–3.67 (2 H, m), 3.77 (3 H, s), 3.82–4.00 (2 H, m), 6.57–6.68 (3 H, m), 6.80–7.03 (5 H, m), 8.20 (1 H, d, J=7 Hz), 8.44 (1 H,

EXAMPLE 8

To a suspension of 4-(2,3-diaminobenzoyl)amino-3-methoxy-N-methyl-N-[4-methyl-2-[5-(4-methylpiperazin-1-yl)carbonylpent-1-yloxy]phenyl]benzamide (200 mg) in water (5 ml) was added 1N hydrochloric acid (1.3 ml) and then dicyandiamide (545 mg) was added to the stirred reaction mixture. The solution was heated under reflux for 24 hours. After cooling, aqueous sodium hydrogen carbonate was added to the mixture and extracted with ethyl acetate. The extract was washed with brine and dried over sodium sulfate. After evaporation of the solvent, the residue was purified by silica gel column chromatography (SiO$_2$, 30 g, 15% methanol in chloroform) to give 4-[2-guanidinobenzimidazol-4-yl]carbonylamino-3-methoxy-N-methyl-N-[4-methyl-2-[5-(4-methylpiperazin-1-yl) carbonylpent-1-yloxy]phenyl]benzamide (100 mg) as yellow amorphous.

NMR (CDCl$_3$, δ): 1.36–1.83 (6 H, m), 2.25 (3 H, s), 2.30 (3 H, s), 2.32–2.48 (6 H, m), 3.34 (3 H, s), 3.43–3.74 (5 H, m), 3.78 (3 H, s), 3.82–3.98 (1 H, m), 6.56 (1 H, s), 6.68 (1 H, d, J=8 Hz), 6.94 (1 H, d, J=8 Hz), 7.02 (1 H, d, J=8 Hz), 7.08–7.18 (2 H, m), 7.36 (1 H, d, J=8 Hz), 7.97 (1 H, d, J=8 Hz), 8.44 (1 H, d, J=8 Hz).

EXAMPLE 9

To a solution of 4-(2,3-diaminobenzoyl)amino-3-methoxy-N-methyl-N-[4-methyl-2-[5-(4-methylpiperazin-1-yl)carbonylpent-1-yloxy]phenyl]benzamide (110 mg) in anhydrous tetrahydrofuran (2 ml) was added 1,1'-thiocarbonyldiimidazole (48 mg) under nitrogen at ambient temperature and stirred at same temperature for 1 day. After being concentrated in vacuo, the residue was diluted with a mixture of chloroform and saturated sodium bicarbonate aqueous solution and the organic layer was separated. The organic layer was washed with water and brine and the solution was dried over magnesium sulfate. The solvent was evaporated in vacuo and the residue was purified by preparative thin-layer chromatography (ethyl acetate-methanol=1:1) to give 4-(2-mercapto-1H-benzimidazol-4-yl)carbonylamino-3-methoxy-N-methyl-N-[4-methyl-2-[5-(4-methylpiperazin-1-yl)carbonylpent-1-yloxy]phenyl] benzamide (96 mg) as a powder.

NMR (CDCl$_3$, δ): 1.48–1.62 (2 H, m), 1.66–1.78 (2 H, m), 1.78–1.90 (2 H, m), 2.28 (3 H, s), 2.31 (3 H, s), 2.33–2.46 (6 H, m), 3.33 (3 H, s), 3.45–3.53 (2 H, m), 3.60–3.70 (2 H, m), 3.81 (3 H, s), 3.84–4.01 (2 H, m), 6.55–6.67 (2 H, m), 6.86 (1 H, d, J=8 Hz), 6.94 (1 H, d, J=8

Hz), 7.03 (1 H, s), 7.12 (2 H, s-like), 7.17–7.40 (2 H, m), 7.70 (1 H, s), 8.20 (1 H, d, J=8 Hz), 8.65 (1 H, s).

EXAMPLE 10

To a suspension of 4-(2,3-diaminobenzoyl)amino-3-methoxy-N-methyl-N-[4-methyl-2-[5-(4-methylpiperazin-1-yl)carbonylpent-1-yloxy]phenyl]benzamide (242 mg) in water (3 ml) was added cyanogen bromide (46 mg) at ambient temperature. The mixture was stirred at the same temperature for 2 hours and then allowed to stand at the same temperature overnight. To the reaction mixture was added saturated aqueous sodium bicarbonate solution and the solution was extracted with chloroform. The organic layer was washed with water, dried over magnesium sulfate and evaporated in vacuo. The residue was purified by preparative thin-layer chromatography (chloroform-methanol=10:1) to give 4-(2-amino-1H-benzimidazol-4-yl)carbonylamino-3-methoxy-N-methyl-N-[4-methyl-2-[5-(4-methylpiperazin-1-yl)carbonylpent-1-yloxy]phenyl]benzamide (67 mg) as a powder.

NMR (CDCl$_3$, δ): 1.40–1.56 (2 H, m), 1.56–1.87 (4 H, m), 2.23 (3 H, s), 2.26 (3 H, s), 2.30–2.44 (6 H, m), 3.33 (3 H, s), 3.41–3.53 (2 H, m), 3.53–3.69 (5 H, m), 3.69–3.83 (1 H, m), 3.83–4.00 (1 H, m), 5.54 (2 H, br peak), 6.50–6.66 (2 H, m), 6.80–6.95 (2 H, m), 6.95–7.10 (2 H, m), 7.69 (1 H, d-like), 8.37 (1 H, d-like).

EXAMPLE 11

To 4-(2,3-diaminobenzoyl)amino-3-methoxy-N-methyl-N-[4-methyl-2-[5-(4-methylpiperazin-1-yl)carbonylpent-1-yloxy]phenyl]benzamide (120 mg) were added acetic acid (47 mg) and water (0.5 ml) and the suspension was stirred at ambient temperature until a clear solution was obtained. After being cooled to 5° C. a cold solution of sodium nitrite (15 mg) in water (0.3 ml) was added all at once to the solution. The reaction mixture as stirred at 5° C. for 5 minutes and then the temperature was raised to 75° C. and stirred for 10 minutes. The reaction mixture was cooled to 20° C. and the solution was stirred in an ice water bath for 1 hour. To the reaction mixture were added saturated aqueous sodium bicarbonate solution and chloroform and the organic layer was separated. The organic layer was washed with saturated aqueous sodium bicarbonate solution and brine and dried over magnesium sulfate. The solvent was evaporated and the residue was purified by preparative thin-layer chromatography (chloroform-methanol=10:1) to give 4-(1H-benzotriazol-4-yl)carbonylamino-3-methoxy-N-methyl-N-[4-methyl-2-[5-(4-methylpiperazin-1-yl)carbonylpent-1-yloxy]phenyl]benzamide (81 mg) to give a powder.

NMR (CDCl$_3$, δ): 1.46–1.62 (2 H, m), 1.65–1.76 (2 H, m), 1.76–1.90 (2 H, m), 2.26 (3 H, s), 2.32–2.45 (7 H, m), 2.45–2.59 (2 H, m), 3.35 (3 H, s), 3.50–3.66 (3 H, m), 3.73–3.89 (5 H, m), 3.89–3.99 (1 H, m), 6.57–6.65 (2 H, m), 6.93 (1 H, d, J=8 Hz), 6.99–7.05 (2 H, m), 7.53 (1 H, t, J=8 Hz), 8.00 (1 H, d, J=8 Hz), 8.10 (1 H, d, J=8 Hz), 8.34 (1 H, d, J=8 Hz), 10.04 (1 H, s).

EXAMPLE 12

To a stirred solution of 4-(2,3-diaminobenzoyl)amino-3-methoxy-N-methyl-N-[4-methyl-2-[5-(4-methylpiperazin-1-yl)carbonylpent-1-yloxy]phenyl]benzamide (145 mg) in a mixture of acetonitrile and benzene [1:4(v/v)] was added methoxycarbonyl isothiocyanate (36 mg) and the reaction mixture was stirred at ambient temperature for 5 minutes. After being added 1,3-dicyclohexylcarbodiimide (73 mg) to the solution, the resulting mixture was stirred at reflux temperature for 5 hours. The reaction mixture was concentrated in vacuo and the residue was dissolved in chloroform. The solution was washed with saturated aqueous sodium bicarbonate solution, water and brine, dried over magnesium sulfate and evaporated in vacuo. The residue was purified by chromatography on silica gel (chromatorex) eluting with chloroform and preparative thin-layer chromatography (chloroform-methanol=10:1) to give 3-methoxy-4-(2-methoxycarbonylamino-1H-benzimidazol-4-yl)carbonylamino-N-methyl-N-[4-methyl-2-[5-(4-methylpiperazin-1-yl)carbonylpent-1-yloxy]phenyl]benzamide (82 mg) as a powder.

NMR (DMSO-d$_6$, δ): 1.36–1.49 (2 H, m), 1.49–1.62 (2 H, m), 1.67–1.83 (2 H, m), 2.13 (3 H, s), 2.15–2.38 (9 H, m), 3.20 (3 H, s), 3.36–3.45 (4 H, m), 3.74 (3 H, s), 3.79–3.90 (4 H, m), 3.90–4.03 (1 H, m), 6.65 (1 H, d, J=8 Hz), 6.82 (1 H, s), 6.89 (1 H, s), 6.93 (1 H, d, J=8 Hz), 7.03 (1 H, d, J=8 Hz), 7.20 (1 H, t, J=8 Hz) 7.67 (1 H, d, J=8 Hz), 7.82 (1 H, d, J=8 Hz), 8.21–8.28 (1 H, m).

EXAMPLE 13

A mixture of 4-(2,3-diaminobenzoyl)amino-3-methoxy-N-methyl-N-[4-methyl-2-[5-(4-methylpiperazin-1-yl)carbonylpent-1-yloxy]phenyl]benzamide (90 mg) and trimethyl orthoformate (1 ml) was refluxed for 4 hours. After removing excess reagent by evaporation, the residue was dissolved in chloroform and the solution was washed with water and saturated aqueous sodium bicarbonate solution. The organic layer was dried over magnesium sulfate and the solvent was evaporated in vacuo. The residue was purified by preparative thin-layer chromatography (chloroform-methanol=10:1) to give 4-(1H-benzimidazol-4-yl)carbonylamino-3-methoxy-N-methyl-N-[4-methyl-2-[5-(4-methylpiperazin-1-yl)carbonylpent-1-yloxy]phenyl]benzamide (51 mg) as a powder.

NMR (CDCl$_3$, δ): 1.48–1.62 (2 H, m), 1.67–1.78 (2 H, m), 1.78–1.91 (2 H, m), 2.21–2.31 (6 H, m), 2.31–2.43 (6 H, m), 3.35 (3 H, s), 3.45–3.56 (2 H, m), 3.60–3.69 (2 H, m), 3.81 (1 H, d-like), 3.81–3.90 (1 H, m), 3.90–4.01 (1 H, m), 6.54–6.65 (2 H, m), 6.84–6.93 (1 H, m), 6.93–7.07 (2 H, m), 7.31–7.50 (1 H, m), 7.59 (1 H×1/2, d, J=8 Hz), 7.68 (1 H×1/2, d, J=8 Hz), 7.98–8.33 (2 H, m), 8.45–8.56 (1 H×1/2, m), 8.79 (1 H×1/2, s).

EXAMPLE 14

To a solution of 4-(2,3-diaminobenzoyl)amino-3-methoxy-N-methyl-N-[4-methyl-2-[5-(4-methylpiperazin-1-yl)carbonylpent-1-yloxy]phenyl]benzamide (200 mg) in acetic acid (1 ml) was added tetramethyl orthocarbonate (66 mg) at ambient temperature and the solution was allowed to stand at the same temperature for 3 days. After being concentrated in vacuo, the residue was diluted with chloroform and saturated sodium bicarbonate aqueous solution. The organic layer was separated and washed with water and brine. The solution was dried over magnesium sulfate and the solvent was evaporated in vacuo. The residue was purified by preparative thin-layer chromatography (chloroform-methanol=10:1) to give 4-(2-methoxy-1H-benzimidazol-4-yl)carbonylamino-3-methoxy-N-methyl-N-[4-methyl-2-[5-(4-methylpiperazin-1-yl)carbonylpent-1-yloxy]phenyl]benzamide (171 mg) as a powder.

NMR (CDCl$_3$, δ): 1.44–1.65 (2 H, m), 1.65–1.76 (2 H, m), 1.76–1.90 (2 H, m), 2.27 (3 H, s), 2.29 (3 H, s), 2.33–2.45 (6 H, m), 3.34 (3 H, s), 3.42–3.54 (2 H, m), 3.58–3.68 (2 H, m), 3.71 (3 H×2/3, s), 3.80 (3 H×1/3, s), 3.82–4.02 (2 H, m), 4.20 (3 H×1/3, s), 4.28 (3 H×2/3, s), 6.53–6.68 (2 H, m), 6.81–7.08 (3 H, m), 7.17–7.43 (3 H, m), 7.70 (1 H×1/3, d, J=8 Hz), 8.06 (1 H×2/3, d, J=8 Hz), 8.22–8.31 (1 H×1/3, m), 8.54 (1 H×2/3, d, J=8 Hz), 8.72 (1 H×1/3, s), 8.90 (1 H×2/3, s).

EXAMPLE 15

The following compounds were obtained according to a similar manner to that of Example 14.

1) 4-(2-Ethoxy-1H-benzimidazol-4-yl)carbonylamino-3-methoxy-N-methyl-N-[4-methyl-2-[5-(4-methylpiperazin-1-yl)carbonylpent-1-yloxy]phenyl]benzamide NMR (CDCl$_3$, δ): 1.44–1.65 (5 H, m), 1.65–1.76 (2 H, m), 1.76–1.90 (2 H, m), 2.25 (3 H, s), 2.29 (3 H, s), 2.31–2.43 (6 H, m), 3.33 (3 H, s), 3.44–3.53 (2 H, m), 3.60–3.68 (2 H, m), 3.74 (3 H×3/4, s), 3.80 (3 H×1/4, s), 3.83–4.01 (2 H, m), 4.61 (2 H×1/4, q, J=7.5 Hz), 4.73 (2 H×3/4, q, J=7.5 Hz), 6.55–6.66 (2 H, m), 6.81–6.99 (2 H, m), 7.02 (1 H, s), 7.20 (1 H, t, J=8 Hz), 7.35 (1 H, d, J=8 Hz), 7.67 (1 H×1/4, d, J=8 Hz), 8.05 (1 H×3/4, d, J=8 Hz), 8.26 (1 H×1/4, d, J=8 Hz), 8.54 (1 H×3/4, d, J=8 Hz), 8.70–8.78 (1 H, m).

2) 3-Methoxy-N-methyl-N-[4-methyl-2-[5-(4-methylpiperazin-1-yl)carbonylpent-1-yloxy]phenyl]-4-(2-propoxy-1H-benzimidazol-4-yl)carbonylaminobenzamide NMR (CD$_3$OD, δ): 1.06 (3 H, t, J=7.5 Hz), 1.42–1.56 (2 H, m), 1.56–1.71 (2 H, m), 1.71–1.96 (4 H, m), 2.20 (3 H, s), 2.25 (3 H, s), 2.28–2.97 (6 H, m), 3.29 (3 H, s), 3.40–3.62 (4 H, m), 3.70 (3 H, s), 3.79–4.01 (2 H, m), 4.56 (2 H, t, J=7 Hz), 6.67 (1 H, d, J=8 Hz), 6.76 (1 H, s), 6.94 (1 H, s), 6.96–7.05 (2 H, m), 7.13 (1 H, t, J=8 Hz), 7.35 (1 H, d, J=8 Hz), 7.82 (1 H, d, J=8 Hz), 8.40 (1 H, d, J=8 Hz).

EXAMPLE 16

A suspension of 4-(2,3-diaminobenzoyl)amino-3-methoxy-N-methyl-N-[4-methyl-2-[5-(4-methylpiperazin-1-yl)carbonylpent-1-yloxy]phenyl]benzamide (100 mg) in acetic acid (1 ml) was refluxed for 8 hours. After being evaporated in vacuo, the residue was dissolved chloroform and the solution was washed with water and saturated aqueous sodium bicarbonate solution. The organic layer was dried over magnesium sulfate and the solvent was evaporated in vacuo. The residue was purified by preparative thin-layer chromatography (chloroform-methanol=10:1) to give 3-methoxy-N-methyl-4-(2-methyl-1H-benzimidazol-4-yl)carbonylamino-N-[4-methyl-2-[5-(4-methylpiperazin-1-yl)carbonylpent-1-yloxy]phenyl]benzamide (84 mg) as a powder.

NMR (CDCl$_3$, δ): 1.43–1.60 (2 H, m), 1.60–1.75 (2 H, m), 1.75–1.89 (2 H, m), 2.25 (3 H, s), 2.29 (3 H, s), 2.31–2.43 (6 H, m), 2.63 (3 H, s), 3.33 (3 H, s), 3.43–3.53 (2 H, m), 3.58–3.68 (2 H, m), 3.73–3.90 (4 H, m), 3.90–4.00 (1 H, m), 6.53–6.64 (2 H, m), 6.82–6.91 (1 H, m), 6.91–7.05 (2 H, m), 7.22–7.33 (1 H×2/3, m), 7.43–7.53 (1 H, m), 7.80–7.90 (1 H×1/3, m), 8.11 (1 H×2/3, d, J=8 Hz), 8.23–8.31 (1 H×1/3, m), 8.47–8.57 (1 H×2/3, m), 8.75 (1 H×1/3, s), 9.83 (1 H×2/3, s), 10.67 (1 H×1/3, s).

EXAMPLE 17

The following compounds were obtained according to a similar manner to that of Example 16.

1) 3-Methoxy-N-methyl-N-[4-methyl-2-[5-(4-methylpiperazin-1-yl)carbonylpent-1-yloxy]phenyl]-4-(2-trifluoromethyl-1H-benzimidazol-4-yl)carbonylaminobenzamide NMR (CDCl$_3$, δ): 1.43–1.62 (2H, m), 1.62–1.77 (2H, m), 1.77–1.94 (2H, m), 3.35 (3H, s), 3.43–3.58 (2H, m), 3.58–3.70 (2H, m), 3.80 (3H, s), 3.82–3.91 (1H, m), 3.91–4.01 (1H, m), 6.53–6.66 (2H, m), 6.90 (1H, d, J=8 Hz), 6.94–7.04 (2H, m), 7.48 (1H, t, J=8 Hz), 7.78 (1H, br peak), 8.08 (1H, br peak), 8.41 (1H, br peak)

2) 4-(2-Ethyl-1H-benzimidazol-4-yl)carbonylamino-3-methoxy-N-methyl-N-[4-methyl-2-[5-(4-methylpiperazin-1-yl)-carbonylpent-1-yloxy]phenyl]benzamide NMR (CDCl$_3$, δ): 1.41–1.75 (7H, m), 1.75–1.90 (2H, m), 2.23–2.31 (6H, m), 2.31–2.42 (6H, m), 2.99 (2H, q, J=7.5 Hz), 3.34 (3H, m), 3.44–3.52 (2H, m), 3.59–3.67 (2H, m), 3.76–3.90 (4H, m), 3.90–4.00 (1H, m), 6.53–6.64 (2H, m), 6.83–7.04 (3H, m), 7.24–7.34 (1H, m), 7.44–7.55 (1H, m), 7.89 (1H×1/3, d, J=8 Hz), 8.14 (1H×2/3, d, J=8 Hz), 8.28 (1H×1/3, d, J=8 Hz), 8.37 (1H×2/3, d, J=8 Hz), 8.78 (1H×1/3, s), 9.56 (1H×2/3, s), 10.75 (1H×1/3, s)

3) 3-Methoxy-N-methyl-N-[4-methyl-2-[5-(4-methylpiperazin-1-yl)carbonylpent-1-yloxy]phenyl]-4-(2-n-propyl-1H-benzimidazol-4-yl)carbonylaminobenzamide NMR (CD$_3$OD, δ): 1.06 (3H, t, J=7.5 Hz), 1.47–1.60 (2H, m), 1.60–1.74 (2H, m), 1.74–1.90 (2H, m), 1.90–2.05 (2H, m), 2.23 (3H, s), 2.28 (3H, s), 2.31–2.47 (6H, m), 2.95 (2H, t, J=7.5 Hz), 3.30 (3H, s), 3.48–3.61 (4H, m), 3.79 (3H, s), 3.84–3.94 (1H, m), 3.94–4.06 (1H, m), 6.70 (1H, d, J=8 Hz), 6.79 (1H, s), 6.97 (1H, s), 6.99–7.08 (2H, m), 7.30 (1H, t, J=8 Hz), 7.94 (1H, d, J=8 Hz), 8.40 (1H, d, J=8 Hz)

4) 4-(2-Isopropyl-1H-benzimidazol-4-yl)carbonylamino-3-methoxy-N-methyl-N-[4-methyl-2-[5-(4-methylpiperazin-1-yl)carbonylpent-1-yloxy]phenyl]benzamide NMR (CDCl$_3$, δ): 1.43–1.59 (8H, m), 1.59–1.75 (2H, m), 1.75–1.90 (2H, m), 2.22–2.30 (6H, m), 2.30–2.42 (6H, m), 3.18–3.30 (1H, m), 3.33 (3H, s), 3.43–3.51 (2H, m), 3.60–3.67 (2H, m), 3.75–3.89 (4H, m), 3.89–4.01 (1H, m), 6.53–6.65 (2H, m), 6.87 (1H, d, J=8 Hz), 6.94 (1H, d, J=8 Hz), 7.03 (1H, s), 7.30 (1H, t, J=8 Hz), 7.45–7.56 (1H, m), 7.90 (1H×1/3, d, J=8 Hz), 8.12 (1H×2/3, d, J=8 Hz), 8.26 (1H×1/3, d, J=8 Hz), 8.54 (1H×2/3, d, J=8 Hz), 8.77 (1H×1/3, s), 9.64 (1H×2/3, s)

EXAMPLE 18

To a solution of 4-(2,3-diaminobenzoyl)amino-3-methoxy-N-methyl-N-[4-methyl-2-[5-(4-methylpiperazin-1-yl)carbonylpent-1-yloxy]phenyl]benzamide (640 mg) in dichloromethane (6 ml) were added pyridine (99 mg) and N-phthaloylglycyl chloride (280 mg) under nitrogen in ice water bath and the mixture was stirred at the same temperature for 2 hours. To the reaction mixture was added methanol (1 ml) at ambient temperature and stirred for additional 30 minutes. The reaction mixture was concentrated in vacuo and the residue was dissolved in pyridine (6 ml). The solution was stirred at 100° C. for 48 hours and the solvent was evaporated in vacuo. The residue was diluted with chloroform and saturated aqueous sodium bicarbonate solution. The organic layer was separated and washed with water and brine. The organic solution was dried over magnesium sulfate and the solvent was evaporated in vacuo. The residue was chromatographed on silica gel eluting with a mixture of chloroform and methanol (50:1~25:1~10:1) to give 3-methoxy-N-methyl-N-[4-methyl-2-[5-(4-methylpiperazin-1-yl)carbonylpent-1-yloxy]phenyl]-4-(2-phthalimidomethyl-1H-benzimidazol-4-yl)carbonylaminobenzamide (410 mg) as a powder.

NMR (CDCl$_3$, δ): 1.43–1.61 (2H, m), 1.61–1.76 (2H, m), 1.76–1.89 (2H, m), 2.27 (3H, s), 2.30 (3H, s), 2.32–2.43 (6H, m), 3.33 (3H, s), 3.45–3.53 (2H, m), 3.59–3.67 (2H, m), 3.81–4.02 (5H, m), 5.18 (2H, s), 6.54–6.65 (2H, m), 6.77–7.03 (3H, m), 7.27–7.38 (1H, m), 7.50 (1H, d, J=8 Hz), 7.64–7.77 (2H, m), 7.77–7.90 (2H, m), 8.10 (1H, d, J=8 Hz), 8.46 (1H, d, J=8 Hz)

EXAMPLE 19

The following compounds were obtained according to a similar manner to that of Example 18

1) 3-Methoxy-N-methyl-N-[4-methyl-2-[5-(4-methylpiperazin-1-yl)carbonylpent-1-yloxy]phenyl]-4-[2-(2-phthalimidoethyl)-1H-benzimidazol-4-yl]carbonylaminobenzamide NMR (CDCl$_3$, δ): 1.46–1.66 (2H, m), 1.66–1.79 (2H, m), 1.79–1.92 (2H, m), 2.20–2.32 (6H, m), 2.32–2.43 (6H, m), 3.33 (3H, s), 3.40 (2H, t, J=7 Hz), 3.44–3.55 (2H, m), 3.55–3.68 (2H, m), 3.81–4.03 (5H, m), 4.23 (2H, t, J=7 Hz), 6.55–6.69 (2H, m), 6.81–7.05 (3H, m), 7.34 (1H, t, J=8 Hz), 7.53–7.62 (2H, m), 7.65–7.76 (2H, m), 7.76–7.91 (1H, m), 8.12 (1H, d, J=8 Hz), 8.42 (1H, d, J=8 Hz)

3-Methoxy-N-methyl-N-[4-methyl-2-[5-(4-methylpiperazin-1-yl)carbonylpent-1-yloxy]phenyl]-4-[2-(2-pyridylmethyl)-1H-benzimidazol-4-yl]carbonylaminobenzamide NMR (CDCl$_3$, δ): 1.46–1.62 (2H, m), 1.62–1.91 (4H, m), 2.22–2.30 (6H, m), 2.30–2.42 (6H, m), 3.34 (3H, s), 3.44–3.52 (2H, m), 3.58–3.67 (2H, m), 3.77–4.02 (5H, m), 4.47 (2H×1/6, s), 4.52 (2H×5/6, s), 6.54–6.65 (2H, m), 6.87 (1H, d, J=8 Hz), 6.96 (1H, d, J=8 Hz), 7.01–7.09 (1H, m), 7.16–7.35 (overlapped in CHCl$_3$), 7.40 (1H×5/6, d, J=8 Hz), 7.48 (1H×1/6, d, J=8 Hz), 7.58 (1H×5/6, d, J=8 Hz), 7.63 (1H×1/6, d, J=8 Hz), 7.66–7.76 (1H, m), 7.89 (1H×1/6, d, J=8 Hz), 8.13 (1H×5/6, d, J=8 Hz), 8.30 (1H×1/6, d, J=8 Hz), 8.51 (1H×5/6, d, J=8 Hz), 8.67 (1H×5/6, d, J=5 Hz), 8.73 (1H×1/5, s-like)

3) 3-Methoxy-N-methyl-N-[4-methyl-2-[5-(4-methylpiperazin-1-yl)carbonylpent-1-yloxy]phenyl]-4-[2-(3-pyridylmethyl)-1H-benzimidazol-4-yl]carbonylaminobenzamide NMR (CDCl$_3$, δ): 1.45–1.58 (2H, m), 1.64–1.75 (2H, m), 1.75–1.89 (2H, m), 2.25 (3H, s), 2.29 (3H, s), 2.32–2.43 (6H, m), 3.34 (3H, s), 3.43–3.53 (2H, m), 3.57–3.66 (2H, m), 3.74 (3H×2/3, s), 3.79 (3H×1/3, s), 3.81–3.91 (1H, m), 3.90–4.00 (1H, m), 4.32 (2H, s), 6.54–6.64 (2H, m), 6.83–6.92 (1H, m), 6.92–7.03 (2H, m), 7.23–7.36 (overlapped in CHCl$_3$), 7.50 (1H, d, J=8 Hz), 7.66 (1H×1/3, d, J=8 Hz), 7.73 (1H×2/3, d, J=8 Hz), 7.91 (1H×1/3, d, J=8 Hz), 8.15 (1H×2/3, d, J=8 Hz), 8.21 (1H×1/3, d, J=8 Hz), 8.48–8.75 (3H, m)

4) 3-Methoxy-N-methyl-N-[4-methyl-2-[5-(4-methylpiperazin-1-yl)carbonylpent-1-yloxy]phenyl]-4-[2-(4-pyridylmethyl)-1H-benzimidazol-4-yl]carbonylaminobenzamide NMR (CDCl$_3$—CD$_3$OD, δ): 1.47–1.60 (2H, m), 1.60–1.76 (2H, m), 1.76–1.89 (2H, m), 2.26 (3H, s), 2.30 (3H, s), 2.32–2.44 (6H, m), 3.33 (3H, s), 3.46–3.54 (2H, m), 3.58–3.64 (2H, m), 3.68 (3H×3/4, s), 3.77 (3H×1/4, s), 3.81–4.01 (2H, m), 4.33 (2H, s), 6.55–6.65 (2H, m), 6.83–6.92 (1H, m), 6.92–7.02 (2H, m), 7.27–7.38 (3H, m), 7.53 (1H, d, J=8 Hz), 8.10 (1H, d, J=8 Hz), 8.45–8.55 (3H, m)

EXAMPLE 20

To a mixture of 4-[(indol-4-yl)carbonyl]amino-3-methoxy-N-methyl-N-[4-methyl-2-[5-(4-methylpiperazin-1-yl)carbonylpent-1-yloxy]phenyl]benzamide (150 mg) and N,N-dimethylaminopyridine (5.9 mg) in acetonitrile (10 ml) was added diethyl dicarbonate (46.6 mg) at ambient temperature. The solution was stirred at ambient temperature for a few hours and stood overnight. The resulting mixture was diluted with water and the aqueous solution was extracted with ethyl acetate. Drying, filtering and removal of solvents afforded a crude product. The crude product was purified by column chromatography (eluent; 2% methanol in chloroform) to give 4-[(ethoxycarbonylindol-4-yl)carbonyl]amino-3-methoxy-N-methyl-N-[4-methyl-2-[5-(4-methylpiperazin-1-yl)carbonylpent-1-yloxy]phenyl]benzamide (126 mg) as a colorless syrup.

NMR (CDCl$_3$, δ): 1.49 (3H, t, J=8 Hz), 1.50–1.59 (2H, m), 1.66–1.76 (2H, m), 1.79–1.88 (2H, m), 2.28 (3H, s), 2.29 (3H, s), 2.32–2.41 (6H, m), 3.33 (3H, s), 3.47–3.51 (2H, m), 3.60–3.66 (2H, m), 3.79 (3H, s), 3.88–4.00 (2H, m), 4.50 (2H, q, J=8 Hz), 6.59 (1H, d, J=8 Hz), 6.64 (1H, s), 6.87 (1H, d, J=8 Hz), 6.96 (1H, d, J=8 Hz), 7.05 (1H, s), 7.18 (1H, d, J=4 Hz), 7.40 (1H, t, J=8 Hz), 7.62 (1H, d, J=8 Hz), 7.75 (1H, d, J=4 Hz), 8.32 (1H, d, J=8 Hz), 8.40 (1H, d, J=8 Hz), 8.57 (1H, s)

EXAMPLE 21

A solution of 4-[[1-(4-toluenesulfonyl)indol-4-yl]-carbonyl]amino-3-methoxy-N-methyl-N-[4-methyl-2-[5-(4-methylpiperazin-1-yl)carbonylpent-1-yloxy]phenyl]benzamide (255 mg) in a mixture of 2N potassium hydroxide aqueous solution (2.5 ml) and methanol (6.0 ml) was stirred at ambient temperature for 3 hours and stood overnight. The resulting mixture was diluted with water and the solution was extracted with ethyl acetate. Drying, filtering and removal of solvents afforded a crude product. The crude product was chromatographed on silica gel (eluent; 3–8% methanol in chloroform) to give 4-[(indol-4-yl)carbonyl]amino-3-methoxy-N-methyl-N-[4-methyl-2-[5-(4-methylpiperazin-1-yl)-carbonylpent-1-yloxy]phenyl]benzamide (154 mg) as a white amorphous powder.

NMR (CDCl$_3$, δ): 1.48–1.59 (2H, m), 1.66–1.88 (4H, m), 2.29 (3H, s), 2.30 (3H, s), 2.32–2.47 (6H, m), 3.33 (3H, s), 3.48–3.53 (2H, m), 3.62–3.69 (2H, m), 3.77 (3H, s), 3.84–4.00 (2H, m), 6.60 (1H, d, J=8 Hz), 6.63 (1H, s), 6.88 (1H, d, J=8 Hz), 6.96 (1H, d, J=8 Hz), 6.99–7.05 (2H, m), 7.21–7.28 (1H, m), 7.35 (1H, d, J=3 Hz), 7.55 (1H, d, J=8 Hz), 7.61 (1H, d, J=8 Hz), 8.38 (1H, d, J=8 Hz), 8.73 (1H, s), 8.82–8.87 (1H, br s)

EXAMPLE 22

To a solution of 4-[(1-pivaloyloxymethylindol-7-yl)-carbonyl]amino-3-methoxy-N-methyl-N-[4-methyl-2-[5-(4-methylpiperazin-1-yl)carbonylpent-1-yloxy]phenyl]benzamide (100 mg) in methanol (4.0 ml) was added 28% sodium methylate in methanol solution (100 mg). The solution was stirred at ambient temperature for a few hours and stood overnight. The resulting mixture was diluted with water and the solution was extracted with ethyl acetate. Drying, filtering and removal of solvents afforded 4-[(indol-7-yl)carbonyl]amino-3-methoxy-N-methyl-[4-methyl-2-[5-(4-methylpiperazin-1-yl)-carbonylpent-1-yloxy]phenyl]benzamide (70 mg) as a slightly yellow syrup.

NMR (CDCl$_3$, δ): 1.49–1.95 (6H, m), 2.27 (3H, s), 2.28 (3H, s), 2.32–2.41 (6H, m), 3.33 (3H, s), 3.47–3.51 (2H, m), 3.60–3.67 (2H, m), 3.80 (3H, m), 3.83–3.95 (2H, m), 6.56–6.65 (3H, m), 6.87 (1H, d, J=8 Hz), 6.98 (1H, d, J=8 Hz), 7.03 (1H, s), 7.16 (1H, t, J=8 Hz), 7.32 (1H, d, J=4 Hz), 7.49 (1H, d, J=8 Hz), 7.83 (1H, d, J=8 Hz), 8.30 (1H, d, J=8 Hz), 8.78 (1H, s)

EXAMPLE 23

The mixture of 4-[(1-tert-butoxycarbonyl-2-ethoxycarbonylindol-4-yl)carbonyl]amino-3-methoxy-N-methyl-N-[4-methyl-2-[5-(4-methylpiperazin-1-yl)

carbonylpent-1-yloxy]phenyl]benzamide (75 mg) in trifluoroacetic acid (2.0 ml) was stirred at ambient temperature for 5 minutes. Trifluoroacetic acid was removed in vacuo and the residue was diluted with aqueous saturated sodium bicarbonate solution. The solution was extracted with ethyl acetate and the organic layer was washed with brine. Drying, filtering and removal of solvents afforded 4-[(2-ethoxycarbonylindol-4-yl)-carbonyl]amino-3-methoxy-N-methyl-N-[4-methyl-2-[5-(4-methylpiperazin-1-yl)carbonylpent-1-yloxy]phenyl]benzamide (50 mg) as a yellow amorphous powder.

NMR (CDCl$_3$, δ): 1.42 (3H, t, J=8 Hz), 1.49–1.60 (2H, m), 1.68–1.90 (4H, m), 2.28 (3H, s), 2.29 (3H, s), 2.32–2.43 (6H, m), 3.33 (3H, s), 3.47–3.52 (2H, m), 3.60–3.68 (2H, m), 3.80 (3H, s), 3.87–4.00 (2H, m), 4.41 (2H, q, J=8 Hz), 6.60 (1H, d, J=8 Hz), 6.63 (1H, s), 6.87 (1H, d, J=8 Hz), 6.96 (1H, d, J=8 Hz), 7.06 (1H, s), 7.39 (1H, t, J=8 Hz), 7.58–7.66 (2H, m), 7.75 (1H, s), 8.35 (1H, d, J=8 Hz), 8.68 (1H, s), 9.22–9.28 (1H, br s)

EXAMPLE 24

A mixture of 4-(3-benzyl-2-methoxymethyl-3H-benzimidazol-4-yl)carbonylamino-3-methoxy-N-methyl-N-[4-methyl-2-[5-(4-methylpiperazin-1-yl)carbonylpent-1-yloxy]phenyl]benzamide (200 mg) and 5% formic acid in methanol solution (10 ml) was refluxed for 24 hours. The reaction mixture was concentrated in vacuo and the residue was dissolved in chloroform. The solution was washed with saturated aqueous sodium bicarbonate solution and the organic layer was dried over magnesium sulfate. The solvent was evaporated in vacuo and the residue was purified by preparative thin-layer chromatography (chloroform-methanol=10:1) to give 3-methoxy-4-(2-methoxymethyl-1H-benzimidazol-4-yl)carbonylamino-N-methyl-N-[4-methyl-2-[5-(4-methylpiperazin-1-yl)carbonylpent-1-yloxy]phenyl]benzamide (48 mg) as a powder.

NMR (CDCl$_3$, δ): 1.24–1.60 (2H, m), 1.60–1.93 (6H, m), 3.33 (3H, s), 3.42–3.60 (5H, m), 3.60–3.76 (2H, m), 3.76–4.04 (5H, m), 4.77 (2H×1/3, s), 4.83 (2H×2/3, s), 6.51–6.67 (2H, m), 6.67–7.10 (3H, m), 7.23–7.56 (2H, m), 7.62 (1H×2/3, d, J=8 Hz), 7.85–7.96 (1H×1/3, m), 7.17 (1H×2/3, d, J=8 Hz), 8.24–8.33 (1H×1/3, m), 8.49 (1H×2/3, d, J=8 Hz), 8.72–8.80 (1H×1/3, m), 9.72 (1H×2/3, s), 10.91 (1H×1/3, s)

EXAMPLE 25

A solution of 3-methoxy-4-[1-(4-methoxybenzyl)-2-(N-methylcarbamoyl)-1H-benzimidazol-4-yl]carbonylamino-N-methyl-N-[4-methyl-2-[5-(4-methylpiperazin-1-yl)carbonylpent-1-yloxy]phenyl]benzamide (130 mg) in trifluoroacetic acid (3 ml) was stirred at 60° C. for 8 hours. The reaction mixture was concentrated in vacuo and the residue was diluted with a mixture of chloroform and saturated aqueous sodium bicarbonate solution. The organic layer was separated and washed with water and brine. The solution was dried over magnesium sulfate and the solvent was evaporated in vacuo. The residue was purified by preparative thin-layer chromatography (chloroform-methanol=10:1) to give 3-methoxy-N-methyl-4-[2-N-methylcarbamoyl)-1H-benzimidazol-4-yl]carbonylamino-N-[4-methyl-2-[5-(4-methylpiperazin-1-yl)-carbonylpent-1-yloxy]phenyl]benzamide (45 mg) as a powder.

NMR (CDCl$_3$, δ): 1.46–1.76 (4H, m), 1.76–1.90 (2H, m), 2.27 (3H, s), 2.29 (3H, s), 2.31–2.42 (6H, m), 3.19 (3H, d, J=5 Hz), 3.34 (3H, s) 3.44–3.51 (2H, m), 3.58–3.65 (2H, m), 3.80–4.01 (5H, m), 6.59 (1H, d, J=8 Hz), 6.64 (1H, s), 6.86 (1H, d, J=8 Hz), 6.96 (1H, d, J=8 Hz), 7.09 (1H, s), 7.50 (1H, t, J=8 Hz), 7.66 (1H, br peak), 7.73 (1H, d, J=8 Hz), 8.25 (1H, d, J=8 Hz), 8.51 (1H, d, J=8 Hz)

EXAMPLE 26

To a solution of 3-methoxy-N-methyl-N-[4-methyl-2-[5-(4-methylpiperazin-1-yl)carbonylpent-1-yloxy]phenyl]-4-(2-phthalimidomethyl-1H-benzimidazol-4-yl)carbonylaminobenzamide (383 mg) in ethanol (5 ml) was added hydrazine monohydrate (19 mg) at ambient temperature and the solution was stirred at 60° C. for 1 hour. The reaction mixture was stirred in an ice water bath for 2 hours and the precipitate was filtered off. The filtrate was evaporated in vacuo and the residue was purified by preparative thin-layer chromatography (chloroform-methanol-ammonia solution (28%)=160:32:1) to give 4-(2-aminomethyl-1H-benzimidazol-4-yl)carbonylamino-3-methoxy-N-methyl-N-[4-methyl-2-[5-(4-methylpiperazin-1-yl)carbonylpent-1-yloxy]phenyl]benzamide (200 mg) as a powder.

NMR (CDCl$_3$, δ): 1.45–1.62 (2H, m), 1.64–1.75 (2H, m), 1.75–1.90 (2H, m), 2.25 (3H, s), 2.29 (3H, s), 2.31–2.48 (6H, m), 3.33 (3H, s) 3.44–3.54 (2H, m), 3.58–3.67 (2H, m), 3.71 (3H, s), 3.79–3.90 (1H, m), 3.90–4.02 (1H, m), 4.20 (2H, br peak), 6.53–6.65 (2H, m), 6.83–7.04 (3H, m), 7.22–7.32 (1H, m), 7.54 (1H, br peak), 7.98 (1H, br peak), 8.47 (1H, br peak)

EXAMPLE 27

The following compound was obtained according to a similar manner to that of Example 26.

4-[2-(2-Aminoethyl)-1H-benzimidazol-4-yl]carbonylamino-3-methoxy-N-methyl-N-[4-methyl-2-[5-4-methylpiperazin-1-yl)carbonylpent-1-yloxy]phenyl]benzamide NMR (CDCl$_3$, δ): 1.43–1.58 (2H, m), 1.58–1.90 (4H, m), 2.25 (3H, s), 2.28 (3H, s), 2.30–2.41 (6H, m), 3.08–3.16 (2H, m), 3.23–3.34 (5H, m), 3.43–3.51 (2H, m), 3.56–3.65 (2H, m), 3.76–3.88 (4H, m), 3.88–4.00 (1H, m), 6.54–6.63 (1H, m), 6.86 (1H, d, J=8 Hz), 6.91–7.01 (2H, m), 7.28 (1H, t, J=8 Hz), 7.60 (1H, d, J=8 Hz), 8.00 (1H, br peak), 8.46 (1H, d, J=8 Hz)

EXAMPLE 28

A solution of 3-methoxy-N-methyl-N-[4-methyl-2-[5-(4-methylpiperazin-1-yl)carbonylpent-1-yloxy]phenyl]-4-(3-nitro-2-trifluoroacetylaminobenzoyl)aminobenzamide (10.5 g) in hydrazine monohydride (100 ml) was stirred at 60° C. for 2 hours and the mixture was diluted with a mixture of water and ethyl acetate. The organic layer was separated and washed with saturated aqueous sodium bicarbonate solution and brine. The organic layer was dried over magnesium sulfate and the solution was concentrated in vacuo. The residue was purified by silica gel column chromatography (3% methanol in chloroform) to give 4-(2-amino-3-nitrobenzoyl)amino-3-methoxy-N-methyl-N-[4-methyl-2-[5-(4-methylpiperazin-1-yl)-carbonylpent-1-yloxy]phenyl]benzamide as a yellow powder (5.90 g).

NMR (CDCl$_3$, δ): 1.47–1.58 (2H, m), 1.60–1.88 (4H, m), 2.28 (3H, s), 2.30 (3H, s), 2.33–2.41 (6H, m), 3.34 (3H, s), 3.48–3.50 (2H, m), 3.62–3.66 (2H, m), 3.78 (3H, s), 3.83–3.97 (2H, m), 6.58–6.72 (3H, m), 6.87 (1H, d, J=6 Hz), 6.97 (1H, d, J=6 Hz), 7.02 (1H, s), 7.21 (1H, d, J=6 Hz), 8.12–8.15 (3H, m), 8.29–8.33 (2H, m)

EXAMPLE 29

The solution of 4-[(2-ethoxycarbonylindol-4-yl)-carbonyl]amino-3-methoxy-N-methyl-N-[4-methyl-2-[5-(4- methylpiperazin-1-yl)carbonylpent-1-yloxy]phenyl]benzamide (100 mg) in a mixture of 1N aqueous sodium hydroxide solution (0.43 ml) and ethanol (4.0 ml) was stirred at ambient temperature for 5.5 hours. The resulting solution was neutralized with 1N hydrochloric acid and methanol was removed in vacuo. The residue was diluted with water and the aqueous layer was extracted with chloroform. Drying, filtering and removal of solvents afforded 4-[(2-carboxyindol-4-yl)carbonyl]amino-3-methoxy-N-methyl-N-[4-methyl-2-[5-(4-methylpiperazin-1-yl)carbonylpent-1-yloxy]phenyl]benzamide (70 mg) as a yellow amorphous.

NMR (DMSO-$d_6$, δ): 1.38–1.58 (4H, m), 1.69–1.79 (2H, m), 2.19 (3H, s), 2.23 (3H, s), 2.26–2.37 (6H, m), 3.19 (3H, s), 3.38–3.47 (3H, m), 3.70 (3H, s), 3.80–4.00 (3H, m), 6.66 (1H, d, J=8 Hz), 6.83 (1H, s), 6.90–6.97 (2H, m), 7.03 (1H, d, J=8 Hz), 7.33 (1H, t, J=8 Hz), 7.47 (1H, s), 7.58–7.67 (2H, m), 7.90 (1H, d, J=8 Hz), 9.20 (1H, s)

EXAMPLE 30

To a mixture of 4-[(2-carboxyindol-4-yl)-carbonyl]amino-3-methoxy-N-methyl-N-[4-methyl-2-[5-(4-methylpiperazin-1-yl)carbonylpent-1-yloxy]phenyl]benzamide (60 mg), N,N-dimethylamine hydrochloride (7.7 mg) and 1-hydroxybenzotriazole (14.5 mg) in N,N-dimethylformamide (3.0 ml) was added a solution of 1-(3-dimethylaminopropyl)-3-ethylcarbodiimide hydrochloride (20.6 mg) in N,N-dimethylformamide (1.0 ml) and the mixture was stirred at ambient temperature for 4 hours. The resulting mixture was diluted with ethyl acetate and the organic layer was washed successively with saturated aqueous sodium bicarbonate solution and brine. Drying, filtering and removal of solvents afforded 4-[(2-dimethylaminocarbonylindol-4-yl)-carbonyl]amino-3-methoxy-N-methyl-N-[4-methyl-2-[5-(4-methylpiperazin-1-yl)carbonylpent-1-yloxy]phenyl]benzamide (60 mg) as a yellow amorphous powder.

NMR (CDCl$_3$, δ): 1.50–1.61 (2H, m), 1.68–1.90 (4H, m), 2.29 (6H, s), 2.32–2.42 (6H, m), 3.18–3.27 (3H, br s), 3.34 (3H, s), 3.43–3.52 (5H, m), 3.60–3.68 (2H, m), 3.78 (3H, s), 3.87–4.00 (2H, m), 6.60 (1H, d, J=8 Hz), 6.64 (1H, s), 6.87 (1H, d, J=8 Hz), 6.96 (1H, d, J=8 Hz), 7.07 (1H, s), 7.34 (1H, t, J=8 Hz), 7.45 (1H, s), 7.52 (1H, d, J=8 Hz), 7.61 (1H, d, J=8 Hz), 8.33 (1H, d, J=8 Hz), 8.62 (1H, s), 9.73–9.78 (1H, br s)

EXAMPLE 31

A solution of 3-methoxy-4-(2-methoxy-1H-benzimidazol-4-yl)carbonylamino-N-methyl-N-[4-methyl-2-[5-(4-methylpiperazin-1-yl)carbonylpent-1-yloxy]phenyl]benzamide (139 mg) in 10% hydrogen chloride in methanol (2 ml) was stirred at ambient temperature for 2 hours and 4N hydrogen chloride in 1,4-dioxane (2 ml) was added to the mixture. After being allowed to stand at ambient temperature overnight, the reaction mixture was concentrated in vacuo and the residue was diluted with a mixture of chloroform and saturated aqueous sodium bicarbonate solution. The organic layer was separated and washed with water and brine. The solution was dried over magnesium sulfate and evaporated in vacuo. The residue was purified by preparative thin-layer chromatography (chloroform-methanol=10:1) to give 4-(2-hydroxy-1H-benzimidazol-4-yl)carbonylamino-3-methoxy-N-methyl-N-[4-methyl-2-[5-(4-methylpiperazin-1-yl)carbonylpent-1-yloxy]phenyl]benzamide (53 mg) as a powder.

NMR (CDCl$_3$, δ): 1.44–1.65 (2H, m), 1.65–1.76 (2H, m), 1.76–1.92 (2H, m), 2.28 (3H, s), 2.30 (3H, s), 2.31–2.43 (6H, m), 3.33 (3H, s), 3.44–3.53 (2H, m), 3.58–3.69 (2H, m), 3.82 (3H, s), 3.85–4.01 (2H, m), 6.55–6.68 (2H, m), 6.87 (1H, d, J=8 Hz), 6.96 (1H, d, J=8 Hz), 7.05 (1H, s), 7.08–7.21 (2H, m), 8.25 (1H, d, J=8 Hz), 8.50 (1H, s), 8.66 (1H, s), 9.43 (1H, br s)

EXAMPLE 32

To a solution of 4-(2-tert-butyldiphenylsiloxymethyl-1H-benzimidazol-4-yl)carbonylamino-3-methoxy-N-methyl-N-[4-methyl-2-[5-(4-methylpiperazin-1-yl)carbonylpent-1-yloxy]phenyl]benzamide (296 mg) in dry tetrahydrofuran (10 ml) was added tetrabutylammonium fluoride (173 mg) in ice water bath under nitrogen and the mixture was stirred at the same temperature for 1 hour. The reaction mixture was concentrated in vacuo and the residue was dissolved in chloroform. The solution was washed with water and brine and dried over magnesium sulfate. The solvent was evaporated in vacuo. The residue was purified by preparative thin-layer chromatography (chloroform-methanol=10:1) to give 4-(2-hydroxymethyl-1H-benzimidazol-4-yl)carbonylamino-3-methoxy-N-methyl-N-[4-methyl-2-[5-(4-methylpiperazin-1-yl)carbonylpent-1-yloxy]phenyl]benzamide (200 mg) as a powder.

NMR (CDCl$_3$, δ): 1.37–1.58 (2H, m), 1.58–1.90 (4H, m), 2.23 (3H, s), 2.28 (3H, s), 2.30–2.44 (6H, m), 3.32 (3H, s), 3.40–3.71 (7H, m), 3.71–3.88 (1H, m), 3.88–4.01 (1H, m), 4.85 (2H, s), 6.58 (2H, s-like), 6.67–6.79 (1H, m), 6.79–6.97 (2H, m), 7.14–7.30 (1H, m), 7.49 (1H, br peak), 7.98 (1H, br peak), 8.36 (1H, d, J=8 Hz)

EXAMPLE 33

A mixture of 4-(2-amino-1H-benzimidazol-4-yl)-carbonylamino-3-methoxy-N-methyl-N-[4-methyl-2-[5-(4-methylpiperazin-1-yl)carbonylpent-1-yloxy]phenyl]benzamide (45 mg) and acetic anhydride (0.5 ml) was stirred at ambient temperature for 1 hour and then allowed to stand at the same temperature overnight. The reaction mixture was concentrated in vacuo and the residue was dissolved in chloroform. The solution was washed successively with saturated aqueous sodium bicarbonate solution, water and brine and the solution was dried over magnesium sulfate. The solvent was evaporated in vacuo and the residue was purified by preparative thin-layer chromatography (chloroform-methanol=10:1) to give 4-(2-acetamido-1H-benzimidazol-4-yl)carbonylamino-3-methoxy-N-methyl-N-[4-methyl-2-[5-(4-methylpiperazin-1-yl)-carbonylpent-1-yloxy]phenyl]benzamide (26 mg) to give a powder.

NMR (CDCl$_3$, δ): 1.36–1.52 (2H, br peak), 1.58–1.82 (4H, m), 2.26 (3H, s), 2.28–2.42 (15H, m), 3.32 (3H, s), 3.43–3.51 (2H, m), 3.51–3.66 (5H, m), 3.75 (1H, br peak), 3.91 (1H, br peak), 6.55–6.65 (2H, m), 6.84–6.95 (2H, m), 6.99 (1H, s), 7.20–7.31 (1H, m), 7.54 (1H, br peak), 8.07 (1H, br peak), 8.34 (1H, d, J=8 Hz)

EXAMPLE 34

To a solution of 4-(2-amino-1H-benzimidazol-4-yl)carbonylamino-3-methoxy-N-methyl-N-[4-methyl-2-[5-(4-methylpiperazin-1-yl)carbonylpent-1-yloxy]phenyl]benzamide (90 mg) in pyridine (1 ml) was added methanesulfonyl chloride (18 mg) in ice water bath under nitrogen and the mixture was stirred at the same temperature for 3 hours. The reaction mixture was concentrated in vacuo and the residue was dissolved in chloroform. The organic layer was washed successively with saturated aqueous sodium bicarbonate solution, water and brine and the solution was dried over magnesium sulfate. The solvent was evaporated in vacuo and the residue was purified by preparative thin-layer chromatography (chloroform-methanol=10:1) to give 4-(2-methanesulfonylamino-1H-benzimidazol-4-yl)carbonylamino-3-methoxy-N-methyl-N-[4-methyl-2-[5-(4-methylpiperazin-1-yl)carbonylpent-1-yloxy]phenyl]benzamide (15 mg) as a powder.

NMR (CDCl$_3$, δ): 1.42–1.58 (2H, m), 1.62–1.95 (4H, m), 2.26 (3H, s), 2.29–2.45 (9H, m), 3.24 (3H, s), 3.34 (3H, s), 3.44–3.52 (2H, m), 3.59–3.67 (2H, m), 3.76–3.89 (4H, m), 3.89–4.00 (1H, m), 6.98 (1H, br s), 6.54–6.65 (2H, m), 6.88 (1H, d, J=8 Hz), 6.94 (1H, d, J=8 Hz), 7.04 (1H, s), 7.23 (1H, t, J=8 Hz), 7.74 (1H, d, J=8 Hz), 8.11 (1H, d, J=8 Hz), 8.40 (1H, d, J=8 Hz)

EXAMPLE 35

The following compound was obtained according to a similar manner to that of Example 34.

4-(2-Benzenesulfonylamino-1H-benzimidazol-4-yl)carbonylamino-3-methoxy-N-methyl-N-[4-methyl-2-[5-(4-methylpiperazin-1-yl)carbonylpent-1-yloxy]phenyl]benzamide NMR (CDCl$_3$, δ): 1.43–1.73 (4H, m), 1.73–1.84 (2H, m), 2.25 (3H, s), 2.30 (3H, s), 2.31–2.42 (6H, m), 3.33 (3H, s), 3.44–3.51 (2H, m), 3.59–3.66 (2H, m), 3.75–3.87 (4H, m), 3.87–4.00 (1H, m), 6.04 (2H, s), 6.54–6.63 (2H, m), 6.86 (1H, d, J=8 Hz), 6.93 (1H, d, J=8 Hz), 7.20 (1H, t, J=8 Hz), 7.48–7.56 (2H, m), 7.65 (1H, t, J=8 Hz), 7.85 (1H, d, J=8 Hz), 7.97 (2H, d, J=8 Hz), 8.08 (1H, d, J=8 Hz), 8.37 (1H, d, J=8 Hz), 11.39 (1H, s)

EXAMPLE 36

To a solution of 4-[(indol-4-yl)carbonyl]amino-3-methoxy-N-methyl-N-[4-methyl-2-[5-(4-methylpiperazin-1-yl)carbonylpent-1-yloxy]phenyl]benzamide (93 mg) in dichloromethane (6.0 ml) was added N,N-dimethylmethylene-ammonium chloride (41.7 mg) at 0° C. and the mixture was stirred at ambient temperature for 1 hour. The resulting mixture was diluted with water and the aqueous solution was extracted with dichloromethane. Drying, filtering and removal of solvents afforded 4-[(3-dimethylaminomethylindol-4-yl)carbonyl]amino-3-methoxy-N-methyl-N-[4-methyl-2-[5-(4-methylpiperazin-1-yl)carbonylpent-1-yloxy]phenyl]benzamide (90 mg) as a colorless syrup.

NMR (CDCl$_3$, δ): 1.50–1.95 (6H, m), 2.28 (3H, s), 2.29 (6H, s), 2.30 (3H, s), 2.33–2.42 (6H, m), 3.34 (3H, s), 3.44–3.52 (2H, m), 3.60–3.66 (2H, m), 3.68 (3H, s), 3.84–4.00 (2H, m), 5.30 (2H, s), 6.58 (1H, d J=8 Hz), 6.62 (1H, s), 6.83 (1H, d, J=8 Hz), 6.93 (1H, d, J=8 Hz), 6.97 (1H, s), 7.10–7.26 (2H, m), 7.35–7.57 (3H, m), 8.23–8.31 (1H, m), 8.36–8.40 (1H, br)

EXAMPLE 37

To a mixture of 4-(2-hydroxymethyl-1H-benzimidazol-4-yl)carbonylamino-3-methoxy-N-methyl-N-[4-methyl-2-[5-(4-methylpiperazin-1-yl)carbonylpent-1-yloxy]phenyl]benzamide (40 mg), triethylamine (31 mg), dimethyl sulfoxide (0.5 ml) and dichloromethane (0.5 ml) was added portionwise sulfur trioxide pyridine complex (29 mg) in water bath and the mixture was stirred at the same temperature for 1 day. The reaction mixture was poured into saturated aqueous sodium bicarbonate solution and the solution was extracted with chloroform. The organic layer was washed with water and brine and the solution was dried over magnesium sulfate. The solvent was evaporated in vacuo and the residue was purified by preparative thin-layer chromatography (chloroform-methanol=10:1) to give 4-(2-formyl-1H-benzimidazol-4-yl)carbonylamino-3-methoxy-N-methyl-N-[4-methyl-2-[5-(4-methylpiperazin-1-yl)carbonylpent-1-yloxy]phenyl]benzamide (6 mg) as a powder.

NMR (CDCl$_3$, δ): 1.47–1.64 (2H, m), 1.64–1.90 (4H, m), 2.25 (3H, s), 2.29 (3H, s), 2.34–2.44 (6H, m), 3.23–3.38 (3H, m), 3.46–3.54 (2H, m), 3.60–3.68 (2H, m), 3.73–4.01 (5H, m), 6.54–6.66 (2H, m), 6.83–7.10 (3H, m), 7.47–7.63 (1H, m), 7.63–7.77 (1H, m), 8.07–8.80 (3H, m), 9.96–10.12 (1H, m), 11.85 (1H, br s)

EXAMPLE 38

To a solution of 4-(2-amino-3-nitrobenzoyl)amino-3-methoxy-N-methyl-N-[4-methyl-2-[5-(4-methylpiperazin-1-yl)carbonylpent-1-yloxy]phenyl]benzamide (50 mg) in ethanol (2 ml) was added 1N hydrochloric acid (0.16 ml) at ambient temperature and allowed to stand at the same temperature for 30 minutes. After being removed the solvent under reduced pressure, the resulting solid was dissolved in distilled water (5 ml) and the solution was filtered through micro filter. The filtrate was lyophilized to give 4-[(2-amino-3-nitro)benzoyl]amino-3-methoxy-N-methyl-N-[4-methyl-2-[5-(4-methylpiperazin-1-yl)carbonylpent-1-yloxy]phenyl]benzamide dihydrochloride (48 mg) as a white powder.

NMR (DMSO-d$_6$, δ): 1.37–1.51 (2H, m) 1.51–1.65 (2H, m), 1.65–1.84 (2H, m), 2.22 (3H, s), 2.33–2.45 (2H, m), 2.77 (3H, s), 2.81–3.46 (9H, m), 3.61 (3H, s), 3.80–3.91 (1H, m), 3.91–4.00 (1H, m), 4.00–4.16 (1H, m), 4.23–4.51 (1H, m), 6.65 (1H, d, J=8 Hz), 6.73 (1H, t, J=8 Hz), 6.82 (1H, s-like), 6.86–6.96 (2H m), 7.05 (1H, d, J=8 Hz), 7.52 (1H, d, J=8 Hz), 7.96 (1H, d, J=8 Hz), 7.99–8.08 (2H, m), 8.21 (1H, d, J=8 Hz), 9.63 (1H, s)

EXAMPLE 39

The following compounds were obtained according to a similar manner to that of Example 38.

1) 4-[(Indol-4-yl)carbonyl]amino-3-methoxy-N-methyl-N-[4-methyl-2-[5-(4-methylpiperazin-1-yl)carbonylpent-1-yloxy]-phenyl]benzamide hydrochloride NMR (DMSO-d$_6$, δ): 1.42–1.63 (4H, m), 1.71–1.80 (2H, m), 2.25 (3H, s), 2.37–2.42 (2H, m), 2.73 (3H, s), 2.89–3.03 (3H, m), 3.20 (3H, s), 3.31–3.48 (3H, m), 3.70 (3H, s), 3.85–4.10 (3H, m), 4.39–4.49 (1H, m), 6.67 (1H, d, J=9 Hz), 6.82 (2H, s), 6.90–6.98 (2H, m), 7.04 (1H, d, J=9 Hz), 7.19 (1H, t, J=8 Hz), 7.51–7.58 (2H, m), 7.62 (1H, d, J=8 Hz), 8.00 (1H, d, J=8 Hz), 9.05 (1H, s)

2) 4-[(1-Methylindol-4-yl)carbonyl]amino-3-methoxy-N-methyl-N-[4-methyl-2-[5-(4-methylpiperazin-1-yl)carbonylpent-1-yloxy]phenyl]benzamide hydrochloride NMR (DMSO-d$_6$, δ): 1.42–1.63 (4H, m), 1.71–1.80 (2H, m), 2.25 (3H, s), 2.40 (2H, t, J=8 Hz), 2.73 (3H, s), 2.90–3.05 (3H, m), 3.19 (3H, s), 3.30–3.45 (3H, m), 3.70 (3H, s), 3.87 (3H, s), 3.88–4.00 (3H, m), 4.39–4.47 (1H, m), 6.67 (1H, d, J=8 Hz), 6.80 (1H, d, J=3 Hz), 6.83 (1H, s), 6.91–6.97 (2H, m), 7.06 (1H, d, J=8 Hz), 7.27 (1H, t, J=8 Hz), 7.51 (1H, d, J=3 Hz), 7.58 (1H, d, J=8 Hz), 7.69 (1H, d, J=8 Hz), 7.98 (1H, d, J=8 Hz), 9.07 (1H, s)

3) 4-[(1-Ethoxycarbonylindol-4-yl)carbonyl]amino-3-methoxy-N-methyl-N-[4-methyl-2-[5-(4-methylpiperazin-1-yl)carbonylpent-1-yloxy]phenyl]benzamide hydrochloride NMR (DMSO-d$_6$, δ): 1.41 (3H, t, J=8 Hz), 1.42–1.63 (4H, m), 1.71–1.81 (2H, m), 2.23 (3H, s), 2.39 (2H, t, J=8 Hz), 2.74 (3H, s), 2.86–3.04 (3H, m), 3.19 (3H, s), 3.30–3.48

(3H, m), 3.67 (3H, s), 3.83–4.00 (4H, m), 4.48 (2H, q, J=8 Hz), 6.66 (1H, d, J=8 Hz), 6.82 (1H, s), 6.90–6.96 (2H, m), 7.05 (1H, d, J=8 Hz), 7.10 (1H, d, J=4 Hz), 7.47 (1H, t, J=8 Hz), 7.72–7.81 (2H, m), 7.83 (1H, d, J=4 Hz), 8.31 (1H, d, J=8 Hz), 9.33 (1H, s)

4) 4-[(1-Isopropylindol-4-yl)carbonyl]amino-3-methoxy-N-methyl-N-[4-methyl-2-[5-(4-methylpiperazin-1-yl)carbonylpent-1-yloxy]phenyl]benzamide hydrochloride NMR (DMSO-$d_6$, δ): 1.41–1.67 (4H, m), 1.48 (6H, d, J=7 Hz), 1.71–1.81 (2H, m), 2.23 (3H, s), 2.39 (2H, t, J=8 Hz), 2.73 (3H, s), 2.90–3.05 (3H, m), 3.19 (3H, s), 3.29–3.45 (3H, m), 3.69 (3H, s), 3.84–4.00 (4H, m), 4.80–4.90 (1H, m), 6.67 (1H, d, J=8 Hz), 6.80–6.87 (2H, m), 6.90–6.97 (2H, m), 7.05 (1H, d, J=8 Hz), 7.25 (1H, t, J=8 Hz), 7.55 (1H, d, J=8 Hz), 7.69 (1H, d, J=3 Hz), 7.77 (1H, d, J=8 Hz), 7.98 (1H, d, J=8 Hz), 9.06 (1H, s)

5) 4-[(3-Dimethylaminomethylindol-4-yl)carbonyl]amino-3-methoxy-N-methyl-N-[4-methyl-2-[5-(4-methylpiperazin-1-yl)carbonylpent-1-yloxy]phenyl]benzamide dihydrochloride NMR (DMSO-$d_6$, δ): 1.42–1.64 (4H, m), 1.71–1.82 (2H, m), 2.24 (3H, s), 2.40 (2H, t, J=8 Hz), 2.70 (3H, s), 2.72 (6H, s), 2.82–3.08 (4H, m), 3.20 (3H, s), 3.38–3.54 (3H, m), 3.68 (3H, s), 3.84–4.11 (3H, m), 5.63–5.72 (2H, br s), 6.66 (1H, d, J=8 Hz), 6.83 (1H, s), 6.90–6.98 (2H, m), 7.04 (1H, d, J=8 Hz), 7.27 (1H, t, J=8 Hz), 7.38–7.52 (2H, m), 7.60–7.78 (2H, m), 8.02–8.18 (2H, m)

6) 4-[(Indol-7-yl)carbonyl]amino-3-methoxy-N-methyl-N-[4-methyl-2-[5-(4-methylpiperazin-1-yl)carbonylpent-1-yloxy]phenyl]benzamide hydrochloride NMR (DMSO-$d_6$, δ): 1.41–1.62 (4H, m), 1.70–1.81 (2H, m), 2.23 (3H, s), 2.39 (2H, t, J=8 Hz), 2.74 (3H, s), 2.88–3.02 (3H, m), 3.20 (3H, s), 3.30–3.42 (3H, m), 3.66 (3H, s), 3.85–4.03 (3H, m), 4.38–4.47 (1H, m), 6.51 (1H, d, J=3 Hz), 6.67 (1H, d, J=8 Hz), 6.83 (1H, s), 6.89–6.98 (2H, m), 7.06 (1H, d, J=8 Hz), 7.10 (1H, d, J=8 Hz), 7.37 (1H, d, J=3 Hz), 7.71–7.80 (3H, m), 9.35 (1H, s)

7) 4-[(1-Methylindol-7-yl)carbonyl]amino-3-methoxy-N-methyl-N-[4-methyl-2-[5-(4-methylpiperazin-1-yl)carbonylpent-1-yloxy]phenyl]benzamide hydrochloride NMR (DMSO-$d_6$, δ): 1.40–1.80 (6H, m), 2.22 (3H, s), 2.39 (2H, t, J=8 Hz), 2.72 (3H, s), 2.91–3.02 (3H, m), 3.18 (3H, s), 3.31–3.48 (3H, m), 3.63 (3H, s), 3.73 (3H, s), 3.87–4.12 (3H, m), 4.39–4.48 (1H, m), 6.51 (1H, d, J=3 Hz), 6.67 (1H, d, J=8 Hz), 6.83 (1H, s), 6.89–7.09 (3H, m), 7.20–7.29 (2H, m), 7.37 (1H, d, J=3 Hz), 7.68 (1H, d, J=8 Hz), 7.80 (1H, d, J=8 Hz), 9.53 (1H, s)

8) 4-[(2-Ethoxycarbonylindol-4-yl)carbonyl]amino-3-methoxy-N-methyl-N-[4-methyl-2-[5-(4-methylpiperazin-1-yl)carbonylpent-1-yloxy]phenyl]benzamide hydrochloride NMR (DMSO-$d_6$, δ): 1.37 (3H, t, J=8 Hz), 1.43–1.63 (4H, m), 1.72–1.80 (2H, m), 2.24 (3H, s), 2.40 (2H, t, J=8 Hz), 2.73 (3H, s), 2.88–3.03 (3H, m), 3.20 (3H, s), 3.28–3.45 ((4H, m), 3.70 (3H, s), 3.87–4.00 (3H, m), 4.37 (2H, q, J=8 Hz), 6.67 (1H, d, J=8 Hz), 6.83 (1H, s), 6.90–6.97 (2H, m), 7.07 (1H, d, J=8 Hz), 7.38 (1H, t, J=8 Hz), 7.56 (1H, s), 7.61–7.69 (2H, m), 7.86 (1H, d, J=8 Hz), 9.27 (1H, s)

9) 4-[(2-Dimethylaminocarbonylindo-4-yl)carbonyl]amino-3-methoxy-N-methyl-N-[4-methyl-2-[5-(4-methylpiperazin-1-yl)-carbonylpent-1-yloxy]phenyl]benzamide hydrochloride NMR (DMSO-$d_6$, δ): 1.42–1.63 (4H, m), 1.72–1.81 (2H, m), 2.25 (3H, s), 2.40 (2H, t, J=8 Hz), 2.74 (3H, s), 2.97–3.13 (3H, m), 3.19 (3H, s), 3.30–3.49 (10H, m), 3.68 (3H, s), 3.88–4.08 (3H, m), 6.67 (1H, d, J=8 Hz), 6.83 (1H, s), 6.90–6.97 (2H, m), 7.05 (1H, d, J=8 Hz), 7.21 (1H, s), 7.30 (1H, t, J=8 Hz), 7.59 (1H, d, J=8 Hz), 7.65 (1H, d, J=8 Hz), 7.90 (1H, d, J=8 Hz), 9.20 (1H, s)

10) 4-[1H-Imidazo[4,5-b]pyridin-7-yl]carbonylamino-3-methoxy-N-methyl-N-[4-methyl-2-[5-(4-methylpiperazin-1-yl)carbonylpent-1-yloxy]phenyl]benzamide trihydrochloride NMR (DMSO-$d_6$, δ): 1.39–1.67 (4H, m), 1.69–1.83 (2H, m), 2.22 (3H, s), 2.39 (2H, t, J=7 Hz), 2.72 and 2.74 (Total 3H, s), 2.80–3.11 (3H, m), 3.20 (3H, s), 3.31–3.57 (3H, m), 3.76 (3H, s), 3.80–4.77 (4H, m), 6.66 (1H, d, J=8 Hz), 6.82 (1H, s), 6.89–7.01 (2H, m), 7.05 (1H, d, J=8 Hz), 7.82 (1H, d, J=7 Hz), 8.28 (1H, d, J=8 Hz), 8.57 (1H, d, J=7 Hz), 8.79 (1H, s)

11) 4-[2-Chloro-1H-benzimidazol-4-yl]carbonylamino-3-methoxy-N-methyl-N-[4-methyl-2-[5-(4-methylpiperazin-1-yl)carbonylpent-1-yloxy]phenyl]benzamide dihydrochloride NMR (DMSO-$d_6$, δ): 1.37–1.66 (4H, m), 1.67–1.83 (2H, m), 2.21 (3H, s), 2.39 (2H, t, J=7 Hz), 2.73 (3H, s), 2.80–3.09 (3H, m), 3.19 (3H, s), 3.29–3.60 (3H, m), 3.71–4.17 (6H, m), 4.43 (1H, m), 6.64 (1H, d, J=8 Hz), 6.81 (1H, s), 6.87–6.99 (2H, m), 7.03 (1H, d, J=8 Hz), 7.41 (1H, dd, J=8, 8 Hz), 7.72 (1H, d, J=8 Hz), 7.96 (1H, d, J=8 Hz), 8.33 (1H, d, J=8 Hz)

12) 4-(2,3-Diaminobenzoyl)amino-3-methoxy-N-methyl-N-[4-methyl-2-[5-(4-methylpiperazin-1-yl)carbonylpent-1-yloxy]phenyl]benzamide trihydrochloride NMR (DMSO-$d_6$, δ): 1.38–1.52 (2H, m), 1.52–1.66 (2H, m), 1.66–1.83 (2H, m), 2.23 (3H, s), 2.40 (2H, t, J=7 Hz), 2.75 (3H, s), 2.81–3.11 (3H, m), 3.18 (3H, s), 3.28–3.50 (3H, m), 3.63 (3H, s), 3.82–3.92 (1H, m), 3.92–4.03 (1H, m), 4.45 (1H, br peak), 6.60–6.77 (2H, m), 6.83 (1H, s-like), 6.87–6.98 (2H, m), 7.05 (1H, d, J=8 Hz), 7.23 (1H, d, J=8 Hz), 7.50 (1H, d, J=8 Hz), 7.60 (1H, d, J=8 Hz), 9.31 (1H, s)

13) 4-[2-Guanidinobenzimidazol-4-yl]carbonylamino-3-methoxy-N-methyl-N-[4-methyl-2-[5-(4-methylpiperazin-1-yl)-carbonylpent-1-yloxy]phenyl]benzamide dihydrochloride NMR (DMSO-$d_6$, δ): 1.31–1.84 (6H, m), 2.22 (3H, s), 2.40 (2H, t, J=7 Hz), 2.74 (3H, s), 2.80–3.11 (3H, m), 3.18 (3H, s), 3.26–3.63 (3H, m), 3.74 (3H, s), 3.80–4.20 (3H, m), 4.33–4.53 (1H, m), 6.64 (1H, d, J=8 Hz), 6.82 (1H, s), 6.92 (1H, d, J=8 Hz), 6.99 (1H, s), 7.04 (1H, d, J=8 Hz), 7.33 (1H, dd, J=8, 8 Hz), 7.69 (1H, d, J=8 Hz), 7.90 (1H, d, J=8 Hz), 8.28–8.41 (1H, m), 8.49–8.80 (3H, m)

14) 4-(1H-Benzimidazol-4-yl)carbonylamino-3-methoxy-N-methyl-N-[4-methyl-2-[5-(4-methylpiperazin-1-yl)carbonylpent-1-yloxy]phenyl]benzamide dihydrochloride NMR (DMSO-$d_6$, δ): 1.40–1.51 (2H, m), 1.51–1.64 (2H, m), 1.69–1.81 (2H, m), 2.22 (3H, s), 2.39 (2H, t, J=7.5 Hz), 2.49 (3H, s), 2.75 (3H, d-like), 2.80–3.07 (3H, m), 3.19 (3H, s), 3.31–3.48 (3H, m), 3.73 (3H, s), 3.77–4.03 (2H, m), 4.03–4.14 (1H, m), 4.38–4.50 (1H, m), 6.65 (1H, d, J=8 Hz), 6.81 (1H, s-like), 6.87–6.98 (2H, m), 7.04 (1H, d, J=8 Hz), 7.43 (1H, t, J=8 Hz), 7.83 (1H, d, J=8 Hz), 7.98 (1H, d, J=8 Hz), 8.24 (1H, br peak), 8.64 (1H, br s), 10.63 (1H, br peak)

15) 4-(2-Hydroxy-1H-benzimidazol-4-yl)carbonylamino-3-methoxy-N-methyl-N-[4-methyl-2-[5-(4-methylpiperazin-1-yl)carbonylpent-1-yloxy]phenyl]benzamide hydrochloride NMR (DMSO-$d_6$, δ): 1.39–1.52 (2H, m), 1.52–1.65 (2H, m), 1.69–1.82 (2H, m), 2.22 (3H, s), 2.39 (2H, t, J=7.5 Hz), 2.76 (3H, d-like), 2.80–3.08 (3H, m), 3.19 (3H, s), 3.27–3.45 (3H, m), 3.64 (3H, s), 3.81–3.91 (1H, m), 3.91–4.01 (1H, m), 4.01–4.14 (1H, m), 4.38–4.50 (1H, m), 6.65 (1H, d, J=8

Hz), 6.83 (1H, s), 6.86–6.96 (2H, m), 6.96–7.12 (3H, m), 7.46 (1H, d, J=8 Hz), 7.66 (1H, d, J=8 Hz) 9.28 (1H, s)

16) 3-Methoxy-N-methyl-4-(2-methyl-1H-benzimidazol-4-yl)-carbonylamino-N-[4-methyl-2-[5-(4-methylpiperazin-1-yl)carbonylpent-1-yloxy]phenyl]benzamide dihydrochloride NMR (DMSO-d$_6$, δ): 1.39–1.51 (2H, m), 1.52–1.65 (2H, m), 1.65–1.82 (2H, m), 2.23 (3H, s), 2.39 (2H, t, J=7.5 Hz), 2.68 (3H, s), 2.75 (3H, d-like), 2.79–3.09 (3H, m), 3.18 (3H, s), 3.30–3.44 (3H, m), 3.72 (3H, s), 3.80–3.90 (1H, m), 3.90–4.00 (1H, m), 4.00–4.13 (1H, m), 4.48–4.50 (1H, m), 6.65 (1H, d, J=8 Hz), 6.82 Hz), (1H, s-like), 6.87–6.98 (2H, m), 7.04 (1H, d, J=8 Hz), 7.39 (1H, br peak), 7.77 (1H, br peak), 7.95 (1H, br peak), 10.67 (1H, br s)

17) 4-(2-Mercapto-1H-benzimidazol-4-yl)carbonylamino-3-methoxy-N-methyl-N-[4-methyl-2-[5-(4-methylpiperazin-1-yl)carbonylpent-1-yloxy]phenyl]benzamide dihydrochroride NMR (DMSO-d$_6$, δ): 1.39–1.52 (2H, m), 1.52–1.65 (2H, m), 1.70–1.82 (2H, m), 2.23 (3H, s), 2.40 (2H, t, J=7 Hz), 2.76 (3H, s), 3.20 (3H, s), 3.65 (3H, s), 3.80–4.06 (2H, m), 6.65 (1H, d, J=8 Hz), 6.83 (1H, s), 7.05 (1H, d, J=8 Hz), 7.20 (1H, t, J=8 Hz), 7.30 (1H, d, J=8 Hz), 7.60 (1H, d, J=8 Hz), 7.64–7.71 (2H, m), 9.11 (1H, s), 9.50 (1H, s)

18) 3-Methoxy-N-methyl-N-[4-methyl-2-[5-(4-methylpiperazin-1-yl)carbonylpent-1-yloxy]phenyl]-4-(2-trifluoromethyl-1H-benzimidazol-4-yl)carbonylaminobenzamide dihydrochloride NMR (DMSO-d$_6$, δ): 1.39–1.53 (2H, m), 1.53–1.65 (2H, m), 1.65–1.83 (2H, m), 2.22 (3H, s), 2.40 (2H, t, J=7 Hz), 2.78 (3H, s), 2.82–3.07 (3H, m), 3.20 (3H, s), 3.28–3.51 (3H, m), 3.75 (3H, s), 3.30–3.91 (1H, m), 3.91–4.03 (1H, m), 4.10 (1H, br peak), 4.43 (1H, br peak), 6.66 (1H, d, J=8 Hz), 6.82 (1H, s), 6.90–7.00 (2H, m), 7.04 (1H, d, J=8 Hz), 7.61 (1H, t, J=8 Hz), 7.94 (1H, d, J=8 Hz), 8.11 (1H, d, J=8 Hz), 8.41 (1H, d, J=8 Hz), 10.33 (1H, br peak), 11.89 (1H, s)

19) 4-(2-Amino-1H-benzimidazol-4-yl)carbonylamino-3-methoxy-N-methyl-N-[4-methyl-2-[5-(4-methylpiperazin-1-yl)-carbonylpent-1-yloxy]phenyl]benzamide dihydrochloride NMR (DMSO-d$_6$, δ): 1.37–1.53 (2H, m), 1.53–1.65 (2H, m), 1.70–1.84 (2H, m), 2.23 (3H, s), 2.39 (2H, t, J=7.5 Hz), 2.75 (3H, s), 2.80–3.10 (3H, m), 3.20 (3H, s), 3.26–3.55 (3H, m), 3.66 (3H, s), 3.78–3.92 (1H, m), 3.91–4.01 (1H, m), 4.07 (1H, br s), 4.43 (1H, br s), 6.65 (1H, d, J=8 Hz), 6.83 (1H, s), 6.87–6.98 (2H, m), 7.04 (1H, d, J=8 Hz), 7.29 (1H, br peak), 7.55 (1H, br peak), 7.55 (1H, br peak), 7.86 (1H, br peak), 8.20 (1H, br peak), 9.75 (1H, br peak), 10.78 (1H, br peak)

20) 4-(2-Acetamido-1H-benzimidazol-4-yl)carbonylamino-3-methoxy-N-methyl-N-[4-methyl-2-[5-(4-methylpiperazin-1-yl)-carbonylpent-1-yloxy]phenyl]benzamide dihydrochloride NMR (CD$_3$OD, δ): 1.50–1.65 (2H, m), 1.65–1.77 (2H, m), 1.77–1.92 (2H, m), 2.28 (3H, s), 2.35 (3H, s), 2.51 (2H, t-like), 2.93 (3H, s), 2.96–3.59 (6H, m), 3.75 (3H, s), 3.81–3.95 (1H, m), 3.95–4.07 (1H, m), 4.15–4.31 (1H, m), 4.57–4.71 (1H, m), 6.70 (1H, d, J=8 Hz), 6.80 (1H, s-like), 6.94 (1H, s-like), 7.00–7.12 (2H, m), 2H, m), 7.47–7.58 (2H, m), 7.81 (1H, d, J=8 Hz), 7.99 (1H, d, J=8 Hz), 8.06 (1H, d, J=8 Hz)

21) 4-(2-Methanesulfonylamino-1H-benzimidazol-4-yl)-carbonylamino-3-methoxy-N-methyl-N-[4-methyl-2-[5-(4-methylpiperazin-1-yl)carbonylpent-1-yloxy]phenyl]benzamide dihydrochloride NMR (CD$_3$OD, δ): 1.50–1.64 (2H, m), 1.64–1.77 (2H, m), 1.77–1.90 (2H, m), 2.28 (3H, s), 2.50 (2H, t, J=7 Hz), 2.92 (3H, s), 2.95–3.20 (3H, m), 3.39–3.60 (5H, m), 3.76 (3H, s), 3.83–3.94 (1H, m), 3.94–4.07 (1H, m), 4.17–4.32 (1H, m), 4.60–4.72 (1H, m), 6.70 (1H, d, J=8 Hz), 6.79 (1H, s), 6.92 (1H, s), 6.99–7.10 (2H, m), 7.30 (1H, t, J=8 Hz), 7.88 (1H, d, J=8 Hz), 7.95 (1H, d, J=8 Hz), 8.18 (1H, d, J=8 Hz)

22) 4-(2-Benzenesulfonylamino-1H-benzimidazol-4-yl)-carbonylamino-3-methoxy-N-methyl-N-[4-methyl-2-[5-(4-methylpiperazin-1-yl)carbonylpent-1-yloxy]phenyl]benzamide dihydrochloride NMR (DMSO-d$_6$, δ): 1.35–1.50 (2H, m), 1.50–1.65 (2H, m), 1.65–1.80 (2H, m), 2.21 (3H, s), 2.38 (2H, t, J=7.5 Hz), 2.75 (3H, d, J=5 Hz), 2.80–3.10 (3H, m), 3.17 (3H, s), 3.25–3.48 (3H, m), 3.73 (3H, s), 3.78–3.90 (1H, m), 3.90–4.00 (1H, m), 4.07 (1H, br d, J=15 Hz), 4.44 (1H, br d, J=15 Hz), 6.54 (1H, d, J=8 Hz), 6.78–6.98 (3H, m), 7.04 (1H, d, J=8 Hz), 7.19 (1H, t, J=8 Hz), 7.53–7.73 (3H, m), 7.73–7.94 (3H, m), 8.12 (2H, d, J=8 Hz), 8.25 (1H, d, J=8 Hz)

23) 4-(1H-Benzotriazol-4-yl)carbonylamino-3-methoxy-N-methyl-N-[4-methyl-2-[5-(4-methylpiperazin-1-yl)carbonylpent-1-yloxy]phenyl]benzamide hydrochloride NMR (DMSO-d$_6$, δ): 1.39–1.52 (2H, m), 1.52–1.66 (2H, m), 1.70–1.83 (2H, m), 2.22 (3H, s), 2.39 (2H, t, J=8 Hz), 2.77 (3H, s), 2.83–3.10 (3H, m), 3.20 (3H, s), 3.25–3.53 (3H, m), 3.77 (3H, s), 3.82–3.93 (1H, m), 3.93–4.03 (1H, m), 4.08 (1H, br peak), 4.45 (1H, br peak), 6.66 (1H, d, J=8 Hz), 6.82 (1H, s), 6.92–7.01 (2H, m), 7.06 (1H, d, J=8 Hz), 7.72 (1H, br peak), 8.06–8.19 (2H, m), 8.36 (1H, br peak), 10.37 (1H, br peak), 11.56 (1H, br peak)

24) 4-(2-Ethyl-1H-benzimidazol-4-yl)carbonylamino-3-methoxy-N-methyl-N-[4-methyl-2-[5-(4-methylpiperazin-1-yl)-carbonylpent-1-yloxy]phenyl]benzamide dihydrochloride NMR (DMSO-d$_6$, δ): 1.37–1.52 (5H, m), 1.52–1.65 (2H, m), 1.68–1.83 (2H, m), 2.23 (3H, s), 2.40 (2H, t, J=7.5 Hz), 2.75 (3H, d, J=5 Hz), 2.82–3.08 (5H, m), 3.18 (3H, s), 3.30–3.60 (3H, m), 3.73 (3H, s), 3.81–3.91 (1H, m), 3.91–4.02 (1H, m), 4.10 (1H, br d, J=15 Hz), 4.45 (1H, br d, J=15 Hz), 6.65 (1H, d, J=8 Hz), 6.81 (1H, s), 6.89–6.99 (2H, m), 7.04 (1H, d, J=8 Hz), 7.30–7.41 (1H, m), 7.73 (1H, d, J=8 Hz), 7.92 (1H, d, J=8 Hz), 8.33 (1H, br peak), 10.49 (1H, br s)

25) 3-Methoxy-N-methyl-N-[4-methyl-2-[5-(4-methylpiperazin-1-yl)carbonylpent-1-yloxy]phenyl]-4-(2-n-propyl-1H-benzimidazol-4-yl)carbonylaminobenzamide dihydrochloride NMR (DMSO-d$_6$, δ): 0.99 (3H, t, J=7.5 Hz), 1.38–1.52 (2H, m), 1.52–1.67 (2H, m), 1.67–1.83 (2H, m), 1.83–1.98 (2H, m), 2.23 (3H, s), 2.40 (2H, t, J=7.5 Hz), 2.76 (3H, d, J=4 Hz), 2.82–3.08 (5H, m), 3.20 (3H, s), 3.33–3.66 (3H, m), 3.73 (3H, s), 3.81–3.93 (1H, m), 3.93–4.03 (1H, m), 4.10 (1H, br d, J=15 Hz), 4.44 (1H, br d, J=15 Hz), 6.65 (1H, d, J=8 Hz), 6.82 (1H, s), 6.89–5.98 (2H, m), 7.04 (1H, d, J=8 Hz), 7.31–7.43 (1H, m), 7.75 (1H, br d, J=8 Hz), 7.94 (1H, br d, J=8 Hz), 8.26 (1H, br peak)

26) 4-(2-Isopropyl-1H-benzimidazol-4-yl)carbonylamino-3-methoxy-N-methyl-N-[4-methyl-2-[5-(4-methylpiperazin-1-yl)carbonylpent-1-yloxy]phenyl]benzamide dihydrochloride NMR (DMSO-d$_6$, δ): 1.37–1.51 (8H, m), 1.51–1.65 (2H, m), 1.65–1.84 (2H, m), 2.23 (3H, s), 2.40 (2H, t, J=7.5 Hz), 2.76 (3H, d, J=4 Hz), 2.83–3.09 (3H, m), 3.19 (3H, s), 3.23–3.43 (4H, m), 3.73 (3H, s), 3.81–3.92 (1H, m), 3.92–4.03 (1H, m), 4.09 (1H, br d, J=15 Hz), 4.45 (1H, br d, J=15 Hz), 6.65 (1H, d, J=8 Hz), 6.81 (1H, s), 6.90–6.97 (2H, m), 7.04 (1H, d, J=8 Hz), 7.34 (1H, t, J=8 Hz), 7.71 (1H, d, J=8 Hz), 7.90 (1H, d, J=8 Hz), 8.38 (1H, br peak)

27) 4-(2-Aminomethyl-1H-benzimidazol-4-yl)carbonylamino-3-methoxy-N-methyl-N-[4-methyl-2-[5-(4-methylpiperazin-1-yl)carbonylpent-1-yloxy]phenyl]benzamide trihydrochloride NMR (DMSO-$d_6$, δ): 1.39–1.53 (2H, m), 1.53–1.66 (2H, m), 1.66–1.83 (2H, m), 2.23 (3H, s), 2.40 (2H, t, J=7 Hz), 2.76 (3H, d-like), 2.82–3.10 (3H, m), 3.19 (3H, s), 3.75 (3H, s), 3.88 (1H, br peak), 3.98 (1H, br peak), 4.04–4.15 (1H, m), 4.38–4.50 (3H, m), 6.65 (1H, d, J=8 Hz), 6.83 (1H, s), 6.95 (2H, br peak), 7.05 (1H, d, J=8 Hz), 7.43 (1H, t, J=8 Hz), 7.85 (1H, d, J=8 Hz), 7.98 (1H, d, J=8 Hz), 8.33 (1H, br peak), 8.75 (2H, br peak)

28) 4-[2-(2-Aminoethyl)-1H-benzimidazol-4-yl]carbonylamino-3-methoxy-N-methyl-N-[4-methyl-2-[5-(4-methylpiperazin-1-yl)carbonylpent-1-yloxy]phenyl]benzamide trihydrochloride NMR (DMSO-$d_6$, δ): 1.38–1.51 (2H, m), 1.51–1.65 (1H, m), 1.65–1.83 (2H, m), 2.22 (3H, s), 2.40 (2H, t, J=7.5 Hz), 2.74 (3H, d, J=4 Hz), 2.80–3.11 (3H, m), 3.30–3.50 (5H, m), 3.92–4.02 (3H, m), 4.10 (1H, br d, J=15 Hz), 4.44 (1H, br d, J=15 Hz), 6.66 (1H, d, J=8 Hz), 6.83 (1H, s), 6.90–7.00 (2H, m), 7.05 (1H, d, J=8 Hz), 7.36 (1H, t, J=8 Hz), 7.75 (1H, d, J=8 Hz), 7.93 (1H, d, J=8 Hz), 8.16–8.31 (3H, m), 8.31–8.42 (1H, m)

29) 3-Methoxy-N-methyl-4-(3-methyl-3H-benzimidazol-4-yl)carbonylamino-N-[4-methyl-2-[5-(4-methylpiperazin-1-yl)-carbonylpent-1-yloxy]phenyl]benzamide dihydrochloride NMR (CD$_3$OD, δ): 1.49–1.66 (2H, m), 1.66–1.79 (2H, m), 1.79–1.94 (2H, m), 2.27 (3H, s), 2.51 (2H, t, J=7.5 Hz), 2.91 (3H, s), 2.95–3.35 (3H, m), 3.35–3.61 (3H, m), 3.71 (3H, s), 3.81–4.07 (2H, m), 4.10 (3H, s), 4.23 (1H, br peak), 4.65 (1H, br peak), 6.69 (1H, d, J=8 Hz), 6.79 (1H, s-like), 6.97 (1H, s), 7.01–7.09 (2H, m), 7.70 (1H, t, J=8 Hz), 7.82 (1H, d, J=8 Hz), 7.95–8.08 (2H, m), 9.34 (1H, s)

30) 3-Methoxy-4-(2-meethoxymethyl-1H-benzimidazol-4-yl)-carbonylamino-N-methyl-N-[4-methyl-2-[5-(4-methylpiperazin-1-yl)carbonylpent-1-yloxy]phenyl]benzamide dihydrochloride NMR (DMSO-$d_6$, δ): 1.38–1.52 (2H, m), 1.52–1.65 (2H, m), 1.65–1.82 (2H, m), 2.22 (3H, s), 2.39 (2H, t, J=7 Hz), 2.75 (3H, d-like), 2.80–3.09 (3H, m), 3.20 (3H, s), 3.32–3.53 (6H, m), 3.77 (3H, s), 3.81–3.91 (1H, m), 3.91–4.00 (1H, m), 4.04–4.14 (1H, m), 4.40–4.50 (1H, m), 4.80 (2H, s), 6.65 (1H, d, J=8 Hz), 6.80 (1H, s-like), 6.89–6.98 (2H, m), 7.04 (1H, d, J=8 Hz), 7.37 (1H, t, J=8 Hz), 7.74 (1H, d, J=8 Hz), 7.94 (1H, d, J=8 Hz), 8.37 (1H, d, J=8 Hz), 10.55 (1H, br s)

31) 4-(1,2-Dimethyl-1H-benzimidazol-4-yl)carbonylamino-3-methoxy-N-methyl-N-[4-methyl-2-[5-(4-methylpiperazin-1-yl)carbonylpent-1-yloxy]phenyl]benzamide dihydrochloride NMR (DMSO-$d_6$, δ): 1.38–1.53 (2H, m), 1.53–1.65 (2H, m), 1.65–1.82 (2H, m), 2.23 (3H, s), 2.40 (2H, t, J=7 Hz), 2.70 (3H, s), 2.75 (3H, d-like), 2.80–3.08 (3H, m), 3.19 (3H, s), 3.31–3.50 (3H, m), 3.85 (3H, s), 3.92–4.01 (1H, m), 4.08 (1H, br d, J=12 Hz), 4.44 (1H, br d, J=12 Hz), 6.66 (1H, d, J=8 Hz), 6.82 (1H, s), 6.90–7.00 (2H, m), 7.05 (1H, d, J=8 Hz), 7.37–7.50 (1H, m), 7.83–7.92 (1H, m), 7.96 (1H, d, J=8 Hz), 10.78 (1H, br peak)

32) 4-(1-Ethyl-2-methyl-1H-benzimidazol-4-yl)carbonylamino-3-methoxy-N-methyl-N-[4-methyl-2-[5-(4-methylpiperazin-1-yl)carbonylpent-1-yloxy]phenyl]benzamide dihydrochloride NMR (DMSO-$d_6$, δ): 1.34 (3H, t, J=7 Hz), 1.40–1.53 (2H, m), 1.53–1.66 (2H, m), 1.66–1.83 (2H, m), 2.23 (3H, s), 2.40 (2H, t, J=7 Hz), 2.72 (3H, s), 2.75 (3H, d-like), 2.81–3.09 (2H, m), 3.20 (3H, s), 3.30–3.52 (4H, m), 3.75 (3H, s), 4.09 (1H, br d, J=12 Hz), 4.35 (2H, q, J=7 Hz), 4.44 (1H, br d, J=12 Hz), 6.65 (1H, d, J=8 Hz), 6.82 (1H, s), 6.90–6.99 (2H, m), 7.04 (1H, d, J=8 Hz), 7.42 (1H, t, J=8 Hz), 7.90 (1H, d, J=8 Hz), 7.96 (1H, d, J=8 Hz), 8.25 (1H, br peak)

33) 3-Methoxy-N-methyl-N-[4-methyl-2-[5-(4-methylpiperazin-1-yl)carbonylpent-1-yloxy]phenyl]-4-(2-methyl-1-propyl-1H-benzimidazol-4-yl)carbonylaminobenzamide dihydrochloride NMR (DMSO-$d_6$, δ): 0.90 (3H, t, J=7 Hz), 1.40–1.52 (2H, m), 1.52–1.65 (2H, m), 1.68–1.86 (4H, m), 2.23 (3H, s), 2.39 (2H, t, J=7 Hz), 2.70 (3H, s), 2.75 (3H, d, J=5 Hz), 2.80–3.07 (3H, m), 3.18 (3H, m), 3.33–3.44 (3H, m), 3.76 (3H, s), 3.86 (1H, br peak), 3.95 (1H, br peak), 4.09 (1H, br d, J=12 Hz), 4.27 (1H, t, J=8 Hz), 4.44 (1H, br d, J=12 Hz), 6.65 (1H, d, J=8 Hz), 6.81 (1H, s), 6.88–6.98 (2H, m), 7.05 (1H, d, J=8 Hz), 7.39 (1H, t, J=8 Hz), 7.87 (1H, d, J=8 Hz), 7.94 (1H, d, J=8 Hz), 8.30 (1H, br peak)

34) 3-Methoxy-N-methyl-4-[2-(N-methylcarbamoyl)-1H-benzimidazol-4-yl]carbonylamino-N-[4-methyl-2-[5-(4-methylpiperazin-1-yl)carbonylpent-1-yloxy]phenyl]benzamide dihydrochloride NMR (DMSO-$d_6$, δ): 1.40–1.53 (2H, m), 1.53–1.65 (2H, m), 1.70–1.83 (2H, m), 2.21 (3H, s), 2.40 (2H, t, J=7 Hz), 2.75 (3H, d, J=5 Hz), 2.80–3.10 (6H, m), 3.20 (3H, s), 3.33–3.50 (3H, m), 3.76 (3H, s), 3.90 (1H, br peak), 3.97 (1H, br peak), 4.09 (1H, br d, J=12 Hz), 4.44 (1H, br d, J=12 Hz), 6.65 (1H, d, J=8 Hz), 6.83 (1H, s), 6.91–6.99 (2H, m), 7.05 (1H, d, J=8 Hz), 7.50 (1H, t, J=8 Hz), 7.79 (1H, d, J=8 Hz), 8.02 (1H, d, J=8 Hz), 8.31 (1H, d, J=8 Hz), 8.41 (1H, q-like)

35) 4-(2-Hydroxymethyl-1H-benzimidazol-4-yl)carbonylamino-3-methoxy-N-methyl-N-[4-methyl-2-[5-(4-methylpiperazin-1-yl)carbonylpent-1-yloxy]phenyl]benzamide dihydrochloride NMR (DMSO-$d_6$, δ): 1.38–1.52 (2H, m), 1.52–1.67 (2H, m), 1.67–1.83 (2H, m), 2.23 (3H, s), 2.40 (2H, t, J=7.5 Hz), 2.78 (3H, d, J=4 Hz), 2.82–3.10 (3H, m), 3.20 (3H, s), 3.75 (3H, s), 3.80–3.91 (1H, m), 3.91–4.01 (1H, m), 4.01–4.17 (1H, m), 4.36–4.52 (1H, m), 4.86 (2H, s), 6.64 (1H, d, J=8 Hz), 6.81 (1H, s), 6.85–6.98 (2H, m), 7.35 (1H, t, J=8 Hz), 7.72 (1H, d, J=8 Hz), 7.90 (1H, d, J=8 Hz), 8.24–8.37 (1H, m), 10.40 (1h, br peak)

36) 4-(Benzoxazol-4-yl)carbonylamino-3-methoxy-N-methyl-N-[4-methyl-2-[5-(4-methylpiperazin-1-yl)carbonylpent-1-yloxy]phenyl]benzamide hydrochloride NMR (DMSO-$d_6$, δ): 1.39–1.51 (2H, m), 1.51–1.65 (2H, m), 1.65–1.82 (2H, m), 2.24 (3H, s), 2.40 (2H, t, J=7.5 Hz), 2.77 (3H, s), 2.81–3.10 (3H, m), 3.20 (3H, s), 3.30–3.45 (3H, m), 3.77 (3H, s), 3.81–3.91 (1H, m), 3.91–4.04 (1H, m), 4.14–4.24 (1H, m), 4.40–4.52 (1H, m), 6.65 (1H, d, J=8 Hz), 6.81 (1H, s-like), 6.91–6.99 (2H, m), 7.07 (1H, d, J=8 Hz), 7.65 (1H, t, J=8 Hz), 8.06–8.14 (2H, m), 8.32 (1H, d, J=8 Hz), 9.14 (1H, s)

37) 3-Methoxy-N-methyl-4-(2-methylimidazol[1,2-a]pyridin-4-yl)carbonylamino-N-[4-methyl-2-[5-(4-methylpiperazin-1-yl)-carbonylpent-1-yloxy]phenyl]benzamide dihydrochloride NMR(DMSO-$d_6$, δ): 1.37–1.53 (2H, m), 1.53–1.65 (2H, m), 1.68–1.84 (2H, m), 2.23 (3H, s), 2.40 (2H, t, J=7 Hz), 2.46 (3H, s), 2.75 (3H, d-like), 2.80–3.08 (3H, m), 3.20 (3H, s), 3.31–3.53 (3H, m), 3.92–4.01 (1H, m), 4.09 (1H, br d, J=12 Hz), 4.45 (1H, br d, J=12 Hz), 6.66 (1H, d, J=8 Hz), 6.83 (1H, s-like), 6.90–7.00 (2H, m), 7.06 (1H, d, J=8 Hz), 7.24 (1H, br peak), 7.99 (1H, br s), 8.07–8.25 (2H, m), 8.76–8.89 (1H, m), 10.94 (1H, br peak)

38) 3-Methoxy-N-methyl-N-[4-methyl-2-[5-(4-methylpiperazin-1-yl)carbonylpent-1-yloxy]phenyl]-4-[2-(2-pyridylmethyl)-1H-benzimidazol-4-yl]carbonylaminobenzamide trihydrochloride NMR (DMSO-$d_6$, $\delta$): 1.39–1.51 (2H, m), 1.51–1.64 (2H, m), 1.67–1.82 (2H, m), 2.23 (3H, s), 2.40 (2H, t, J=7.5 Hz), 2.75 (3H, d, J=5 Hz), 2.80–3.07 (3H, m), 3.20 (3H, s), 3.33–3.44 (3H, m), 3.64 (3H, s), 3.66–4.00 (overlapped in $H_2O$), 4.02–4.14 (1H, m), 4.39–4.50 (1H, m), 4.67 (2H, s), 6.65 (1H, s, J=8 Hz), 6.81 (1H, s), 6.85–6.96 (2H, m), 7.03 (1H, d, J=8 Hz), 7.38 (1H, t, J=8 Hz), 7.48–7.57 (1H, m), 7.67 (1H, d, J=8 Hz), 7.76 (1H, d, J=8 Hz), 7.93 (1H, d, J=8 Hz), 7.98–8.09 (1H, m), 8.20–8.29 (1H, m), 8.61–8.67 (1H, m)

39) 3-Methoxy-N-methyl-N-[4-methyl-2-[5-(4-methylpiperazin-1-yl)carbonylpent-1-yloxy]phenyl]-4-[2-(3-pyridylmethyl)-1H-benzimidazol-4-yl]carbonylaminobenzamide trihydrochloride NMR (DMSO-$d_6$, $\delta$): 1.39–1.51 (2H, m), 1.51–1.65 (2H, m), 1.65–1.83 (2H, m), 2.23 (3H, s), 2.39 (2H, t, J=7.5 Hz), 2.74 (3H, s), 2.80–3.10 (3H, m), 3.20 (3H, s), 3.29–3.52 (3H, m), 3.66 (3H, s), 3.80–3.92 (1H, m), 3.92–4.02 (1H, m), 4.10 (1H, br peak), 4.43 (1H, br peak), 4.61 (2H, s), 6.67 (1H, d, J=8 Hz), 6.83 (1H, s), 6.89–6.99 (2H, m), 7.04 (1H, d, J=8 Hz), 7.37 (1H, t, J=8 Hz), 7.75 (1H, d, J=8 Hz), 7.86–7.99 (2H, m), 8.24–8.35 (1H, m), 8.44 (1H, d, J=8 Hz), 8.76–8.86 (1H, m), 8.99 (1H, s-like).

40) 3-Methoxy-N-methyl-N-[4-methyl-2-[5-(4-methylpiperazin-1-yl)carbonylpent-1-yloxy]phenyl]-4-[2-(4-pyridylmethyl)-1H-benzimidazol-4-yl]carbonylaminobenzamide trihydrochloride NMR (DMSO-$d_6$, $\delta$): 1.38–1.51 (2H, m), 1.51–1.66 (2H, m), 1.66–1.83 (2H, m), 2.22 (3H, s), 2.39 (2H, t, J=7.5 Hz), 2.74 (3H, s), 2.80–3.09 (3H, m), 3.19 (3H, s), 3.30–3.44 (3H, m), 3.63 (3H, s), 3.65–4.00 (overlapped in $H_2O$), 4.08 (1H, br peak), 4.44 (1H, br peak), 4.72 (2H, s), 6.65 (1H, d, J=8 Hz), 6.82 (1H, s), 6.87–6.95 (2H, m), 7.03 (1H, d, J=8 Hz), 7.39 (1H, t, J=8 Hz), 7.78 (1H, d, J=8 Hz), 7.94 (1H, d, J=8 Hz), 8.05 (2H, d, J=5 Hz), 8.25–8.35 (1H, m), 8.88 (2H, d, J=5 Hz).

41) 3-Methoxy-4-(2-methoxycarbonylamino-1H-benzimidazol-4-yl)carbonylamino-N-methyl-N-[4-methyl-2-[5-(4-methylpiperazin-1-yl)carbonylpent-1-yloxy]phenyl]benzamide dihydrochloride NMR (DMSO-$d_6$, $\delta$): 1.40–1.52 (2H, m), 1.52–1.66 (2H, m), 1.66–1.81 (2H, m), 2.23 (3H, s), 2.38 (2H, t, J=7.5 Hz), 2.75 (3H, d, J=5 Hz), 2.81–3.08 (3H, m), 3.19 (3H, s), 3.32–3.47 (3H, m), 3.74 (3H, s), 3.79–3.91 (4H, m), 3.91–4.02 (4H, m), 4.07 (1H, br d, J=15 Hz), 4.44 (1H, br d, J=15 Hz), 6.67 (1H, d, J=8 Hz), 6.82 (1H, s), 6.88 (1H, s), 6.94 (1H, d, J=8 Hz), 7.05 (1H, d, J=8 Hz), 7.23 (1H, t, J=8 Hz), 7.69 (1H, d, J=8 Hz), 7.83 (1H, d, J=8 Hz), 8.25 (1H, d, J=8 Hz).

Preparation 33

The following compound was obtained by using 2-amino-4-nitro-1H-benzimidazole as a starting compound according to a similar manner to that of Preparation 1.

2-[(Methylsulfonyl)amino]-4-nitro-1H-benzimidazole

NMR (DMSO-$d_6$, $\delta$): 3.61 (3H, s), 7.16 (1H, t, J=8 Hz), 7.75 (2H, br peak), 7.83 (1H, d, J=8 Hz), 7.95 (1H, d, J=8 Hz).

Preparation 34

The following compounds were obtained according to a similar manner to that of Preparation 5.

1) N-(2-Chloroethyl)-2-nitrobenzamide

NMR (CDCl$_3$, $\delta$): 3.72–3.89 (4H, m), 6.27 (1H, br), 7.56 (1H, m), 7.60 (1H, dd, J=8, 8 Hz), 7.70 (1H, dd, J=8, 8 Hz), 8.10 (1H, d, J=8 Hz).

2) N-(3-Chloropropyl)-2-nitrobenzamide

NMR (CDCl$_3$, $\delta$): 2.09–2.20 (2H, m), 3.56–3.73 (4H, m), 6.15 (1H, br s), 7.50 (1H, d, J=8 Hz), 7.59 (1H, dd, J=8, 8 Hz), 7.67 (1H, dd, J=8, 8 Hz), 8.05 (1H, d, J=8 Hz).

3) N-[1-(Hydorxymethyl)cyclopentyl]-2-nitrobenzamide

NMR (CDCl$_3$, $\delta$): 1.61–2.00 (8H, m), 3.62 (1H, t, J=7 Hz), 3.80 (2H, d, J=7 Hz), 6.00 (1H, s), 7.52 (1H, m), 7.59 (1H, m), 7.68 (1H, t, J=8, 8 Hz), 8.07 (1H, d, J=8 Hz).

Preparation 35

The following compounds were obtained according to a similar manner to that of Preparation 8.

1) Benzyl 1-tert-butoxycarbonyl-3-tert-butyldiphenyl-silyloxymethylindole-4-carboxylate NMR (CDCl$_3$, $\delta$): 1.09 (9H, s), 1.67 (9H, s), 5.03 (2H, s), 5.19 (2H, s), 7.27–7.43 (12H, m), 7.66–7.78 (6H, m), 8.43 (1H, d, J=8 Hz).

2) 2-tert-Butyldiphenylsiloxymethyl-4-nitro-1H-benzimidazole

NMR (CDCl$_3$, $\delta$): 1.15 (9H, s), 5.08 (2H, s), 7.30–7.51 (7H, m), 7.70 (4H, d-like), 8.00 (1H, d, J=8 Hz), 8.15 (1H, d, J=8 Hz).

Preparation 36

To a solution of benzyl 2-hydroxymethylindole-4-carboxylate (456 mg) and imidazole (364 mg) in N,N-dimethylformamide (10 ml) was added tert-butyldiphenylsilyl chloride (802 mg) and the solution was stirred at ambient temperature for 2 hours. The resulting mixture was diluted with ethyl acetate (30 ml) and washed successively with water and brine. The organic layer was dried over magnesium sulfate and concentrated in vacuo. The residue was purified be silica gel column chromatography (eluent; n-hexane:ethyl acetate=15:1) to give benzyl 2-tert-butyldiphenylsilyloxymethylindole-4-carboxylate (810 mg).

NMR (CDCl$_3$, $\delta$): 1.09 (9H, s), 4.93 (2H, s), 5.42 (2H, s), 6.89 (1H, s), 7.19 (1H, t, J=8 Hz), 7.30–7.54 (12H, m), 7.68 (4H, d, J=8 Hz), 7.92 (1H, d, J=8 Hz), 8.32–8.37 (1H, br).

Preparation 37

The following compound was obtained by using methyl 2-formyl-1-methoxymethoxyindole-4-carboxylate as a starting compound according to a similar manner to that of Preparation 10.

Methyl 2-hydroxymethylindole-4-carboxylate

NMR (DMSO-$d_6$, $\delta$): 3.88 (3H, s), 4.67 (2H, d, J=6 Hz), 5.37 (1H, t, J=6 Hz), 6.80 (1H, s), 7.13 (1H, t, J=8 Hz), 7.60 (1H, d, J=8 Hz), 7.69 (1H, d, J=8 Hz).

Preparation 38

The following compounds were obtained according to a similar manner to that of Preparation 12.

1) 1-tert-Butoxycarbonyl-2-ethoxycarbonylindoline-4-carboxylic acid

NMR (DMSO-$d_6$, $\delta$): 1.22 (3H, t, J=8 Hz), 1.45 (9H, s), 3.37 (1H, dd, J=8, 16 Hz), 3.78 (1H, dd, J=10, 16 Hz), 4.17 (2H, q, J=8 Hz), 4.90 (1H, dd, J=8, 10 Hz), 7.32 (1H, t, J=8 Hz), 7.51 (1H, d, J=8 Hz), 7.94–8.03 (1H, m).

2) 1-tert-Butoxycarbonyl-3-tert-butyldiphenylsilyloxymethylindole-4-carboxylic acid NMR (CDCl$_3$, δ): 1.08 (9H, s), 1.68 (9H, s), 5.10 (2H, s), 7.28–7.41 (7H, m), 7.65–7.70 (4H, m), 7.77 (1H, s), 7.88 (1H, d, J=9 Hz), 8.52 (1H, d, J=9 Hz).

3) 1-tert-Butoxycarbonyl-2-phthalimidomethylindole-4-carboxylic acid

NMR (CDCl$_3$, δ): 1.69 (9H, s), 5.15 (2H, s), 6.86 (1H, s), 7.37 (1H, t, J=8 Hz), 7.80 (1H, d, J=8 Hz), 7.89–8.03 (4H, m), 8.28 (1H, d, J=8 Hz).

4) 1-tert-Butoxycarbonyl-2-methylindole-4-carboxylic acid

NMR (CDCl$_3$, δ): 1.70 (9H, s), 2.67 (3H, s), 7.13 (1H, s), 7.30 (1H, t, J=9 Hz), 8.03 (1H, d, J=9 Hz), 8.40 (1H, d, J=9 Hz).

Preparation 39

To a solution of benzyl 1-tert-butoxycarbonyl-2-tert-butyldiphenylsilyloxymethylindole-4-carboxylate (762 mg) in 5.0% formic acid-methanol (20.0 ml) was added 10% palladium on carbon (100 mg) and the mixture was stirred under nitrogen atmosphere at ambient temperature for 2 hours. The resulting solution was filtered through a bed of celite and the filtrate was concentrated in vacuo. The residue was diluted with chloroform (10 ml) and the solution was washed successively with water and brine. The organic layer was dried over magnesium sulfate and concentrated in vacuo to give 1-tert-butoxycarbonyl-2-tert-butyldiphenylsilyloxymethylindole-4-carboxylic acid (597 mg).

NMR (CDCl$_3$, δ): 1.13 (9H, s), 1.49 (9H, s), 5.05 (2H, s), 7.29–7.43 (7H, m), 7.57 (1H, s), 7.71 (4H, d, J=8 Hz), 8.08 (1H, d, J=8 Hz), 8.44 (1H, d, J=8 Hz).

Preparation 40

To a solution of benzyl 1-tert-butoxycarbonylindole-6-carboxylate (1.27 g) in 5.0% formic acid-methanol (20.0 ml) was added 10% palladium on carbon (1.27 g) and the mixture was stirred under nitrogen atmosphere at ambient temperature for 4 hours and stand overnight. The resulting solution was filtered through a bed of celite and the filtrate was concentrated in vacuo. The residue was diluted with chloroform and the solution was washed successively with water and brine. The organic layer was dried over magnesium sulfate and concentrated in vacuo. The residue was triturated with ether:n-hexane (1:5) to give 1-tert-butoxycarbonylindoline-6-carboxylic acid (761 mg).

NMR (DMSO-d$_6$, δ): 1.50 (9H, s), 3.11 (2H, t, J=11 Hz), 3.96 (2H, t, J=11 Hz), 7.28 (1H, d, J=8 Hz), 7.54 (1H, d, J=8 Hz), 8.20–8.30 (1H, br).

Preparation 41

To a solution of benzyl 1-tert-butoxycarbonylindole-6-carboxylate (450 mg) in 5.0% formic acid-methanol (10.0 ml) was added 10% palladium on carbon (153 mg) and the mixture was stirred under nitrogen atmosphere at ambient temperature for 4 hours. The resulting solution was filtered through a bed of celite and the filtrate was concentrated in vacuo. The residue was diluted with chloroform and the solution was washed successively with water and brine. The organic layer was dried over magnesium sulfate and concentrated in vacuo. The residue was triturated with ether:n-hexane (1:5) to give 1-tert-butoxycarbonylindole-6-caroxylic acid (302 mg).

NMR (DMSO-d$_6$, δ): 1.67 (9H, s), 6.80 (1H, d, J=3 Hz), 7.69 (1H, d, J=8 Hz), 7.83 (1H, d, J=8 Hz), 7.86 (1H, d, J=3 Hz), 8.75 (1H, s).

Preparation 42

The following compound was obtained by using 3-methoxy-4-methoxycarbonyl-N-[4-methyl-2-(4-phthalimidobut-1-yloxy)]-phenylbenzamide as a starting compound according to a similar manner to that of Preparation 15.

3-Methoxy-4-methoxycarbonyl-N-methyl-N-[4-methyl-2-(4-phthalimidobut-1-yloxy)]phenylbenzamide NMR (CDCl$_3$, δ): 1.77–1.91 (4H, m), 2.23 (3H, s), 3.31 (3H, s), 3.69 (3H, s), 3.77 (2H, t, J=7.5 Hz), 3.81 (3H, s), 3.82–3.99 (2H, m), 6.40–6.50 (2H, m), 6.82 (1H, d, J=8 Hz), 6.88 (1H, d, J=8 Hz), 6.90 (1H, s), 7.55 (1H, d, J=8 Hz), 7.65–7.73 (2H, m), 7.81–7.88 (2H, m).

Preparation 43

The following compound was obtained according to a similar manner to that of Preparation 42.

3-Methoxy-4-nitro-N-methyl-N-[4-methyl-2-(5-phthalimidopent-1-yloxy)]phenylbenzamide NMR (CDCl$_3$, δ): 1.46–1.58 (2H, m), 1.70–1.91 (4H, m), 2.27 (3H, s), 3.30 (3H, s), 3.74 (2H, t, J=7.5 Hz), 3.79 (3H, s), 3.85–3.95 (2H, m), 6.57–6.63 (2H, m), 6.82 (1H, d, J=8 Hz), 6.94 (1H, d, J=8 Hz), 7.06 (1H, s), 7.61 (1H, d, J=8 Hz), 7.68–7.75 (2H, m), 7.80–7.85 (2H, m).

Preparation 44

The following compounds were obtained according to a similar manner to that of Preparation 17.

1) 2-Benzyloxymethyl-1-tert-butoxycarbonylindoline-4-carboxylic acid

NMR (CDCl$_3$, δ): 1.50 (9H, s), 3.45–3.59 (3H, m), 3.67 (1H, dd, J=4, 10 Hz), 4.52 (2H, s), 4.57–4.67 (1H, br), 7.21–7.38 (7H, m), 7.70 (1H, d, J=8 Hz).

2) 3-Formylindole-4-carboxylic acid

NMR (DMSO-d$_6$, δ): 7.31 (1H, t, J=8 Hz), 7.73 (2H, d, J=8 Hz), 8.27 (1H, d, J=3 Hz), 10.45 (1H, s).

3) 2-Hydroxymethylindole-4-carboxylic acid

NMR (CDCl$_3$, δ): 4.65 (2H, s), 5.27–5.40 (1H, br), 6.82 (1H, s), 7.10 (1H, t, J=8 Hz), 7.57 (1H, d, J=8 Hz), 7.67 (1H, d, J=8 Hz).

4) 4-Carboxy-3-methoxy-N-methyl-N-(4-methyl-2-nitrophenyl)benzamide

NMR (CDCl$_3$, δ): 2.24 (3H, s), 3.43 (3H, s), 3.97 (3H, s), 6.80 (1H, d, J=8 Hz), 7.09 (1H, s), 7.20 (1H, d, J=8 Hz), 7.34 (1H, d, J=8 Hz), 7.60 (1H, s), 7.89 (1H, d, J=8 Hz).

5) 4-Carboxy-3-methoxy-N-methyl-N-[2-(4-tert-butoxycarbonylaminobut-1-yl)oxy-4-methyl]phenylbenzamide NMR (CDCl$_3$, δ): 1.45 (9H, s), 1.60–1.72 (2H, m), 1.76–1.87 (2H, m), 2.26 (3H, s), 3.19 (2H, t, J=7.5 Hz), 3.32 (3H, s), 3.81–3.97 (2H, m), 3.89 (3H, s), 6.57–6.62 (2H, m), 7.85 (1H, d, J=8 Hz), 7.98 (1H, d, J=8 Hz), 7.07 (1H, s), 7.90 (1H, s).

6) 4-Carboxy-N-[2-[4,4-dimethyl(2,5-oxazolinyl)]phenyl]-N-methyl-3-methoxybenzamide NMR (CDCl$_3$, δ): 1.36 (3H, s), 1.37 (3H, s), 3.37 (3H, s), 3.81 (3H, s), 4.02–4.18 (2H, m), 7.01–7.18 (3H, m), 7.21–7.39 (2H, m), 7.79 (1H, m), 7.91 (1H, d, J=8 Hz).

7) 4-Carboxy-3-methoxy-N-methyl-N-[2-(morpholin-4-yl)phenyl]benzamide

NMR (CDCl$_3$, δ): 2.28–2.43 (2H, m), 2.78–2.92 (2H, m), 3.52 (3H, s), 3.59–3.85 (7H, m), 6.86 (1H, d, J=8 Hz), 7.04 (1H, s), 7.08–7.18 (2H, m), 7.21 (1H, d, J=8 Hz), 7.29 (1H, dd, J=8, 8 Hz), 7.92 (1H, d, J=8 Hz).

8) 4-Carboxy-3-methoxy-N-methyl-N-[2-(1-pyrrolyl)phenyl]benzamide

NMR (CDCl$_3$, δ): 3.51 (3H, s), 3.88 (3H, s), 6.25 (2H, s), 6.32–6.41 (2H, m), 6.53 (1H, d, J=8 Hz), 6.60 (1H, s), 7.11 (1H, m), 7.26–7.52 (3H, m), 7.75 (1H, d, J=8 Hz).

9) 4-Carboxy-3-methoxy-N-methyl-N-(2-piperidinophenyl)-benzamide

NMR (CDCl$_3$, δ): 1.41–1.71 (6H, m), 2.20–2.36 (2H, m), 2.68–2.83 (2H, m), 3.52 (3H, s), 3.79 (3H, s), 6.83 (1H, d, J=8 Hz), 6.96–7.30 (5H, m), 7.92 (1H, d, J=8 Hz).

10) 4-Carboxy-N-methyl-3-methoxy-N-[2-(4-methyl-1-piperazinyl)phenyl]benzamide

NMR (DMSO-d$_6$, δ): 2.22 (3H, s), 2.23–2.50 (6H, m), 2.70–2.91 (2H, m), 3.36 (3H, s), 3.50 (3H, s), 6.81 (1H, s), 6.86–7.00 (2H, m), 7.10 (1H, m), 7.19 (1H, m), 7.32–7.46 (2H, m).

11) 4-Carboxy-3-methoxy-N-methyl-N-[2-(2,5-oxazolyl)phenyl]-benzamide

NMR (CDCl$_3$, δ): 3.46 (3H, s), 3.78 (3H, s), 6.77–6.85 (2H, m), 7.23–7.46 (4H, m), 7.75–7.91 (3H, m).

12) 4-Carboxy-N-methyl-3-methoxy-N-[2-(2,5-oxazolinyl)-phenyl]benzamide

NMR (CDCl$_3$, δ): 3.41 (3H, s), 3.82 (3H, s), 4.02–4.17 (2H, m), 4.32–4.50 (2H, m), 7.00–7.08 (2H, m), 7.15 (1H, d, J=8 Hz), 7.28 (1H, dd, J=8, 8 Hz), 7.38 (1H, dd, J=8, 8 Hz), 7.77 (1H, m), 7.89 (1H, d, J=8 Hz).

13) 4-Carboxy-N-methyl-3-methoxy-N-[2-(3H,4H,5H-2,6-oxazinyl)phenyl]benzamide

NMR (CDCl$_3$, δ): 1.94–2.08 (2H, m), 3.42 (3H, s), 3.58 (2H, t, J=7 Hz), 3.78 (3H, s), 4.29–4.41 (2H, m), 6.84–7.37 (4H, m), 7.48–7.60 (2H, m), 7.90 (1H, d, J=8 Hz).

14) N-[2-(1-(Aza-3-oxaspiro[4.4]non-1-en-2-yl)phenyl]-4-carboxy-3-methoxy-N-methylbenzamide NMR (CDCl$_3$, δ): 1.61–1.77 (4H, m), 1.82–2.04 (4H, m), 3.38 (3H, s), 3.82 (3H, s), 4.16–4.28 (2H, m), 7.06–7.16 (3H, m), 7.22–7.39 (2H, m), 7.77 (1H, m), 7.92 (1H, d, J=8 Hz).

15) 2-Carbamoyl-1-(4-methoxybenzyl)-1H-benzimidazole-4-carboxylic acid

NMR (DMSO-d$_6$, δ): 3.69 (3H, s), 5.89 (3H, s), 6.86 (2H, d, J=8 Hz), 7.23 (2H, d, J=8 Hz), 7.30 (1H, t, J=8 Hz), 7.66 (1H, d, J=8 Hz), 7.72 (1H, d, J=8 Hz), 7.89 (1H, br s), 9.30 (1H, br peak).

16) 2-(N,N-Dimethylcarbamoyl)-1-(4-methoxybenzyl)-1H-benzimidazole-4-carboxylic acid NMR (DMSO-d$_6$, δ): 2.91 (3H, s), 3.05 (3H, s), 3.71 (3H, s), 5.49 (2H, s), 6.89 (2H, d, J=8 Hz), 7.22 (2H, d, J=8 Hz), 7.42 (1H, t, J=8 Hz), 7.82 (1H, d, J=8 Hz), 7.92 (1H, d, J=8 Hz).

17) 2-[1-(Benzyloxycarbonyl)-4-piperidyl]-1H-benzimidazole-4-carboxylic acid

NMR (DMSO-d$_6$, δ): 1.69–1.88 (2H, m), 1.95–2.08 (2H, m), 2.99 (2H, br peak), 3.24–3.59 (1H, m), 4.08–4.19 (2H, m), 5.10 (2H, s), 7.23–7.47 (6H, m), 7.79 (1H, d, J=8 Hz), 7.85 (1H, d, J=8 Hz).

18) 2-(N-tert-Butoxycarbonylaminomethyl)-1-methyl-1H-benzimidazole-4-carboxylic acid NMR (DMSO-d$_6$, δ): 1.36 (9H, s), 4.01 (3H, s), 4.77 (2H, d, J=5 Hz), 7.16–7.31 (2H, m), 8.11 (1H, d, J=8 Hz), 8.23 (1H, d, J=8 Hz).

19) 2-(N-tert-Butoxycarbonylaminomethyl)-3-methyl-3H-benzimidazole- 4-carboxylic acid NMR (DMSO-d$_6$, δ): 1.40 (9H, s), 3.96 (3H, s), 4.65 (2H, d, J=6 Hz), 7.52 (1H, t, J=8 Hz), 7.77 (1H, br peak), 7.87 (1H, d, J=8 Hz), 7.95 (1H, d, J=8 Hz).

20) 2-Methylthio-1H-benzimidazole-4-carboxylic acid

NMR (DMSO-d$_6$, δ): 2.68 (3H, s), 7.22 (1H, t, J=8 Hz), 7.70 (1H, d, J=8 Hz), 7.76 (1H, d, J=8 Hz).

21) 2-Methylsulfonyl-1H-benzimidazole-4-carboxylic acid

NMR (DMSO-d$_6$, δ): 3.56 (3H, s), 7.50 (1H, t, J=8 Hz), 8.01 (1H, d, J=8 Hz), 8.09 (1H, br peak).

22) 2-Sulfamoyl-1H-benzimidazole-4-carboxylic acid

NMR (DMSO-d$_6$, δ): 7.46 (1H, t, J=8 Hz), 7.89–8.02 (3H, m), 8.07 (1H, d, J=8 Hz).

23) 2-Methyl-1H-pyrazolo[1,5-b][1,2,4]triazole-7-carboxylic acid

NMR (DMSO-d$_6$, δ): 2.43 (3H, s), 7.82 (1H, s).

24) 2-(4-Pyridyl)-1H-benzimidazole-4-carboxylic acid

NMR (DMSO-d$_6$, δ): 7.37 (1H, t, J=8 Hz), 7.89 (1H, d, J=8 Hz), 8.00 (1H, d, J=8 Hz), 8.27 (1H, d, J=6 Hz), 8.74 (1H, d, J=6 Hz).

25) 2-(3-Pyridyl)-1H-benzimidazole-4-carboxylic acid

NMR (DMSO-d$_6$, δ): 7.40 (1H, t, J=8 Hz), 7.72 (1H, t, J=8 Hz), 7.90 (1H, d, J=8 Hz), 8.01 (1H, d, J=8 Hz), 8.77–8.80 (2H, m), 9.52 (1H, s).

26) 2-(2-Pyridyl)-1H-benzimidazole-4-carboxylic acid

NMR (DMSO-d$_6$, δ): 7.39 (1H, t, J=8 Hz), 7.57 (1H, t, J=7 Hz), 7.87 (1H, d, J=8 Hz), 7.98–8.06 (2H, m), 8.35 (1H, d, J=8 Hz), 8.79 (1H, d, J=4 Hz).

27) 2-Dimethylaminomethyl-1H-benzimidazole-4-carboxylic acid

NMR (DMSO-d$_6$, δ): 2.89 (6H, s), 4.68 (2H, s), 7.39 (1H, t, J=8 Hz), 7.90 (1H, d, J=8 Hz), 8.00 (1H, d, J=8 Hz).

28) 2-(4-Methylpiperazin-1-yl)methyl-1H-benzimidazole-4-carboxylic acid

NMR (DMSO-d$_6$, δ): 2.50 (3H, s), 2.72 (4H, br s), 2.88 (4H, br s), 3.87 (2H, s), 7.27 (1H, t, J=8 Hz), 7.77 (1H, d, J=8 Hz), 7.82 (1H, d, J=8 Hz).

29) 2-(4-Dimethylaminopiperidino)methyl-1H-benzimidazole-4-carboxylic acid

NMR (DMSO-d$_6$, δ): 1.90 (2H, br s), 2.10–2.20 (2H, m), 2.52–2.70 (7H, m), 3.15–3.50 (6H, m), 7.30 (1H, t, J=8 Hz), 7.82 (1H, d, J=8 Hz), 7.90 (1H, d, J=8 Hz).

30) 2-Morpholinomethyl-1H-benzimidazole-4-carboxylic acid

NMR (DMSO-d$_6$, δ): 2.50 (4H, br s), 3.88 (4H, br s), 4.72 (2H, s), 7.40 (1H, t, J=8 Hz), 7.90 (1H, d, J=8 Hz), 7.99 (1H, d, J=8 Hz).

31) 2H-1,4-Benzoxazin-3-one-8-carboxylic acid

NMR (DMSO-d$_6$, δ): 4.62 (2H, s), 6.96–7.05 (2H, m), 7.30 (1H, d, J=8 Hz).

Preparation 45

The following compounds were obtained according to a similar manner to that of Preparation 25.

1) 4-Amino-3-methoxy-N-methyl-N-[2-(5-tert-butoxycarbonyl-aminopent-1-yl)oxy-4-methyl]phenylbenzamide NMR (CDCl$_3$, δ): 1.42 (9H, s), 1.42–1.59 (4H, m), 1.70–1.81 (2H, m), 2.28 (9H, s), 3.06–3.17 (2H, m), 3.31 (3H, s), 3.61 (3H, s), 3.76–3.93 (2H, m), 3.87 (2H, s), 4.69 (1H, br), 6.43 (1H, d, J=8 Hz), 6.57–6.63 (2H, m), 6.80–6.85 (2H, m), 6.89 (1H, d, J=8 Hz).

2) tert-Butyl 4-amino-1H-benzimidazole-1-carboxylate

NMR (CDCl$_3$, δ): 1.68 (9H, s), 4.37 (2H, s), 6.61 (1H, d, J=8 Hz), 7.16 (1H, dd, J=8, 8 Hz), 7.32 (1H, d, J=8 Hz), 8.30 (1H, s).

3) 2-[4,4-Dimethyl(2,5-oxazolinyl)]phenylamine

NMR (CDCl$_3$, δ): 1.39 (6H, s), 4.00 (2H, s), 6.06–6.28 (2H, br), 6.60–6.73 (2H, m), 7.19 (1H, m), 7.68 (1H, d, J=8 Hz).

4) 4-Amino-N-[2-[4,4-dimethyl(2,5-oxazolinyl)phenyl]-N-methyl-3-methoxybenzamide NMR (CDCl$_3$, δ): 1.32 (6H, s), 3.38 (3H, s), 3.58 (3H, s), 3.86 (2H, br s), 4.07 (2H, s), 6.41 (1H, d, J=8 Hz), 6.78–6.90 (2H, m), 7.12 (1H, d, J=8 Hz), 7.22 (1H, dd, J=8, 8 Hz), 7.35 (1H, dd, J=8, 8 Hz), 7.79 (1H, d, J=8 Hz).

5) 4-Amino-3-methoxy-N-methyl-N-[2-(morpholin-4-yl)phenyl]benzamide

NMR (CDCl$_3$, δ): 2.52–2.68 (2H, m), 2.77–2.93 (2H, m), 3.46 (3H, s), 3.59 (3H, s), 3.63–3.82 (4H, m), 6.45 (1H, d, J=8 Hz), 6.84 (1H, s), 6.86–6.96 (2H, m), 7.04 (1H, dd, J=8, 8 Hz), 7.12–7.23 (2H, m).

6) 2-(4-Methyl-1-piperazinyl)phenylamine

NMR (CDCl$_3$, δ): 2.37 (3H, s), 2.46–2.75 (4H, m), 2.88–3.04 (4H, m), 3.94 (2H, br s), 6.75 (2H, dd, J=8, 8 Hz), 6.92 (1H, dd, J=8, 8 Hz), 7.02 (1H, d, J=8 Hz).

7) 2-(2,5-Oxazolyl)phenylamine

NMR (CDCl$_3$, δ): 6.70–6.83 (2H, m), 7.16–7.28 (2H, m), 7.64 (1H, s), 7.86 (1H, m).

8) 2-(1-Aza-3-oxaspiro[4.4]non-1-en-2-yl)phenylamine

NMR (CDCl$_3$, δ): 1.52–2.06 (8H, m), 4.12 (2H, s), 6.10 (2H, br s), 6.59–6.73 (2H, m), 7.18 (1H, dd, J=8, 8 Hz), 7.66 (1H, d, J=8 Hz).

9) 4-Amino-2-methoxy-1H-benzimidazole

NMR (DMSO-d$_6$, δ): 4.01 (3H, s), 4.84 (2H, s), 6.30 (1H, d, J=8 Hz), 6.47 (1H, br peak), 6.74 (1H, t, J=8 Hz).

10) 4-Amino-2-[2-(dimethylamino)ethyl]-1H-benzimidazole

NMR (CDCl$_3$, δ): 2.39 (6H, s), 2.71 (2H, t, J=5 Hz), 3.07 (2H, t, J=5 Hz), 4.23 (2H, br peak), 6.50 (1H, d, J=8 Hz), 6.84 (1H, d, J=8 Hz), 7.00 (1H, t, J=8 Hz).

11) 4-Amino-1-(tert-butoxycarbonyl)-2-[[2-[N-(tert-butoxy-carbonyl)-N-methylamino]ethyl]amino]-1H-benzimidazole NMR (CDCl$_3$, δ): 1.45 (9H, s), 1.69 (9H, s), 2.93 (3H, s), 3.51–3.65 (2H, m), 3.65–3.88 (2H, m), 6.57 (1H, d, J=8 Hz), 6.88 (1H, t, J=8 Hz), 7.02 (1H, d, J=8 Hz).

12) 4-Amino-1-(tert-butoxycarbonyl)-2-[[2-[(tert-butoxy)carbonylamino]ethyl]methylamino]-1H-benzimidazole NMR (CDCl$_3$, δ): 1.35 (9H, s), 1.70 (9H, s), 3.03 (3H, s), 3.41–3.55 (2H, m), 3.61–3.77 (2H, m), 6.14 (1H, br peak), 6.59 (1H, d, J=8 Hz), 6.91–7.10 (2H, m).

13) 4-Amino-1-(tert-butoxycarbonyl)-2-[[2-(dimethylamino)-ethyl]amino]-1H-benzimidazole NMR (CDCl$_3$, δ): 1.69 (9H, s), 2.43 (6H, br s), 2.80 (2H, br peak), 2.69–2.81 (2H, m), 6.56 (1H, d, J=8 Hz), 6.85 (1H, t, J=8 Hz), 7.06 (1H, d, J=8 Hz).

14) 4-Amino-2-[[2-(dimethylamino)ethyl]methylamino]-1H-benzimidazole

NMR (DMSO-d$_6$, δ): 2.20 (6H, s), 2.45 (2H, t, J=5 Hz), 3.11 (3H, s), 3.52 (2H, t, J=5 Hz), 6.18 (1H, d, J=8 Hz), 6.44 (1H, d, J=8 Hz), 6.60 (1H, t, J=8 Hz).

Preparation 46

The following compounds were obtained according to a similar manner to that of Preparation 31.

1) Methyl-2-carbamoyl-1-(4-methoxybenzyl)-1H-benzimidazole-4-carboxylate

NMR (CDCl$_3$, δ): 3.74 (3H, s), 4.04 (3H, s), 5.65 (1H, br s), 5.98 (2H, s), 6.80 (2H, d, J=8 Hz), 7.15 (1H, d, J=8 Hz), 7.40 (1H, t, J=8 Hz), 7.63 (1H, d, J=8 Hz), 7.86 (1H, br s), 8.03 (1H, d, J=8 Hz).

2) Methyl 2-(N,N-dimethylcarbamoyl)-1-(4-methoxybenzyl)-1H-benzimidazole-4-carboxylate NMR (CDCl$_3$, δ): 3.10 (3H, s), 3.19 (3H, s), 3.76 (3H, s), 4.01 (3H, s), 5.54 (2H, s), 6.80 (2H, d, J=8 Hz), 7.12 (2H, d, J=8 Hz), 7.35 (1H, t, J=8 Hz), 7.58 (1H, d, J=8 Hz), 7.99 (1H, d, J=8 Hz).

Preparation 47

The following compounds were obtained by using ethyl 2-phthalimidomethyl-1H-benzimidazole-4-carboxylate as a starting compound according to a similar manner to that of Preparation 31.

1) Ethyl 1-methyl-2-phthalimidomethyl-1H-benzimidazole-4-carboxylate

NMR (CDCl$_3$, δ): 1.26 (3H, t, J=7.5 Hz), 3.95 (3H, s), 4.35 (2H, q, J=7.5 Hz), 5.20 (2H, s), 7.32 (1H, t, J=8 Hz), 7.52 (1H, d, J=8 Hz), 7.70–7.80 (2H, m), 7.84–7.95 (3H, m)

2) Ethyl 3-methyl-2-phthalimidomethyl-3H-benzimidazole-4-carboxylate

NMR (CDCl$_3$, δ):1.45 (3H, t, J=7.5 Hz), 4.06 (3H, s), 4.43 (2H, q, J=7.5 Hz), 5.15 (2H, s), 7.21 (1H, t, J=8 Hz), 7.71–7.80 (3H, m), 7.85 (1H, d, J=8 Hz), 7.87–7.94 (2H, m)

Preparation 48

To a solution of benzyl 2-tert-butyldiphenyl-silyloxymethylindole-4-carboxylate (805 mg) and N,N-dimethylaminopyridine (189 mg) in acetonitrile (15 ml) was added di-tert-butyl dicarbonate (507 mg) and the mixture was stirred at ambient temperature for 20 minutes. The resulting mixture was diluted with ethyl acetate (30 ml) and washed successively with saturated sodium bicarbonate aqueous solution and brine. The organic layer was dried over magnesium sulfate and concentrated in vacuo. The residue was purified by silica gel column chromatography (eluent; n-hexane:ethyl acetate=15:1) to give benzyl 1-tert-butoxycarbonyl-2-tert-butylidphenylsilyloxymethylindole-4-carboxylate (762 mg).

NMR (CDCl$_3$, δ):1.12 (9H, s), 1.47 (9H, s), 5.01 (2H, s), 5.47 (2H, s), 7.27–7.50 (12H, m), 7.55 (1H, s), 7.71 (4H, d, J=8 Hz), 8.01 (1H, d, J=8 Hz), 8.39 (1H, d, J=8 Hz)

Preparation 49

The following compounds were obtained according to a similar manner to that of Preparation 48.

1) Methyl 2-benzyloxymethyl-1-tert-butoxycarbonylindoline-4-carboxylate

NMR (CDCl$_3$, δ):1.50 (9H, s), 3.42–3.53 (3H, m) 3.67 (1H, dd, J=4, 12 Hz), 3.89 (3H, s), 4.50 (2H, s), 4.56–4.67 (1H, br), 7.20–7.38 (7H, m), 7.60 (1H, d, J=8 Hz)

2) Benzyl 1-tert-butoxycarbonyl-3-formylindole-4-carboxylate

NMR (CDCl$_3$, δ):1.68 (9H, s), 5.43 (2H, s), 7.32–7.49 (6H, m), 7.92 (1H, d, J=8 Hz), 8.37 (1H, s), 8.49 (1H, d, J=8 Hz), 10.47 (1H, s)

3) Benzyl 1-tert-butoxycarbonyl-2-formylindole-4-carboxylate

NMR (CDCl$_3$, δ):1.72 (9H, s), 5.45 (2H, s) 7.34–7.45 (3H, m), 7.47–7.57 (3H, m), 8.07 (1H, d, J=9 Hz), 8.10 (1H, s), 8.43 (1H, d, J=9 Hz), 10.40 (1H, s)

4) Benzyl 1-tert-butoxycarbonyl-2-methylindole-4-carboxylate

NMR (CDCl$_3$, δ):1.70 (9H, s), 2.61 (3H, s), 5.40 (2H, s), 7.07 (1H, s), 7.22–7.28 (1H, m), 7.31–7.43 (3H, m), 7.47–7.52 (2H, m), 7.97 (1H, d, J=8 Hz), 8.35 (1H, d, J=8 Hz)

5) Benzyl 1-tert-butoxycarbonylindole-6-carboxylate

NMR (CDCl$_3$, δ):1.67 (9H, s), 5.39 (2H, s), 6.61 (1H, d, J=3 Hz), 7.32–7.42 (3H, m), 7.46–7.50 (2H, m), 7.59 (1H, d, J=8 Hz), 7.78 (1H, d, J=3 Hz), 7.97 (1H, d, J=8 Hz) 8.86 (1H, s)

6) 3-Methoxy-4-methoxycarbonyl-N-methyl-N-[4-methyl-2-[4-(tert-butoxycarbonylamino)but-1-yloxy]]phenylbenzamide NMR (CDCl$_3$, δ):1.42 (9H, s), 1.57–1.70 (2H, m), 1.72–1.86 (2H, m), 2.23 (3H, s), 3.19 (2H, t, J=7.5 Hz), 3.31 (3H, s), 3.69 (3H, s), 3.78–3.96 (2H, m), 3.82 (3H, s), 6.55–6.60 (2H, m), 6.87 (1H, d, J=8 Hz), 6.91 (1H, d, J=8 Hz), 6.94 (1H, s), 7.57 (1H, d, J=8 Hz)

7) tert-Butyl 4-nitro-1H-benzimidazole-1-carboxylate

NMR (CDCl$_3$, δ):1.72 (9H, s), 7.53 (1H, dd, J=8, 8 Hz), 8.20 (1H, d, J=8 Hz), 8.39 (1H, d, J=8 Hz), 8.61 (1H, s)

8) 1-(tert-Butoxycarbonyl)-2-[[2-[N-(tert-butoxycarbonyl)-N-methylamino]ethyl]amino]-4-nitro-1H-benzimidazole NMR (CDCl$_3$, δ):1.41 (9H, s), 1.71 (9H, s), 2.95 (3H, s), 3.60 (1H, t-like, J=5 Hz), 3.84 (1H, q-like, J=5 Hz), 7.04 (1H, t, J=8 Hz), 7.31 (1H, d, J=8 Hz), 8.00 (1H, d, J=8 Hz)

9) 1-(tert-Butoxycarbonyl)-2-[[2-[(tert-butoxy)carbonylamino]ethyl]methylamino]-4-nitro-1H-benzimidazole NMR (CDCl$_3$, δ):1.39 (9H, s), 1.69 (9H, s), 3.11 (3H, s), 3.50 (2H, q-like, J=5 Hz), 3.80 (2H, t-like, J=5 Hz), 6.01 (1H, br peak), 7.11 (1H, t, J=8 Hz), 7.88 (1H, d, J=8 Hz), 8.03 (1H, d, J=8 Hz)

10) 1-(tert-Butoxycarbonyl)-2-[[2-(dimethylamino)ethyl]amino]-4-nitro-1H- benzimidazole NMR (CDCl$_3$, δ):1.72 (9H, s), 2.55 (6H, br peak), 3.00 (2H, br peak), 3.92 (2H, br peak), 7.07 (1H, t, J=8 Hz), 7.84 (1H, br peak), 7.90 (1H, d, J=8 Hz), 8.01 (1H, d, J=8 Hz)

Preparation 50

The following compounds were obtained according to a similar manner to that of Example 1.

1) 3-Methoxy-4-methoxycarbonyl-N-methyl-N-(4-methyl-2-nitrophenyl)benzamide

NMR (CDCl$_3$, δ):2.35 (3H, s), 3.37 (3H, s), 3.70 (3H, s), 3.80 (3H, s), 6.80 (1H, d, J=8 Hz), 6.91 (1H, s), 7.11 (1H, d, J=8 Hz), 7.30 (1H, d, J=8 Hz), 7.54 (1H, d, J=8 Hz), 7.63 (1H, s)

2) 3-Methoxy-4-methoxycarbonyl-N-[4-methyl-2-(4-phthalimidobut-1-yloxy)]phenylbenzamide NMR (CDCl$_3$, δ):1.87–1.96 (4H, m), 2.31 (3H, s), 3.78 (2H, m), 3.91 (3H, s), 3.98 (3H, s), 4.10 (2H, m), 6.70 (1H, s), 6.79 (1H, d, J=8 Hz), 7.35 (1H, d, J=8 Hz), 7.62 (1H, s), 7.66–7.74 (2H, m), 7.79–7.87 (2H, m), 7.96 (1H, d, J=8 Hz), 8.33 (1H, d, J=8 Hz), 8.52 (1H, s)

3) 3-Methoxy-4-nitro-N-[4-methyl-2-(5-phthalimidopent-1-yloxy)]phenylbenzamide

NMR (CDCl$_3$, δ):1.48–1.60 (2H, m), 1.70–1.82 (2H, m), 1.85–1.95 (2H, m), 2.31 (3H, s), 3.69 (2H, t, J=7.5 Hz), 4.02 (3H, s), 4.04 (2H, t, J=7.5 Hz), 6.71 (1H, s), 6.81 (1H, d, J=8 Hz), 7.39 (1H, d, J=8 Hz), 7.66–7.72 (2H, m), 7.76–7.74 (2H, m), 7.98 (1H, d, J=8 Hz), 8.32 (1H, d, J=8 Hz), 8.52 (1H, s)

Preparation 51

The following compounds were obtained according to a similar manner to that of Example 7.

1) 4-Amino-2-phthalimidomethyl-1H-benzimidazole

NMR (DMSO-d$_6$, δ):4.95 (2H, s), 5.10 (2H, br s), 6.30 (1H, d, J=8 Hz), 6.57 (1H, d, J=8 Hz), 6.82 (1H, t, J=8 Hz), 7.83–8.02 (4H, m)

2) 4-Amino-2-(2-phthalimidomethyl)-1H-benzimidazole

NMR (DMSO-d$_6$, δ):3.11 (2H, br peak), 4.00 (2H, br peak), 5.01 (2H, br peak), 6.28 (1H, br peak), 6.60 (1H, br peak), 6.80 (1H, br peak), 7.85 (4H, br peak)

3) 4-Amino-2-tert-butyldiphenylsiloxymethyl-1H-benzimidazole

NMR (CD$_3$OD, δ):109 (9H, s), 4.91 (2H, s), 6.53 (1H, d, J=8 Hz), 6.88 (1H, d, J=8 Hz), 6.99 (1H, d, J=8 Hz), 7.32–7.50 (6H, m), 7.66–7.75 (4H, m)

4) 4-Amino-2-[(tert-butoxy)carbonylamino]-1H-benzimidazole

NMR (CDCl$_3$, δ):1.69 (9H, s), 6.58 (1H, d, J=8 Hz), 6.90 (1H, t, J=8 Hz), 7.06 (1H, d, J=8 Hz)

5) 4-Amino-2-[(methylsulfonyl)amino]-1H-benzimidazole

NMR (DMSO-d$_6$, δ):3.40 (3H, s), 4.90 (2H, s), 6.41–6.51 (1H, m), 6.65 (2H, s), 6.71–6.81 (2H, m)

6) 4-Amino-2-methoxymethyl-1H-benzimidazole

NMR (DMSO-d$_6$, δ):3.32 (3H×⅔, s), 3.37 (3H×⅓, s), 4.55 (2H×⅔, s), 4.60 (2H×⅓, s), 5.65 (2H, s), 6.26–6.40 (1H, m), 6.62 (1H×⅔, d, J=8 Hz), 6.73–6.90 (1H+1H×⅓, m)

7) 4-Amino-2-(n-propyl)-1H-benzimidazole

NMR (CDCl$_3$, δ):1.00 (3H, t, J=7.5 Hz), 1.83 (2H, m), 2.86 (2H, t, J=7.5 Hz), 4.26 (2H, br s), 6.50 (1H, d, J=8 Hz), 6.80 (1H, d, J=8 Hz), 7.00 (1H, t, J=8 Hz)

8) 4-Amino-2-isopropyl-1H-benzimidazole

NMR (CDCl$_3$, δ):1.43 (6H, d, J=7.5 Hz), 3.23 (1H, m), 4.28 (2H, br s), 6.50 (1H, d, J=8 Hz), 6.80 (1H, br peak), 7.01 (1H, t, J=8 Hz), 8.84 (1H, br s)

9) 4-Amino-2-(3-pyridyl)-1H-benzimidazole

NMR (DMSO-d$_6$, δ):5.30 (2H, br s), 6.38 (1H, d, J=8 Hz), 6.73 (1H, d, J=8 Hz), 6.93 (1H, t, J=8 Hz), 7.56 (1H, dd, J=5, 8 Hz), 8.43 (1H, d, J=8 Hz), 8.93 (1H, d, J=5 Hz), 9.30 (1H, s)

10) 4-Amino-2-(N,N-dimethylaminomethyl)-1H-benzimidazole

NMR (CDCl$_3$, δ):2.41 (6H, s), 3.83 (2H, s), 6.50 (1H, d, J=8 Hz), 6.83 (1H, d, J=8 Hz), 7.04 (1H, t, J=8 Hz)

11) 4-Amino-2-(1-imidazolyl)methyl-1H-benzimiazole

NMR (DMSO-d$_6$, δ):5.16 (2H, s), 5.38 (2H, s), 6.33 (1H, d, J=8 Hz), 6.67 (1H, d, J=8 Hz), 6.86 (1H, t, J=8 Hz), 6.91 (1H, s), 7.23 (1H, s), 7.77 (1H, s)

12) 4-Amino-2-[(4-methylpiperazin-1-yl)methyl]-1H-benzimidazole

NMR (DMSO-d$_6$, δ):2.15 (3H, s), 2.20–2.49 (8H, m), 3.61 (2H×⅔, s), 3.65 (2H×⅓, s), 5.10 (2H×⅔, s), 5.20 (2H×⅓, s), 6.28 (1H×⅔, d, J=8 Hz), 6.33 (1H×⅓, d, J=8 Hz), 6.60 (1H×⅔, d, J=8 Hz), 6.73–6.86 (1H+1H×⅓, m)

13) 4-Amino-2-(morpholin-4-ylmethyl)-1H-benzimidazole

NMR (CDCl$_3$, δ):2.50–2.60 (4H, m), 3.68–3.76 (4H, m), 3.79 (2H, s), 4.28 (2H, br peak), 6.51 (1H, d, J=8 Hz), 6.83 (1H, d, J=8 Hz), 7.03 (1H, t, J=8 Hz)

14) 4-Amino-2-(pyrrolidin-1-ylmethyl)-1H-benzimidazole

NMR (CDCl$_3$, δ):1.83–2.00 (2H, m), 2.71–2.83 (2H, m), 4.03 (2H, s), 6.50 (1H, d, J=8 Hz), 6.85 (1H, d, J=8 Hz), 7.03 (1H, t, J=8 Hz)

15) 4-Amino-2-(piperidinomethyl)-1H-benzimidazole

NMR (CDCl$_3$, δ):1.47–1.63 (2H, m), 1.73–1.86 (4H, m), 2.73 (4H, br peak), 4.01 (2H, s), 4.26 (2H, br peak), 6.51 (1H, d, J=8 Hz), 6.90 (1H, d, J=8 Hz), 7.05 (1H, t, J=8 Hz)

16) 4-Amino-2-[2-(4-methylpiperazin-1-yl)ethyl]-1H-benzimidazole

NMR (DMSO-d$_6$, δ):2.18 (3H, s), 2.22–2.53 (8H, m), 2.72 (2H, t, J=7.5 Hz), 2.91 (2H, t, J=7.5 Hz), 5.02 (2H, br peak), 6.29 (1H, d, J=8 Hz), 6.61 (1H, d, J=8 Hz), 6.80 (1H, t, J=8 Hz)

17) 4-Amino-2-(4-methylpiperazin-1-yl)-1H-benzimidazole

NMR (DMSO-d$_6$, δ):2.22 (3H, s), 2.36–2.46 (4H, m), 3.36–3.49 (4H, m), 4.70 (2H×⅔, br s), 4.82 (2H ×⅓, br s), 6.20 (1H×⅓, d, J=8 Hz), 6.23 (1H×⅔, d, J=8 Hz), 6.45 (1H×⅔, d, J=8 Hz), 6.52 (1H ×⅓, d, J=8 Hz), 6.62 (1H×⅔, t, J=8 Hz), 6.68 (1H×⅓, t, J=8 Hz)

18) 4-Amino-2-dimethylamino-1H-benzimidazole

NMR (DMSO-d$_6$, δ):3.21 (6H, s), 5.73 (2H, br peak), 6.46 (1H, d, J=8 Hz), 6.57 (1H, d, J=8 Hz), 6.93 (1H, t, J=8 Hz)

19) 4-Amino-2-(1-imidazolyl)-1H-benzimidazole

NMR (DMSO-d$_6$, δ):5.20 (2H, br s), 6.42 (1H, d, J=8 Hz), 6.72 (1H, br peak), 6.94 (1H, t, J=8 Hz), 7.20 (1H, s), 7.85 (1H, s), 8.40 (1H, s)

20) 4-Amino-2-(1,2,4-tetrazol-1-yl)-1H-benzimidazole

NMR (DMSO-$d_6$, δ):5.31 (2H, br peak), 6.43 (1H, d, J=8 Hz), 6.85 (1H, br peak), 6.95 (1H, t, J=8 Hz), 8.42 (1H, s), 9.34 (1H, s)

21) 4-Amino-2-[(2-methoxyethyl)amino]-1H-benzimidazole

NMR (DMSO-$d_6$, δ):3.30 (3H, s), 3.45–3.60 (4H, m), 6.32 (1H, d, J=8 Hz), 6.50 (1H, d, J=8 Hz), 6.75 (1H, t, J=8 Hz), 7.55 (1H, br peak)

Preparation 52

The following compound was obtained according to a similar manner to that of Example 14.

Methyl 2-formyl -1H-benzimidazole-4-carboxylate

NMR (DMSO-$d_6$, δ): 3.97 (3H, s), 7.50 (1H, t, J=8 Hz), 8.03 (1H, d, J=8 Hz), 8.11 (1H, d, J=8 Hz), 10.06 (1H, s)

Preparation 53

The following compound was obtained according to a similar manner to that of Example 16.

2-Methoxymethyl-4-nitro-1H-benzimidazole

NMR (CDCl$_3$, δ):3.59 (3H, s), 4.85 (2H, s), 7.40 (1H, t, J=8 Hz), 8.08 (1H, d, J=8 Hz), 8.18 (1H, d, J=8 Hz)

Preparation 54

To a solution of ethyl 2,3-diaminobenzoate (4.72 g) and pyridine (2.49 g) in dichloroethane (50 ml) was added chloroacetyl chloride (3.11 g) in chloroform (10 ml) at −70° C. and the reaction mixture was stood overnight. After the reaction mixture was concentrated in vacuo, the residue was diluted with ethnaol (50 ml). To the solution was added p-toluenesulfonic acid (249 mg) and the reaction mixture was refluxed for 2 hours. After the reaction mixture was concentrated in vacuo, the reside was diluted with ethyl acetate and satureated sodium hydrogen carbonate aqueous solution. The organic layer was separated and washed with brine. The solution was dried over magnesium sulfate and concentrated in vacuo. The residue was purified by silica gel column chromatography (n-hexane:ethyl acetate=4:1) to give ethyl 2-chloromethyl-1H-benzimidazole-4-carboxylate (2.98 g).

NMR (CDCl$_3$, δ):0.94 (3H, t, J=7 Hz), 4.47 (2H, q, J=7 Hz), 4.86 (2H, s), 7.32 (1H, t, J=8 Hz), 7.93 (2H, d, J=8 Hz)

Preparation 55

The following compounds were obtained according to a similar manner to that of Preparation 54.

1) 4-Nitro-2-(n-propyl)-1H-benzimidazole

NMR (CDCl$_3$, δ):1.08 (3H, t, J=7.5 Hz), 1.94 (2H, m), 2.99 (2H, t, J=7.5 Hz), 7.34 (1H, t, J=8 Hz), 8.03 (1H, d, J=8 Hz), 8.13 (1H, d, J=8 Hz)

2) 2-Isopropyl-4-nitro-1H-benzimidazole

NMR (CDCl$_3$, δ):1.51 (6H, d, J=7.5 Hz), 3.32 (1H, m), 7.34 (1H, t, J=8 Hz), 8.06 (1H, d, J=8 Hz), 8.12 (1H, d, J=8 Hz)

3) 4-Nitro-2-(3-pyridyl)-1H-benzimidazole

NMR (DMSO-$d_6$, δ):7.47 (1H, t, J=8 Hz), 7.63 (1H, dd, J=5, 8 Hz), 8.17 (2H, d, J=8 Hz), 8.69 (1H, dd, J=8, 2 Hz), 8.74 (1H, dd, J=5, 2 Hz), 9.47 (1H, d, J=2 Hz)

4) 2-(2-Chloroethyl)-4-nitro-1H-benzimidazole

NMR (CDCl$_3$, δ):3.49 (2H, t, J=7 Hz), 4.04 (2H, t, J=7 Hz), 7.39 (1H, t, J=8 Hz), 8.06 (1H, d, J=8 Hz), 8.17 (1H, d, J=8 Hz)

5) Ethyl 2-(3-pyridyl)-1H-benzimidazole-4-carboxylate

NMR (CDCl$_3$, δ):1.47 (3H, t, J=7 Hz), 4.48 (3H, q, J=7 Hz), 7.36 (1H, t, J=8 Hz), 7.46–7.50 (1H, m), 7.93 (1H, d, J=8 Hz), 8.03 (1H, d, J=8 Hz), 8.42 (1H, d, J=8 Hz), 8.73 (1H, d, J=3 Hz), 9.32 (1H, s)

6) Ethyl 2-(2-pyridyl)-1H-benzimidazole-4-carboxylate

NMR (CDCl$_3$, δ):1.48 (3H, t, J=7 Hz), 4.50 (2H, q, J=7 Hz), 7.31–7.40 (2H, m), 7.86 (1H, t, J=8 Hz), 7.97 (1H, d, J=8 Hz), 8.03 (1H, d, J=8 Hz), 8.40 (1H, d, J=8 Hz), 8.68 (1H, d, J=3 Hz)

Preparation 56

The following compounds were obtained according to a similar manner to that of Example 26.

1) 3-Methoxy-4-methoxycarbonyl-N-methyl-N-[4-methyl-2-(4-aminobut-1-yloxy)]phenylbenzamide 2) 3-Methoxy-N-methyl-4-nitro-N-[2-(5-tert-butoxycarbonyl-aminopent-1-yl)oxy-4-methyl]phenylbenzamide NMR (CDCl$_3$, δ):1.44 (9H, s), 1.47–1.68 (4H, m), 1.73–1.87 (2H, m), 2.29 (3H, s), 3.10–3.18 (2H, m), 3.31 (3H, s), 3.79 (3H, s), 3.84–3.95 (2H, m), 6.58–6.62 (2H, m), 6.88 (1H, d, J=8 Hz), 6.95 (1H, d, J=8 Hz), 7.09 (1H, s), 7.62 (1H, d, J=8 Hz)

3) Ethyl 2-aminomethyl-1-methyl-1H-benzimidazole-4-carboxylate

NMR (CDCl$_3$, δ):1.45 (3H, t, J=7.5 Hz), 3.84 (3H, s), 4.20 (2H, s), 4.49 (2H, q, J=7.5 Hz), 7.31 (1H, t, J=8 Hz), 7.51 (1H, d, J=8 Hz), 7.93 (1H, d, J=8 Hz)

4) Ethyl 2-aminomethyl-3-methyl-3H-benzimidazole-4-carboxylate

NMR (CDCl$_3$, δ):1.43 (3H, t, J=7.5 Hz), 3.93 (3H, s), 4.15 (2H, s), 4.43 (2H, q, J=7.5 Hz), 7.25 (1H, t, J=8 Hz), 7.76 (1H, d, J=8 Hz), 7.90 (1H, d, J=8 Hz)

Preparation 57

The following compounds were obtained according to a similar manner to that of Example 30.

1) Methyl 2-carbamoyl-1H-benzimidazole-4-carboxylate

NMR (DMSO-$d_6$, δ):3.94 (3H, s), 7.36 (1H, t, J=8 Hz), 7.82–7.92 (2H, m), 7.97 (1H, d, J=8 Hz), 8.26 (1H, br s)

2) Methyl 2-(N,N-dimethylcarbamoyl)-1H-benzimidazole-4-carboxylate

NMR (CDCl$_3$, δ):3.21 (3H, s), 3.80 (3H, s), 4.02 (3H, s), 7.38 (1H, t, J=8 Hz), 8.04 (2H, d, J=8 Hz)

3) 2-(N,N-Dimethylcarbamoyl)-4-nitro-1H-benzimidazole

NMR (DMSO-$d_6$, δ):3.10 (3H, s), 3.33 (3H, s), 7.51 (3H, t, J=8 Hz), 8.09–8.25 (2H, m)

Preparation 58

To a suspension of 3-formylindole-4-carboxylic acid (390 mg) and potassium carbonate (285 mg) in N,N-dimethylformamide (10 ml) was added benzyl bromide (353 mg) at ambient temperature and the mixture was stirred for 4 hours. The resulting mixture was diluted with ethyl acetate and water, then the layers were separated. The organic layer was washed with brine, dried over magnesium sulfate and concentrated in vacuo. The residual solid was triturated with diethyl ether:n-hexane (1:6) to give benzyl 3-formylindole-4-carboxylate (520 mg).

NMR (DMSO-$d_6$, δ):5.37 (2H, s), 7.28–7.48 (7H, m), 7.62 (1H, d, J=8 Hz), 7.75 (1H, d, J=8 Hz), 8.36 (1H, s), 10.22 (1H, s)

Preparation 59

The following compounds were obtained according to a similar manner to that of Preparation 58.

1) Benzyl 2-hydroxymethylindole-4-carboxylate
NMR (CDCl$_3$, δ):4.88 (1H, d, J=6 Hz), 5.44 (2H, s), 7.03 (1H, s), 7.22 (1H, t, J=8 Hz), 7.32–7.43 (3H, m), 7.47–7.52 (2H, m), 7.56 (1H, d, J=8 Hz), 7.94 (1H, d, J=8 Hz), 8.52–8.58 (1H, br)

2) Benzyl 2-methylindole-4-carboxylate
NMR (CDCl$_3$, δ):2.48 (3H, s), 5.44 (2H, s), 6.88 (1H, s), 7.13 (1H, t, J=8 Hz), 7.30–7.52 (6H, m), 7.90 (1H, d, J=8 Hz), 8.03–8.10 (1H, br)

Preparation 60

To a solution of benzyl 1-tert-butoxycarbonyl-3-formylindole-4-carboxylate (363 mg) in methanol (15 ml) was added sodium borohydride (109 mg) at 0° C. and the mixture was stirred for 5 minutes. The resulting mixture was diluted with water and the solution was neutralized with 1N hydrochloric acid. The solution was extracted with ethyl acetate, and then the organic solution was washed successively with saturated sodium bicarbonate aqueous solution and brine, dried over magnesium sulfate and concentrated in vacuo to afford benzyl 1-tert-butoxycarbonyl-3-hydroxymethylindole-4-carboxylate (365 mg).

NMR (CDCl$_3$, δ):1.67 (9H, s), 4.11 (1H, t, J=8 Hz), 4.72 (2H, d, J=8 Hz), 5.43 (2H, s), 7.30–7.51 (6H, m), 7.71 (1H, s), 7.92 (1H, d, J=8 Hz), 8.49 (1H, d, J=8 Hz)

Preparation 61

The following compound was obtained according to a similar manner to that of Preparation 60.

Benzyl 1-tert-butoxycarbonyl-2-hydroxymethylindole-4-carboxylate
NMR (CDCl$_3$, δ):1.73 (9H, s), 3.58 (1H, t, J=9 Hz), 4.82 (2H, d, J=9 Hz), 5.42 (2H, s), 7.30–7.42 (5H, m), 7.47–7.50 (2H, m), 8.00 (1H, d, J=8 Hz), 8.22 (1H, d, J=8 Hz)

Preparation 62

To a solution of 3-methoxy-4-methoxycarbonylbenzoic acid (800 mg) in dichloromethane (15 ml) was added oxalyl chloride (0.664 ml) and 1 drop of N,N-dimethylformamide and the mixture was stirred at ambient temperature for 2 hours. After being removed a solvent by evaporation, residual acid chloride in dichloromethane (5 ml) was added to a mixture of 2-[4,4-dimethyl(2,5-oxazolinyl)]phenylamine (724 mg) and triethylamine (770 mg) in dichloromethane (15 ml) at 0° C. and the mixture was stirred at ambient temperature for 2 hours. After being removed a solvent by evaporation, the residue was diluted with ethyl acetate and washed successively with 1N hydrochloric acid, saturated aqueous sodium hydrogencarbonate and brine and dried over sodium sulfate. The solvent was removed by rotary evaporation to give N-[2-[4,4-dimethyl (2,5-oxazolinyl)]phenyl]-3-methoxy-4-methoxycarbonylbenzamide (1.46 g).

NMR (CDCl$_3$, δ):1.44 (6H, s), 3.94 (3H, s), 4.01 (3H, s), 4.12 (3H, s), 7.16 (1H, dd, J=8, 8 Hz), 7.53 (1H, dd, J=8, 8 Hz), 7.72 (1H, d, J=8 Hz), 7.78 (1H, s), 7.85–7.94 (2H, m), 8.92 (1H, d, J=8 Hz)

Preparation 63

The following compounds were obtained according to a similar manner to that of Preparation 62.

1) N-[2-[4,4-Dimethyl(2,5-oxazolinyl)]phenyl]-3-methoxy-4-nitrobenzamide
NMR (CDCl$_3$, δ):1.43 (6H, s), 4.08 (3H, s), 4.13 (2H, s), 7.18 (1H, dd, J=8 Hz), 7.56 (1H, dd, J=8, 8 Hz), 7.78 (1H, d, J=8 Hz), 7.86–8.00 (3H, m), 8.91 (1H, d, J=8 Hz)

2) 3-Methoxy-4-methoxycarbonyl-N-[2-(morpholin-4-yl)phenyl]benzamide
NMR (CDCl$_3$, δ):2.87–2.98 (4H, m), 3.82–3.90 (4H, m), 3.91 (3H, s), 4.00 (3H s), 7.09–7.18 (1H, m), 7.20–7.30 (1H, m), 7.39 (1H, d, J=8 Hz), 7.66 (1H, s), 7.92 (1H, d, J=8 Hz), 8.54 (1H, d, J=8 Hz), 9.58 (1H, s)

3) 3-Methoxy-N-[2-(morpholin-4-yl)phenyl]-4-nitrobenzamide
NMR (CDCl$_3$, δ):2.88–3.08 (4H, br), 3.82–3.99 (4H, br), 4.08 (3H, s), 7.12–7.36 (3H, m), 7.46 (1H, m), 7.82 (1H, s), 7.97 (1H, d, J=8 Hz), 8.48 (1H, m)

4) 3-Methoxy-4-methoxycarbonyl-N-[2-(1-pyrrolyl)phenyl]-benzamide
NMR (CDCl$_3$, δ):3.90 (3H, s), 3.92 (3H, s), 642–6.49 (2H, m), 6.82–6.90 (2H, m), 7.04–7.12 (1H, m), 7.18–7.32 (2H, m), 7.39 (1H, d, J=8 Hz), 7.48 (1H, dd, J=8, 8 Hz), 7.70–7.83 (2H, m), 8.62 (1H, d, J=8 Hz)

5) 3-Methoxy-4-methoxycarbonyl-N-(2-piperidinophenyl)-benzamide
NMR (CDCl$_3$, δ):1.54–1.81 (6H, m), 2.79–2.90 (4H, m), 3.92 (3H, s), 4.01 (3H, s), 7.04–7.15 (1H, m), 7.20 (1H, dd, J=8, 8 Hz), 7.42 (1H, d, J=8 Hz), 7.66 (3H, s), 7.93 (1H, d, J=8 Hz), 8.54 (1H, d, J=8 Hz), 9.68 (1H, s)

6) 3-Methoxy-4-nitro-N-(2-piperidinophenyl)benzamide
NMR (CDCl$_3$, δ):1.56–1.82 (6H, m), 2.78–2.92 (4H, m), 4.06 (3H, s), 7.08–7.29 (3H, m), 7.44 (1H, m), 7.77 (1H, s), 7.97 (1H, d, J=8 Hz), 8.51 (1H, d, J=8 Hz), 9.71 (1H, s)

7) 3-Methoxy-4-methoxycarbonyl-N-[2-(4-methyl-1-piperazinyl)phenyl]benzamide
NMR (CDCl$_3$, δ):2.38 (3H, s), 2.48–2.79 (4H, br), 2.91–3.02 (4H, m), 3.94 (3H, s), 4.02 (3H, s), 7.11 (1H, dd, J=8, 8 Hz), 7.18–7.30 (2H, m), 7.42 (1H, d, J=8 Hz), 7.65 (1H, s), 7.92 (1H, d, J=8 Hz), 8.54 (1H, d, J=8 Hz), 9.58 (1H, s)

8) 3-Methoxy-N-[2-(4-methyl-1-piperazinyl)phenyl]-4-nitrobenzamide
NMR (CDCl$_3$, δ):2.42 (3H, s), 2.53–2.80 (4H, m), 2.92–3.06 (4H, m), 4.07 (3H, s), 7.11–7.20 (1H, m), 7.21–7.32 (2H, m), 7.45 (1H, m), 7.79 (1H, s), 7.98 (1H, d, J=8 Hz), 8.52 (1H, d, J=8 Hz)

9) 3-Methoxy-4-methoxycarbonyl-N-[2-(2,5-oxazolyl)phenyl]-benzamide
NMR (CDCl$_3$, δ):1.63 (1H, br s), 3.94 (3H, s), 4.04 (3H, s), 7.22 (1H, dd, J=8, 8 Hz), 7.31 (1H, s), 7.53 (1H, m), 7.72–7.82 (3H, m), 7.94 (1H, d, J=8 Hz), 8.09 (1H, m), 8.98 (1H, d, J=8 Hz)

10) 3-Methoxy-4-methoxycarbonyl-N-[2-(2,5-oxazolinyl)-phenyl]benzamide
NMR (CDCl$_3$, δ):3.92 (3H, s), 4.02 (3H, s), 4.20 (9H, t, J=8 Hz), 4.44 (9H, t, J=8 Hz), 7.14 (1H, dd, J=8, 8 Hz), 7.54 (1H, dd, J=8, 8 Hz), 7.69 (1H, d, J=8 Hz), 7.75 (1H, s), 7.87–7.96 (2H, m), 8.95 (1H, d, J=8 Hz)

11) 3-Methoxy-4-methoxycarbonyl-N-[2-(3H,4H,5H-2,6-oxazinyl)phenyl]benzamide
NMR (CDCl$_3$, δ):1.98–2.11 (2H, m), 3.71 (2H, t, J=7 Hz), 3.93 (3H, s), 4.00 (3H, s), 4.43 (2H, t, J=7 Hz), 7.09 (1H, dd, J=8, 8 Hz), 7.47 (1H, dd, J=8, 8 Hz), 7.56 (1H, d, J=8 Hz), 7.70 (1H, s), 7.89 (1H, d, J=8 Hz), 7.93 (1H, d, J=8 Hz), 8.89 (1H, d, J=8 Hz)

12) N-[2-(1-Aza-3-oxaspiro[4.4]non-1-en-2-yl)phenyl]-3-methoxy-4-methoxycarbonylbenzamide
NMR (CDCl$_3$, δ): 1.70–1.84 (4H, m), 1.85–2.09 (4H, m), 3.93 (3H, s), 4.00 (3H, s), 4.26 (2H, s), 7.15 (1H, dd, J=8, 8 Hz), 7.52 (1H, dd, J=8, 8 Hz), 7.69 (1H, d, J=8 Hz), 7.77 (1H, s), 7.84 (1H, d, J=8 Hz), 7.91 (1H, d, J=8 Hz), 8.94 (1H, d, J=8 Hz)

Preparation 64

To a solution of N-[2-[4,4-dimethyl(2,5-oxazolinyl)]-phenyl]-3-methoxy-4-methoxycarbonylbenzamide (1.45 g)

in N,N-dimethylformamide (18 ml) was added portionwise sodium hydride (167 mg) at 0° C. and the mixture was stirred at 0° C. for 30 minutes. Methyl iodide (0.283 ml) was added to the mixture and the solution was stirred at 0° C. for 1 hour. The reaction was quenched with water and then the aqueous solution was extracted with ethyl acetate. The organic layer was washed with brine and dried over sodium sulfate. The solvent was evaporated in vacuo to give N-[2-[4,4-dimethyl-(2,5-oxazolinyl)]phenyl]-N-methyl-3-methoxy-4-methoxycarbonylbenzamide (1.5 g).

NMR (CDCl$_3$, δ): 1.35 (3H, s), 1.36 (3H, s), 3.33 (3H, s), 3.63 (3H, s), 4.00–4.14 (2H, m), 6.93–7.09 (3H, m), 7.18–7.36 (2H, m), 7.57 (1H, d, J=8 Hz), 7.78 (1H, d, J=8 Hz)

Preparation 65

The following compounds were obtained according to a similar manner to that of Preparation 64.

1) N-[2-[4,4-Dimethyl(2,5-oxazolinyl)]phenyl]-N-methyl-3-methoxy-4-nitrobenzamide NMR (CDCl$_3$, δ): 1.38 (3H, s), 1.39 (3H, s), 3.35 (3H, s), 3.71 (3H, s), 4.02–4.16 (2H, m), 7.00–7.10 (2H, m), 7.21 (1H, s), 7.23–7.39 (2H, m), 7.63 (1H, d, J=8 Hz), 7.80 (1H, m)

2) 3-Methoxy-4-methoxycarbonyl-N-methyl-N-[2-(morpholin-4-yl)phenyl]benzamide

NMR (CDCl$_3$, δ): 2.32–2.48 (2H, m), 2.78–2.91 (2H, m), 3.50 (3H, s), 3.61 (3H, s), 3.62–3.80 (4H, m), 3.82 (3H, s), 6.86 (1H, d, J=8 Hz), 6.91 (1H, s), 7.02–7.32 (4H, m), 7.59 (1H, d, J=8 Hz)

3) 3-Methoxy-N-methyl-N-[2-(morpholin-4-yl)phenyl]-4-nitrobenzamide

NMR (CDCl$_3$, δ): 2.28–2.45 (2H, m), 2.77–2.92 (2H, m), 3.50 (3H, s), 3.57–3.82 (7H, m), 6.87 (1H, d, J=8 Hz), 7.02 (1H, s), 7.04–7.18 (2H, m), 7.19–7.33 (2H, m), 7.61 (1H, d, J=8 Hz)

4) 3-Methoxy-4-methoxycarbonyl-N-methyl-N-[2-(1-pyrrolyl)phenyl]benzamide

NMR (CDCl$_3$, δ): 3.43 (3H, s), 3.66 (3H, s), 3.81 (3H, s), 6.25 (2H, s), 6.38–6.51 (3H, m), 6.56 (1H, s), 7.12 (1H, m), 7.21–7.51 (4H, m)

5) 3-Methoxy-4-methoxycarbonyl-N-methyl-N-(2-piperidinophenyl)benzamide

NMR (CDCl$_3$, δ): 1.43–1.72 (6H, m), 2.29–2.44 (2H, m), 2.70–2.84 (2H, m), 3.50 (3H, s), 3.60 (3H, s), 3.81 (3H, s), 6.84 (1H, d, J=8 Hz), 6.90 (1H, s), 6.98–7.09 (2H, m), 7.15 (1H, dd, J=8, 8 Hz), 7.22 (1H, d, J=8 Hz), 7.59 (1H, d, J=8 Hz)

6) 3-Methoxy-N-methyl-4-nitro-N-(2-piperidinophenyl)-benzamide

NMR (CDCl$_3$, δ): 1.42–1.76 (6H, m), 2.23–2.41 (2H, m), 2.70–2.87 (2H, m), 3.53 (3H, s), 3.68 (3H, s), 6.87 (1H, d, J=8 Hz), 7.01 (1H, s), 7.03–7.14 (2H, m), 7.20 (1H, dd, J=8, 8 Hz), 7.27 (1H, m), 7.64 (1H, d, J=8 Hz)

7) N-Methyl-3-methoxy-4-methoxycarbonyl-N-[2-(4-methyl-1-piperazinyl)phenyl]benzamide NMR (CDCl$_3$, δ): 2.34 (3H, s), 2.39–2.61 (6H, m), 2.82–2.99 (2H, m), 3.49 (3H, s), 3.61 (3H, s), 3.82 (3H, s), 6.81–6.93 (2H, m), 7.00–7.11 (2H, m), 7.12–7.29 (2H, m), 7.60 (1H, d, J=8 Hz)

8) N-Methyl-3-methoxy-N-[2-(4-methyl-1-piperazinyl)phenyl]-4-nitrobenzamide

NMR (CDCl$_3$, δ): 2.34 (3H, s), 2.35–2.62 (6H, m), 2.85–3.00 (2H, m), 3.52 (3H, s), 3.68 (3H, s), 6.89 (1H, d, J=8 Hz), 7.01 (1H, s), 7.04–7.32 (4H, m), 7.64 (1H, d, J=8 Hz)

9) 3-Methoxy-4-methoxycarbonyl-N-methyl-N-[2-(2,5-oxazolyl)phenyl]benzamide

NMR (CDCl$_3$, δ): 3.45 (3H, s), 3.60 (3H, s), 3.80 (3H, s), 6.69 (1H, d, J=8 Hz), 6.72 (1H, s), 7.22–7.42 (4H, m), 7.48 (1H, d, J=8 Hz), 7.76 (1H, s), 7.89 (1H, d, J=8 Hz)

10) N-Methyl-3-methoxy-4-methoxycarbonyl-N-[2-(2,5-oxazolinyl)phenyl]benzamide

NMR (CDCl$_3$, δ): 3.40 (3H, s), 3.67 (3H, s), 3.81 (3H, s), 4.02–4.12 (2H, m), 4.30–4.46 (2H, m), 6.88–6.98 (2H, m), 7.12 (1H, d, J=8 Hz), 7.24 (1H, dd, J=8, 8 Hz), 7.35 (H, dd, J=8, 8 Hz), 7.57 (1H, d, J=8 Hz), 7.76 (1H, d, J=8 Hz)

11) N-Methyl-3-methoxy-4-methoxycarbonyl-N-[2-(3H,4H,5H-2,6-oxazinyl)phenyl]benzamide NMR (CDCl$_3$, δ): 1.92–2.08 (2H, m), 3.40 (3H, s), 3.58 (2H, t, J=7 Hz), 3.64 (3H, s), 3.82 (3H, s), 4.27–4.40 (2H, m), 6.93–7.00 (1H, m), 7.01–7.09 (2H, m), 7.16–7.28 (2H, m), 7.51–7.65 (2H, m)

12) N-[2-(1-Aza-3-oxaspiro[4.4]non-1-en-2-yl)phenyl]-3-methoxy-4-methoxycarbonyl-N-methylbenzamide NMR (CDCl$_3$, δ): 1.59–1.77 (4H, m), 1.80–2.05 (4H, m), 3.36 (3H, s), 3.65 (3H, s), 3.80 (3H, s), 4.15–4.27 (2H, m), 6.93–7.03 (2H, m), 7.06 (1H, d, J=8 Hz), 7.18–7.35 (2H, m), 7.58 (1H, d, J=8 Hz), 7.75 (1H, m)

Preparation 66

To a solution of 2-(1-pyrrolyl)nitrobenzene (1.11 g) in ethanol (30 ml) were added iron powder (1.65 g) and acetic acid (3.54 g) and the mixture was refluxed for 1 hour. The reaction mixture was filtered through a bed of celite and the filtrate was concentrated in vacuo. The residue was diluted with a mixture of ethyl acetate and saturated aqueous sodium bicarbonate solution and the mixture was filtered through a bed of celite again. The organic layer was separated and washed with water and brine. The solution was dried over sodium sulfate and the solvent was evaporated in vacuo to give 2-(1-pyrrolyl)phenylamine (860 mg).

NMR (CDCl$_3$, δ): 3.72 (2H, br s), 6.31–6.40 (2H, m), 6.72–6.90 (4H, m), 7.10–7.24 (2H, m)

Preparation 67

The following compounds were obtained according to a similar manner to that of Preparation 66.

1) 4-Amino-3-methoxy-N-methyl-N-(2-piperidinophenyl)-benzamide

NMR (CDCl$_3$, δ): 1.43–1.71 (6H, m), 2.54–2.68 (2H, m), 2.71–2.86 (2H, m), 3.46 (3H, s), 3.57 (3H, s), 3.86 (2H, s), 6.41 (1H, d, J=8 Hz), 6.83 (1H, s), 6.86–7.00 (3H, m), 7.07–7.19 (2H, m)

2) 4-Amino-N-methyl-3-methoxy-N-[2-(4-methyl-1-piperazinyl)phenyl]benzamide

NMR (CDCl$_3$, δ): 2.35 (3H, s), 2.41–2.61 (4H, m), 2.66–2.80 (2H, m), 2.84–3.00 (2H, m), 3.46 (3H, s), 3.58 (3H, s), 3.88 (2H, s), 6.42 (1H, d, J=8 Hz), 6.82 (1H, s), 6.86–7.06 (3H, m), 7.09–7.21 (2H, m)

3) 2-(2,5-Oxazolinyl)phenylamine

NMR (CDCl$_3$, δ): 4.10 (2H, t, J=8 Hz), 4.34 (2H, t, J=8 Hz), 6.60–6.76 (2H, m), 7.20 (1H, dd, J=8, 8 Hz), 7.71 (1H, d, J=8 Hz)

4) 2-(3H,4H,5H-2,6-Oxazinyl)phenylamine

NMR (CDCl$_3$, δ): 1.91–2.02 (2H, m), 3.63 (2H, t, J=7 Hz), 4.35 (2H, t, J=7 Hz), 6.20 (2H, br s), 6.56–6.68 (2H, m), 7.12 (1H, dd, J=8, 8 Hz), 7.70 (1H, d, J=8 Hz)

5) 4-Amino-2-(N,N-dimethylcarbamoyl)-1H-benzimidazole

NMR (DMSO-d$_6$, δ): 3.06 (3H×3/5, s), 3.09 (3H×2/5, s), 3.65 (3H×3/5, s), 3.19 (3H×2/5, s), 5.35 (2H×3/5, s), 5.48 (2H×2/5, s), 6.36 (1H×3/5, d, J=8 Hz), 6.45 (1H×2/5, d, J=8

Hz), 6.66 (1H×3/5, d, J=8 Hz), 6.88–7.02 (1H+1H×2/5, m), 7.15 (1H, br peak)

Preparation 68

To a solution of 3-nitro-1,2-phenylenediamine (1.0 g) and triethylamine (793 mg) in dichloromethane (3 ml) under nitrogen was added portionwise phthalyglycyl chloride (1.61 g) in ice water bath and the mixture was stirred at the same temperature for 2 hours. The reaction mixture was washed with saturated sodium bicarbonate aqueous solution, dried over magnesium sulfate and evaporated in vacuo. To the resulting crude product was added polyphosphoric acid (5 ml) and stirred at 130° C. for 3 hours. After the mixture was cooled at ambient temperature, ammonia solution (28%) was added to the reaction mixture in ice water bath. The precipitate was collected by vacuum filtration to give 2-phthalimidomethyl-4-nitro-1H-benzimidazole (1.35 g).

NMR (DMSO-$d_6$, δ): 5.13 (2H, s), 7.36 (1H, t, J=8 Hz), 7.86–8.05 (5H, m), 8.11 (1H, d, J=8 Hz)

Preparation 69

The following compound was obtained according to a similar manner to that of Preparation 68.

4-Nitro-2-(2-phthalimidoethyl)-1H-benzimidazole

NMR (DMSO-$d_6$, δ): 3,28 (2H, t, J=7.5 Hz), 4.05 (2H, t, J=7.5 Hz), 7.34 (1H, t, J=8 Hz), 7.78–7.90 (4H, m), 7.96 (1H, d, J=8 Hz), 8.08 (1H, d, J=8 Hz)

Preparation 70

To a solution of 2-chloro-4-nitro-1H-benzimidazole (300 mg) in N-methyl-2-pyrrolidone (4 ml) was added imidazole (517 mg) and the mixture was stirred at 80° C. for 8 hours. The reaction mixture was poured into brine and extracted with a mixture of chloroform and methanol. The organic layer was dried over magnesium sulfate and evaporated in vacuo. The residue was chromatographed on silica gel eluting with a mixture of chloroform and methanol (100-0-30-1) to give 2-(1-imidazolyl)-4-nitro-1H-benzimidazole (175 mg).

NMR (DMSO-$d_6$, δ): 7.21 (1H, s), 7.46 (1H, t, J=8 Hz), 8.05–8.19 (3H, m), 8.70 (1H, s)

Preparation 71

The following compound was obtained according to a similar manner to that of Preparation 70.

4-Nitro-2-(1,2,4-tetrazol-1-yl)-1H-benzimidazole

NMR (DMSO-$d_6$, δ): 7.50 (1H, t, J=8 Hz), 8.06 (1H, br peak), 8.17 (1H, d, J=8 Hz), 8.50 (1H, s), 9.53 (1H, s)

Preparation 72

A mixture of 2-chloro-4-nitro-1H-benzimidazole (300 mg) and N,N-dimethylethylenediamine (2 ml) were stirred at 80° C. for 8 hours. The reaction mixture was poured into saturated sodium bicarbonate aqueous solution and extracted with a mixture of chloroform and methanol. The organic layer was washed with brine, dried over magnesium sulfate and evaporated in vacuo. The resiude was washed with diisopropyl ether to give 2-[[2-(dimethylamino)ethyl]amino]-4-nitro-1H-benzimidazole (113 mg).

NMR (CDCl$_3$, δ): 2.65 (3H, s), 2.90–2.98 (2H, m), 3.55–3.64 (2H, m), 7.11 (1H, t, J=8 Hz), 7.69 (1H, d, J=8 Hz), 7.87 (1H, d, J=8 Hz)

Preparation 73

The following compounds were obtained according to a similar manner to that of Preparation 72.

1) 2-(4-Methylpiperazin-1-yl)-4-nitro-1H-benzimidazole

NMR (CDCl$_3$, δ): 2.42 (3H, s), 2.58–2.72 (4H, m), 3.63–3.80 (4H, m), 7.19 (1H, t, J=8 Hz), 7.68 (1H, d, J=8 Hz), 7.85 (1H, d, J=8 Hz), 9.44 (1H, br s)

2) 2-Dimethylamino-4-nitro-1H-benzimidazole

NMR (CDCl$_3$, δ): 3.30 (6H, s), 7.21 (1H, t, J=8 Hz), 7.76 (1H, d, J=8 Hz), 7.86 (1H, d, J=8 Hz)

3) 2-[(2-Aminoethyl)methylamino]-4-nitro-1H-benzimidazole

NMR (CDCl$_3$, δ): 3.09 (2H, t, J=5 Hz), 3.26 (3H, s), 3.60 (2H, t, J=5 Hz), 7.15 (1H, t, J=8 Hz), 7.61 (1H, d, J=8 Hz), 7.83 (1H, d, J=8 Hz)

4) 2-[(2-Methylamino)ethyl]amino-4-nitro-1H-benzimidazole

NMR (CDCl$_3$, δ): 2.68 (3H, s), 3.09 (2H, t-like, J=5 Hz), 3.59 (2H, t-like, J=5 Hz), 7.02 (1H, t, J=8 Hz), 7.51 (1H, d, J=8 Hz), 7.74 (1H, d, J=8 Hz)

5) 2-[[2-(Dimethylamino)ethyl]methylamino]-4-nitro-1H-benzimidazole

NMR (CDCl$_3$, δ): 2.58 (6H, s), 2.81–2.91 (2H, m), 3.34 (3H, s), 3.50–3.60 (2H, m), 7.09 (1H, t, J=8 Hz), 7.70 (1H, d, J=8 Hz), 7.83 (1H, d, J=8 Hz)

6) 2-[(2-Methoxyethyl)amino]-4-nitro-1H-benzimidazole

NMR (CDCl$_3$, δ): 3.50 (3H, s), 3.60–3.71 (4H, m), 5.60 (1H, br peak), 7.15 (1H, t, J=8 Hz), 7.63 (1H, d, J=8 Hz), 7.83 (1H, d, J=8 Hz)

Preparation 74

To a solution of ethyl 2-chloromethyl-1H-benzimidazole-4-carboxylate (250 mg) in dichloroethane (2.5 ml) was added morpholine (183 mg) under ice bath cooling and the reaction mixture was stirred at ambient temperature for 15 hours. To the reaction mixture was added morpholine (91 mg) and stirred at 80° C. for 6 hours. After the reaction mixture was concentrated in vacuo, the residue was diluted with chloroform and saturated sodium hydrogen carbonate aqueous solution. The organic layer was separated and washed with brine. The solution was dried over magnesium sulfate and concentrated in vacuo. The residue was purified by silica gel column chromatography (methanol:chloroform=1:9) to give ethyl-2-morpholinomethyl-1H-benzimidazole-4-carboxylate (219 mg).

NMR (CDCl$_3$, δ): 1.47 (3H, t, J=7 Hz), 2.57–2.60 (4H, m), 3.75–3.77 (4H, m), 3.86 (2H, s), 4.47 (2H, q, J=8 Hz), 7.28 (1H, t, J=8 Hz), 7.90 (1H, d, J=8 Hz), 7.91 (1H, d, J=8 Hz)

Preparation 75

The following compounds were obtained according to a similar manner to that of Preparation 74.

1) 2-(N,N-Dimethylaminomethyl)-4-nitro-1H-benzimidazole

NMR (CDCl$_3$, δ): 2.36 (6H, s), 3.81 (2H, s), 7.35 (1H, t, J=8 Hz), 8.03 (1H, d, J=8 Hz), 8.15 (1H, d, J=8 Hz)

2) 2-(1-Imidazolyl)methyl-4-nitro-1H-benzimidazole

NMR (DMSO-$d_6$, δ): 5.53 (2H, s), 6.91 (1H, s), 7.28 (1H, s), 7.40 (1H, t, J=8 Hz), 7.80 (1H, s), 8.08 (1H, d, J=8 Hz), 8.14 (1H, d, J=8 Hz)

3) 2-[(4-Methylpiperazin-1-yl)methyl]-4-nitro-1H-benzimidazole

NMR (CDCl$_3$, δ): 2.40 (3H, s), 2.49–2.82 (8H, m), 3.91 (2H, s), 7.35 (1H, t, J=8 Hz), 8.04 (1H, d, J=8 Hz), 8.16 (1H, d, J=8 Hz)

4) 2-Morpholin-4-ylmethyl)-4-nitro-1H-benzimidazole

NMR (CDCl$_3$, δ): 2.55–2.69 (4H, m), 3.73–3.85 (4H, m), 3.89 (2H, s), 7.35 (1H, t, J=8 Hz), 8.05 (1H, d, J=8 Hz), 8.15 (1H, d, J=8 Hz)

5) 4-Nitro-2-(pyrrolidin-1-ylmethyl)-1H-benzimidazole

NMR (CDCl$_3$, δ): 1.96 (4H, br s), 2.86 (4H, br s), 4.19 (2H, s), 7.36 (1H, t, J=8 Hz), 8.03 (1H, d, J=8 Hz), 8.16 (1H, d, J=8 Hz)

6) 4-Nitro-2-(piperidinomethyl)-1H-benzimidazole

NMR (CDCl$_3$, δ): 1.58 (2H, br peak), 1.73 (4H, br peak), 2.65 (4H, br peak), 4.00 (2H, br s), 7.36 (1H, t, J=8 Hz), 8.03 (1H, d, J=8 Hz), 8.17 (1H, d, J=8 Hz)

7) 2-[2-(Dimethylamino)ethyl]-4-nitro-1H-benzimidazole

NMR (CDCl$_3$, δ): 2.50 (6H, s), 2.83 (2H, t, J=7 Hz), 3.18 (2H, t, J=8 Hz), 7.30 (1H, t, J=8 Hz), 8.00 (1H, d, J=8 Hz), 8.11 (1H, d, J=8 Hz)

8) 2-[2-(4-Methylpiperazin-1-yl)ethyl]-4-nitro-1H-benzimidazole

NMR (CDCl$_3$, δ): 2.41 (3H, s), 2.70 (8H, br peak), 2.89 (2H, t, J=5 Hz), 3.18 (2H, t, J=5 Hz), 7.32 (1H, t, J=8 Hz), 8.01 (1H, d, J=8 Hz), 8.13 (1H, d, J=8 Hz)

9) Ethyl 2-dimethylaminomethyl-1H-benzimidazole-4-carboxylate

NMR (CDCl$_3$, δ): 1.44 (3H, t, J=7 Hz), 2.33 (6H, s), 3.77 (2H, s), 4.45 (2H, q, J=7 Hz), 7.27 (1H, t, J=8 Hz), 7.88–7.92 (2H, m)

10) Ethyl 2-(4-methylpiperazin-1-yl)methyl-1H-benzimidazole-4-carboxylate

NMR (CDCl$_3$, δ): 1.47 (3H, t, J=7 Hz), 2.51 (4H, br s), 2.62 (4H, br s), 3.86 (2H, s), 4.47 (2H, q, J=8 Hz), 7.26 (1H, t, J=8 Hz), 7.90 (2H, d, J=8 Hz)

11) Ethyl 2-(4-dimethylaminopiperidino)methyl-1H-benzimidazole-4-carboxylate

NMR (CDCl$_3$, δ): 1.46 (3H, t, J=7 Hz), 1.61 (2H, dt, J=2, 8 Hz), 1.82 (1H, br s), 2.12–2.23 (4H, m), 2.28 (6H, s), 2.92–2.98 (2H, m), 3.82 (2H, s), 4.48 (2H, q, J=7 Hz), 7.28 (1H, t, J=8 Hz), 7.89 (2H, d, J=8 Hz)

Preparation 76

A suspension of 2-methyl-4-nitrobenzimidazole (2.2 g) in 1,4-dioxane (35 ml) was treated with triethylamine (2.51 g) and di-tert-butyl dicarbonate (5.42 g). After 15 minutes, to the reaction mixture was added N,N-dimethylaminopyridine (catalytic amount). The solution was stirred a further 20 hours and concentrated in vacuo and the residue was dissolved in ethyl acetate. The solution was washed with 1N hydrochloric acid, water, saturated aqueous sodium hydrogen carbonate and brine. The organic layer was dried over magnesium sulfate. The solvent was evaporated in vacuo and the residue was purified by silica gel column chromatography (chloroform) to give tert-butyl 2-methyl-4-nitro-1H-benzimidazole-1-carboxylate (3.0 g).

NMR (CDCl$_3$, δ): 1.73 (9H, s), 2.93 (3H, s), 7.41 (1H, dd, J=8, 8 Hz), 8.13 (1H, d, J=8 Hz), 8.29 (1H, d, J=8 Hz)

Preparation 77

The following compounds were obtained according to a similar manner to that of Preparation 76.

1) Ethyl 2-(N-tert-butoxycarbonylaminomethyl)-1-methyl-1H-benzimidazole-4-carboxylate NMR (CDCl$_3$, δ): 1.40–1.50 (12H, m), 3.34 (3H, s), 4.49 (2H, q, J=7.5 Hz), 4.70 (2H, d, J=7 Hz), 5.48 (1H, br peak), 7.33 (1H, t, J=8 Hz), 7.53 (1H, d, J=8 Hz), 7.94 (1H, d, J=8 Hz)

2) Ethyl 2-(N-tert-butoxycarbonylaminomethyl)-3-methyl-3H-benzimidazole-4-carboxylate NMR (CDCl$_3$, δ): 1.44 (3H, t, J=7.5 Hz), 1.48 (9H, s), 3.93 (3H, s), 4.44 (2H, q, J=7.5 Hz), 4.64 (2H, d, J=5 Hz), 5.51 (1H, br peak), 7.25 (1H, t, J=8 Hz), 7.77 (1H, d, J=8 Hz), 7.88 (1H, d, J=8 Hz)

3) 2-[(tert-Butoxy)carbonylamino]-4-nitro-1H-benzimidazole

NMR (DMSO-d$_6$, δ): 1.68 (9H, s), 7.11 (1H, t, J=8 Hz), 7.84–8.00 (3H, m)

Preparation 78

To a solution of N-(2-chloroethyl)-2-nitrobenzamide (3.63 g) in acetonitrile (100 ml) was slowly added 40% potassium fluoride on alumina (10 g). This slurry was stirred at ambient temperature for 24 hours. The potassium fluoride on alumina was filtered through a bed of celite, washed with ethyl acetate. The solvent was evaporated to give 2-(2,5-oxazolinyl)nitrobenzene (3.0 g).

NMR (CDCl$_3$, δ): 4.09 (2H, t, J=8 Hz), 4.45 (2H, t, J=8 Hz), 7.58–7.69 (2H, m), 7.80–7.89 (2H, m)

Preparation 79

The following compound was obtained according to a similar manner to that of Preparation 78.

2-(2-Nitrophenyl)-4H,5H,6H-1,3-oxazine

NMR (CDCl$_3$, δ): 1.96–2.11 (2H, m), 3.56–3.68 (2H, m), 4.25–4.37 (2H, m), 7.54 (1H, dd, J=8, 8 Hz), 7.61 (1H, dd, J=8, 8 Hz), 7.71 (1H, d, J=8 Hz), 7.85 (1H, d, J=8 Hz)

Preparation 80

The following compound was obtained according to a similar manner to that of Example 84.

Benzyl 2-formylindole-4-carboxylate

NMR (DMSO-d$_6$, δ): 5.45 (2H, s), 7.30–7.55 (6H, m), 7.73–7.82 (2H, m), 7.88 (1H, d, J=8 Hz), 9.93 (1H, s)

Preparation 81

The following compound was obtained according to a similar manner to that of Example 107.

4-Methyl-1-(2-nitrophenyl)piperazine

NMR (CDCl$_3$, δ): 2.36 (3H, s), 2.52–2.61 (4H, m), 3.03–3.12 (4H, m), 7.03 (1H, dd, J=8, 8 Hz), 7.15 (1H, d, J=8 Hz), 7.48 (1H, dd, J=8, 8 Hz), 7.75 (1H, d, J=8 Hz)

Preparation 82

To a solution of indole-4-carboxylic acid (500 mg) in methanol (9 ml) and conc. hydrochloric acid (1.0 ml) was added a portion of sodium cyanoborohydride (487 mg) at 0° C. and the mixture was stirred at ambient temperature for 1 hour. The suspension was diluted with water (10 ml) and then the clear solution was neutralized with 2N sodium hydroxide aqueous solution. Methanol was removed and the aqueous solution was diluted with dioxane (15 ml) and 1N sodium hydroxide aqueous solution (10 ml). To the mixture was added portionwise di-tert-butyl dicarbonate (813 mg) and the solution was stirred at ambient temperature for 2 hours. The solution was neutralized with 1N hydrochloric acid and diluted with ethyl acetate (30 ml). The resulting solution was washed with brine, dried over magnesium sulfate and concentrated in vacuo. The solid was triturated with diethyl ether:n-hexane (1:9) to give 1-tert-butoxycarbonylindoline-4-carboxylic acid (727 mg).

NMR (DMSO-d$_6$, δ): 1.50 (9H, s), 3.36 (2H, t, J=9 Hz), 3.92 (2H, t, J=9 Hz), 7.27 (1H, t, J=8 Hz), 7.49 (1H, d, J=8 Hz), 7.80–7.94 (1H, br)

Preparation 83

To a solution of methyl trans-2-[β-(dimethylamino)vinyl]-3-nitrobenzoate (3.16 g) in tetrahydrofuran (20 ml)

and pyridine (3.57 ml) was added dropwise benzyloxyacetyl chloride (4.2 g) at ambient temperature and the mixture was refluxed for 3 hours. The resulting mixture was diluted with ethyl acetate and the solution was washed successively with water, saturated sodium bicarbonate aqueous solution and brine. Drying, filtering and removal of solvents afforded a crude product. The crude product was purified by column chromatography to give 2-[β-(dimethylamino)-α-(benzyloxyacetyl)vinyl]-3-nitrobenzoate (3.32 g).

NMR (CDCl$_3$, δ): 2.70–2.80 (6H, br s), 3.80 (3H, s), 4.08–4.16 (2H, br s), 4.50 and 4.51 (Total 2H, s), 7.28–7.38 (5H, m), 7.49 (1H, t, J=8 Hz), 7.79 (1H, d, J=8 Hz), 7.80 (1H, s), 7.89 (1H, d, J=8 Hz)

Preparation 84

A solution of 2-[β-(dimethylamino)-α-(benzyloxyacetyl)-vinyl]-3-nitrobenzoate (3.31 g) and p-toluenesulfonic acid hydrate (632 mg) in 1,4-dioxane (15 ml) and water (5 ml) was refluxed for 24 hours. The resulting mixture was evaporated in vacuo and the residue was diluted with ethyl acetate. The organic layer was washed successively with water and brine. Drying, filtering and removal of solvents afforded a crude product as a dark-red oil. The crude product was purified by silica gel column chromatography (eluent; hexane:ethyl acetate=3:1) to give 3-benzyloxymethyl-5-nitroisocoumarin (1.0 g).

NMR (CDCl$_3$, δ): 4.40 (2H, s), 4.69 (2H, s), 7.29–7.42 (5H, m), 7.43 (1H, s), 7.62 (1H, t, J=8 Hz), 8.47 (1H, d, J=8 Hz), 8.60 (1H, d, J=8 Hz),

Preparation 85

A solution of 3-benzyloxymethyl-5-nitroisocoumarin (850 mg) in methanol (40.0 ml) was treated with aqueous titanium trichloride (11.2 ml), added as a single portion. After stirring 2 hours at ambient temperature, water (100 ml) and chloroform (120 ml) was added. The whole was carefully basified with saturated sodium bicarbonate aqueous solution and the organic layer was separated. The aqueous layer was further extracted with chloroform (120 ml) and the combined extract was washed with water, dried over magnesium sulfate, and concentrated to afford 3-benzyloxymethyl-5-aminoisocoumarin (806 mg).

NMR (CDCl$_3$, δ): 3.89–4.00 (2H, br), 4.38 (2H, s), 4.69 (2H, s), 6.50 (1H, s), 7.01 (1H, d, J=9 Hz), 7.29 (1H, t, J=9 Hz), 7.30–7.40 (5H, m), 7.73 (1H, d, J=9 Hz)

Preparation 86

A mixture of 5-amino-3-benzyloxymethylisocoumarin (800 mg) and sodium methylate in methanol (768 mg) was stirred at ambient temperature for 20 minutes. After removal of solvents, water (40 ml) was added to the residue and the whole was extacted with chloroform. The extract was washed with water, dried over magnesium sulfate, and evaporated to dryness to leave a crude product, which was purified by silica gel column chromatography with n-hexane:ethyl acetate (6:1) as an eluent to afford methyl 2-benzyloxymethylindole-4-carboxylate (660 mg).

NMR (CDCl$_3$, δ): 3.98 (3H, s), 4.57 (2H, s), 4.78 (2H, s), 7.08 (1H, s), 7.22 (1H, t, J=8 Hz), 7.29–7.39 (5H, m), 7.54 (1H, d, J=8 Hz), 7.90 (1H, d, J=8 Hz), 8.50–8.56 (1H, br)

Preparation 87

To a solution of methyl 2-benzyloxymethylindole-4-carboxylate (650 mg) in methanol (27 ml) and concentrated hydrochloric acid (3.0 ml) was added sodium cyanoborohydride (968 mg) with ice-bath stirring and the mixture was stirred at ambient temperature for 2.5 hours. The resulting mixture was diluted with water (30 ml) and basified with saturated sodium bicarbonate aqueous solution. The mixture was extracted with ethyl acetate (40 ml) and the organic layer was washed successively with water and brine, dried over magnesium sulfate and concentrated in vacuo. The residue was purified by silica gel column chromatography (eluent; n-hexane:ethyl acetate=6:1) to give methyl 2-benzyloxymethylindoline-4-carboxylate (550 mg).

NMR (CDCl$_3$, δ): 3.02 (1H, dd, J=8, 17 Hz), 3.41–3.58 (3H, m), 3.88 (3H, s), 4.08–4.18 (1H, m), 4.33–4.41 (1H, br), 4.55 (2H, s), 6.74 (1H, d, J=8 Hz), 7.08 (1H, t, J=8 Hz), 7.28–7.39 (6H, m)

Preparation 88

The Vilsmeier reagent was prepared by the dropwise addition of phosphoryl oxychloride (0.75 mg) to cooled N,N-dimethylformamide (20.0 ml) under constant stirring. A solution of methyl indole-4-carboxylate in N,N-dimethylformamide (12.0 ml) was added to the above solution at 0° C. and the solution was stirred for 30 minutes. The mixture was diluted with water (40 ml) and the solution was neutralized with saturated sodium bicarbonate aqueous solution and extracted with ethyl acetate (60 ml). The organic layer was washed successively with water and brine, dried over magnesium sulfate and concentrated invacuo. The solid was triturated with diethyl ether (7 ml) to give methyl 3-formylindole-4-carboxylate (792 mg).

NMR (CDCl$_3$, δ): 4.00 (3H, s), 7.32 (1H, t, J=9 Hz), 7.64 (1H, d, J=9 Hz), 7.83 (1H, d, J=9 Hz), 8.06 (1H, d, J=3 Hz), 9.78–9.88 (1H, br), 10.53 (1H, s)

Preparation 89

To a solution of 2,2,6,6-tetramethylpiperidine (1.97 g) in tetrahydrofuran (24.0 ml) was added dropwise n-butyllithium (6.8 ml, 1.64M solution in n-hexane) at −40° C. and the mixture was stirred at 0° C. for 30 minutes. A solution of methyl 1-methoxymethoxyindole-4-carboxylate (1.64 g) in tetrahydrofuran (12.0 ml) was added t the above solution at −60° C. and the solution was stirred at the same temperature for 30 minutes. A solution of N,N-dimethylformamide (662 mg) in tetrahydrofuran (9.0 ml) was added to the reaction mixture at −60° C. and the solution was stirred at the same temperature for 2 hours. The temperature was raised to −320° C. and the reaction was quenched with saturated ammonium chloride aqueous solution. The aqueous solution was extracted with ethyl acetate (80 ml) and the organic layer was washed with brine. Drying, filtering and removal of solvents afforded a crude product. The crude product was purified by silica gel column chromatography (eluent; n-hexane:ethyl acetate=9:1) to give methyl 2-formyl-1-methoxymethoxyindole-4-carboxylate (1.15 g).

NMR (CDCl$_3$, δ): 3.67 (3H, s), 4.01 (3H, s), 5.34 (2H, s), 7.50 (1H, t, J=9 Hz), 7.77 (1H, d, J=9 Hz), 7.81 (1H, s), 7.98 (1H, d, J=9 Hz), 9.98 (1H, s)

Preparation 90

To a solution of benzyl 1-tert-butoxycarbonyl-2-hydroxymethylindole-4-carboxylate (465 mg), phthalimide (179 mg) and triphenylphosphine (640 mg) in tetrahydrofuran (15.0 ml) was added diethyl azodicarboxylate (425 mg) and the mixture was stirred at ambient temperature for 1 hour. The resulting mixture was concentrated in vacuo and the residue was chromatographed on silica gel with n-hexane:ethyl acetate (6:1). The solid was triturated with methanol to give benzyl 1-tert-butoxycarbonyl-2-phthalimidomethylindole-4-carboxylate (440 mg).

NMR (CDCl$_3$, δ): 1.72 (9H, s), 5.27 (2H, s), 5.29 (2H, s), 6.95 (1H, s), 7.21–7.34 (6H, m), 7.75–7.81 (2H, m), 7.89–7.94 (2H, m), 7.96 (1H, d, J=8 Hz), 8.37 (1H, d, J=8 Hz)

Preparation 91

The mixture of tert-butyl 2-methyl-4-nitro-1H-benzimidazole-1-carboxylate (3.0 g) and 10% palladium on carbon (300 mg) in methanol (25 ml) and 1,4-dioxane (60 ml) was hydrogenated under atmospheric pressure at ambient temperature for 11 hours. The reaction mixture was filtered through a bed of celite and the filtrate was concentrated in vacuo to give crude product. The solid was washed with diisopropyl ether/n-hexane (½) to give 4-amino-2-methyl-1H-benzimidazole-1-carboxylate (2.0 g).

NMR (CDCl$_3$, δ): 1.70 (9H, s), 2.79 (3H, s), 4.28 (2H, br), 6.58 (1H, d, J=8 Hz), 7.06 (1H, dd, J=8, 8 Hz), 7.25 (1H, d, J=8 Hz)

Preparation 92

A solution of N-[(1-hydroxymethyl)cyclopentyl]-2-nitrobenzamide (2.1 g) in thionyl chloride (5.8 ml) was stirred at ambient temperature for 1 hour. To the reaction mixture was added diethyl ether and the resulting precipitate was filtered. The collected precipitate was dissolved in ethyl acetate and 1N sodium hydroxide. The organic layer was washed with brine and dried over magnesium sulfate and concentrated to give 4-aza-3-(2-nitrophenyl)-2-oxaspiro[4.4]-non-3-ene (1.95 g).

NMR (CDCl$_3$, δ): 1.62–1.79 (4H, m), 1.82–2.10 (4H, m), 4.26 (2H, s), 7.54–7.67 (2H, m), 7.80 (1H, d, J=8 Hz), 7.88 (1H, d, J=8 Hz)

Preparation 93

To a suspension of methyl 2-formyl-1H-benzimidazole-4-carboxylate (460 mg) in a mixture of water (3.2 ml) and t-butyl alcohol (12 ml) were added 2-methyl-2-butene (700 mg) and sodium dihydrogenphosphate (387 mg) in water bath. To the mixture was added portionwise sodium chlorite (901 mg) and stirred for 1 day at same temperature. The reaction mixture was cooled in an ice bath, adjusted to pH 4 with 1N hydrochloric acid and the precipitate was collected by vacuum filtration. The precipitate was washed with ethyl acetate and methanol to give methyl 2-carboxy-1H-benzimidazole-4-carboxylate (400 mg).

MASS (ES−) (m/z): 219

Preparation 94

To a solution of 3-ethoxycarbonyl-1,2-phenylenediamine (790 mg) in tetrahydrofuran (10 ml) was added 1,1'-thiocarbonyldiimidazole (1.02 g) in ice water bath and the mixture was stirred for 20 hours at ambient temperature. The reaction solvent was concentrated in vacuo and the residue was washed with chloroform and collected by vacuum filtration to give ethyl 2-mercapto-1H-benzimidazole-4-carboxylate (665 mg).

NMR (DMSO-d$_6$, δ): 1.33 (3H, t, J=7.5 Hz), 4.42 (2H, q, J=7.5 Hz), 7.23 (1H, t, J=8 Hz), 7.38 (1H, d, J=8 Hz), 7.66 (1H;, d, J=8 Hz)

Preparation 95

To a solution of ethyl 2-mercapto-1H-benzimidazole-4-carboxylate (500 mg) were added iodomethane (351 mg) and potassium carbonate (622 mg) at ambient temperature and the mixture was stirred for 20 hours at same temperature. The reaction mixture was poured into water and extracted with chloroform. The organic layer was washed with water and brine, dried over magnesium sulfate and evaporated in vacuo. The residue was washed with diisopropyl ether to give ethyl 2-methylthio-1H-benzimidazole-4-carboxylate (310 mg).

NMR (CDCl$_3$, δ): 1.44 (3H, t, J=7.5 Hz), 3.80 (3H, s), 4.44 (2H, q, J=7.5 Hz), 7.24 (1H, t, J=8 Hz), 7.77–7.88 (23H, m)

Preparation 96

To a solution of ethyl 2-methylthio-1H-benzimidazole-4-carboxylate (200 mg) in dichloromethane (4 ml) was added dropwise a solution of m-chloroperroxybenzoic acid (292 mg) in dichloromethane (4 ml) in ice water bath under nitrogen and the mixture was stirred for 4 hours at the same temperature. The reaction mixture was poured into water and extracted with dichloromethane. The organic layer was washed with water, dried over magnesium sulfate and evaporated in vacuo. The residue was purified by preparative thin-layer chromatography (chloroform:ethyl acetate:methanol=16:1:1) to give ethyl 2-methylsulfonyl-1H-benzimidazole-4-carboxylate (102 mg).

NMR (CDCl$_3$, δ): 1.48 (3H, t, J=7.5 Hz), 3.42 (3H, s), 4.50 (2H, q, J=7.5 Hz), 7.49 (1H, t, J=8 Hz), 8.06–8.16 (2H, m)

Preparation 97

To a suspension of ethyl 2-mercapto-1H-benzimidazole-4-carboxylate (950 mg) in 20% acetic acid aqueous solution (30 ml) at 0° C. was bubbled chlorine for 30 minutes. The resulting crude product was collected by vacuum filtration and added portionwise to ammonia aqueous solution (28%, 10 ml) in ice water bath. The reaction mixture was stirred at ambient temperature for 1 hour and adjusted to pH 5 with 1N hydrochloric acid. The precipitate was collected by vacuum filtration to give ethyl 2-sulfamoyl-1H-benzimidazole-4-carboxylate (775 mg).

NMR (DMSO-d$_6$, δ): 1.38 (3H, t, J=7.5 Hz), 4.43 (2H, q, J=7.5 Hz), 7.47 (1H, t, J=8 Hz), 7.97 (1H, d, J=8 Hz), 8.04 (1H, d, J=8 Hz)

Preparation 98

Thionyl chloride (8.3 ml) was added dropwise to 2-hydroxymethyl-4-nitro-1H-benzimidazole (1.15 g) at 0° C. and the suspension was then heated at reflux for 3 hours. The excess of thionyl chloride was removed in vacuo, and the residue was poured into ice and adjusted to pH 7 with saturated sodium bicarbonate aqueous solution. The precipitate was collected by vacuum filtration and washed water to give 2-chloromethyl-4-nitro-1H-benzimidazole (1.32 g).

NMR (DMSO-d$_6$, δ): 4.98 (2H, s), 7.39 (1H, t, J=8 Hz), 8.09 (1H, d, J=8 Hz), 8.13 (1H, d, J=8 Hz)

Preparation 99

To a solution of 2,4-dihydroxy-8-methylquinazoline (1.00 g) in mixture of 2-methyl-2-propanol (20 ml) and water (20 ml) was added potassium permanganate (3.59 g) and magnesium sulfate (1.37 g) and the reaction mixture was stirred at 90° C. for 15 hours. After the reaction mixture was filtered through a bed of celite, the filtrate was diluted with water. The solution was adjusted to pH 4 with 1N hydrochloric acid. The formed precipitate was collected by vacuum filtration to give 2,4-dihydroxyquinazoline-8-carboxylic acid (390 mg).

NMR (DMSO-d$_6$, δ): 7.31 (1H, t, J=8 Hz), 8.19 (1H, d, J=8 Hz), 8.18 (1H, d, J=8 Hz)

Preparation 100

To a solution of ethyl 3-aminopyrazole-4-carboxylate (5.00 g) in carbon tetrachloride (70 ml) was added triethyl orthoacetate (6.53 g) and the reaction mixture was stirred at 90° C. for 3 hours. After the reaction mixture was concentrated in vacuo, the residue was purified by silica gel (Chromatorex, Fuji Silysia Chemical Ltd.) column chromatography (n-nexane:ethyl acetate=1:2) to give ethyl 3-(1-aza-2-ethoxyprop-1-enyl)pyrazole-4-carboxylate (4.94 g).

NMR (CDCl$_3$, δ): 1.27–1.36 (6H, m), 1.92 (3H, s), 4.22–4.36 (4H, m), 7.91 (1H, s)

Preparation 101

To a solution of ethyl 3-(1-aza-2-ethoxyprop-1-enyl) pyrazole-4-carboxylate (4.90 g) in N,N-dimethylformamide (50 ml) was added hydroxylamine hydrochloride (15.1 g) and stirred at ambient temperature for 3 hours. The reaction mixture was concentrated in vacuo and the residue was diluted with water. The solution was adjusted to pH 7 with 1N hydrochloric acid. The formed precipitate was collected by vacuum filtration to give ethyl 3-[[1-(hydroxyimino) ethyl]-amino]pyrazole-4-carboxylate (1.52 g).

NMR (DMSO-d$_6$, δ): 1.27 (3H, t, J=8 Hz), 2.20 (3H, s), 4.22 (2H, q, J=8 Hz), 8.16 (1H, s), 8.07 (1H, s), 9.82 (1H, s)

Preparation 102

To a solution of ethyl 3-[[1-(hydroxyimino)ethyl]amino]-pyrazole-4-carboxylate (1.50 g) and pyridine (1.12 g) in N,N-dimethylformamide (20 ml) was added dropwise p-toluenesulfonyl chloride (1.39 g) under ice bath cooling and stirred at ambient temperature for 3 hours. The reaction mixture was diluted with ethyl acetate and water. The organic layer was separated and washed with saturated sodium hydrogen carbonate aqueous solution and brine. The solution was dried over magnesium sulfate and concentrated in vacuo to give ethyl 3-[1-(p-toluenesulfonyloxyimino) ethyl]amino-1H-pyrazole-4-carboxylate (2.14 g).

NMR (CDCl$_3$, δ): 1.42 (3H, t, J=8 Hz), 2.30 (3H, s), 2.43 (3H, s), 4.38 (2H, q, J=8 Hz), 7.33 (2H, d, J=8 Hz), 7.90–7.93 (3H, m), 9.10 (1H, s)

Preparation 103

A solution of ethyl 3-[1-(p-toluenesulfonyloxyimino)-ethyl]amino-1H-pyrazole-4-carboxylate (1.00 g) and pyridine (240 mg; in ethanol (20 ml) was refluxed for 3 hours. The reaction mixture was concentrated in vacuo and the residue was diluted with water. The solution was adjusted to pH 4 with 1N hydrochloric acid. The formed precipitate was collected by vacuum filtration to give ethyl 2-methyl-1H-pyrazole[1,5-b][1,2,4]triazole-7-carboxylate (240 mg).

NMR (DMSO-d$_6$, δ): 1.29 (3H, t, J=8 Hz), 2.45 (3H, s), 4.23 (2H, q, J=8 Hz), 7.85 (1H, s)

Preparation 104

To a solution of ethyl 3-aminophthalic acid (1.00 g) in ethanol (10 ml) was added formamidine hydrochloride (444 mg) and refluxed for 12 hours. After cooling, the formed precipitate was collected by vacuum filtration and the precipitate was washed with ethanol to give 4-hydroxyquinazoline-5-carboxylic acid (504 mg).

NMR (DMSO-d$_6$, δ): 7.52–7.62 (2H, m), 7.72 (1H, t, J=8 Hz), 8.13 (1H, s)

Preparation 105

To a solution of ethyl 3-nitro-2-aminobenzoate (700 mg) in N,N-dimethylaniline (7 ml) was added dropwise isonicotinoyl chloride (2.96 g) at 120° C. for 3 hours. After cooling, the reaction mixture was diluted with ethyl acetate and saturated sodium hydrogen carbonate aqueous solution. The organic layer was separated and washed with brine. The solution was dried over magnesium sulfate and concentrated in vacuo. The residue was purified by silica gel column chromatography (n-hexane:ethyl acetate=9:1) to give ethyl 3-nitro-2-(4-pyridyl)carbonylaminobenzoate (200 mg).

NMR (CDCl$_3$, δ): 1.42 (3H, t, J=7 Hz), 4.43 (2H, q, J=7 Hz), 7.26 (1H, s), 7.40 (1H, t, J=7 Hz), 7.82–7.84 (2H, m), 8.15 (1H, d, J=8 Hz), 8.31 (1H, d, J=8 Hz), 8.85 (1H, d, J=7 Hz)

Preparation 106

To a solution of ethyl 3-nitro-2-(4-pyridyl)-carbonylaminobenzoate (200 mg) in ethanol (2 ml) was added iron (177 mg) and acetic acid (381 mg) at ambient temperature and the reaction mixture was stirred at 60° C. for 2 hours. After the reaction mixture was filtered through a bed a celite, the filtrate was concentrated in vacuo. The residue was diluted with chloroform and saturated sodium hydrogen carbonate aqueous solution. The organic layer was separated and washed with brine. The solution was dried over magnesium sulfate and concentrated in vacuo to give ethyl 2-(4-pyridyl)-1H-benzimidazole-4-carboxylate (150 mg).

NMR (CDCl$_3$, δ): 1.48 (3H, t, J=7 Hz), 4.40 (2H, q, J=7 Hz), 7.38 (1H, t, J=8 Hz), 7.90–8.00 (3H, m), 8.05 (1H, d, J=8 Hz), 8.82 (1H, d, J=6 Hz)

Preparation 107

To a solution of ethyl 3-amino-2-hydroxybenzoate (500 mg), sodium hydrogen carbonate (927 mg) and benzyltributylammonium bromide (983 mg) in chloroform (10 ml) was added dropwise chloroacetyl chloride (374 mg) in chloroform (3 ml) under ice bath cooling. The reaction mixture was stirred at ambient temperature for 1 hour and at 60° C. for 2 hours. To the reaction mixture was added dropwise chloroacetyl chloride (312 mg) in chloroform (3 ml) under ice bath cooling and stirred at 60° C. for 2 hours. After the reaction mixture was concentrated in vacuo, the residue was diluted with chloroform and saturated sodium hydrogen carbonate aqueous solution. The organic layer was separated and washed with brine. The solution was dried over magnesium sulfate and concentrated in vacuo to give ethyl 2H-1,4-benzoxazin-3-one-8-carboxylate (460 mg).

NMR (CDCl$_3$, δ): 1.38 (3H, t, J=7 Hz), 4.36 (2H, q, J=8 Hz), 4.71 (2H, s), 6.96–7.00 (2H, m), 7.47–7.52 (1H, m), 9.04 (1H, s)

EXAMPLE 40

The following compounds were obtained according to a similar manner to that of Example 1.
1) 4-(Imidazo[(1,5-a]pyridine-1-carbonyl)amino-3-methoxy-N-methyl-N-[4-methyl-2-[5-(4-methylpiperazin-1-yl) carbonylpent-1-yloxy]phenyl]benzamide NMR (CDCl$_3$, δ): 1.48–1.58 (2H, m), 1.65–1.88 (4H, m), 2.27 (3H, s), 2.29 (3H, s), 2.32–2.40 (6H, m), 3.33 (3H, s), 3.46–3.51 (2H, m), 3.59–3.67 (2H, m), 3.80 (3H, s), 3.81–3.99 (2H, m), 6.58 (1H, d, J=8 Hz), 6.62 (1H, s), 6.74–6.87 (2H, m), 6.93 (1H, d, J=8 Hz), 7.00 (1H, s), 7.02–7.09 (1H, m), 8.01 (1H, d, J=8 Hz), 8.03 (1H, s), 8.29 (1H, d, J=9 Hz), 8.36 (1H, d, J=8 Hz), 9.60 (1H, s)

2) 4-[(1-tert-Butoxycarbonyl-2-ethoxycarbonylindolin-4-yl)carbonyl]amino-3-methoxy-N-methyl-N-[4-methyl-2-[5-(4-methylpiperazin-1-yl) carbonylpent-1-yloxy]phenyl]benzamide NMR (CDCl$_3$, δ): 1.28 (3H, t, J=8 Hz), 1.52 (9H, s), 1.55–1.88 (6H, m), 2.28 (3H, s), 2.31 (3H, s), 2.32–2.43 (6H, m), 3.32 (3H, s), 3.42–3.53 (3H, m), 3.60–3.67 (2H, m), 3.78 (3H, s), 3.80–4.00 (3H, m), 4.19 (2H, q, J=8 Hz), 4.82–4.91 (1H, d, J=8 Hz), 6.92 (1H, d, J=8 Hz), 7.02 (1H, s), 7.20 (1H, d, J=8 Hz), 7.26–7.32 (1H, m), 8.02–8.10 (1H, m), 8.20 (1H, d, J=8 Hz), 8.42 (1H, s)

3) 4-[(1-tert-Butoxycarbonylindolin-4-yl)carbonyl]amino-3-methoxy-N-methyl-N-[4-methyl-2-[5-(4-methylpiperazin-1-yl) carbonylpent-1-yloxy]phenyl]benazmide NMR (CDCl$_3$, δ): 1.48–1.60 (2H, m), 1.56 (9H, s), 1.66–1.88 (4H, m), 2.28 (3H, s), 2.30 (3H, s), 2.31–2.42 (6H, m), 3.31 (3H, s), 3.40 (2H, t, J=9 Hz), 3.47–3.51 (2H, m), 3.59–3.67 (2H, m), 3.78 (3H, s), 3.84–4.04 (4H, m), 6.58 (1H, d, J=8 Hz), 6.62 (1H, s), 6.84 (1H, d, J=8 Hz), 6.92 (1H, d, J=8 Hz), 7.02 (1H, s), 7.20 (1H, t, J=8 Hz), 7.23–7.29 (1H, m), 8.01 (1H, s), 8.23 (1H, d, J=8 Hz), 8.38 (1H, s)

4) 4-[(2-Benzyloxymethyl-1-tert-butoxycarbonylindolin-4-yl) carbonyl]amino-3-methoxy-N-methyl-N-[4-methyl-2-[5-(4-methylpiperazin-1-yl) carbonylpent-1-yloxy]phenyl]-benzamide NMR (CDCl$_3$, δ): 1.50 (9H, s), 1.51–1.58 (2H, m), 1.66–1.87 (4H, m), 2.28 (3H, s), 2.30 (3H, s), 2.32–2.41 (6H, m), 3.32 (3H, s), 3.41–3.53 (5H, m), 3.59–3.67 (3H, m), 3.76 (3H, s), 3.83–3.99 (2H, m), 4.48 (2H, s), 4.57–4.65 (1H, br), 6.58 (1H, d, J=8 Hz), 6.63 (1H, s), 6.84 (1H, d, J=8 Hz), 6.92 (1H, d, J=8 Hz), 7.02 (1H, s), 7.19–7.30 (8H, m), 8.26 (1H, d, J=8 Hz), 8.38 (1H, s)

5) 4-[(1-Tert-Butoxycarbonyl-3-tert-butyldiphenylsilyloxymethylindol-4-yl) carbonyl]amino-3-methoxy-N-methyl-N-[4-methyl-2-[5-(4-methylpiperazin-1-yl)carbonylpent-1-yloxy]phenyl]benzamide NMR (CDCl$_3$, δ): 0.90 (9H, s), 1.50–1.60 (2H, m), 1.67 (9H, s), 1.68–1.89 (4H, m), 2.22 (3H, s), 2.30 (3H, s), 2.32–2.42 (6H, m), 3.33 (3H, s), 3.46–3.51 (2H, m), 3.60–3.67 (5H, m), 3.87–3.98 (2H, m), 4.88 (2H, s), 6.53 (1H, d, J=8 Hz), 6.62 (1H, s), 6.83 (1H, d, J=8 Hz), 6.93 (1H, d, J=8 Hz), 6.98 (1H, s), 7.21–7.41 (8H, m), 7.50–7.59 (5H, m), 8.16 (1H, s), 8.26 (1H, d, J=8 Hz), 8.34 (1H, d, J=8 Hz)

6) 4-[(1-tert-Butoxycarbonyl-2-tert-butyldiphenylsilyoxymethylindol-4-yl) carbonyl]amino-3-methoxy-N-methyl-N-[4-methyl-2-[5-(4-methylpiperazin-1-yl) carbonylpent-1-yloxy]phenyl]benzamide NMR (CDCl$_3$, δ): 0.90 (9H, s), 1.50–1.60 (2H, m), 1.67 (9H, s), 1.68–1.89 (4H, m), 2.22 (3H, s), 2.30 (3H, s), 2.32–2.42 (6H, m), 3.33 (3H, s), 3.46–3.51 (2H, m), 3.60–3.67 (5H, m), 3.87–3.98 (2H, m), 4.88 (2H, s), 6.53 (1H, d, J=8 Hz), 6.62 (1H, s), 6.83 (1H, d, J=8 Hz), 6.93 (1H, d, J=8 Hz), 6.98 (1H, s), 7.21–7.41 (8H, m), 7.50–7.59 (5H, m), 8.16 (1H, s), 8.26 (1H, d, J=8 Hz), 8.34 (1H, d, J=8 Hz)

7) 4-[(1-tert-Butoxycarbonyl-2-phthalimidomethylindol-4-yl) carbonyl]amino-3-methoxy-N-methyl-N-[4-methyl-2-[5-(4-methylpiperazin-1-yl) carbonylpent-1-yloxy]phenyl]benzamide NMR (CDCl$_3$, δ): 1.46–1.57 (2H, m), 1.64–1.85 (4H, m), 1.73 (9H, s), 2.25 (3H, s), 2.30 (3H, s), 2.32–2.41 (6H, m), 3.30 (3H, s), 3.44–3.51 (2H, m), 3.60–3.67 (2H, m), 3.72 (3H, s), 3.81–3.96 (2H, m), 5.29 (2H, s), 6.54 (1H, d, J=8 Hz), 6.59 (1H, s), 6.78 (1H, s), 6.83 (1H, d, J=8 Hz), 6.98 (1H, s), 7.32 (1H, t, J=8 Hz), 7.54 (1H, d, J=8 Hz), 7.77–7.81 (2H, m), 7.88–7.93 (2H, m), 8.03 (1H, s), 8.18 (1H, d, J=8 Hz), 8.31 (1H, d, J=8 Hz), 8.42 (1H, s)

8) 4-[(1-tert-Butoxycarbonyl-2-methylindol-4-yl)carbonyl]-amino-3-methoxy-N-methyl-N-[4-methyl-2-[5-(4-methylpiperazin-1-yl) carbonylpent-1-yloxy]phenyl]benzamide NMR (CDCl$_3$, δ): 1.48–1.60 (2H, m), 1.65–1.90 (4H, m), 1.69 (9H, s), 2.28 (3H, s), 2.29 (3H, s), 2.32–2.43 (6H, m), 2.62 (3H, s), 3.33 (3H, s), 3.47–3.53 (2H, m), 3.60–3.68 (2H, m), 3.78 (3H, s), 3.86–4.00 (2H, m), 6.59 (1H, d, J=8 Hz), 6.63 (1H, s), 6.83–6.98 (3H, m), 7.05 (1H, s), 7.24–7.31 (1H, m), 7.57 (1H, d, J=8 Hz), 8.28–8.37 (2H, m), 8.53 (1H, s)

9) 4-[(1-tert-Butoxycarbonylindolin-6-yl)carbonyl]amino-3-methoxy-N-methyl-N-[4-methyl-2-[5-(4-methylpiperazin-1-yl) carbonylpent-1-yloxy]phenyl]benzamide NMR (CDCl$_3$, δ): 1.50–1.63 (2H, m), 1.58 (9H, s), 1.67–1.88 (4H, m), 2.28 (3H, s), 2.30 (3H, s), 2.32–2.42 (6H, m), 3.12 (2H, t, J=8 Hz), 3.32 (3H, s), 3.46–3.51 (2H, m), 3.60–3.67 (2H, m), 3.77 (3H, s), 3.85–3.99 (2H, m), 4.03 (2H, t, J=8 Hz), 6.58 (1H, d, J=8 Hz), 6.63 (1H, s), 6.84 (1H, d, J=8 Hz), 6.90 (1H, d, J=8 Hz), 7.00 (1H, s), 7.21 (1H, d, J=8 Hz), 7.45 (1H, d, J=8 Hz), 8.24 (1H, d, J=8 Hz), 8.47 (1H, s)

10) 4-[(1-Butoxydcarbonylindol-6-yl)carbonyl]amino-3-methoxy-N-methyl-N-[4-methyl-2-[5-(4-methylpiperazin-1-yl) carbonylpent-1-yloxy]phenyl]benzamide NMR (CDCl$_3$, δ): 1.48–1.59 (2H, m), 1.67–1.90 (4H, m), 1.70 (9H, s), 2.28 (3H, s), 2.30 (3H, s), 2.32–2.42 (6H, m), 3.33 (3H, s), 3.47–3.52 (2H, m), 3.60–3.67 (2H, m), 3.79 (3H, s), 3.83–4.00 (2H, m), 6.58 (1H, d, J=8 Hz), 6.61 (1H, d, J=3 Hz), 6.63 (1H, s), 6.86 (1H, d, J=8 Hz), 6.93 (1H, d, J=8 Hz), 7.03 (1H, s), 7.62 (1H, d, J=9 Hz), 7.72 (1H, d, J=9 Hz), 7.75 (1H, d, J=3 H z), 8.30 (1H, d, J=8 Hz), 8.60 (1H, s), 8.67 (1H, s)

11) 3-Methoxy-N-methyl-N-[4-methyl-2-[5-(4-methylpiperazin-1-yl) carbonylpent-1-yloxy]phenyl]-4-(quinolin-8-yl)-carbonylaminobenzamide NMR (CDCl$_3$, δ): 1.48–1.59 (2H, m), 1.65–1.76 (2H, m), 1.78–1.89 (2H, m), 2.24 (3H, s), 2.26 (3H, s), 2.31–2.41 (6H, m), 3.32 (3H, s), 3.43–3.50 (2H, m), 3.58–3.66 (2H, m), 3.83–3.99 (2H, m), 3.88 (3H, s), 6.54–6.64 (2H, m), 6.87 (1H, d, J=8 Hz), 6.97 (1H, d, J=8 Hz), 7.03 (1H, s), 7.50 (1H, dd, J=8, 7 Hz), 7.70 (1H, t, J=8 Hz), 7.87 (1H, d, J=8 Hz), 8.31 (1H, d, J=8 Hz), 8.50 (1H, d, J=8 Hz), 8.88 (1H, d, J=7 Hz), 8.98 (1H, m)

12) 4-(3-Hydroxy-1H-indazol-4-yl)carbonylamino-3-methoxy-N-methyl-N-[4-methyl-2-[5-(4-methylpiperazin-1-yl) carbonylpent-1-yloxy]phenyl]benzamide NMR (CDCl$_3$, δ): 1.47–1.58 (2H, m), 1.66–1.78 (2H, m), 1.78–1.89 (2H, m), 2.27 (3H, s), 2.37 (3H, s), 2.43–2.54 (6H, m), 3.33 (3H, s), 3.52–3.57 (2H, m), 3.64–3.72 (2H, m), 3.79 (3H, s), 3.85–4.00 (2H, m), 6.54–6.65 (2H, m), 6.80–7.02 (3H, m), 7.34–7.49 (2H, m), 7.58 (1H, d, J=8 Hz), 8.26 (1H, d, J=8 Hz), 9.32 (1H, br)

13) 3-Methoxy-N-methyl-N-(4-methyl-2-benzyloxyphenyl)-4-[2-(tert-butoxycarbonyl) aminomethyl-1H-benzimidazol-4-yl]carbonylaminobenzamide NMR (CDCl$_3$, δ): 1.48 (9H, s), 2.23 (3H, s), 3.39 (3H, s), 3.61 (3H, s), 4.52 (2H, d, J=7 Hz), 4.87 (1H, d, J=12 Hz), 5.03 (1H, d, J=12 Hz), 5.60 (1H, br), 6.60–6.70 (2H, m), 6.85–7.00 (3H, m), 7.21–7.40 (6H, m), 7.48 (1H, d, J=8 Hz), 8.10 (1H, d, J=8 Hz), 8.47 (1H, d, J=8 Hz)

14) N-(2,4-Dimethylphenyl)-3-methoxy-N-methyl-4-[2-(tertbutoxycarbonylaminomethyl)-1H-benzimidazol-4-yl]carbonylaminobenzamide NMR (CDCl$_3$, δ): 1.50 (9H, s), 2.14 (3H, s), 2.25 (3H, s), 3.37 (3H, s), 3.74 (3H, s), 4.57 (2H, d, J=7 Hz), 5.64 (1H, br), 6.86–6.99 (7H, m ), 7.31 (1H, t, J=8 Hz), 7.51 (1H, br), 8.10 (1H, br), 8.47 (1H, br)

15) 3-Methoxy-N-(2-methoxy-4-methylphenyl)-N-methyl-4-[2-(tert-butoxycarbonylaminomethyl)-1H-benzimidazol-4-yl]-carbonylaminobenzamide NMR (CDCl$_3$, δ): 1.49 (9H, s), 2.28 (3H, s), 3.34 (3H, s), 3.71 (3H, s), 3.77 (3H, s), 4.57 (2H, d, J=7 Hz), 5.69 (1H, br), 6.56–6.63 (2H, m), 6.86–6.98 (3H, m), 7.29 (1H, t, J=8 Hz), 7.50 (1H, d, J=8 Hz), 8.09 (1H, d, J=8 Hz), 8.50 (1H, d, J=8 Hz)

16) 3-Methoxy-N-methyl-N-[4-methyl-2-[4-(4-methylpiperazin-1-yl) carbonylphenylmethoxy]phenyl]-4-[2-(tert-butoxy-carbonyl) aminomethyl-1H-benzimidazol-4-yl]carbonylaminobenzamide MASS (m/z): 776

17) 3-Methoxy-N-methyl-N-[4-methyl-2-[3-(4-methylpiperazin-1-yl) carbonylprop-1-yloxy]phenyl]-4-[2-(tert-butoxy-carbonylaminomethyl)-1H-benzimidazol-4-yl]carbonylamino-benzamide NMR (CDCl$_3$, δ): 1.50 (9H, s), 2.06–2.17 (2H, m), 2.26 (3H, s), 2.31–2.39 (4H, m), 2.50 (2H, t, J=7.5 Hz), 3.33 (3H, s), 3.43–3.50 (2H, m), 3.52–3.70 (2H, m), 3.81 (3H, s), 3.85–4.06 (2H, m), 4.58 (2H, m), 6.60–6.68 (2H, m), 6.89–7.05 (3H, m), 7.33 (1H, t, J=8 Hz), 7.51 (1H, d, J=8 Hz), 8.12 (1H, d, J=8 Hz), 8.51 (1H, d, J=8 Hz)

18) 3-Methoxy-N-methyl-N-[4-methyl-2-[4-(4-methylpiperazin-1-yl) carbonylbut-1-yloxy]phenyl]-4-[2-(tert-butoxy-carbonyl) aminomethyl-1H-benzimidazol-4-yl]carbonylamino-benzamide NMR (CDCl$_3$, δ): 1.51 (9H, s), 1.64–1.73 (2H, m), 1.76–1.88 (2H, m), 2.26 (6H, s), 2.28 (3H, s), 2.32—2.47 (6H, m), 3.33 (3H, s), 3.43–3.51 (2H, m), 3.58–3.68 (2H, m), 3.76–4.00 (5H, m), 4.60 (2H , m), 5.83 (1H, br), 6.41 (1H, d, J=8Hz), 6.54–6.64 (2H, m), 6.78–7.03 (3H, m), 7.42 (1H, d, J=8Hz), 8.10 (1H, d, J=8Hz), 8.50 (1H, d, J=8Hz)

19) N-[2-(4-Ethoxycarbonylpent-1-yloxy)-4-methylphenyl]-3-methoxy-N-methyl-4-(3-nitro-2-phthalimidomethylcarbonylaminophenyl) carbonylaminobenzamide NMR (CDCl$_3$, δ) : 1.24 (3H, t, J=7.5Hz), 1.44–1.58 (2H, m), 1.64–1.77 (2H, m), 1.77–1.90 (2H, m), 2.28 (3H, s), 2.33 (2H, t, J=7.5Hz), 3.34 (3H, s), 3.72 (3H, s), 3.82–4.00 (2H, m), 4.11 (2H, q, J=7.5Hz), 4.49 (2H, m), 6.60–6.68 (2H, m), 6.88 (1H, d, J=8Hz), 6.98 (1H, s), 7.38 (1H, t, J=8Hz), 7.72–7.90 (6H, m), 8.02 (1H, d, J=8Hz), 8.40 (1H, s)

20) 4-[2-Carbamoyl-1-(4-methoxybenzyl)-1H-benzimidazol-4-yl]carbonylamino-3-methoxy-N-methyl-N-[4-methyl-2-[5-(4-methylpiperazin-1-yl)carbonylpent-1-yloxy]phenyl]benzamide NMR (CDCl$_3$, δ) : 1.47–1.63 (2H, m), 1.63–1.77 (2H, m), 1.77–1.91 (2H, m), 2.24 (3H, s), 2.29 (3H, s), 2.31–2.42 (6H, m), 3.33 (3H, s), 3.43–3.53 (2H, m), 3.58–3.68 (2H, m), 3.75 (3H, s), 3.80–3.90 (4H, m), 3.90–4.00 (1H, m), 5.98 (2H, s), 6.02 (1H, br s), 6.55–6.65 (2H, m), 6.81 (2H, d, J=8Hz), 6.88 (1H, d, J=8Hz), 6.98 (1H, d, J=8Hz), 7.10 (1H, s), 7.21 (2H, d, J=8Hz), 7.48 (1H, t, J=8Hz), 7.62 (1H, d, J=8Hz), 7.84 (1H, d, J=8Hz), 8.24 (1H, d, J=8Hz), 8.51 (1H, d, J=8Hz)

21) 4-[2-(N,N-Dimethylcarbamoyl)-1-(4-methoxybenzyl)-1H-benzimidazol-4-yl]carbonylamino-3-methoxy-N-methyl-N-[4-methyl-2-[5-(4-methylpiperazin-1-yl) carbonylpent-1-yloxy]phenyl]benzamide NMR (CDCl$_3$, δ) : 1.49–1.64 (2H, m), 1.64–1.78 (2H, m), 1.78–1.90 (2H, m), 2.27 (3H, s), 2.30 (3H, s), 2.33–2.44 (6H, m), 3.13 (3H, s), 3.19 (3H, s), 3.34 (3H, s), 3.46–3.54 (2H, m), 2.60–3.69 (2H, m), 3.74–3.81 (6H, m), 3.81–4.01 (2H, m), 5.55 (2H, s), 6.58 (1H, d, J=8Hz), 6.64 (1H, s), 6.80–6.90 (3H, m), 6.84 (1H, d, J=8Hz), 7.06 (1H, s), 7.16 (2H, d, J=8Hz), 7.44 (1H, t, J=8Hz), 7.56 (1H, d, J=8Hz), 8.24 (1H, d, J=8Hz), 8.47 (1H, d, J=8Hz)

22) 4-[2-[1-(Benzyloxycarbonyl)-4-piperidyl]-1H-benzimidazol-4-yl]carbonylamino-3-methoxy-N-methyl-N-[4-methyl-2-[5-(4-methylpiperazin-1-yl)-carbonylpent-1-yloxy]phenyl]benzamide NMR (DMSO-d$_6$, δ) : 1.37–1.49 (2H, m), 1.49–1.61 (2H, m), 1.67–1.79 (2H, m), 1.79–1.92 (2H, m), 2.07–2.35 (14H, m), 3.07 (2H, br peak), 3.15–3.29 (4H, m), 3.29–3.46 (4H, m), 3.68 (3H, s), 3.84 (1H, br peak), 3.94 (1H, br peak), 4.11–4.22 (2H, m), 5.11 (2H, s), 6.63 (1H, d, J=8Hz), 6.81 (1H, s), 6.88–6.97 (2H, m), 7.04 (1H, d, J=8Hz), 7.26–7.45 (6H, m), 7.70 (1H, d, J=8Hz), 7.90 (1H, d, J=8Hz), 8.43 (1H, d, J=8Hz)

23) 4-[2-(N-tert-Butoxycarbonylaminomethyl)-1-methyl-1H-benzimidazol-4-yl]carbonylamino-3-methoxy-N-methyl-N-[4-methyl-2-[5-(4-methylpiperazin-1-yl) carbonylpent-1-yloxy]phenyl]benzamide NMR (CDCl$_3$, δ) : 1.44–1.56 (11H, m), 1.64–1.75 (2H, m), 1.74–1.88 (2H, m), 2.26 (6H, s), 2.30–2.40 (6H, m), 3.33 (3H, s), 3.43–3.50 (2H, m), 3.58–3.66 (2H, m), 3.81 (3H, s), 3.83–4.00 (5H, m), 4.68 (2H, d, J=5Hz), 5.90 (1H, br peak), 6.54–6.64 (2H, m), 6.88 (1H, d, J=8Hz), 6.95 (1H, d, J=8Hz), 7.09 (1H, s), 7.41 (1H, t, J=8Hz), 7.51 (1H, d, J=8Hz), 8.18 (1H, d, J=8Hz), 8.53 (1H, d, J=8Hz)

24) 4-[2-(N-tert-Butoxycarbonylaminomethyl)-3-methyl-3H-benzimidazol-4-yl]carbonylamino-3-methoxy-N-methyl-N-[4-methyl-2-[5-(4-methylpiperazin-1-yl) carbonylpent-1-yloxy]phenyl]benzamide NMR (CDCl$_3$, δ) : 1.40–1.61 (2H, m), 1.61–1.91 (4H, m), 2.22–2.32 (6H, m), 2.32–2.44 (6H, m), 3.33 (3H, s), 3.43–3.55 (2H, m), 3.58–3.69 (2H, m), 3.74 (3H, s), 3.82 (3H, s), 3.87–4.03 (2H, m), 4.62 (2H, d, J=5Hz), 5.55 (1H, br peak), 6.60 (1H, d, J=8Hz), 6.66 (1H, s), 6.80–6.90 (1H, m), 6.96 (1H, d, J=8Hz), 7.04 (1H, s), 7.23–7.32 (1H, m), 7.43 (1H, d, J=8Hz), 7.84 (1H, d, J=8Hz), 8.28 (1H, d, J=8Hz), 8.34 (1H, s).

25) 4-(2-Methylthio-1H-benzimidazol-4-yl)carbonylamino-3-methoxy-N-methyl-N-[4-methyl-2-[5-(4-methylpiperazin-1-yl)carbonylpent-1-yloxy]phenyl]benzamide NMR (DMSO$_6$, δ) : 1.35–1.49 (2H, m), 1.49–1.62 (2H, m), 1.67–1.80 (2H, m), 2.12 (3H, s), 2.15–2.34 (9H, m), 2.85 (3H, s), 3.19 (3H, s), 3.37–3.46 (4H, m), 3.73 (3H, s), 3.89 (1H, br peak), 3.96 (1H, br peak), 6.65 (1H, d, J=8Hz), 6.82 (1H, s), 6.89–6.99 (2H, m), 7.03 (1H, d, J=8Hz), 7.28 (1H, t, J=8Hz), 7.61 (1H, d, J=8Hz), 7.87 (1H, d, J=8Hz), 8.39 (1H, d, J=8Hz)

26) 3-Methoxy-N-methyl-N-[4-methyl-2-[5-(4-methylpiperazin-1-yl)carbonylpent-1-yloxy]phenyl]-4-(2-methylsulfonyl-1H-benzimidazol-4-yl) carbonylaminobenzamide NMR (CDCl$_3$, δ): 1.46–1.63 (2H, m), 1.63–1.78 (2H, m), 1.78–1.90 (2H, m), 2.24 (3H, s), 2.29 (3H, s), 2.33–2.44 (6H, m), 3.33 (3H, s), 3.41 (3H, s), 3.44–3.53 (2H, m), 3.60–3.69 (2H, m), 3.76–3.90 (4H, m), 3.90–4.02 (1H, m), 6.53–6.64 (2H, m), 6.88 (1H, d, J=8Hz), 6.92–7.02 (2H, m), 27) 3-Methoxy-N-methyl-N-[4-methyl-2-[5-(4-methylpiperazin-1-yl)carbonylpent-1-yloxy]phenyl]-4-(2-sulfamoyl-1H-benzimidazol-4-yl)carbonylaminobenzamide NMR (DMSO-$d_6$, δ) : 1.36–1.50 (2H, m), 1.50–1.64 (2H, m), 1.68–1.81 (2H, m), 2.19 (3H, s), 2.23 (3H, s), 2.34–2.38 (6H, m), 3.19 (3H, s), 3.39–3.50 (4H, m), 3.76 (3H, s), 3.87 (1H, br peak), 3.96 (1H, br peak), 6.64 (1H, d, J=8Hz), 6.83 (1H, s), 6.89 (1H, s), 6.95 (1H, d, J=8Hz), 7.03 (1H, d, J=8Hz), 7.50 (1H, d, J=8Hz), 7.82 (1H, d, J=8Hz), 7.98–8.10 (3H, m), 8.36 (1H, d, J=8Hz)

28) 4-(2,4-Dihydroxyquinazolin-8-yl)carbonylamino-3-methoxy-N-methyl-N-[4-methyl-2-[5-(4-methylpiperazin-1-yl)carbonylpent-1-yloxy]phenyl]benzamide NMR (DMSO-$d_6$, δ) : 1.38–1.52 (2H, m), 1.52–1.63 (2H, m), 1.70–1.80 (2H, m), 2.22 (3H, s), 2.23 (3H, s), 2.32–2.43 (6H, m), 3.18 (3H, s), 3.40–3.46 (4H, m), 3.63 (3H, s), 3.80–4.00 (2H, m), 6.65 (1H, d, J=8Hz), 6.82 (1H, s), 6.90–6.93 (2H, m), 7.05 (1H, d, J=8Hz), 7.30 (1H, t, J=8Hz), 7.53 (1H, d, J=8Hz), 8.12 (1H, d, J=8Hz), 8.23 (1H, d, J=8Hz)

29) 3-Methoxy-N-methyl-N-[4-methyl-2-[5-(4-methylpiperazin-1-yl)carbonylpent-1-yloxy]phenyl]-4-(2-methyl-1H-pyrazolo[1,5-b][1,2,4]triazol-7-yl)carbonylaminobenzamide NMR (DMSO-$d_6$, δ) : 1.40–1.50 (2H, m), 1.50–1.62 (2H, m), 1.70–1.80 (2H, m), 2.23 (6H, s), 2.29–2.37 (6H, m), 2.39 (3H, s), 3.19 (3H, s), 3.43–3.47 (4H, m), 3.64 (3H, s), 3.43–3.47 (4H, m), 3.64 (3H, s), 3.80–4.00 (4H, m), 6.63 (1H, d, J=8Hz), 6.78–6.90 (3H, m), 7.01 (1H, d, J=8Hz), 7.73 (1H, d, J=8Hz), 8.05 (1H, s), 8.88 (1H, s)

30) 4-(4-Hydroxyquinazolin-5-yl)carbonylamino-3-methoxy-N-methyl-N-[4-methyl-2-[5-(4-methylpiperazin-1-yl)carbonylpent-1-yloxy[phenyl]benzamide NMR (CDCl$_3$, δ) : 1.40–1.55 (2H, m), 1.65–1.80 (4H, m), 2.27 (3H, s), 2.30 (3H, s), 2.33–2.43 (6H, m), 3.33 (3H, s), 3.50 (2H, t, J=7Hz), 3.60–3.67 (5H, m), 3.77–3.97 (2H, m), 6.60–6.65 (2H, m), 6.90–6.95 (2H, m), 7.02 (1H, s), 7.50–7.53 (1H, m), 7.77–7.80 (1H, m), 7.92 (1H, s), 7.98 (1H, s), 8.33 (1H, d, J=8Hz)

31) 4-(2-Dimethylaminomethyl-1H-benzimidazol-4-yl)carbonylamino-3-methoxy-N-methyl-N-[4-methyl-2-[5-(4-methylpiperazino-1-yl)carbonylpent-1-yloxy]phenyl]benzamide NMR (CDCl$_3$, δ) : 1.50–1.60 (2H, m), 1.60–1.78 (2H, m), 1.78–1.90 (2H, m), 2.25 (3H, s), 2.27 (3H, s), 2.33–2.40 (12H, m) 3.33 (3H, s), 3.48 (2H, t, J=7Hz), 3.62 (2H, t, J=7Hz), 3.75–4.00 (7H, m), 6.55–6.62 (2H, m), 6.85 (1H, d, J=8Hz), 6.94 (1H, d, J=8Hz), 7.01 (1H, s), 7.33 (1H, t, J=8Hz), 7.57 (1H, d, J=8Hz), 8.15 (1H, d, J=8Hz), 8.50 (1H, d, J=8Hz)

32) 3-Methoxy-N-methyl-N-[4-methyl-2-[5-(4-methylpiperazin-1-yl)carbonylpent-1-yloxy]phenyl]-4-[2-(4-methylpiperazin-1-yl)methyl-1H-benzimidazol-4-yl]carbonylaminobenzamide NMR (CDCl$_3$, δ) : 1.50–1.60 (2H, m), 1.67–1.78 (2H, m), 1.78–1.86 (2H, m), 2.26–2.38 (12H, m), 2.48 (4H, br s), 2.62 (4H, br s), 3.32 (3H, s), 3.47 (2H, t, J=7Hz), 3.62 (2H, t, J=7Hz), 3.80–4.00 (7H, m), 6.54–6.63 (2H, m), 6.86 (1H, d, J=8Hz), 6.93–7.03 (2H, m), 7.28–7.37 (1H, m), 7.58 (1H, d, J=8Hz), 8.15 (1H, d, J=8Hz), 8.52 (1H, d, J=8Hz)

33) 4-[2-(4-Dimethylaminopiperidino)methyl-1H-benzimidazol-4-yl]carbonylamino-3-methoxy-N-methyl-N-[4-methyl-2-[5-(4-methylpiperazin-1-yl)carbonylpent-1-yloxy]phenyl]benzamide NMR (CDCl$_3$, δ) : 1.50–1.93 (8H, m), 2.13–2.40 (17H, m), 2.92–3.00 (2H, m), 3.32 (3H, s), 3.48 (2H, t, J=7Hz), 3.62 (2H, t, J=7Hz), 3.82–4.00 (7H, m), 6.54–6.62 (2H, m), 6.86(1H, d, J=8Hz), 6.93–7.05 (2H, m), 7.35 (1H, t, J=8Hz), 7.59 (1H, d, J=8Hz), 8.15 (1H, d, J=8Hz), 8.50 (1H, d, J=8Hz)

34) 3-Methoxy-N-methyl-N-[4-methyl-2-[5-(4-methylpiperazin-1-yl)carbonylpent-1-yloxy]phenyl]-4-(2-morpholinomethyl-1H-benzimidazol-4-yl)carbonylaminobenzamide NMR (CDCl$_3$, δ) : 1.50–1.60 (2H, m), 1.66–1.77 (2H, m), 1.78–1.90 (2H, m), 2.25 (3H, s), 2.28 (3H, s), 2.35–2.40 (6H, m), 2.53–2.62 (4H, m), 3.33 (3H, s), 3.50 (2H, t, J=7Hz), 3.63 (2H, t, J=7Hz), 3.73–3.77 (4H, m), 3.81–4.01 (7H, m), 6.56–6.63 (2H, m), 6.87 (1H, d, J=8Hz), 6.96–7.07 (2H, m), 7.28–7.38 (1H, m), 7.50–7.60 (1H, m), 8.17 (1H, d, J=8Hz), 8.52 (1H, d, J=8Hz)

EXAMPLE 41

The following compound was obtained according to a similar manner to that of Example 4.

1) N-[2-[4,4-Dimethyl(2,5-oxazolinyl)]phenyl]-3-methoxy-N-methyl-4-(3-nitro-2-trifluoroacetylaminobenzoyl)aminobenzamide NMR (CDCl$_3$, δ) : 1.36 (3H, s), 1.37 (3H, s), 3.39 (3H, s), 3.63 (3H, s), 4.10 (2H, s), 6.71–6.60 (6H, m), 7.77 (1H, d, J=8Hz), 7.95 (1H, d, J=8Hz), 8.09 (1H, d, J=8Hz), 8.18 (1H, d, J=8Hz)

2) 3-Methoxy-N-methyl-N-[2-(morpholin-4-yl)phenyl]-4-(3-nitro-2-trifluoroacetylaminobenzoyl)aminobenzamide NMR (CDCl$_3$, δ) : 2.18–2.63 (2H, m), 2.74–2.93 (2H, m), 3.48 (3H, s), 3.54–3.82 (7H, m), 6.87–7.40 (7H, m), 7.91–8.24 (3H, m)

3) 3-Methoxy-N-methyl-N-[2-(4-methyl-1-piperazinyl)phenyl]-4-(3-nitro-2-trifluoroacetylaminobenzoyl)aminobenzamide NMR (CDCl$_3$, δ) : 2.30–3.00 (11H, m), 3.46 (3H, s), 3.59 (3H, s), 6.85–6.96 (2H, m), 7.04 (1H, d, J=8Hz), 7.11–7.24 (2H, m), 7.25–7.39 (2H, m), 7.94 (1H, d, J=8Hz), 8.15 (1H, d, J=8Hz), 8.24 (1H, d, J=8Hz)

4) 3-Methoxy-N-methyl-4-(3-nitro-2-trifluoroacetylaminobenzoyl)amino-N-(2-piperidinophenyl)benzamide NMR (CDCl$_3$, δ) : 1.42–1.74 (6H, m), 2.36–2.65 (2H, m), 2.70–2.88 (2H, m), 3.42–3.76 (6H, m), 6.39–8.24 (10H, m)

EXAMPLE 42

The following compounds were obtained according to a similar manner to that of Example 7.

1) N-(2-Acetoxy-4-methylphenyl)-4-(2,3-diaminophenyl)carbonylamino-3-methoxy-N-methylbenzamide NMR (CDCl$_3$, δ) : 2.30 (6H, sx2), 3.35 (3H, s), 3.70 (3H, s), 6.67 (1H, t, J=8Hz), 6.81–7.05 (6H, m), 8.29 (1H, d, J=8Hz), 8.45 (1H, s)

2) 4-(2,3-Diaminophenyl)carbonylamino-3-methoxy-N-(2-methoxycarbonyl-4-methylphenyl)-N-methylbenzamide NMR (CDCl$_3$, δ) : 2.31 (3H, s), 3.40 (3H, s), 3.71 (3H, s), 3.85 (3H, s), 6.62 (1H, t, J=8Hz), 6.80 (1H, d, J=8Hz), 6.88 (1H, d, J=8Hz), 6.93 (1H, s), 7.02 (1H, d, J=8Hz), 7.10 (1H, d, J=8Hz), 7.59 (1H, s), 8.19 (1H, d, J=8Hz), 8.42 (1H, s)

3) 4-(2,3-Diaminophenyl)carbonylamino-3-methoxy-N-methyl-N-[2-(4-phthalimidobut-1-yloxy)-4-methylphenyl]benzamide

EXAMPLE 43

The following compounds were obtained according to a similar manner to that of Example 13.

1) N-(2-Acetoxy-4-methylphenyl)-4-(1H-benzimidazol-4-yl)carbonylamino-3-methoxy-N-methylbenzamide NMR (CDCl$_3$, δ) : 2.27 (3H, s), 2.30 (3H, s), 3.35 (3H, s), 3.74 (3H, s), 6.86 (1H, s), 6.90–7.03 (3H, m), 7.11 (1H, d, J=8Hz), 7.39 (1H, t, J=8Hz,), 7.76 (1H, d, J=8Hz), 7.95 (1H, d, J=8Hz), 8.18 (1H, s), 8.49 (1H, d, J=8Hz)

2) 4-(1H-Benzimidazol-4-yl)carbonylamino-3-methoxy-N-(2-methoxycarbonyl-4-methylphenyl)-N-methylbenzamide NMR (CDCl$_3$, δ) : 2.30 (3H, s), 3.41 (3H, s), 3.70 (3H, s), 3.82 (3H, s), 6.82–6.90 (2H, m), 7.13 (1H, d, J=8Hz), 7.24 (1H, d, J=8Hz), 7.33 (1H, t, J=8Hz), 7.57 (1H, s), 7.72 (1H, d, J=8Hz), 7.98 (1H, d, J=8Hz), 8.10 (1H, s), 8.41 (1H, d, J=8Hz)

EXAMPLE 44

The following compounds were obtained according to a similar manner to that of Example 16.

1) 3-Methoxy-N-methyl-4-(2-methyl-1H-benzimidazol-4-yl)carbonylamino-N-[2-(4-phthalimidobut-1-yloxy)-4-methylphenyl]benzamide NMR (CDCl$_3$, δ) : 1.77–1.92 (4H, m), 2.22 (3H, s), 2.64 (3H, s), 3.31 (3H, s), 3.69–3.80 (5H, m), 3.89 (1H, m), 3.97 (1H, m), 6.53–6.61 (3H, m), 6.85 (1H, d, J=8Hz), 6.90–6.97 (2H, m), 7.25 (1H, t, J=8Hz), 7.59–7.70 (3H, m), 7.78–7.90 (3H, m), 8.40 (1H, d, J=8Hz)

2) 3-Methoxy-N-(2-methoxycarbonyl-4-methylphenyl)-N-methyl-4-(2-methyl-1H-benzimidazol-4-yl)carbonylaminobenzamide NMR (CDCl$_3$, δ) : 2.30 (3H, s), 2.60 (3H, s), 3.41 (3H, s), 3.70 (3H, s), 3.83 (3H, s), 6.81–6.89 (2H, m), 7.13 (1H, d, J=8Hz), 7.22–7.30 (2H, m), 7.51–7.58 (2H, m), 7.90 (1H, d, J=8Hz), 8.41 (1H, d, J=8Hz)

EXAMPLE 45

The following compounds were obtained according to a similar manner to that of Example 18.

1) 3-Methyl-N-methyl-N-[4-methyl-2-[5-(4-methylpiperazin-1-yl)carbonylpent-1-yloxy]phenyl]-4-[2-(3-phthalimidopropyl)-1H-benzimidazol-4-yl]carbonylaminobenzamide NMR (CDCl$_3$, δ) : 1.47–1.60 (2H, m), 1.68–1.77 (2H, m), 1.78–1.90 (2H, m), 2.26 (3H, s), 2.28 (3H, s), 2.30–2.40 (8H, m), 3.00 (2H, t, J=7Hz), 3.32 (3H, s), 3.48 (2H, t, J=7Hz), 3.63 (2H, t, J=7Hz), 3.80–4.00 (7H, m), 6.55–6.62 (2H, m), 6.87 (1H, d, J=8Hz), 6.96 (1H, d, J=8Hz), 7.02 (1H, s), 7.32 (1H, t, J=8Hz), 7.60 (1H, d, J=8Hz), 7.66–7.87 (5H, m), 8.10 (1H, d, J=8Hz), 8.49 (1H, d, J=8Hz)

2) 3-Methoxy-N-[4-methyl-2-[5-(4-methylpiperazin-1-yl)carbonylpent-1-yloxy]phenyl]-4-(2-phenyl-1H-benzimidazol-4-yl)carbonylaminobenzamide NMR (DMSO-d$_6$, δ) : 1.40–1.50 (2H, m), 1.50–1.63 (2H, m), 1.70–1.90 (2H, m), 2.13 (3H, m), 2.17–2.23 (4H, m), 2.22 (3H, s), 2.31 (2H, t, J=7Hz), 3.20 (3H, s), 3.39 (4H, br s), 3.87 (3H, s), 3.85–4.00 (2H, m), 6.65 (1H, d, J=8Hz), 6.83 (1H, s), 6.94 (1H, d, J=8Hz), 7.00 (1H, s), 7.04 (1H, d, J=8Hz), 7.40 (1H, t, J=8Hz), 7.57–7.69 (3H, m), 7.80 (1H, d, J=8Hz), 7.97 (1H, d, J=8Hz), 8.32–8.37 (3H, m), 8.50 (1H, d, J=8Hz)

EXAMPLE 46

The following compounds were obtained according to a similar manner to that of Example 23.

1) 4-[(2-Ethoxycarbonylinodolin-4-yl)carbonyl]amino-3-methoxy-N-methyl-N-[4-methyl-2-[5-(4-methylpiperazin-1-yl)carbonylpent-1-yloxy]phenyl]benzamide NMR (CDCl$_3$, δ) : 1.27 (3H, t, J=8Hz), 1.48–1.59 (2H, m), 1.67–1.89 (4H, m), 2.29 (3H, s), 2.31 (3H, s), 2.36–2.45 (6H, m), 3.32 (3H, s), 3.48–3.53 (2H, m), 3.61–3.72 (3H, m), 3.77 (3H, s), 3.84–4.00 (2H, m), 4.09–4.23 (3H, m), 4.41 (1H, dd, J=7, 9Hz), 4.55–4.60 (1H, br s), 6.59 (1H, d, J=8Hz), 6.62 (1H, s), 6.80–6.88 (2H, m), 6.92 (1H, d, J=8Hz), 6.99–7.05 (2H, m), 7.15 (1H, t, J=8Hz), 8.23 (1H, d, J=8Hz), 8.40 (1H, s)

2) 4-[(Indolin-4-yl)carbonyl]amino-3-methoxy-N-methyl-N-[4-methyl-2-[5-(4-methylpiperazin-1-yl)carbonylpent-1-yloxy]phenyl]benamide NMR (CDCl$_3$, δ) : 1.49–1.59 (2H, m), 1.67–1.88 (4H, m), 2.28 (3H, s), 2.30 (3H, s), 2.32–2.42 (6H, m), 3.32 (3H, s), 3.36 (2H, t, J=9Hz), 3.47–3.52 (2H, m), 3.56–3.66 (4H, m), 3.78 (3H, s), 3.84–3.99 (2H, m), 6.59 (1H, d, J=8Hz), 6.63 (1H, s), 6.73 (1H, d, J=8Hz), 6.86 (1H, d, J=8Hz), 6.90 (1H, d, J=8Hz), 6.97–7.03 (2H, m), 7.09 (1H, t, J=8Hz), 8.27 (1H, d, J=8Hz), 8.39 (1H, s)

3) 4-[(2-Hydroxymethylindolin-4-yl)carbonyl]amino-3-methoxy-N-methyl-N-[4-methyl-2-[5-(4-methylpiperazin-1-yl)carbonylpent-1-yloxy]phenyl]benzamide NMR (CDCl$_3$, δ) : 1.47–1.57 (2H, m), 1.65–1.86 (4H, m), 2.28 (3H, s), 2.32 (3H, s), 2.34–2.45 (6H, m), 3.06–3.17 (1H, m), 3.32 (3H, s), 3.41–3.52 (3H, m), 3.57 (1H, dd, J=8, 13Hz), 3.60–3.67 (2H, m), 3.70 (1H, dd, J=5, 13Hz), 3.77 (3H, s), 3.83–3.98 (2H, m), 4.02–4.10 (1H, m), 6.59 (1H, d, J=8Hz), 6.62 (1H, s), 6.74 (1H, d, J=8Hz), 6.87 (1H, d, J=8Hz), 6.92 (1H, d, J=8Hz), 6.98 (1H, d, J=8Hz), 7.01 (1H, s), 7.10 (1H, t, J=8Hz), 8.25 (1H, d, J=8Hz), 8.39 (1H, s)

4) 4-[(Indolin-6-yl)carbonyl]amino-3-methoxy-N-methyl-N-[4-methyl-2-[5-(4-methoxypiperazin-1-yl)carbonylpent-1-yloxy]phenyl]benzamide NMR (CDCl$_3$, δ) : 1.48–1.58 (2H, m), 1.64–1.87 (4H, m), 2.28 (3H, s), 2.30 (3H, s), 2.32–2.42 (6H, m), 3.07 (2H, t, J=8Hz), 3.32 (3H, s), 3.46–3.51 (2H, m), 3.60 (2H, t, J=8Hz), 3.61–3.68 (2H, m), 3.77 (3H, s), 3.83–3.98 (2H, M), 6.58 (1H, d, J=8Hz), 6.62 (1H, s), 6.84 (1H, d, J=8Hz), 6.91 (1H, d, J=8Hz), 6.99–7.16 (3H, m), 8.27 (1H, d, J=8Hz), 8.44 (1H, s)

5) 4-[2-[[2-(Dimethylamino)ethyl]amino]-1H-benzimidazol-4-yl]carbamoyl-3-methoxy-N-methyl-N-[4-methyl-2-[5-(4-methylpiperazin-1-yl)carbonylpent-1-yloxy]phenyl]benzamide NMR (DMSO-d$_6$, δ) : 1.35–1.50 (2H, m), 1.50–1.66 (2H, m), 1.66–1.85 (2H, m), 2.14 (3H, s), 2.17–2.39 (15H, m), 2.45–2.60 (2H, m), 3.21 (3H, s), 3.27– 3.53 (3H, m), 3.80–4.01 (5H,m), 6.46–6.54 (1H, m), 6.60–6.71 (1H, m), 6.72–6.85 (2H, m), 6.90 (1H, d, J=8Hz), 6.95–7.04 (3H, m), 7.81–7.94 (2H, m)

EXAMPLE 47

The following compounds were obtained according to a similar manner to that of Example 25.

1) 4-[2-Carbamoyl-1H-benzimidazol-4-yl]carbonylamino-3-methoxy-N-methyl-N-[4-methyl-2-[5-(4-methylpiperazin-1-yl)carbonylpent-1-yloxy]phenyl]benzamide NMR (CDCl$_3$, δ) : 1.44–1.66 (2H, m), 1.66–1.80 (2H, m), 1.80–1.93 (2H, m), 2.26 (3H, s), 2.30 (3H, s), 2.32–2.46 (6H, m), 3.35 (3H, s), 3.45–3.54 (2H, m), 3.60–3.71 (2H, m), 3.79–3.92 (4H, m), 3.92–4.03 (1H, m), 6.32 (1H, br peak), 6.56–6.69 (2H, m), 6.90 (1H, d, J=8Hz), 6.94–7.04 (1H, m), 7.10 (1H, s), 7.48–7.61 (2H, m), 7.73 (1H, d, J=8Hz), 8.28 (1H, d, J=8Hz), 8.47–8.57 (1H, m)

2) 4-[2-(N,N-Dimethylcarbamoyl)-1H-benzimidazol-4-yl]carbonylamino-3-methoxy-N-methyl-N-[4-methyl-2-(5-(4-methylpiperazin-1-yl)carbonylpent-1-yloxy]phenyl]benamide NMR (CDCl$_3$, δ) : 1.45–1.64 (2H, m), 1.64–1.78 (2H, m), 1.78–1.92 (2H, m), 2.26 (3H, s), 2.29 (3H, s), 2.31–2.43

(6H, m), 3.25 (3H, s), 3.33 (3H, s), 3.43–3.53 (2H, m), 3.59–3.68 (2H, m), 3.70–4.03 (8H, m), 6.54–6.69 (2H, m), 6.86 (1H, d, J=8Hz), 6.93 (1H, d, J=8Hz), 7.09 (1H, s), 7.49 (1H, br peak), 7.71 (1H, br peak), 8.25 (1H, br peak), 8.34 (1H, d, J=8Hz)

EXAMPLE 48

The following compounds were obtained according to a similar manner to that of Example 26.

1) 4-(2-Aminomethyl-1H-benzimidazol-4-yl)carbonylamino-N-(2-(5-ethoxycarbonylpent-1-yloxy)-4-methyphenyl]-3-methoxy-N-methylbenzamide 2) 4-(2-Aminomethyl-1H-benzimidazol-4-yl)carbamoyl-3-methoxy-N-methyl-N-[4-methyl-2-[5-(4-methylpiperazin-1-yl)carbonylpent-1-yloxy]penyl]benzamide NMR (DMSO-$d_6$, δ) : 1.36–1.50 (2H, m), 1.50–1.64 (2H, m), 1.70–1.82 (2H, m), 2.15 (3H, s), 2.17–2.40 (9H, m), 3.21 (3H, s), 3.37–3.47 (4H, m), 3.81–4.04 (7H, m), 6.64 (1H, d, J=8Hz), 6.81 (1H, s), 6.99–7.14 (4, m), 7.14–7.24 (1H, m), 7.90 (1H, br peak), 8.09 (1H, br peak)

3) 4-[2-(2-Aminoethyl)-1H-benzimidazol-4-yl]carbamoyl-3-methoxy-N-methyl-N-[4-methyl-2-[5-(4-methylpiperazin-1-yl)carbonylpent-1-yloxy]phenyl]benzamide NMR (DMSO-$d_6$, δ) : 1.36–1.51 (2H, m), 1.51–1.64 (2H, m), 1.70–1.83 (2H, m), 2.14 (3H, s), 2.17–2.38 (9H, m), 2.94 (2H, t, J=5Hz), 3.09 (2H, t, J=5Hz), 3.21 (3H, s), 3.24–3.49 (4H, m), 3.84–4.04 (5H, m), 6.64 (1H, d, J=8Hz), 6.81 (1H, s), 7.02 (1H, d, J=8Hz), 7.06–7.20 (4H, m), 7.85–7.94 (1H, m), 8.00–8.10 (1H, m)

EXAMPLE 49

The following compounds were obtained according to a similar manner to that of Example 29.

1) 4-(2-Amino-3-nitrobenzoyl)amino-N-[2-[4,4-dimethyl(2,5-oxazolinyl)]phenyl]-3-methoxy-N-methylbenzamide NMR (CDCl$_2$, δ) : 1.35 (6H, s), 3.39 (3H, s), 3.67 (3H, s), 4.09 (2H, s), 6.68 (1H, dd, J=8, 8Hz), 6.99 (1H, s), 7.05 (1H, d, J=8Hz), 7.14 (1H, d, J=8Hz), 7.27 (1H, dd, J=8, 8Hz), 7.37 (1H, dd, J=8, 8Hz), 7.70 (1H, d, J≦8Hz), 7.79 (1H, d, J=8Hz), 8.04–8.23 (3H, m), 8.25–8.36 (2H, m)

2) 4-(2-Amino-3-nitrobenzoyl)amino-3-methoxy-N-methyl-N-[2-(morpholin-4-yl)phenyl]benzamide NMR (CDCl$_3$, δ) : 2.45–2.63 (2H, m), 2.80–2.98 (2H, m), 3.49 (3H, s), 3.63–3.86 (7H, m), 6.69 (1H, dd, J=8, 8Hz), 6.92 (1H, d, J=8Hz), 7.02 (1H, m), 7.05–7.16 (2H, m), 7.17–7.30 (2H, m), 7.72 (1H, d, J=8Hz), 8.10–8.22 (3H, m), 8.28–8.40 (2H, m)

3) 4-(2-Amino-3-nitrobenzoyl)amino-3-methoxy-N-methyl-N-(2-piperidinophenyl)benzamide NMR (CDCl$_3$, δ) : 1.43–1.72 (6H, m), 2.42–2.56 (2H, m), 2.73–2.87 (2H, m), 3.50 (3H, s), 3.71 (3H, s), 6.68 (1H, dd, J=8, 8Hz), 6.90 (1H, d, J=8Hz), 6.97–7.07 (3H, m), 7.12–7.22 (2H, m), 7.73 (1H, d, J=8Hz), 8.11–8.22 (3H, m), 8.28–8.39 (2H, m)

4) 4-(2-Amino-3-nitrobenzoyl)amino-3-methyl-N-methyl-N-[2-(4-methyl-1-piperazinyl)phenyl]benzamide NMR (CDCl$_3$, δ) : 2.40 (3H, s), 2.45–2.73 (6H, m), 2.89–3.04 (2H, m), 3.50 (3H, s), 3.69 (3H, s), 6.68 (1H, dd, J=8, 8Hz), 6.89–7.01 (2H, m), 7.02–7.12 (2H, m), 7.15–7.29 (2H, m), 7.72 (1H, d, J=8Hz), 8.09–8.24 (3H, m), 8.28–8.38 (2H, m)

EXAMPLE 50

The following compound was obtained according to a similar manner to that of Example 29.

4-(2-Carboxyphenylcarbamoyl)-3-methoxy-N-methyl-N-[4-methyl-2-[5-(4-methylpiperazin-1-yl)carbonylpent-1-yloxy]-phenyl]benzamide NMR (DMSO-$d_6$, δ) : 1.38–1.65 (2H, m), 1.70–1.85 (2H, m), 2.21 (3H, s), 2.30–2.60 (6H, m), 2.68–2.91 (3H, m), 3.17 (3H, s), 3.20 (3H, s), 3.66 (3H, s), 3.83–4.03 (3H, m), 6.10 (1H, d, J=8Hz), 6.82–7.02 (3H, m), 7.43–7.52 (2H, m), 7.63–7.70 (2H, m), 7.91–8.01 (2H, m), 8.67 (1H, d, J=8Hz)

EXAMPLE 51

The following compound was obtained by using 4-(1H-benzimidazol-4-yl)carbonylamino-N-(2-methoxycarbonyl-4-methylphenyl)-3-methoxy-N-methylbenzamide as a starting compound according to a similar manner to that of Example 29.

4-(1H-Benzimidazol-4-yl)carbonylamino-N-(2-carboxy-4-methylphenyl)-3-methoxy-N-methylbenzamide NMR (DMSO-$d_6$, δ) : 2.29 (3H, s), 3.28 (3H, s), 3.70 (3H, s), 6.80–6.89 (2H, m), 7.28–7.43 (3H, m), 7.51 (1H, s), 7.80 (1H, d, J=8Hz), 7.94 (1H, d, J=8Hz), 8.31 (1H, m), 8.53 (1H, s)

EXAMPLE 52

The following compound was obtained according to a similar manner to that of Example 51.

N-(2-Carboxy-4-methylphenyl)-3-methoxy-N-methyl-4-(2-methyl-1H-benzimidazol-4-yl)carbonylaminobenzamide NMR (DMSO-$d_6$, δ) : 2.29 (3H, s), 2.65 (3H, s), 3.29 (3H, s), 3.73 (3H, s), 6.80–6.89 (2H, m), 7.28–7.38 (3H, m), 7.51 (1H, s), 7.70 (1H, d, J=8Hz), 7.89 (1H, d, J=8Hz), 8.30 (1H, br)

EXAMPLE 53

The following compounds were obtained according to a similar manner to that of Example 30.

1) 4-[(2-Carbamoylindol-4-yl)carbonyl]amino-3-methoxy-N-methyl-N-[4-methyl-2-[5-(4-methylpiperazin-1-yl)carbonylpent-1-yloxy]phenyl]benzamide NMR (CDCl$_3$, δ): 1.47–1.56 (2H, m), 1.63–1.87 (4H, m), 2.28 (3H, s), 2.29 (3H, s), 2.31–2.42 (6H, m), 3.33 (3H, s), 3.47–3.51 (2H, m), 3.58–3.65 (2H, m), 3.74 (3H, s), 3.85–4.00 (2H, m), 6.59–6.66 (2H, m), 6.91 (1H, d, J=8 Hz), 6.98–7.03 (2H, m), 7.35 (1H, t, J=8 Hz), 7.52 (1H, d, J=8 Hz), 7.57–7.63 (2H, m), 8.32 (1H, d, J=8 Hz), 8.60 (1H, s), 9.88 (1H, s)

2) 4-[[2-(N-Methylcarbamoyl)indol-4-yl]carbonyl]amino-3-methoxy-N-methyl-N-[4-methyl-2-[5-(4-methylpiperazin-1-yl)carbonylpent-1-yloxy]phenyl]benzamide NMR (CDCl$_3$, δ): 1.45–1.56 (2H, m), 1.63–1.86 (4H, m), 2.27 (3H, s), 2.29 (3H, s), 2.30–2.42 (6H, m), 3.04 and 3.06 (Total 3H, s), 3.34 (3H, s), 3.47–3.52 (2H, m), 3.57–3.63 (2H, m), 3.75 (3H, s), 3.83–4.00 (2H, m), 6.58–6.64 (2H, m), 6.90 (1H, d, J=8 Hz), 6.98–7.03 (2H, m), 7.32 (1H, t, J=8 Hz), 7.46 (1H, s), 7.51 (1H, d, J=8 Hz), 7.60 (1H, d, J=8 Hz), 8.02 (1H, s), 8.33 (1H, d, J=8 Hz), 8.59 (1H, s), 9.76 (1H, s)

3) 4-[2-(N,N-Dimethylcarbamoyl)phenylcarbamoyl]-3-methoxy-N-methyl-N-[4-methyl-2-[5-(4-methylpiperazin-1-yl)carbonylpent-1-yloxy]phenyl]benzamide NMR (CDCl$_3$, δ): 1.49–1.59 (2H, m), 1.67–1.89 (4H, m), 2.27 (3H, s), 2.30 (3H, s), 2.32–2.42 (6H, m), 2.93 (3H, s), 3.12 (3H, s), 3.35 (3H, s), 3.47–3.52 (2H, m), 3.60–3.67 (2H, m), 3.84–3.98 (2H, m), 3.92 (3H, s), 6.58 (1H, d, J=8 Hz), 6.61 (1H, s), 6.83 (1H, d, J=8 Hz), 6.98 (1H, d, J=8 Hz), 7.01 (1H, s), 7.10 (1H, t, J=8 Hz), 7.20 (1H, d, J=8 Hz), 7.40 (1H, t, J=8 Hz), 8.01 (1H, d, J=8 Hz), 8.39 (1H, d, J=8 Hz)

EXAMPLE 54

The following compounds were obtained according to a similar manner to that of Example 32.

1) 4-[(1-tert-Butoxycarbonyl-3-hydroxymethylindol-4-yl) carbonyl]amino-3-methoxy-N-methyl-[4-methyl-2-[5-(4-methylpiperazin-1-yl)carbonylpent-1-yloxy]phenyl]benzamide NMR (CDCl$_3$, δ): 1.49–1.61 (2H, m), 1.66 (9H, s), 1.67–1.89 (4H, m), 2.29 (3H, s), 2.30 (3H, s), 2.32–2.42 (6H, m), 3.34 (3H, s), 3.46–3.51 (2H, m), 3.60–3.67 (2H, m), 3.76 (3H, s), 3.88–4.01 (2H, m), 4.61 (2H, s), 6.61 (1H, d, J=8 Hz), 6.67 (1H, s), 6.87 (1H, d, J=8 Hz), 6.93 (1H, d, J=8 Hz), 7.07 (1H, s), 7.37 (1H, t, J=8 Hz), 7.44 (1H, d, J=8 Hz), 7.68 (1H, s), 8.29 (1H, d, J=8 Hz), 8.39–8.47 (2H, m)

2) 4-(2-Hydroxymethyl-1H-benzimidazol-4-yl)carbamoyl-3-methoxy-N-methyl-[4-methyl-2-[5-(4-methylpiperazin-1-yl)carbonylpent-1-yloxy]phenyl]benzamide NMR (DMSO-d$_6$, δ): 1.40–1.50 (2H, m), 1.50–1.63 (2H, m), 1.69–1.82 (2H, m), 2.14 (3H, s), 2.17–2.37 (9H, m), 3.21 (3H, s), 3.37–3.48 (4H, m), 3.83–4.03 (5H, m), 4.72 (2H, d, J=5 Hz), 5.74 (1H, br peak), 6.64 (1H, d, J=8 Hz), 6.80 (1H, s), 6.99–7.23 (5H, m), 7.90 (1H, d, J=8 Hz), 8.09 (1H, d, J=8 Hz)

EXAMPLE 55

The following compounds were obtained according to similar manners to those of Examples 4 and 28.

1) 4-(2-Amino-3-nitrophenyl)carbonylamino-3-methoxy-N-(2-methoxycarbonyl-4-methylphenyl)-N-methylbenzamide NMR (CDCl$_3$, δ): 2.23 (3H, s), 3.39 (3H, s), 3.75 (3H, s), 3.89 (3H, s), 6.67 (1H, t, J=8 Hz), 6.83 (1H, d, J=8 Hz), 6.97 (1H, s), 7.12 (1H, d, J=8 Hz), 7.27 (1H, d, J=8 Hz), 7.59 (1H, s), 7.70 (1H, d, J=8 Hz), 8.04–8.18 (3H, m), 8.12 (1H, d, J=8 Hz)

2) 4-(2-Amino-3-nitrophenyl)carbonylamino-3-methoxy-N-[2-(4-methoxyphenylmethyloxy)-4-methylphenyl]-N-methylbenzamide NMR (CDCl$_3$, δ): 2.28 (3H, s), 3.37 (3H, s), 3.66 (3H, s), 3.81 (3H, s), 4.87 (1H, d, J=12 Hz), 5.01 (1H, d, J=12 Hz), 6.60–6.73 (3H, m), 6.85–6.99 (4H, m), 7.23–7.31 (3H, m), 7.71 (1H, d, J=8 Hz), 8.10–8.19 (3H, m), 8.29–8.34 (2H, m)

3) 4-(2-Amino-3-nitrophenyl)carbonylamino-3-methoxy-N-methyl-N-[2-(5-tert-butoxycarbonylaminopent-1-yl)oxy-4-methyl]phenylbenzamide NMR (CDCl$_3$, δ): 1.41 (9H, s), 1.45–1.60 (4H, m), 1.75–1.84 (2H, m), 2.28 (3H, s), 3.09–3.18 (2H, m), 3.31 (3H, s), 3.78 (3H, s), 3.80–3.97 (2H, m), 4.67 (1H, br), 6.58–6.63 (2H, m), 6.69 (1H, t, J=8 Hz), 6.89 (1H, d, J=8 Hz), 6.96 (1H, d, J=8 Hz), 7.03 (1H, s), 7.71 (1H, d, J=8 Hz), 8.13 (1H, d, J=8 Hz), 8.29–8.37 (3H, m)

EXAMPLE 56

The following compounds were obtained according to similar manners to those of Examples 7 and 16.

1) N-(2-Amino-4-methylphenyl)-3-methoxy-N-methyl-4-(2-methyl-1H-benzimidazol-4-yl)carbonylaminobenzamide NMR (CDCl$_3$, δ): 2.18 (3H, s), 2.76 (3H, s), 3.31 (3H, s), 3.80 (3H, s), 6.37 (1H, d, J=8 Hz), 6.53 (1H, s), 6.66 (1H, d, J=8 Hz), 7.00–7.08 (2H, m), 7.26 (1H, t, J=8 Hz), 7.60 (1H, d, J=8 Hz), 7.86 (1H, br), 8.44 (1H, d, J=8 Hz)

2) 3-Methoxy-N-methyl-4-(2-methyl-1H-benzimidazol-4-yl)carbonylamino-N-[2-(5-tert-butoxycarbonylaminopent-1-yl)oxy-4-methyl]phenylbenzamide NMR (CDCl$_3$, δ): 1.42 (9H, s), 1.42–1.60 (4H, m), 1.72–1.85 (2H, m), 2.28 (3H, s), 2.67 (3H, s), 3.08–3.17 (2H, m), 3.36 (3H, s), 3.60–3.97 (2H, m), 3.78 (3H, s), 4.80 (1H, br), 6.57–6.63 (2H, m), 6.80–7.08 (3H, m), 7.30 (1H, m), 7.59 (1H, m), 7.91 (1H, br), 8.45 (1H, m)

3) N-[2-[4,4-Dimethyl(2,5-oxazolinyl)]phenyl]-3-methoxy-N-methyl-4-(2-methyl-1H-benzimidazol-4-yl)carbonylaminobenzamide NMR (CDCl$_3$, δ): 1.33 (3H, s), 1.35 (3H, s), 1.60 (3H, s), 3.41 (3H, s), 3.68 (3H, s), 4.04–4.14 (2H, m), 6.95 (1H, s), 7.07 (1H, d, J=8 Hz), 7.14 (1H, d, J=8 Hz), 7.18–7.39 (4H, m), 7.59 (1H, d, J=8 Hz), 7.80 (1H, d, J=8 Hz), 7.90 (1H, d, J=8 Hz), 8.47 (1H, d, J=8 Hz)

4) 3-Methoxy-N-methyl-4-(2-methyl-1H-benzimidazol-4-yl)carbonylamino-N-[2-(morpholin-4-yl)phenyl]benzamide NMR (DMSO-d$_6$, δ): 2.25–2.44 (2H, m), 2.62 (3H, s), 2.72–2.90 (2H, m), 3.20–3.80 (10H, m), 6.87–6.99 (2H, m), 7.05 (1H, d, J=8 Hz), 7.09–7.26 (2H, m), 7.30 (1H, dd, J=8, 8 Hz), 7.42 (1H, d, J=8 Hz), 7.67 (1H, d, J=8 Hz), 7.87 (1H, d, J=8 Hz), 8.41 (1H, m)

3) 3-Methoxy-N-methyl-4-(2-methyl-1H-benzimidazol-4-yl)carbonylamino-N-(2-piperidinophenyl)benzamide NMR (CDCl$_3$, δ): 1.41–1.72 (6H, m), 2.36–2.53 (2H, m), 2.66 (3H, s), 2.70–2.87 (2H, m), 3.51 (3H, s), 3.71 (3H, s), 6.88 (1H, d, J=8 Hz), 6.93–7.33 (7H, m), 7.62 (1H, d, J=8 Hz), 7.90 (1H, d, J=8 Hz), 8.42 (1H, d, J=8 Hz)

6) 3-Methoxy-N-methyl-4-(2-methyl-1H-benzimidazol-4-yl)carbonylamino-N-[2-(4-methyl-1-piperazinyl)phenyl]benzamide NMR (CDCl$_3$, δ): 2.40 (3H, br s), 2.46–2.70 (9H, m), 2.86–3.01 (2H, m), 3.51 (3H, s), 3.70 (3H, s), 6.82–6.98 (2H, m), 7.02–7.21 (3H, m), 7.22–7.36 (2H, m), 7.43–7.54 (1H, m), 8.11 (1H, d, J=8 Hz), 8.58 (1H, d, J=8 Hz)

EXAMPLE 57

To a solution of 2-(4-pyridyl)-1H-benzimidazole-4-carboxylic acid (155 mg) in dichloromethane (2 ml) was added oxalyl chloride (0.056 ml) and N,N-dimethylformamide (2 drops) and stirred at ambient temperature for 2 hours. The reaction mixture was concentrated in vacuo to give 2-(4-pyridyl)-1H-benzimidazole-4-carbonyl chloride. To a solution of 4-amino-3-methoxy-N-methyl-N-[4-methyl-2-[5-(4-methylpiperazin-1-yl)carbonylpent-1-yloxy]phenyl]benzamide (76.8 mg) and triethylamine (65 mg) in dichloromethane (5 mL) was added 2-(4-pyridyl)-1H-benzimidazole-4-carbonyl chloride in dichloromethane (2 ml) under ice bath cooling and stirred at ambient temperature for 6 hours. After the reaction mixture was concentrated in vacuo, the residue was diluted with chloroform and saturated sodium hydrogen carbonate aqueous solution. The organic layer was separated and washed with brine. The solution was dried over magnesium sulfate and concentrated in vacuo. The residue was purified by silica gel (Chromatorex, Fuji Silysia Chemical Ltd.) column chromatography (methanol:chloroform=1:49). To the purified product was added water and 1N hydrochloric acid (0.51 ml). The solution was lyophilized to give 3-methoxy-N-methyl-N-[4-methyl-2-[5-(4-methylpiperazin-1-yl)carbonylpent-1-yloxy]phenyl]-4-[2-(4-pyridyl)-1H-benzimidazol-4-yl]carbonylaminobenzamide trichloride (120 mg).

NMR (DMSO-d$_6$, δ): 1.42–1.52 (2H, m), 1.52–1.62 (2H, m), 1.73–1.83 (2H, m), 2.22 (3H, s), 2.41 (2H, t, J=7 Hz), 2.73 (3H, s), 2.82–3.07 (4H, m), 3.21 (3H, s), 3.32–3.52

(3H, m), 3.88 (3H, s), 3.90–4.13 (2H, m), 4.40–4.50 (1H, m), 6.66 (1H, d, J=8 Hz), 6.83 (1H, s), 6.98 (1H, d, J=8 Hz), 7.03 (1H, s), 7.07 (1H, d, J=8 Hz), 7.55 (1H, t, J=8 Hz), 7.94 (1H, d, J=8 Hz), 8.07 (1H, d, J=8 Hz), 8.48 (1H, d, J=8 Hz), 8.75 (2H, br s)

EXAMPLE 58

The following compounds were obtained according to a similar manner to that of Example 57.

1) 3-Methoxy-N-methyl-N-[4-methyl-2-[5-(4-methylpiperazin-1-yl)carbonylpent-1-yloxy]phenyl]-4-[2-(3-pyridyl)-1H-benzimidazol-4-yl]carbonylaminobenzamide trihydrochloride NMR (DMSO-$d_6$, δ): 1.40–1.52 (2H, m), 1.52–1.65 (2H, m), 1.70–1.83 (2H, m), 2.22 (3H, s), 2.40 (2H, t, J=7 Hz), 2.73 (3H, s), 2.85–3.12 (4H, m), 3.21 (3H, s), 3.35–3.53 (3H, m), 3.88 (3H, s), 3.92–4.13 (2H, m), 4.40–4.45 (1H, m), 6.66 (1H, d, J=8 Hz), 6.83 (1H, s), 6.96 (1H, d, J=8 Hz), 7.01 (1H, s), 7.06 (1H, d, J=8 Hz), 7.48 (1H, t, J=8 Hz), 7.89 (1H, d, J=8 Hz), 8.03 (1H, d, J=8 Hz), 8.13 (1H, t, J=8 Hz), 8.48 (1H, d, J=8 Hz), 9.00 (1H, br s), 9.12 (1H, d, J=8 Hz), 9.67 (1H, br s)

2) 3-Methoxy-N-methyl-N-[4-methyl-2-[5-(4-methylpiperazin-1-yl)carbonylpent-1-yloxy]phenyl]-4-[2-(2-pyridyl)-1H-benzimidazol-4-yl]carbonylaminobenzamide trihydrochloride NMR (DMSO-$d_6$, δ): 1.40–1.52 (2H, m), 1.52–1.63 (2H, m), 1.68–1.82 (2H, m), 2.22 (3H, s), 2.37 (2H, t, J=7 Hz), 2.72 (3H, s), 2.82–3.10 (4H, m), 3.20 (3H, s), 3.33–3.56 (3H, m), 3.85 (3H, s), 3.90–4.10 (2H, m), 4.40–4.45 (1H, m), 6.62 (1H, t, J=8 Hz), 6.80–7.06 (4H, m), 7.43 (1H, t, J=8 Hz), 7.63 (1H, t, J=7 Hz), 7.79 (1H, d, J=8 Hz), 7.98 (1H, d, J=8 Hz), 8.17 (1H, t, J=8 Hz), 8.48 (1H, t, J=8 Hz), 8.82 (1H, d, J=5 Hz)

3) 4-(2H-1,4-Benzoxazin-3-oxo-8-yl)carbonylamino-3-methoxy-N-methyl-N-[4-methyl-2-[5-(4-methylpiperazin-1-yl)carbonylpent-1-yloxy]phenyl]benzamide hydrochloride NMR (DMSO-$d_6$, δ): 1.40–1.51 (2H, m), 1.51–1.63 (2H, m), 1.70–1.80 (2H, m), 2.22 (3H, s), 2.37 (2H, t, J=7 Hz), 2.73 (3H, s), 2.80–3.04 (4H, m), 3.17 (3H, s), 3.36–3.50 (3H, m), 3.73 (3H, s), 3.80–4.15 (2H, m), 4.40–4.47 (1H, m), 4.89 (2H, s), 6.64 (1H, d, J=8 Hz), 6.80 (1H, s), 6.88–6.93 (2H, m), 7.03 (1H, d, J=8 Hz), 7.10–7.13 (2H, m), 7.59–7.62 (1H, m), 8.22 (1H, d, J=8 Hz)

EXAMPLE 59

The following compound was obtained by using N-(2-phthalimido-4-methylphenyl)-2-amino-3-methyoxy-N-methylbenzamide as a starting compound according to a similar manner to that of Example 4.

N-(2-Amino-4-methylphenyl)-4-(2-amino-3-nitrophenyl)carbonylamino-3-methoxy-N-methylbenzamide NMR (CDCl$_3$, δ): 2.20 (3H, s), 3.30 (3H, s), 3.79 (3H, s), 3.89 (2H, br s), 6.39 (1H, d, J=8 Hz), 6.52 (1H, s), 6.63–6.71 (2H, m), 7.05 (1H, d, J=8 Hz), 7.10 (1H, s), 7.70 (1H, d, J=8 Hz), 8.12 (2H, br s), 8.20 (1H, d, J=8 Hz), 8.31 (1H, d, J=8 Hz), 8.34 (1H, br)

EXAMPLE 60

A mixture of N-[2-(5-ethoxycarbonylpent-1-yloxy)-4-methylphenyl]-3-methoxy-N-methyl-4-(3-nitro-2-phthalimidomethylcarbonylaminophenyl)carbonylaminobenzamide (3.96 g), iron powder (1.42 g) and acetic acid (3.05 g) in ethanol (50 ml) was refluxed for 4 hours and the solvent was removed under reduce pressure. The residue was stirred in a mixture of chloroform (100 ml) and saturated aqueous sodium hydrogen carbonate (100 ml) for 30 minutes and the solution was filtered through a bed of celite. The organic phase was separated and washed with brine. The solution was dried over magnesium sulfate and the solvent was evaporated in vacuo. The residue was solidified with diethyl ether to give N-[2-(5-ethoxycarbonylpent-1-yloxy)-4-methylphenyl]-3-methoxy-N-methyl-4-(2-phthalimidomethyl-1H-benzimidazol-4-yl)carbonylaminobenzamide (3.64 g).

NMR (CDCl$_3$, δ): 1.24 (3H, t, J=7.5 Hz), 1.46–1.57 (2H, m), 1.63–1.75 (2H, m), 1.75–1.88 (2H, m), 2.25 (3H, s), 2.34 (2H, t, J=7.5 Hz), 3.31 (3H, s), 3.74–4.00 (2H, m), 4.02 (3H, s), 4.12 (2H, q, J=7.5 Hz), 5.21 (2H, s), 6.53–6.63 (2H, m), 6.86 (11H, d, J=8 Hz), 6.93 (1H, d, J=8 Hz), 7.03 (1H, s), 7.35 (1H, t, J=8 Hz), 7.53 (1H, d, J=8 Hz), 7.68–7.78 (2H, m), 7.84–7.93 (2H, m), 8.14 (1H, d, J=8 Hz), 8.50 (1H, d, J=8 Hz).

EXAMPLE 61

To a solution of 4-(2,3-diaminobenzoyl)amino-3-methoxy-N-methyl-N-[4-methyl-2-[5-(4-methylpiperazin-1-yl)carbonylpent-1-yloxy]phenyl]benzamide (240 mg) in acetonitrile (1 ml) was added cyanoacetic acid (662 mg). The solution was heated at 100° C. for 8 hours. After cooling, aqueous sodium hydrogen carbonate was added to the mixture and extracted with ethyl acetate. The extract was washed with brine and dried over sodium sulfate. After evaporation of the solvent, the residue was purified by silica gel column chromatography (7% methanol in chloroform) and preparative thin-layer chromatography (ethyl acetate:methanol=1:1) to give 4-[[2-cyanomethyl-1H-benzimidazol-4-yl]carbonylamino]-3-methoxy-N-methyl-N-[4-methyl-2-[5-(4-methylpiperazin-1-yl)carbonylpent-1-yloxy]phenyl]benzamide (80 mg).

NMR (CDCl$_3$, δ): 1.42–1.94 (6H, m), 2.24 (3H, s), 2.29 (3H, s), 2.32–2.48 (6H, m), 3.36 (3H, s), 3.43–3.55 (2H, m), 3.55–4.21 (9H, m), 6.50–6.68 (2H, m), 6.78 (1H, br), 6.81–7.02 (2H, m), 7.20–7.31 (1H, m), 7.36–7.48 (1H, m), 8.08 (1H, d, J=8 Hz), 8.47 (1H, d, J=8 Hz)

EXAMPLE 62

A solution of 4-(2,3-diaminobenzoyl)amino-3-methoxy-N-methyl-N-[4-methyl-2-[5-(4-methylpiperazin-1-yl)carbonylpent-1-yloxy]phenyl]benzamide (100 mg) and mercaptoacetic acid (448 mg) was heated at 80° C. for 5 hours. The reaction mixture was diluted with chloroform and washed with aqueous sodium hydrogen carbonate. The extract was dried over sodium sulfate. After evaporation of the solvent, the residue was purified by silica gel column chromatography (10% methanol in chloroform) to give 3-methoxy-4-(2-mercaptomethyl-1H-benzimidazol-4-yl)carbonylamino-N-methyl-N-[4-methyl-2-[5-(4-methylpiperazin-1-yl)carbonylpent-1-yloxy]phenyl]benzamide (60 mg).

NMR (CDCl$_3$, δ): 1.42–1.90 (6H, m), 2.19–2.47 (12H, m), 3.34 (3H, s), 3.49 (2H, m), 3.57–4.07 (9H, m), 6.51–6.68 (2H, m), 6.81–7.05 (3H, m), 7.31 (1H, dd, J=8, 8 Hz), 7.51 (1H, d, J=8 Hz), 8.12 (1H, d, J=8 Hz), 8.50 (1H, m)

EXAMPLE 63

A solution of 4-(2,3-diaminobenzoyl)amino-3-methoxy-N-methyl-N-[4-methyl-2-[5-(4-methylpiperazin-1-yl)carbonylpent-1-yloxy]phenyl]benzamide (150 mg), butyrolactone (628 mg) and p-toluenesulfonic acid (139 mg) was heated at 100° C. for 4 hours. The reaction mixture was diluted with chloroform and washed with aqueous sodium hydrogen carbonate. The extract was dried over sodium sulfate. After evaporation of the solvent, the residue was purified by silica gel column chromatography (10% methanol in chloroform) and then preparative thin-layer chromatography (chloroform/methanol=20/3) to give 4-[2-(3-hydroxypropyl)-1H-benzimidazol-4-yl]carbonylamino-3-methoxy-N-methyl-N-[4-methyl-2-[5-(4-methylpiperazin-1-yl)carbonylpent-1-yloxy]phenyl]benzamide (70 mg).

NMR (CDCl$_3$, δ): 1.44–1.59 (2H, m), 1.63–1.88 (4H, m), 2.01–2.14 (2H, m), 2.25 (3H, s), 2.27 (3H, s), 2.30–2.43 (6H, m), 2.90–3.03 (2H, m), 3.34 (3H, s), 3.42–3.52 (2H, m), 3.56–4.02 (9H, m), 6.52–6.66 (2H, m), 6.78–7.03 (3H, m), 7.24 (1H, dd, J=8, 8 Hz), 7.46 (1H, m), 8.07 (1H, m), 8.52 (1H, m)

EXAMPLE 64

To a mixture of 4-(2,3-diaminobenzoyl)amino-3-methoxy-N-methyl-N-[4-methyl-2-[5-(4-methylpiperazin-1-yl)carbonylpent-1-yloxy]phenyl]benzamide (140 mg) and sodium carbonate (14 mg) in ethyl acetate (1.5 ml) was added dropwise a solution of 1,1-dichloro-1,1-diphenoxymethane (67 mg) in ethyl acetate (1 ml) in water bath and the mixture was stirred at same temperature for 5 hours. The reaction mixture was evaporated in vacuo and dissolved in chloroform. The organic layer was washed with water, dried over magnesium sulfate and evaporated in vacuo. The residue was purified by preparative thin-layer chromatography (chloroform:methanol=10:1) to give 3-methoxy-N-methyl-N-[4-methyl-2-[5-(4-methylpiperazin-1-yl)carbonylpent-1-yloxy]phenyl]-4-(2-phenoxy-1H-benzimidazol-4-yl)carbonylaminobenzamide (18 mg).

NMR (DMSO-d$_6$, δ): 1.33–1.48 (2H, m), 1.48–1.62 (2H, m), 1.62–1.78 (2H, m), 2.14 (3H, s), 2.17–2.35 (9H, m), 3.09 (3H, s), 3.17 (3H, s), 3.36–3.45 (4H, m), 3.76–3.87 (1H, m), 3.87–3.99 (1H, m), 6.64 (1H, d, J=8 Hz), 6.75 (1H, s), 6.81 (1H, s), 6.88 (1H, d, J=8 Hz), 7.00 (1H, d, J=8 Hz), 7.25–7.38 (2H, m), 7.45–7.52 (4H, m), 7.60 (1H, d, J=8 Hz), 7.88 (1H, d, J=8 Hz), 8.25 (1H, d, J=8 Hz)

EXAMPLE 65

A mixture of 4-(2,3-diaminobenzoyl)amino-3-methoxy-N-methyl-N-[4-methyl-2-[5-(4-methylpiperazin-1-yl)carbonylpent-1-yloxy]phenyl]benzamide (150 mg) and diphenyl N-sulfamoylcarbonimidate (85 mg) in dichloromethane (8 ml) was refluxed for 24 hours under nitrogen. The reaction mixture was poured into water and extracted with chloroform. The organic layer was washed with water, driver over magnesium sulfate and evaporated in vacuo. The residue was purified by preparative thin-layer chromatography (chloroform:methanol=10:1/chloroform:methanol=6:1) to give 3-methoxy-N-methyl-N-[4-methyl-2-[5-(4-methylpiperazin-1-yl)carbonylpent-1-yloxy]phenyl]-4-(2-sulfamoylamino-1H-benzimidazol-4-yl)carbonylaminobenzamide (38 mg).

NMR (DMSO-d$_6$, δ): 1.37–1.50 (2H, m), 1.50–1.64 (2H, m), 1.64–1.82 (2H, m), 2.23 (6H, s), 2.27–2.43 (6H, m), 3.19 (3H, s), 3.40–3.51 (4H, m), 3.70 (3H, s), 3.80–4.03 (2H, m), 6.30 (2H, br peak), 6.65 (1H, d, J=8 Hz), 6.82 (1H, s), 6.86–6.95 (2H, m), 7.03 (1H, d, J=8 Hz), 7.07 (1H, t, J=8 Hz), 7.32 (1H, d, J=8 Hz), 7.70 (1H, d, J=8 Hz), 7.91 (1H, br peak), 10.48 (1H, br peak), 11.49 (1H, br peak)

EXAMPLE 66

A suspension of 4-(2,3-diaminobenzoyl)amino-3-methoxy-N-methyl-N-[4-methyl-2-[5-(4-methylpiperazin-1-yl)carbonylpent-1-yloxy]phenyl]benzamide (150 mg) and diphenyl-N-cyanocarbonimidate (64 mg) in 2-propanol (2 ml) was refluxed for 3 hours under nitrogen. The reaction mixture was evaporated in vacuo and dissolved in chloroform. The organic solution was washed with water, dried over magnesium sulfate and evaporated in vacuo. The residue was purified by preparative thin-layer chromatography (chloroform:ethyl) acetate:methanol=8:1:1/chloroform:methanol=10:1) to give 4-(2-cyanoamino-1H-benzimidazol-4-yl)carbonylamino-3-methoxy-N-methyl-N-[4-methyl-2-[5-(4-methylpiperazin-1-yl)carbonylpent-1-yloxy]phenyl]benzamide (45 mg).

NMR (DMSO-d$_6$, δ): 1.38–1.51 (2H, m), 1.51–1.66 (2H, m), 1.66–1.81 (2H, m), 2.23 (3H, s), 2.35 (2H, t, J=7 Hz), 2.60 (2H, br s), 2.80–2.99 (4H, m), 3.20 (3H, s), 3.50–3.68 (2H, m), 3.74–3.90 (3H, m), 3.90–4.02 (1H, m), 6.65 (1H, d, J=8 Hz), 6.80–6.95 (4H, m), 7.03 (1H, d, J=8 Hz), 7.07 (1H, d, J=8 Hz), 7.55 (1H, d, J=8 Hz), 8.29–8.40 (1H, m)

EXAMPLE 67

A mixture of 4-(2,3-diaminophenyl)carbonylamino-3-methoxy-N-methyl-N-[4-methyl-2-[5-(4-methylpiperazin-1-yl)carbonylpent-1-yloxy]phenyl]benzamide (200 mg), glyoxal (47 mg) and sodium hydrogen sulfite (169 mg) in ethanol (15 ml) was refluxed for 5 hours. The solution was diluted with chloroform (30 ml) and the solution was washed with water and brine. The organic solution was dried over magnesium sulfate and the solvent was evaporated in vacuo to give an oil. The crude product was purified by silica gel column (1% methanol in chloroform) to give 3-methoxy-N-methyl-N-[4-methyl-2-[5-(4-methylpiperazin-1-yl)carbonylpent-1-yloxy]phenyl]-4-(quinoxalin-5-yl)carbonylaminobenzamide (131 mg).

NMR (CDCl$_3$, δ): 1.49–1.60 (2H, m), 1.63–1.77 (2H, m), 1.77–1.90 (2H, m), 2.27 (3H, s), 2.32 (3H, s), 2.33–2.46 (6H, m), 3.31 (3H, s), 3.45–3.53 (2H, m), 3.60–3.69 (2H, m), 3.74–4.00 (2H, m), 3.81 (3H, s), 6.54–6.66 (2H, m), 6.87 (1H, d, J=8 Hz), 6.98 (1H, d, J=8 Hz), 7.06 (1H, s), 8.18–8.27 (3H, m), 8.52 (1H, s), 8.75 (1H, s), 8.93 (2H, s)

EXAMPLE 68

To a solution of 4-[N-[1-[(tert-butyl)oxycarbonyl]benzimidazol-4-yl]carbamoyl]-N-[2-[4,4-dimethyl(2,5-oxazolinyl)]phenyl]-3-methoxy-N-methylbenzamide (400 mg) in dichloromethane (10 ml) was added trifluoroacetic acid (4 ml). The mixture was stirred at ambient temperature for 3 hours. The reaction mixture was concentrated in vacuo and the residue was diluted with a mixture of chloroform and saturated aqueous sodium bicarbonate solution. The organic layer was separated and washed with water and brine. The solution was dried over magnesium sulfate and the solvent was evaporated in vacuo. The residue was purified by column chromatography (chloroform:methanol=100:3) to give 4-[N-(1H-benzimidazol-4-yl)carbamoyl]-N-[2-[4,4-dimethyl(2,5-oxazolinyl)]phenyl]-3-methoxy-N-methylbenzamide (290 mg).

NMR (CDCl$_3$, δ): 1.38 (3H, s), 1.39 (3H, s), 3.40 (3H, s), 3.84 (3H, s), 4.01–4.17 (2H, m), 7.05–7.45 (7H, m), 7.62 (1H, d, J=8 Hz), 7.79 (1H, d, J=8 Hz), 7.96 (1H, s), 8.07 (1H, d, J=8 Hz)

EXAMPLE 69

The following compounds were obtained according to a similar manner to that of Example 68.

1) 4-[N-(1H-Benzimidazol-4-yl)carbamoyl]-3-methoxy-N-methyl-N-[2-(morpholin-4-yl)phenyl]benzamide NMR (CDCl₃, δ): 2.30–2.48 (2H, m), 2.77–2.94 (2H, m), 3.52 (3H, s), 3.60–3.94 (7H, m), 6.75–7.37 (9H, m), 7.59–8.43 (3H, m)

2) 4-[N-(1H-Benzimidazol-4-yl)carbamoyl]-3-methoxy-N-methyl-N-[2-(1-pyrrolyl)phenyl]benzamide NMR (CDCl₃, δ): 3.50 (3H, s), 3.91 (3H, s), 6.21–6.30 (2H, m), 6.38–6.46 (2H, m), 6.56–6.68 (2H, m), 7.06–7.53 (7H, m), 7.87–8.07 (2H, m)

3) 3-Methoxy-N-methyl-4-[N-(2-methyl-1H-benzimidazol-4-yl)carbamoyl]-N-[2-(4-methyl-1-piperazinyl)phenyl]benzamide NMR (CDCl₃, δ): 2.39 (3H, s), 2.41–2.68 (9H, m), 2.86–3.01 (2H, m), 3.52 (3H, s), 3.84 (3H, s), 6.89 (1H, d, J=8 Hz), 6.99 (1H, s), 7.07–7.36 (7H, m), 8.10 (1H, d, J=8 Hz)

4) 3-Methoxy-N-methyl-4-[N-(2-methyl-1H-benzimidazol-4-yl)carbamoyl]-N-[2-(2,5-oxazolyl)phenyl]benzamide NMR (CDCl₃, δ): 2.60 (3H, s), 3.48 (3H, s), 3.80 (3H, s), 6.78–6.87 (2H, m), 7.13 (1H, dd, J=8, 8 Hz), 7.28–7.47 (7H, m), 7.78 (1H, s), 7.88 (1H, m), 7.95 (1H, d, J=8 Hz)

EXAMPLE 70

The solution of 4-[(1-tert-butoxycarbonyl-2-phthalimidomethylindol-4-yl)carbonyl]amino-3-methoxy-N-methyl-N-[4-methyl-2-[5-(4-methylpiperazin-1-yl)carbonylpent-1-yloxy]phenyl]benzamide (312 mg) in ethanol (5.0 ml) and 1N sodium hydroxide aqueous solution (1.76 ml) was stirred at ambient temperature for 6 hours. The resulting solution was diluted with water and extracted with chloroform. The organic layer was dried over magnesium sulfate and concentrated in vacuo to afford 4-[(2-aminomethylindol-4-yl)carbonyl]amino-3-methoxy-N-methyl-N-[4-methyl-2-[5-(4-methylpiperazin-1-yl)carbonylpent-1-yloxy]phenyl]benzamide (228 mg).

NMR (DMSO-d₆, δ): 1.38–1.62 (4H, m), 1.68–1.80 (2H, m), 2.15 (3H, s), 2.18–2.37 (6H, m), 2.23 (3H, s), 3.19 (3H, s), 3.26–3.48 (3H, m), 3.69 (3H, s), 3.80–4.01 (3H, m), 4.18 (2H, s), 6.67 (1H, d, J=8 Hz), 6.83 (1H, s), 6.90–6.98 (2H, m), 7.14 (1H, d, J=8 Hz), 7.20 (1H, t, J=9 Hz), 7.56 (1H, d, J=9 Hz), 7.62 (1H, d, J=9 Hz), 7.95 (1H, d, J=8 Hz), 9.06 (1H, s)

EXAMPLE 71

The following compounds were obtained according to a similar manner to that of Example 70.

1) 4-[(2-Methylindol-4-yl)carbonyl]amino-3-methoxy-N-methyl-N-[4-methyl-2-[5-(4-methylpiperazin-1-yl)carbonylpent-1-yloxy]phenyl]benzamide NMR (CDCl₃, δ): 1.46–1.60 (2H, m), 1.66–1.88 (4H, m), 2.28 (6H, s), 2.32–2.42 (6H, m), 2.48 (3H, s), 3.33 (3H, s), 3.44–3.51 (2H, m), 3.58–3.67 (2H, m), 3.78 (3H, s), 3.85–4.00 (2H, m), 6.59 (1H, d, J=8 Hz), 6.63 (1H, s), 6.70 (1H, s), 6.87 (1H, d, J=8 Hz), 6.93 (1H, d, J=8 Hz), 7.04 (1H, s), 7.17 (1H, t, J=8 Hz) 7.42 (1H, d, J=8 Hz), 7.57 (1H, d, J=8 Hz), 8.30–8.40 (2H, m), 8.71 (1H, s)

2) 4-[(3-Hydroxymethylindol-4-yl)carbonyl]amino-3-methoxy-N-methyl-N-[4-methyl-2-[5-(4-methylpiperazin-1-yl)carbonylpent-1-yloxy]phenyl]benzamide NMR (CDCl₃, δ): 1.49–1.89 (6H, m), 2.29 (3H, s), 2.30 (3H, s), 2.32–2.42 (6H, m), 3.34 (3H, s), 3.46–3.51 (2H, m), 3.60–3.66 (2H, m), 3.77 (3H, s), 3.89–4.00 (2H, m), 4.68 (2H, s), 6.62 (1H, d, J=8 Hz), 6.67 (1H, s), 6.87 (1H, d, J=8 Hz), 6.92 (1H, d, J=8 Hz), 7.07 (1H, s), 7.22 (1H, t, J=8 Hz), 7.29 (1H, s), 7.36 (1H, d, J=8 Hz), 7.52 (1H, d, J=8 Hz), 8.32 (1H, d, J=8 Hz), 8.48–8.52 (2H, br s)

3) 4-[(Indol-6-yl)carbonyl]amino-3-methoxy-N-methyl-N-[4-methyl-2-[5-(4-methylpiperazin-1-yl)carbonylpent-1-yloxy]phenyl]benzamide NMR (CDCl₃, δ): 1.47–1.58 (2 H, m), 1.65–1.87 (4 H, m), 2.28 (3 H, s), 2.29 (3 H, s), 2.31–2.41 (6 H, m), 3.33 (3 H, s), 3.45–3.51 (2 H, m), 3.59–3.67 (2 H, m), 3.77 (3 H, s), 3.83–3.99 (2 H, m), 6.58–6.64 (3 H, m), 6.88 (1 H, d, J=8 Hz), 6.94 (1 H, d, J=8 Hz), 7.03 (1 H, s), 7.37 (1 H, t, J=3 Hz), 7.50 (1 H, d, J=9 Hz), 7.68 (1 H, d, J=9 Hz), 7.98 (1 H, s), 8.32 (1 H, d, J=8 Hz), 8.60 (1 H, s), 8.83–8.88 (1 H, br s).

EXAMPLE 72

The following compound was obtained by using 3-methoxy-N-methyl-4-[2-[[2-((N-tert-butoxycarbonyl)methylamino)ethyl]amino-1-tert-butoxycarbonyl-1H-benzimidazol-4-yl]carbamoyl-N-[4-methyl-2-[5-(4-methylpiperazin-1-yl)carbonylpent-1-yloxy]phenyl]benzamide as a starting compound according to a similar manner to that of Example 23.

3-Methoxy-N-methyl-4-[2-[[2-(methylamino)ethyl]amino]1-H-benzimidazol-4-yl]carbamoyl-N-[4-methyl-2-[5-(4-methylpiperazin-1-yl)carbonylpent-1-yloxy]phenyl]benzamide NMR (CDCl₃, δ): 1.36–1.50 (2 H, m), 1.50–1.64 (2 H, m), 1.64–1.82 (2 H, m), 2.15 (3 H, s), 2.17–2.36 (9 H, m), 2.40 (3 H, s), 2.88 (2 H, t, J=5 Hz), 3.22 (3 H, s), 3.25–3.55 (7 H, m), 3.81–4.02 (5 H, m), 6.64 (1 H, d, J=8 Hz), 6.70–6.85 (3 H, m), 6.90 (1 H, d, J=8 Hz), 7.00 (1 H, d, J=8 Hz), 7.03–7.13 (2 H, m), 7.77–7.90 (2 H, m).

EXAMPLE 73

The following compound was obtained according to a similar manner to that of Example 72.

4-[2-[(2-Aminoethyl)methylamino]-1H-benzimidazol-4-yl]carbamoyl-3-methoxy-N-methyl-N-[4-methyl-2-[5-(4-methylpiperazin-1-yl)carbonylpent-1-yloxy]phenyl]benzamide NMR (DMSO-d₆, δ): 1.37–1.50 (2 H, m), 1.50–1.63 (2 H, m), 1.68–1.82 (2 H, m), 2.14 (3 H, s), 2.16–2.38 (9 H, m), 2.93 (2 H, t, J=5 Hz), 3.14 (3 H, s), 3.21 (3 H, s), 3.36–3.47 (4 H, m), 3.55 (2 H, t, J=5 Hz), 3.81–4.02 (2 H, m), 6.63 (1 H, d, J=8 Hz), 6.76–6.87 (2 H, m), 6.91 (1 H, d, J=8 Hz), 7.00 (1 H, d, J=8 Hz), 7.04–7.12 (2 H, m), 7.88 (1 H, d, J=8 Hz), 7.95 (1 H, d, J=8 Hz).

EXAMPLE 74

The following compound was obtained by using 4-[2-tert-butoxycarbonylamino-1H-benzimidazol-4-yl]carbamoy-3-methoxy-N-methyl-N-[4-methyl-2-[5-(4-methylpiperazin-1-yl)carbonylpent-1-yloxy]phenyl]benzamide as a starting compound according to a similar manner to that of Example 23.

4-[2-Amino-1H-benzimidazol-4-yl]carbamoyl-3-methoxy-N-methyl-N-[4-methyl-2-[5-(4-methylpiperazin-1-yl)carbonylpent-1-yloxy]phenyl]benzamide NMR (DMSO-d₆, δ): 1.37–1.50 (2 H, m), 1.50–1.65 (2 H, m), 1.65–1.82 (2 H, m), 2.14 (3 H, s), 2.17–2.38 (9 H, m), 3.23 (3 H, s), 3.36–3.48 (4 H, m), 3.67–4.05 (5 H, m), 6.20 (2 H, br peak), 6.65 (1 H, d, J=8 Hz), 6.73–6.93 (3 H, m), 6.96–7.14 (3 H, m), 7.84–7.92 (2 H, m).

EXAMPLE 75

The following compounds were obtained according to a similar manner to that of Preparation 13.

1) 4-(2-Aminomethyl-1-methyl-1H-benzimidazol-4-yl)carbonylamino-3-methoxy-N-methyl-N-[4-methyl-2-[5-(4-methylpiperazin-1-yl)carbonylpent-1-yloxy]phenyl]benzamide NMR (CDCl$_3$, δ): 1.44–1.75 (4 H, m), 1.75–1.90 (2 H, m), 2.25 (3 H, s), 2.28 (3 H, s), 2.30–2.41 (6 H, m), 3.32 (3 H, s), 3.43–3.52 (2 H, m), 3.57–3.66 (2 H, m), 3.74–3.90 (7 H, m), 3.95 (1 H, br peak), 4.20 (2 H, s), 6.53–6.63 (2 H, m), 6.87 (1 H, d, J=8 Hz), 6.98 (1 H, d, J=8 Hz), 7.03 (1 H, s), 7.37 (1 H, t, J=8 Hz), 7.46 (1 H, d, J=8 Hz), 8.15 (1 H, d, J=8 Hz), 8.55 (1 H, d, J=8 Hz).

2) 4-(2-Aminomethyl-3-methyl-3H-benzimidazol-4-yl)carbonylamino-3-methoxy-N-methyl-N-[4-methyl-2-[5-(4-methylpiperazin-1-yl)carbonylpent-1-yloxy]phenyl]benzamide NMR (CDCl$_3$, δ): 1.48–1.62 (2 H, m), 1.62–1.93 (4 H, m), 2.30 (3 H, s), 2.32–2.41 (5 H, m), 2.41–2.55 (4 H, m), 3.33 (3 H, s), 3.51–3.60 (2 H, m), 3.60–3.77 (5 H, m), 3.81 (3 H, s), 3.87–4.03 (2 H, m), 4.13 (2 H, br peak), 6.61 (1 H, d, J=8 Hz), 6.65 (1 H, s), 6.88 (1 H, d, J=8 Hz), 6.97 (1 H, d, J=8 Hz), 7.03 (1 H, s), 7.22–7.30 (1 H, m), 7.42 (1 H, d, J=8 Hz), 7.86 (1 H, br peak), 8.30 (1 H, d, J=8 Hz), 8.35 (1 H, s).

EXAMPLE 76

A solution of 3-methoxy-N-methyl-N-(4-methyl-2-benzyloxyphenyl)-4-[2-(tert-butoxycarbonyl)aminomethyl-1H-benzimidazol-4-yl]carbonylaminobenzamide (260 mg) in 90% trifluoroacetic acid (2 ml) was stirred at ambient temperature for 2 hours and the solvent was evaporated in vacuo. The residue was stirred with chloroform (10 ml) and saturated aqueous sodium hydrogencarbonate (10 ml) and the organic phase was separated. The solution was washed with brine and dried over magnesium sulfate. The solvent was evaporated in vacuo and the residue was purified by NH type silica gel column (chloroform) to give 4-(2-aminomethyl-1H-benzimidazol-4-yl)carbonylamino-3-methoxy-N-methyl-N-(4-methyl-2-benzyloxyphenyl)benzamide (130 mg).

NMR (CDCl$_3$, δ): 2.22 (3 H, s), 3.39 (3 H, s), 3.57 (3 H, s), 4.15 (2 H, s), 4.88 (1 H, d, J=12 Hz), 5.04 (1 H, d, J=12 Hz), 6.60–6.70 (2 H, m), 6.85–7.01 (3 H, m), 7.32 (1 H, m), 7.38 (5 H, s), 7.46 (1 H, br s), 8.08 (1 H, br s), 8.47 (1 H, br s).

EXAMPLE 77

The following compounds were obtained according to a similar manner to that of Example 76.

1) 4-(2-Aminomethyl-1H-benzimidazol-4-yl)carbonylamino-N-(2,4-dimethylphenyl)-3-methoxy-N-methylbenzamide NMR (DMSO-d$_6$, δ): 2.11 (3 H, s), 2.19 (3 H, s), 3.21 (3 H, s), 3.72 (3 H, s), 4.08 (2 H, s), 6.88–7.05 (4 H, m), 7.14 (1 H, d, J=8 Hz), 7.31 (1 H, t, J=8 Hz), 7.71 (1 H, d, J=8 Hz), 7.89 (1 H, d, J=8 Hz), 8.40 (1 H, d, J=8 Hz).

2) 4-(2-Aminomethyl-1H-benzimidazol-4-yl)carbonylamino-3-methoxy-N-(2-methoxy-4-methylphenyl)-N-methylbenzamide NMR (CDCl$_3$, δ): 2.25 (3 H, s), 3.34 (3 H, s), 3.67 (3 H, s), 3.70 (3 H, s), 4.15 (2 H, s), 6.55–6.63 (2 H, m), 6.82–7.00 (3 H, m), 7.26 (1 H, t, J=8 Hz), 7.48 (1 H, br), 8.08 (1 H, br), 8.52 (1 H, br).

3) 4-(2-Aminomethyl-1H-benzimidazol-4-yl)carbonylamino-3-methoxy-N-methyl-N-[4-methyl-2-[4-(4-methylpiperazin-1-yl)carbonylphenylmethoxy]phenyl]benzamide NMR (CDCl$_3$, δ): 2.26 (3 H, s), 2.30 (3 H, s), 2.31–2.50 (4 H, m), 3.40 (3 H, s), 3.40–3.51 (2 H, m), 3.62 (3 H, s), 3.68–3.83 (2 H, m), 4.17 (2 H, s), 4.88 (1 H, d, J=12 Hz), 5.07 (1 H, d, J=12 Hz), 6.62 (1 H, s), 6.70 (1 H, d, J=8 Hz), 6.87–6.94 (2 H, m), 7.03 (1 H, d, J=8 Hz), 7.20–7.44 (5 H, m), 7.52 (1 H, m), 7.99 (1 H, br), 8.46 (1 H, m).

4) 4-(2-Aminomethyl-1H-benzimidazol-4-yl)carbonylamino-3-methoxy-N-methyl-N-[4-methyl-2-[3-(4-methylpiperazin-1-yl)carbonylprop-1-yloxy]phenyl]benzamide NMR (CDCl$_3$, δ): 2.05–2.16 (2 H, m), 2.23 (3 H, s), 2.30–2.41 (4 H, m), 2.52 (2 H, t, J=7.5 Hz), 3.33 (3 H, s), 3.43–3.50 (2 H, m), 3.59–3.65 (2 H, m), 3.75 (3 H, s), 3.86–4.06 (2 H, m), 4.21 (2 H, s), 6.58–6.67 (2 H, m), 6.90–7.02 (3 H, m), 7.28 (1 H, t, J=8 Hz), 7.56 (1 H, br), 8.06 (1 H, br), 8.49 (1 H, br).

5) 4-(2-Aminomethyl-1H-benzimidazol-4-yl)carbonylamino-3-methoxy-N-methyl-N-[4-methyl-2-[4-(4-methylpiperazin-1-yl)carbonylbut-1-yloxy]phenyl]benzamide NMR (CDCl$_3$, δ): 1.76–1.93 (4 H, m), 2.25 (3 H, s), 2.28 (3 H, s), 2.31–2.47 (4 H, m), 3.33 (3 H, s), 3.49 (1 H, m), 3.60–3.74 (5 H, m), 3.86 (1 H, m), 3.96 (1 H, m), 4.17 (2 H, s), 6.59–6.65 (2 H, m), 6.86–6.95 (2 H, m), 7.00 (1 H, d, J=8 Hz), 7.21 (1 H, t, J=8 Hz), 7.39 (1 H, m), 8.02 (1 H, m), 8.50 (1 H, m).

6) 4-(2-Aminomethyl-1H-benzimidazol-4-yl)carbonylamino-3-methoxy-N-methyl-N-[4-methyl-2-(5-piperazin-1-ylcarbonylpent-1-yloxy)phenyl]benzamide NMR (DMSO-d$_6$, δ): 1.39–1.52 (2 H, m), 1.52–1.63 (2 H, m), 1.70–1.81 (2 H, m), 2.22 (3 H, s), 2.37 (2 H, t, J=7.5 Hz), 2.98–3.13 (4 H, m), 3.20 (3 H, s), 3.61–3.71 (4 H, m), 3.77 (3 H, s), 3.88 (1 H, m), 3.97 (1 H, m), 4.42 (2 H, s), 6.66 (1 H, d, J=8 Hz), 6.83 (1 H, s), 6.92–6.99 (2 H, m), 7.05 (1 H, d, J=8 Hz), 7.41 (1 H, t, J=8 Hz), 7.83 (1 H, d, J=8 Hz), 7.97 (1 H, d, J=8 Hz), 8.35 (1 H, br).

7) 4-(2-Aminomethyl-1H-benzimidazol-4-yl)carbonylamino-N-[2-(5-carbamoylpent-1-yloxy)-4-methylphenyl]-3-methoxy-N-methylbenzamide NMR (CDCl$_3$, δ): 1.46–1.57 (2 H, m), 1.66–1.82 (4 H, m), 2.20–2.30 (2 H, m), 2.23 (3 H, s), 3.32 (3 H, s), 3.61 (3H, s), 3.76 (1 H, m), 3.91 (1 H, m), 4.12 (2 H, s), 5.93 (1 H, br), 6.32 (1 H, br), 6.54–6.63 (2 H, m), 6.73 (1 H, s), 6.93 (1 H, d, J=8 Hz), 7.01 (1 H, d, J=8 Hz), 7.18 (1 H, t, J=8 Hz), 7.43 (1 H, m), 7.90 (1 H, m), 8.46 (1 H, d, J=8 Hz).

8) 4-(2-Aminomethyl-1H-benzimidazol-4-yl)carbonylamino-N-[2-(5-dimethylcarbamoylpent-1-yloxy)-4-methylphenyl]-3-methoxy-N-methylbenzamide NMR (DMSO-d$_6$, δ): 1.48–1.60 (2 H, m), 1.66–1.77 (2 H, m), 1.77–1.90 (2 H, m), 2.28 (3 H, s), 2.38 (2 H, t, J=7.5 Hz), 2.93 (3 H, s), 3.00 (3 H, s), 3.35 (3 H, s), 3.72 (3 H, s), 3.85 (1 H, m), 3.96 (1 H, m), 4.17 (2 H, s), 6.55–6.63 (2 H, m), 6.86 (1 H, d, J=8 Hz), 6.91 (1 H, s), 6.97 (1 H, d, J=8 Hz), 7.24 (1 H, t, J=8 Hz), 7.49 (1 H, br), 8.05 (1 H, br), 8.50 (1 H, br).

9) 4-(2-Aminomethyl-1H-benzimidazol-4-yl)carbonylamino-N-[2-[5-(2,2-dimethylhydrazino)carbonylpent-1-yloxy]-4-methylphenyl]-3-methoxy-N-methylcarbonylaminobenzamide NMR (CDCl$_3$, δ): 1.42–1.62 (2 H, m), 1.62–1.90 (4 H, m), 2.12 (2 H, t, J=7.5 Hz), 2.27 (3 H, s), 2.50 (3 H, s), 2.58 (3 H, s), 3.34 (3 H, s), 3.71 (3 H, s), 3.77–4.00 (2 H, m), 4.20 (2 H, s), 6.27 (1 H, br), 6.52–6.67 (2 H, m), 6.83–7.11 (3 H, m), 7.24 (1 H, m), 7.50 (1 H, br), 8.07 (1 H, br), 8.53 (1 H, br).

10) 4-(2-Aminomethyl-1H-benzimidazol-4-yl)carbonylamino-3-methoxy-N-methyl-N-[4-methyl-2-[5-(4-oxopiperidin-1-yl)carbonylpent-1-yloxy]phenyl]benzamide NMR (CDCl$_3$, δ): 1.41–1.60 (2 H, m), 1.60–1.89 (4 H, m), 2.21 (3 H, s), 2.30–2.50 (6 H, m), 3.30 (3 H, s), 3.41–3.98 (6 H, m), 4.22 (2 H, s), 6.51–6.62 (2 H, m), 6.78–6.99 (3 H, m), 7.24 (1 H, m), 7.55 (1 H, br), 7.96 (1 H, br), 8.45 (1 H, br).

11) 4-(2-Aminomethyl-1H-benzimidazol-4-yl)carbonylamino-N-[2-[5-(4-hydroxypiperidin-1-yl)carbonylpent-1-yloxy]-4-methylphenyl]-3-methoxy-N-methylbenzamide NMR (CDCl$_3$, δ): 1.35–1.54 (4 H, m), 1.54–1.72 (2 H, m), 1.72–1.91 (4 H, m), 2.24 (3 H, s), 2.28–2.41 (2 H, m), 2.95–3.21 (2 H, m), 3.30 (3 H, s), 3.46–3.98 (4 H, m), 3.70 (3 H, s), 4.09 (1 H, m), 4.20 (2 H, s), 6.52–6.63 (2 H, m), 6.78–6.97 (3 H, m), 7.13 (1 H, m), 7.41 (1 H, br), 7.88 (1 H, br), 8.38 (1 H, d, J=8 Hz).

12) 4-(2-Aminomethyl-1H-benzimidazol-4-yl)carbonylamino-N-[2-[5-[N-(2-dimethylaminoeth-1-yl)-N-methylaminocarbonyl]pent-1-yloxy]-4-methylphenyl]-3-methoxy-N-methylbenzamide NMR (CDCl$_3$, δ): 1.31–1.52 (2 H, m), 1.59–1.81 (4 H, m), 2.23 (3 H, s), 2.30–2.41 (2 H, m), 2.73–2.88 (2 H, m), 2.85 (6 H, sx2), 3.05 (3 H, s), 3.29 (1 H, s), 3.55–3.94 (4 H, m), 4.46 (2 H, m), 6.52–6.63 (2 H, m), 6.67 (1 H, s), 6.82–7.10 (3 H, m), 7.31 (1 H, m), 7.75 (1 H, m), 8.33 (1 H, m).

EXAMPLE 78

The following compound was obtained according to similar manners to those of Examples 38 and 76.

4-(2-Aminomethyl-1H-benzimidazol-4-yl)carbonylamino-N-[2-(6-hydroxyhex-1-yl)oxy-4-methyl]phenyl-3-methoxy-N-methylbenzamide dihydrochloride NMR (DMSO-d$_6$, δ): 1.31–1.50 (4 H, m), 1.67–1.76 (2 H, m), 2.21 (3 H, s), 3.18 (3 H, s), 3.40 (2 H, t, J=7.5 Hz), 3.74 (3 H, s), 3.74–3.85 (2 H, m), 3.85 (1 H, m), 3.97 (1 H, m), 4.45 (1 H, m), 4.79 (2 H, m), 6.64 (1 H, d, J=8 Hz), 6.81 (1 H, s), 7.90 (1 H, d, J=8 Hz), 6.97 (1 H, s), 7.03 (1 H, d, J=8 Hz), 7.39 (1 H, t, J=8 Hz), 7.77 (1 H, d, J=8 Hz), 7.94 (1 H, d, J=8 Hz), 8.34 (1 H, d, J=8 Hz), 8.71 (1 H, br).

EXAMPLE 79

To the solution of 3-methoxy-N-methyl-N-[4-methyl-2-[5-(4-methylpiperazin-1-yl)carbonylpent-1-yloxy]phenyl]-4-[2-(3-phthalimidopropyl)-1H-benzimidazol-4-yl]carbonylaminobenzamide (160 mg) in ethanol (5 ml) was added hydrazine hydrate (49 mg) and stirred at ambient temperature for 6 hours. After the reaction mixture was concentrated in vacuo, the residue was purified by preparative thin-layer chromatography (methanol:chloroform:28% ammonia solution=3:5:1). To the purified product was added water and 1N hydrochloric acid (0.51 ml). The solution was lyophilized to give 4-[2-(3-aminopropyl)-1H-benzimidazol-4-yl]carbonylamino-3-methoxy-N-methyl-N-[4-methyl-2-[5-(4-methylpiperazin-1-yl)carbonylpent-1-yloxy]phenyl] benzamide trihydrochloride (70 mg).

NMR (DMSO-d$_6$, δ): 1.42–1.50 (2 H, m), 1.50–1.63 (2 H, m), 1.70–1.82 (2 H, m), 2.12–2.22 (2 H, m), 2.22 (3 H, s), 2.40 (2 H, t, J=7 Hz), 2.73 (3 H, s), 2.80–3.17 (6 H, m), 3.20 (3 H, s), 3.33–3.57 (4 H, m), 3.72 (3 H, s), 3.87–4.10 (3 H, m), 4.40–4.47 (1 H, m), 6.63 (1 H, d, J=8 Hz), 6.82 (1 H, s), 6.90–6.93 (2 H, m), 7.04 (1 H, d, J=8 Hz), 7.43 (1 H, t, J=8 Hz), 7.82 (1 H, d, J=8 Hz), 7.97–8.13 (2 H, m), 8.21 (2 H, br s).

EXAMPLE 80

The solution of 4-[(1-tert-butoxycarbonyl-2-tert-butyldiphenylsilyloxymethylindol-4-yl)carbonyl]amino-3-methoxy-N-methyl-N-[4-methyl-2-[5-(4-methylpiperazin-1-yl)carbonylpent-1-yloxy]phenyl]benzamide (615 mg) in 1N sodium hydroxide aqueous solution (3.1 ml) and methanol (10 ml) was stirred at ambient temperature overnight. The resulting solution was neutralized with 1N hydrochloric acid and extracted with ethyl acetate (20 ml). The organic layer was washed with brine, dried over magnesium sulfate and concentrated in vacuo. The residue was purified by silica gel column chromatography (eluent; 8–10% methanol in chloroform) to give 4-[(2-hydroxymethylindol-4-yl)carbonyl]amino-3-methoxy-N-methyl-N-[4-methyl-2-[5-(4-methylpiperazin-1-yl)carbonylpent-1-yloxy]phenyl] benzamide (362 mg).

NMR (CDCl$_3$, δ): 1.44–1.57 (2 H, m), 1.63–1.85 (4 H, m), 2.27 (3 H, s), 2.29 (3 H, s), 2.30–2.40 (6 H, m), 3.33 (3 H, s), 3.43–3.50 (2 H, m), 3.57–3.63 (2 H, m), 3.70 (3 H, s), 3.82–3.99 (2 H, m), 4.80 (2 H, s), 6.59–6.67 (2 H, m), 6.77 (1 H, s), 6.89 (1 H, d, J=8 Hz), 6.95 (1 H, d, J=8 Hz), 6.98 (1 H, s), 7.18 (1 H, t, J=8 Hz), 7.42 (1 H, d, J=8 Hz), 7.57 (1 H, d, J=8 Hz), 8.32 (1 H, d, J=8 Hz), 8.64 (1 H, s), 8.98–9.03 (1 H, br s).

EXAMPLE 81

The following compound was obtained by using 4-[(1-tert-butoxycarbonyl-2-benzyloxymethylindolin-4-yl)carbonyl]amino-3-methoxy-N-methyl-N-[4-methyl-2-[5-(4-methylpiperazin-1-yl)carbonylpent-1-yloxy]phenyl] benzamide as a starting compound according to a similar manner to that of Preparation 10.

4-[(1-tert-Butoxycarbonyl-2-hydroxymethylindolin-4-yl)carbonyl]amino-3-methoxy-N-methyl-N-[4-methyl-2-[5-(4-methylpiperazin-1-yl)carbonylpent-1-yloxy]phenyl] benzamide NMR (DMSO-d$_6$, δ): 1.40–1.61 (4 H, m), 1.50 (9 H, s), 1.69–1.79 (2 H, s), 2.23 (3 H, s), 2.35–2.42 (2 H, m), 2.69 (3 H, s), 2.98–3.22 (9 H, m), 3.28–3.54 (5 H, m), 3.64 (3 H, s), 3.84–4.00 (2 H, m), 4.10–4.18 (1 H, br), 4.31–4.40 (1 H, m), 4.89 (1 H, t, J=5 Hz), 6.65 (1 H, d, J=8 Hz), 6.82 (1 H, s), 6.88–6.92 (2 H, m), 7.03 (1 H, d, J=8 Hz), 7.20–7.33 (2 H, m), 7.76 (1 H, d, J=8 Hz), 9.13 (1 H, s).

EXAMPLE 82

To an ice bath cooled solution of 4-(2-aminomethyl-1 H-benzimidazol-4-yl)carbonylamino-N-[2-(5-ethoxycarbonylpent-1-yloxy)-4-methylphenyl]-3-methoxy-N-methylbenzamide (2.95 g) in dichloromethane (30 ml) were added triethylamine (496 mg) and di-tert-butyl dicarbonate (1.07 g) and the mixture was stirred at ambient temperature for 3 hours. The solution was washed successively with water, 10% hydrochloric acid, saturated aqueous sodium hydrogencarbonate and brine and the organic phase was dried over magnesium sulfate. The solvent was evaporated in vacuo and the residue was purified by silica gel column (1% methanol in chloroform) to give N-[2-(5-ethoxycarbonylpent-1-yloxy)-4-methylphenyl]-3-methoxy-N-methyl-4-[2-(tert-butoxycarbonylamino)methyl-1H-benzimidazol-4-yl]carbonylaminobenzamide (2.65 g).

NMR (CDCl$_3$, δ): 1.24 (3 H, t, J=7.5 Hz), 1.41–1.55 (2 H, m), 1.48 (9 H, s), 1.63–1.84 (4 H, m), 2.23 (3 H, s), 2.31 (2 H, t, J=7.5 Hz), 3.32 (3 H, s), 3.78 (3 H, s), 3.78–3.98 (2 H, m), 4.12 (2 H, q, J=7.5 Hz), 4.58 (2 H, m), 5.68 (1 H, br t, J=7 Hz), 6.53–6.63 (2 H, m), 6.83–7.04 (3 H, m), 7.30 (1 H, t, J=8 Hz), 7.50 (1 H, d, J=8 Hz), 8.11 (1 H, d, J=8 Hz), 8.49 (1 H, d, J=8 Hz).

EXAMPLE 83

The solution of 4-[(2-ethoxycarbonylindolin-4-yl) carbonyl]amino-3-methoxy-N-methyl-N-[4-methyl-2-[5-(4-methylpiperazin-1-yl)carbonylpent-1-yloxy]phenyl] benzamide (175 mg) in ammonia-methanol solution (8.0 ml) was stood overnight at ambient temperature. The solvent was evaporated in vacuo and the residue was purified by silica gel column chromatography (eluent; 8–10% methanol in chloroform) to give 4-[(2-carbamoylindolin-4-yl) carbonyl]amino-3-methoxy-N-methyl-N-[4-methyl-2-[5-(4-methylpiperazin-1-yl)carbonylpent-1-yloxy]phenyl] benzamide (160 mg).

NMR (CDCl$_3$, δ): 1.48–1.58 (2 H, m), 1.64–1.87 (4 H, m), 2.28 (3 H, s), 2.30 (3 H, s), 2.32–2.41 (6 H, m), 3.32 (3 H, s), 3.46–3.51 (2 H, m), 3.59–3.65 (2 H, m), 3.77 (3 H, s), 3.84–3.98 (3 H, m), 4.38–4.49 (2 H, m), 5.46–5.50 (1 H, br s), 6.59 (1 H, d, J=8 Hz), 6.62 (1 H, s), 6.69–6.74 (1 H, br), 6.85 (1 H, d, J=8 Hz), 6.91 (1 H, d, J=8 Hz), 7.01 (1 H, s), 7.09 (1 H, d, J=8 Hz), 7.18 (1 H, t, J=8 Hz), 8.22 (1 H, d, J=8 Hz), 8.37 (1 H, s).

EXAMPLE 84

To a solution of 4-[(2-hydroxymethylindol-4-yl)carbonyl] amino-3-methoxy-N-methyl-N-[4-methyl-2-[5-(4-methylpiperazin-1-yl)carbonylpent-1-yloxy]phenyl] benzamide (295 mg) in dichloromethane (8.0 ml) was added manganese(IV) oxide (196 mg) and the mixture was stirred at ambient temperature for 3 hours. The resulting mixture was filtered through a bed of celite and the filtrate was concentrated in vacuo. The residue was triturated with diethyl ether-n-hexane (1:3) to give 4-[(2-formylindol-4-yl) carbonyl]amino-3-methoxy-N-methyl-N-[4-methyl-2-[5-(4-methylpiperazin-1-yl)carbonylpent-1-yloxy]phenyl] benzamide (255 mg).

NMR (CDCl$_3$, δ): 1.49–1.61 (2 H, m), 1.68–1.89 (4 H, m), 2.28 (3 H, s), 2.29 (3 H, s), 2.31–2.43 (6 H, m), 3.36 (3 H, s), 3.47–3.52 (2 H, m), 3.60–3.68 (2 H, m), 3.78 (3 H, s), 3.86–4.00 (2 H, m), 6.60 (1 H, d, J=8 Hz), 6.65 (1 H, s), 6.88 (1 H, d, J=8 Hz), 6.98 (1 H, d, J=8 Hz), 7.07 (1 H, s), 7.46 (1 H, t, J=8 Hz), 7.58 (1 H, d, J=8 Hz), 7.62 (1 H, d, J=8 Hz), 7.84 (1 H, s), 8.35 (1 H, d, J=8 Hz), 8.62 (1 H, s), 9.44–9.50 (1 H, br s), 9.89 (1 H, s).

EXAMPLE 85

A solution of 4-(2-aminomethyl-1H-benzimidazol-4-yl) carbonylamino-3-methoxy-N-methyl-N-(2-benzyloxy-4-methylphenyl)benzamide (120 mg) in methanol (15 ml) was stirred under atmospheric pressure of hydrogen in the presence of palladium hydroxide (20 mg) at ambient temperature overnight. After removal of the catalyst by filtration, the filtrate was evaporated in vacuo to give 4-(2-aminomethyl-1H-benzimidazol-4-yl)carbonylamino-3-methoxy-N-methyl-N-(2-hydroxy-4-methylphenyl)benzamide (85 mg).

NMR (DMSO-d$_6$, δ): 2.13 (3 H, s), 3.19 (3 H, s), 3.77 (3 H, s), 4.63 (2 H, m), 6.47 (1 H, d, J=8 Hz), 6.69 (1 H, s), 6.86 (1 H, d, J=8 Hz), 6.97 (1 H, d, J=8 Hz), 7.03 (1 H, s), 7.42 (1 H, t, J=8 Hz), 7.83 (1 H, d, J=8 Hz), 7.98 (1 H, d, J=8 Hz), 8.30 (1 H, br), 8.78 (2 H, br).

EXAMPLE 86

The following compound was obtained by using 4-(2-amino-3-nitrophenyl)carbonylamino-N-[2-(4-methoxybenzyloxy)-4-methylphenyl)-3-methoxy-N-methylbenzamide as a starting compound according to a similar manner to that of Example 85.

4-(2-Amino-3-nitrophenyl)carbonylamino-N-(2-hydroxy-4-methylphenyl)-3-methoxy-N-methylbenzamide NMR (CDCl$_3$, δ): 2.23 (3 H, s), 3.37 (3 H, s), 3.67 (3 H, s), 6.48–7.02 (7 H, m), 7.63 (1 H, d, J=8 Hz), 8.03–8.13 (3 H, m), 8.21–8.30 (2 H, m).

EXAMPLE 87

The following compound was obtained by using N-[2-(5-ethoxycarbonylpent-1-yloxy)-4-methylphenyl]-3-methoxy-N-methyl-4-[2-(tert-butoxycarbonylamino)methyl-1H-benzimidazol-4-yl]carbonylaminobenzamide as a starting compound according to a similar manner to that of Example 29.

N-[2-(5-Carboxypent-1-yloxy)-4-methylphenyl]-3-methoxy-N-methyl-4-[2-(tert-butoxycarbonylamino) methyl-1H-benzimidazol-4-yl]carbonylaminobenzamide NMR (CDCl$_3$, δ): 1.50 (9 H, s), 1.50–1.63 (2 H, m), 1.69–1.85 (4 H, m), 2.24 (3 H, s), 2.36–2.50 (2 H, m), 3.33 (3 H, s), 3.63 (3 H, s), 3.80 (1 H, m), 3.95 (1 H, m), 4.54 (2 H, m), 6.09 (1 H, br), 6.52–6.63 (2 H, m), 6.78–7.01 (3 H, m), 7.22 (1 H, t, J=8 Hz), 7.48 (1 H, m), 7.90 (1 H, m), 8.39 (1 H, m).

EXAMPLE 88

A mixture of N-[2-(5-carboxypent-1-yloxy)-4-methylphenyl]-3-methoxy-N-methyl-4-[2-(tert-butoxycarbonylamino)methyl-1H-benzimidazol-4-yl] carbonylaminobenzamide (200 mg), 4-(tert-butoxycarbonyl)piperazine (66.3 mg), 1-(3-dimethylaminopropyl)-3-ethylcarbodiimide hydrochloride (68.3 mg) and 1-hydroxybenztriazol (48.1 mg) in N,N-dimethylformamide (5 ml) was stirred at ambient temperature overnight and the mixture was diluted with ethyl acetate. The solution was washed successively with saturated aqueous sodium hydrogen carbonate solution, water and brine and dried over magnesium sulfate. The solvent was evaporated and the residue was purified by silica gel column (chloroform) to give 3-methoxy-N-methyl-N-[4-methyl-2-[5-(4-tert-butoxycarbonylpiperazin-1-yl) carbonylpent-1-yloxy]phenyl]-4-[2-(tert-butoxycarbonyl) aminomethyl-1H-benzimidazol-4-yl] carbonylaminobenzamide (250 mg).

NMR (CDCl$_3$, δ): 1.45–1.56 (2 H, m), 1.45 (9 H, s), 1.50 (9 H, s), 1.62–1.87 (4 H, m), 2.26 (3 H, s), 2.35 (2 H, t, J=7.5 Hz), 3.32 (3 H, s), 3.35–3.47 (6 H, m), 3.51–3.60 (2 H, m), 3.77–3.99 (2 H, m), 3.82 (3 H, s), 4.37 (2 H, m), 5.74 (1 H, br), 6.55–6.62 (2 H, m), 6.84–7.03 (3 H, m), 7.31 (1 H, t, J=8 Hz), 7.51 (1 H, d, J=8 Hz), 8.12 (1 H, d, J=8 Hz), 8.50 (1 H, d, J=8 Hz).

EXAMPLE 89

The following compounds were obtained according to a similar manner to that of Example 88.
1) 3-Methoxy-N-methyl-N-[4-methyl-2-[5-(4-oxopiperidin-1-yl)carbonylpent- 1-yloxy]phenyl]-4-[2-(tert-butoxycarbonyl)aminomethyl-1H-benzimidazol-4-yl] carbonylaminobenzamide NMR (CDCl$_3$, δ): 1.47–1.60 (2 H, m), 1.47 (9 H, s), 1.70–1.88 (4 H, m), 2.23 (3 H, s), 2.37–2.57 (2 H, m), 3.33 (3 H, s), 3.69–3.99 (4 H, m), 3.80 (3 H, s), 4.60 (2 H, d, J=7 Hz), 5.75 (1 H, br), 6.55–6.66 (2 H, m), 6.85–7.01 (3 H, m), 7.31 (1 H, t, J=8 Hz), 7.59 (1 H, d, J=8 Hz), 8.00 (1 H, d, J=8 Hz), 8.46 (1 H, d, J=8 Hz).

2) N-[2-(5-Carbamoylpent-1-yloxy)-4-methylphenyl]-3-methoxy-N-methyl-4-[2-(tert-butoxycarbonylamino)methyl-1H-benzimidazol-4-yl]carbonylaminobenzamide NMR (CDCl$_3$, δ): 1.50 (9 H, s), 1.60–1.86 (6 H, m), 2.21–2.30 (2 H, m), 2.26 (3 H, s), 3.33 (3 H, s), 3.70 (3 H, s), 3.72–3.97 (2 H, m), 4.56 (2 H, m), 6.57–6.68 (2 H, m), 6.93–7.05 (3 H, m), 7.33 (1 H, m), 7.54 (1 H, m), 8.01 (1 H, s), 8.11 (1 H, d, J=8 Hz), 8.50 (1 H, m).

3) N-[2-(5-Dimethylcarbamoylpent-1-yloxy)-4-methylphenyl]-3-methoxy-N-methyl-4-[2-(tert-butoxycarbonylamino)methyl-1H-benzimidazol-4-yl]carbonylaminobenzamide NMR (CDCl$_3$, δ): 1.45–1.57 (2 H, m), 1.49 (9 H, s), 1.64–1.85 (4 H, m), 2.27 (3 H, s), 2.35 (2 H, t, J=7.5 Hz), 2.92 (3 H, s), 3.00 (3 H, s), 3.34 (3 H, s), 3.79 (3 H, s), 3.84 (1 H, m), 3.94 (1 H, m), 4.58 (2 H, d, J=7 Hz), 5.72 (1 H, br), 6.55–6.64 (2 H, m), 6.90 (1 H, d, J=8 Hz), 6.92–7.01 (2 H, m), 7.28 (1 H, t, J=8 Hz), 7.48 (1 H, d, J=8 Hz), 8.02 (1 H, s), 8.10 (1 H, d, J=8 Hz), 8.50 (1 H, d, J=8 Hz).

4) N-[2-[5-(2,2-Dimethylhydrazino)carbonylpent-1-yloxy]-4-methylphenyl]-3-methoxy-N-methyl-4-[2-(tert-butoxycarbonylamino)methyl-1H-benzimidazol-4-yl]carbonylaminobenzamide NMR (CDCl$_3$, δ): 1.41–1.58 (2 H, m), 1.50 (9 H, s), 1.63–1.89 (4 H, m), 2.13 (2 H, t, J=7.5 Hz), 2.27 (3 H, s), 2.50 (3 H, s), 2.58 (3 H, s), 3.35 (3 H, s), 3.72–4.01 (2 H, m), 3.79 (3 H, s), 4.58 (2 H, m), 5.81 (1 H, br), 6.52–6.67 (2 H, m), 6.84–7.05 (3 H, m), 7.30 (1 H, t, J=8 Hz), 7.49 (1 H, m), 8.11 (1 H, m), 8.51 (1 H, m).

5) N-[2-[5-[N-(2-Dimethylaminoeth-1-yl)-N-methylaminocarbonyl]pent-1-yloxy]-4-methylphenyl]-3-methoxy-N-methyl-4-[2-(tert-butoxycarbonyl)aminomethyl-1H-benzimidazol-4-yl]carbonylaminobenzamide NMR (CDCl$_3$, δ): 1.41–1.56 (2 H, m), 1.48 (9 H, s), 1.61–1.74 (2 H, m), 1.74–1.85 (2 H, m), 2.24 (3 H, s), 2.32 (6 H, s), 2.32–2.44 (2 H, m), 2.53 (2 H, t, J=7.5 Hz), 3.32 (3 H, s), 3.52 (2 H, t, J=7.5 Hz), 3.78 (3 H, s), 3.86 (1 H, m), 3.96 (1 H, m), 4.58 (2 H, m), 5.92 (1 H, br), 6.53–6.61 (2 H, m), 6.87 (1 H, d, J=8 Hz), 6.91–7.02 (2 H, m), 7.29 (1 H, t, J=8 Hz), 7.50 (1 H, m), 8.11 (1 H, d, J=8 Hz), 8.49 (1 H, m).

EXAMPLE 90

The following compound was obtained by using 4-(1H-benzimidazol-4-yl)carbonylamino-N-(2-carboxy-4-methylphenyl)-3-methoxy-N-methylbenzamide as a starting compound according to a similar manner to that of Example 88.

4-(1H-Benzimidazol-4-yl)carbonylamino-N-(2-carbamoyl-4-methylphenyl)-3-methoxy-N-methylbenzamide NMR (CDCl$_3$, δ): 2.29 (3 H, s), 3.45 (3 H, s), 3.71 (3 H, s), 6.93 (1 H, d, J=8 Hz), 7.00–7.10 (2 H, m), 7.14–7.43 (3 H, m), 7.67 (1 H, d, J=8 Hz), 7.93 (1 H, d, J=8 Hz), 8.09 (1 H, s), 8.31 (1 H, d, J=8 Hz).

EXAMPLE 91

The following compound was obtained according to a similar manner to that of Example 90.

N-(2-Dimethylcarbamoyl-4-methylphenyl)-3-methoxy-N-methyl-4-(2-methyl-1H-benzimidazol-4-yl)carbonylamino-benzamide NMR (CDCl$_3$, δ): 2.31 (3H, s), 2.56 (3H, s), 2.99 (6H, s), 3.42 (3H, s), 3.76 (3H, s), 6.89–7.32 (6H, m), 7.44 (1H, d, J=8 Hz), 8.08 (1H, d, J=8 Hz), 8.59 (1H, br)

EXAMPLE 92

To a solution of 3-methoxy-N-methyl-N-[4-methyl-2-[5-(4-oxopiperidin-1-yl)carbonylpent-1-yloxy]phenyl]-4-[2-(tert-butoxycarbonyl)aminomethyl-1H-benzimidazol-4-yl]-carbonylaminobenzamide (150 mg) in methanol (5 ml) was added sodium borohydride (7.52 mg) under an ice bath cooling and the mixture was stirred at the same temperature for 1 hour. The mixture was diluted with chloroform and the solution was washed with water and brine. The organic phase was dried over magnesium sulfate and the solvent was evaporated in vacuo to give N-[2-[5-(4-hydroxypiperidin-1-yl)carbonylpent-1-yloxy]-4-methylphenyl]-3-methoxy-N-methyl-4-[2-tert-butoxycarbonyl)aminomethyl-1H-benzimidazol-4-yl]carbonylaminobenzamide (150 mg).

NMR (CDCl$_3$, δ): 1.48 (9H, s), 1.48–1.57 (2H, m), 1.64–1.94 (8H, m), 2.27 (3H, s), 2.30–2.41 (2H, m), 3.03–3.23 (2H, m), 3.33 (3H, s), 3.79 (3H, s), 3.80–3.97 (4H, m), 4.12 (1H, m), 4.61 (2H, d, J=7 Hz), 5.86 (1H, br), 6.54–6.63 (2H, m), 6.84–7.00 (3H, m), 7.32 (1H, t, J=8 Hz), 7.59 (1H, d, J=8 Hz), 7.98 (1H, br), 8.43 (1H, d, J=8 Hz)

EXAMPLE 93

A mixture of 4-(2-amino-3-nitrophenyl)carbonylamino-N-(2-hydroxy-4-methylphenyl)-3-methoxy-N-methylbenzamide (400 mg), acetic anhydride (90.7 mg) and triethylamine (89.9 mg) in dichloromethane (20 ml) was stirred in an ice bath for 4 hours. The mixture was diluted with chloroform and the solution was washed with water and brine. The organic phase was dried over magnesium sulfate and the solvent was evaporated in vacuo to give N-(2-acetoxy-4-methylphenyl)-4-(2-amino-3-nitrophenyl)carbonylamino-3-methoxy-N-methylbenzamide (425 mg).

NMR (CDCl$_3$, δ): 2.21 (3H, s), 2.30 (3H, s), 3.35 (3H, s), 3.72 (3H, s), 6.68 (1H, t, J=8 Hz), 6.88 (1H, s), 6.92–7.01 (2H, m), 7.10 (1H, d, J=8 Hz), 7.70 (1H, d, J=8 Hz), 8.14 (2H, br), 8.23 (1H, d, J=8 Hz), 8.22 (1H, d, J=8 Hz), 8.36 (1H, br)

EXAMPLE 94

A mixture of 4-(2-amino-3-nitrophenyl)carbonylamino-N-(2-hydroxy-4-methylphenyl)-3-methoxy-N-methylbenzamide (520 mg), N-(4-bromobutyl)phthalimide (326 mg) and potassium carbonate (160 mg) in N,N-dimethylformamide (10 ml) was heated at 60° C. for 8 hours. The mixture was diluted with ethyl acetate and the solution was washed with water and brine. The organic phase was dried over magnesium sulfate and the solvent was evaporated in vacuo. The crude oil was purified by silica gel column (1% methanol in chloroform) to give 4-(2-amino-3-nitrophenyl)carbonylamino-3-methoxy-N-methyl-N-[2-(4-phthalimidobut-1-yloxy)-4-methylphenyl]-benzamide (670 mg).

NMR (CDCl$_3$, δ): 1.78–1.96 (4H, m), 2.27 (3H, s), 3.31 (3H, s), 3.68–3.80 (5H, m), 3.92 (1H, m), 4.00 (1H, m), 6.57–6.72 (3H, m), 6.81–3.08 (3H, m), 7.66–7.73 (2H, m), 7.81–7.88 (2H, m), 8.09–8.21 (2H, m), 8.32 (1H, m)

EXAMPLE 95

The following compound was obtained by using N-[2-(4-phthalimidobut-1-yloxy)-4-methylphenyl]-3-methoxy-N-methyl-4-(2-methyl-1H-benzimidazol-4-yl)carbonylaminobenzamide as a starting compound according to a similar manner to that of Example 26.

N-[2-(4-Aminobut-1-yloxy)-4-methylphenyl]-3-methoxy-N-methyl-4-(2-methyl-1H-benzimidazol-4-yl)carbonylamino-benzamide NMR (CDCl$_3$, δ): 1.53–1.70 (2H, m), 1.75–1.86 (2H, m), 2.23 (3H, s), 2.57 (3H, s), 2.77 (2H, t, J=7.5 Hz), 3.34 (3H, s), 3.66 (3H, s), 3.80 (1H, m), 3.92 (1H, m), 6.54–6.61 (2H, m), 6.81–6.92 (2H, m), 6.98 (1H, d, J=8 Hz), 7.21 (1H, t, J=8 Hz), 7.51 (1H, br), 7.94 (1H, br), 8.45 (1H, br)

EXAMPLE 96

The following compound was obtained according to a similar manner to that of Example 95.

N-[2-(6-Aminohex-1-yl)oxy-4-methyl]phenyl-3-methoxy-N-methyl-4-[2-(tert-butoxycarbonyl)aminomethyl-1H-benzimidazol-4yl]carbonylaminobenzamide NMR (CDCl$_3$, δ): 1.33–1.50 (4H, m), 1.48 (9H, s), 1.52–1.63 (2H, m), 1.68–1.80 (2H, m), 2.25 (3H, s), 2.79 (2H, t, J=7.5 Hz), 3.32 (3H, s), 3.72 (3H, s), 3.78 (1H, m), 3.90 (1H, m), 4.52 (2H, m), 6.02 (1H, br), 6.51–6.62 (2H, m), 6.86–7.00 (3H, m), 7.20 (1H, t, J=8 Hz), 7.48 (1H, d, J=8 Hz), 7.91 (1H, d, J=8 Hz), 8.32 (1H, d, J=8 Hz)

EXAMPLE 97

The following compound was obtained by using N-[2-(5-tert-butoxycarbonylaminopent-1-yl)oxy-4-methyl]phenyl-3-methoxy-N-methyl-4-(2-methyl-1H-benzimidazol-4-yl)-carbonylaminobenzamide as a starting compound according to a similar manner to that of Example 23.

N-[2-(5-Aminopent-1-yl)oxy-4-methyl]phenyl-3-methoxy-N-methyl-4-(2-methyl-1H-benzimidazol-4-yl)carbonylamino-benzamide NMR (CDCl$_3$, δ): 1.40–1.53 (2H, m), 1.53–1.64 (2H, m), 1.71–1.80 (2H, m), 2.25 (3H, s), 2.59 (3H, s), 2.78 (2H, t, J=7.5 Hz), 3.35 (3H, s), 3.68 (3H, s), 3.76 (1H, m), 3.92 (1H, m), 6.51–6.62 (2H, m), 6.83 (1H, s), 6.91 (1H, d, J=8 Hz), 7.00 (1H, d, J=8 Hz), 7.22 (1H, t, J=8 Hz), 7.52 (1H, d, J=8 Hz), 7.90 (1H, br), 8.41 (1H, d, J=8 Hz)

EXAMPLE 98

The following compound was obtained according to a similar manner to that of Example 97.

N-[2-(4-Aminobut-1-yl)oxy-4-methyl]phenyl-3-methoxy-N-methyl-4-(2-methyl-1H-benzimidazol-4-yl)carbamoylbenzamide MASS (m/z): 516

EXAMPLE 99

To a solution of N-[2-(4-aminobut-1-yloxy)-4-methylphenyl]-3-methoxy-N-methyl-4-(2-methyl-1H-benzimidazol-4-yl)carbonylaminobenzamide (120 mg) in dichloromethane (10 ml) was added acetic anhydride (23.8 mg) and the mixture was stirred at ambient temperature for 1 hour. The solution was washed with water and brine and dried over magnesium sulfate and the solvent was evaporated in vacuo. The residue was purified by silica gel column (2% methanol in chloroform) and the product was solidified with diethyl ether to give N-[2-(4-acetylaminobut-1-yloxy)-4-methylphenyl]-3-methoxy-N-methyl-4-(2-methyl-1H-benzimidazol-4-yl)-carbonylaminobenzamide (87 mg).

NMR (CDCl$_3$, δ): 1.58–1.86 (2H, m), 2.08 (3H, s), 2.26 (3H, s), 2.69 (3H, s), 3.19–3.41 (2H, m), 3.35 (3H, s), 3.73–3.87 (2H, m), 3.76 (3H, s), 6.23 (1H, br), 6.51–6.78 (3H, m), 6.90–7.10 (3H, m), 7.27 (1H, m), 7.59 (1H, d, J=8 Hz), 7.91 (1H, d, J=8 Hz), 8.45 (1H, d, J=8 Hz)

EXAMPLE 100

A mixture of N-[2-(4-aminobut-1-yloxy)-4-methylphenyl]-3-methoxy-N-methyl-4-(2-methyl-1H-benzimidazol-4-yl)-carbonylaminobenzamide (150 mg), 37% formaldehyde solution (43.7 mg) and sodium cyanoborohydride (18.3 mg) in methanol (10 ml) was stirred at ambient temperature for 6 hours. The mixture was diluted with chloroform and the solution was washed with saturated aqueous sodium hydrogen carbonate and brine. The organic phase was dried over magnesium sulfate and the solvent was evaporated in vacuo. The crude product was purified by silica gel column (5% methanol in chloroform) to give N-[2-(4-dimethylaminobut-1-yloxy)-4-methylphenyl]-3-methoxy-N-methyl-4-(2-methyl-1H-benzimidazol-4-yl)-carbonylaminobenzamide (142 mg).

NMR (CDCl$_3$, δ): 1.67–1.87 (4H, m), 2.25 (3H, s), 2.35 (6H, s), 2.46–2.61 (2H, m), 2.61 (3H, s), 3.32 (3H, s), 3.73 (3H, s), 3.81 (1H, m), 3.94 (1H, m), 6.53–6.64 (2H, m), 6.81–7.01 (3H, m), 7.24 (1H, t, J=8 Hz), 7.46 (1H, br), 8.03 (1H, br), 8.50 (1H, br)

EXAMPLE 101

The following compound was obtained according to similar manners to those of Preparation 25 and Example 38.

N-(2-Amino-4-methylbenzyl)-3-methoxy-N-methyl-4-(2-methylbenzimidazol-4-yl)carbamoylbenzamide dihydrochloride NMR (DMSO-d$_6$, δ): 2.60 (3H, s), 2.79 (3H, s), 4.00 (3H, s), 4.03 (3H, s), 7.45–7.62 (3H, m), 7.69–7.81 (3H, m), 7.96 (1H, s), 8.03–8.11 (2H, m)

EXAMPLE 102

A mixture of N-(2-carboxy-4-methylphenyl)-3-methoxy-N-methyl-4-(2-methyl-1H-benzimidazol-4-yl)carbonylamino-benzamide (350 mg), diphenylphosphorylazide (224 mg) and triethylamine (82.5 mg) in dioxane (10 mg) was heated at 80° C. for 6 hours. After evaporation, the residual oil was subjected to silica gel column and the column was eluted with 5% methanol in chloroform. Object fractions were collected and evaporated in vacuo and the residue was solidified from chloroform to give N-(2-amino-4-methylphenyl)-3-methoxy-N-methyl-4-(2-methyl-1-H-benzimidazol-4-yl)carbonylamino-benzamide (280 mg).

NMR (DMSO-d$_6$, δ): 2.10 (3H, s), 2.64 (3H, s), 3.11 (3H, s), 4.80 (3H, s), 5.41 (2H, s), 6.13 (1H, d, J=8Hz), 6.48–6.55 (2H, m), 7.02 (1H, d, J=8 Hz), 7.09 (1H, s), 7.30 (1H, t, J=8 Hz), 7.57 (1H, d, J=8 Hz), 7.86 (1H, d, J=8 Hz), 8.40 (1H, d, J=8 Hz)

EXAMPLE 103

The following compound was obtained according to a similar manner to that of Example 102.

N-(2-Amino-4-methylphenyl)-4-(1H-benzimidazol-4-yl)carbonylamino-3-methoxy-N-methylbenzamide NMR (DMSO-d$_6$, δ): 2.08 (3H, s), 3.11 (3H, s), 3.76 (3H, s), 5.41 (2H, s), 6.14 (1H, d, J=8 Hz), 6.47–6.53 (2H, m), 7.02 (1H, d, J=8 Hz), 7.09 (1H, s), 7.40 (1H, t, J=8 Hz), 7.81 (1H, d, J=8 Hz), 7.97 (1H, d, J=8Hz), 8.35 (1H, d, J=8 Hz), 8.52 (1H, s)

EXAMPLE 104

A mixture of N-[2-(5-carboxypent-1-yloxy)-4-methylphenyl]-3-methoxy-N-methyl-4-[2-(tert-butoxycarbonyl)-aminomethyl-1H-benzimidazol-4-yl]carbonylaminobenzamide (850 mg), N-hydroxysuccinimide (145 mg) and N,N'-dicyclohexyl-carbodiimide (260 mg) in tetrahydrofuran (20 ml) was stirred at ambient temperature overnight and the resulting insoluble urea was filtered off. To the filtrate was added lithium borohydride (55 mg) and the mixture was stirred at ambient temperature for 5 hours. The mixture was diluted with chloroform and the solution was washed successively with 1N hydrochloric acid, saturated aqueous sodium hydrogen carbonate and brine. The organic phase was dried over magnesium sulfate and the solvent was evaporated in vacuo. The crude product was purified by silica gel column (5% methanol in chloroform) to give N-[2-(6-hydroxyhex-1-yl)oxy-4-methyl]phenyl-3-methoxy-N-methyl-4-[2-(tert-butoxycarbonyl)aminomethyl-1H-benzimidazol-4-yl]carbonylaminobenzamide (340 mg).

NMR (CDCl$_3$, δ): 1.40–1.51 (2H, m), 1.48 (9H, s), 1.57–1.65 (2H, m), 1.71–1.82 (2H, m), 2.25 (3H, s), 3.35 (3H, s), 3.61–3.69 (2H, m), 3.73 (3H, s), 3.80 (1H, m), 3.91 (1H, m), 4.59 (2H, d, J=7 Hz), 5.92 (1H, br t, J=7 Hz), 6.56–6.63 (2H, m), 6.89–7.01 (3H, m), 7.29 (1H, t, J=8 Hz), 7.55 (1H, d, J=8 Hz), 7.96 (1H, d, J=8 Hz), 8.41 (1H, d, J=8 Hz)

EXAMPLE 105

A mixture of N-[2-(6-hydroxyhex-1-yl)oxy-4-methyl]-phenyl-3-methoxy-N-methyl-4-[2-(tert-butoxycarbonyl)-aminomethyl-1H-benzimidazol-4-yl]carbonylaminobenzamide (210 mg), mesyl chloride (36.5 mg) and triethylamine (32.2 mg) in dichloromethane (10 ml) was stirred in an ice bath for 2 hours. The mixture was diluted with chloroform and the solution was washed successively with 1N hydrochloric acid, saturated aqueous sodium hydrogen carbonate and brine. The organic phase was dried over magnesium sulfate and the solvent was evaporated in vacuo to give N-[2-(6-methanesulfonyloxyhex-1-yl)oxy-4-methyl]phenyl-3-methoxy-N-methyl-4-[2-(tert-butoxycarbonyl)aminomethyl-1H-benzimidazol-4-yl]carbonylaminobenzamide (235 mg).

NMR (CDCl$_3$, δ): 1.40–1.56 (4H, m), 1.49 (9H, s), 1.71–1.82 (2H, m), 2.28 (3H, s), 3.00 (3H, s), 3.36 (3H, s), 3.81 (3H, s), 3.81 (1H, m), 3.91 (1H, m), 4.22 (2H, t, J=7.5 Hz), 4.58 (2H, d, J=7 Hz), 5.61 (1H, br), 6.56–6.63 (2H, m), 6.90 (1H, d, J=8 Hz), 6.95 (1H, d, J=8 Hz), 7.00 (1H, s), 7.30 (1H, t, J=8 Hz), 7.55 (1H, br), 8.10 (1H, br), 8.48 (1H, br)

EXAMPLE 106

A mixture of N-[2-(6-methanesulfonyloxyhex-1-yl)oxy-4-methyl]phenyl-3-methoxy-N-methyl-4-[2-(tert-butoxycarbonyl)-aminomethyl-1H-benzimidazol-4-yl] carbonylaminobenzamide (235 mg) and potassium phthalimide (88.5 mg) in dimethyl sulfoxide (10 ml) was heated at 50° C. for 6 hours. The mixture was diluted with ethyl acetate and the solution was washed with water and brine. The organic phase was dried over magnesium sulfate and the solvent was evaporated in vacuo. The crude product was purified by silica gel column (1% methanol in chloroform) to give 3-methoxy-N-methyl-N-[2-(6-phthalimido-hex-1-yl)oxy-4-methyl]phenyl-4-[2-(tert-butoxycarbonyl)-aminomethyl-1H-benzimidazol-4-yl] carbonylaminobenzamide (224 mg).

NMR (CDCl$_3$, δ): 1.36–1.54 (4H, m), 1.48 (9H, s), 1.64–1.87 (4H, m), 2.26 (3H, s), 2.61 (3H, s), 3.32 (3H, s), 3.69 (2H, t, J=7.5 Hz), 3.79 (3H, s), 3.79 (1H, m), 3.90 (1H, m), 4.60 (1H, d, J=7 Hz), 5.72 (1H, br), 6.54–6.63 (2H, m), 6.81–7.01 (3H, m), 7.31 (1H, t, J=8 Hz), 7.60 (1H, d, J=8 Hz), 7.70 (1H, m), 7.76 (1H, m), 7.80–7.88 (2H, m), 7.99 (1H, br), 8.41 (1H, d, J=8 Hz)

EXAMPLE 107

A solution of 4-[2-chloro-1H-benzimidazol-4-yl] carbonylamino-3-methoxy-N-methyl-N-[4-methyl-2-[5-(4-methylpiperazin-1-yl)carbonylpent-1-yloxy]phenyl] benzamide (70 mg) and N-methylpiperazine (106 mg) was heated at 80° C. for 2.5 hours. The excess of N-methylpiperazine was evaporated in vacuo and the residue was purified by preparative thin-layer chromatography (chloroform:methanol=10:1) to give 3-methoxy-N-methyl-N-[4-methyl-2-[5-(4-methylpiperazin-1-yl)carbonylpent-1-yloxy]phenyl]-4-[2-(4-methylpiperazin-1-yl)-1H-benzimidazol-4-yl]carbonylaminobenzamide (66 mg).

NMR (CDCl$_3$, δ): 1.43–1.60 (2H, m), 1.62–1.93 (4H, m), 2.23 (3H, s), 2.27 (3H, s), 2.30–2.43 (9H, m), 2.47–2.60 (4H, m), 3.34 (3H, s), 3.42–3.52 (2H, m), 3.54–3.72 (9H, m), 3.74–4.00 (2H, m), 6.50–6.67 (2H, m), 6.78–7.09 (4H, m), 7.21 (1H, m), 7.92 (1H, m), 8.58 (1H, m)

EXAMPLE 108

The following compounds were obtained according to a similar manner to that of Example 107.

1) 3-Methoxy-N-methyl-N-[4-methyl-2-[5-(4-methylpiperazin-1-yl)carbonylpent-1-yloxy]phenyl]-4-[2-(morpholin-4-yl)-1H-benzimidazol-4-yl] carbonylaminobenzamide NMR (CDCl$_3$, δ): 1.45–1.60 (2H, m), 1.62–1.95 (4H, m), 2.25 (3H, s), 2.30 (3H, s), 2.32–2.44 (6H, m), 3.33 (3H, s), 3.41–3.52 (5H, m), 3.53–3.68 (6H, m), 3.75–4.00 (6H, m), 6.50–6.65 (2H, m), 6.73 (1H, s), 6.84 (1H, m), 6.91 (1H, m), 7.03 (1H, m), 7.23 (1H, m), 7.93 (1H, m), 8.59 (1H, m)

2) 4-[(2-Dimethylamino-1H-benzimidazol-4-yl) carbonylamino]-3-methoxy-N-methyl-N-[4-methyl-2-[5-(4-methylpiperazin-1-yl)carbonylpent-1-yloxy]phenyl] benzamide NMR (CDCl$_3$, δ): 1.42–1.59 (2H, m), 1.61–1.96 (4H, m), 2.24 (3H, s), 2.29 (3H, s), 2.31–2.44 (6H, m), 3.12 (6H, s), 3.32 (3H, s), 3.38–3.53 (5H, m), 3.57–3.69 (2H, m), 3.72–4.00 (2H, m), 6.50–6.64 (2H, m), 6.70 (1H, s), 6.78–7.08 (3H, m), 7.16–7.29 (1H, m), 7.91 (1H, m), 8.60 (1H, m), 9.28 (1H, s)

3) 4-[2-[4-(Dimethylamino)piperidino]-1H-benzimidazol-4-yl]carbonylamino-3-methoxy-N-methyl-N-[4-methyl-2-[5-(4-methylpiperazin-1-yl)carbonylpent-1-yloxy]phenyl]-benzamide NMR (CDCl$_3$, δ): 1.29–2.00 (10H, m), 2.19–2.48 (18H, m), 2.67 (1H, m), 2.97–3.16 (2H, m), 3.33 (3H, s), 3.42–4.01 (9H, m), 4.18–4.46 (2H, m), 6.50–6.66 (2H, m), 6.78–7.08 (4H, m), 7.21 (1H, d, J=8 Hz), 7.92 (1H, d, J=8 Hz), 8.01 (1H, s), 8.59 (1H, m), 9.59 (1H, m)

4) 4-[[2-Dimethylamino)amino-1H-benzimidazol-4-yl]-carbonylamino]-3-methoxy-N-methyl-N-[4-methyl-2-[5-[4-methylpiperazin-1-yl)carbonylpent-1-yloxy]phenyl]-benzamide NMR (CDCl$_3$, δ): 1.21–1.36 (2H, m), 1.46–1.70 (4H, m), 2.12–2.38 (12H, m), 3.17 (3H, s), 3.25–3.54 (7H, m), 3.56–3.92 (8H, m), 6.39 (2H, s), 6.50 (1H, s), 6.60 (1H, d, J=8 Hz), 6.69 (1H, d, J=8 Hz), 6.72 (1H, s), 6.97 (1H, d, J=8 Hz), 7.20 (1H, dd, J=8, 8 Hz), 7.72 (1H, d, J=8 Hz), 7.98 (1H, d, J=8 Hz), 8.60 (1H, d, J=8 Hz)

5) 4-[2-[(2-Aminoethyl)methylamino]-1H-benzimidazol-4-yl]-carbonylamino]-3-methoxy-N-methyl-N-[4-methyl-2-[5-(4-methylpiperazin-1-yl)carbonylpent-1-yloxy]phenyl]-benzamide NMR (CDCl$_3$, δ): 1.43–1.59 (2H, m), 1.61–1.90 (4H, m), 2.26 (3H, s), 2.28 (3H, s), 2.30–2.44 (6H, m), 2.98–3.07 (2H, m), 3.29 (3H, s), 3.33 (3H, s), 3.41–3.52 (4H, m), 3.56–3.66 (2H, m), 3.70 (3H, s), 3.77–4.00 (2H, m), 6.52–6.66 (2H, m), 6.80–7.06 (4H, m), 7.22 (1H, m), 7.89 (1H, m), 8.56 (1H, m)

6) 4-[[2-[[2-(Dimethylamino)ethyl]amino]-1H-benzimidazol-4-yl]carbonylamino]-3-methoxy-N-methyl-N-[4-methyl-2-[5-(4-methylpiperazin-1-yl)carbonylpent-1-yloxy]phenyl]-benzamide NMR (CDCl$_3$, δ): 1.43–1.58 (2H, m), 1.62–1.88 (4H, m), 2.20–2.42 (18H, m), 2.52–2.62 (2H, m), 3.23 (3H, s), 3.42–3.56 (4H, m), 3.58–3.67 (2H, m), 3.72 (3H, s), 3.77–4.00 (2H, m), 5.69 (1H, m), 6.53–6.65 (2H, m), 6.87 (1H, d, J=8Hz), 6.91–7.00 (2H, m), 7.03 (1H, dd, J=8 Hz), 7.24 (1H, d, J=8 Hz), 7.82 (1H, d, J=8 Hz), 8.50 (1H, d, J=8 Hz)

EXAMPLE 109

The following compound was obtained by using 3-methoxy-N-methyl-N-[4-methyl-2-[5-(4-methylpiperazin-1-yl)-carbonylpent-1-yloxy]phenyl]-4-[2-(1-benzyloxycarbonyl-4-piperidyl)-1H-benzimidazol-4-yl]carbonylaminobenzamide as a starting compound according to a similar manner to that of Example 24.

3-Methoxy-N-methyl-N-[4-methyl-2-[5-(4-methylpiperazin-1-yl)carbonylpent-1-yloxy]phenyl]-4-[2-(4-piperidyl)-1H-benzimidazol-4-yl]carbonylaminobenzamide NMR (DMSO-d$_6$, δ): 1.37–1.50 (2H, m), 1.50–1.63 (2H, m), 1.68–1.81 (2H, m), 1.85–2.04 (2H, m), 2.13 (3H, s), 2.15–2.37 (11H, m), 2.83–2.98 (2H, m), 3.11–3.49 (10H, m), 3.79 (3H, s), 3.83–4.05 (2H, m), 6.65 (1H, d, J=8 Hz), 6.84 (1H, s), 6.92 (1H, d, J=8 Hz), 6.96 (1H, s), 7.03 (1H, d, J=8 Hz), 7.33 (1H, t, J=8 Hz), 7.70 (1H, d, J=8 Hz), 7.91 (1H, d, J=8 Hz), 8.43 (1H, d, J=8 Hz)

EXAMPLE 110

4-(2-Formyl-1H-benzimidazol-4-yl)carbonylamino-3-methoxy-N-methyl-N-[4-methyl-2-[5-(4-methylpiperazin-1-yl)carbonylpent-1-yloxy]phenyl]benzamide (158 mg), hydroxylamine hydrochoride (25 mg), sodium acetate (30 mg) and ethanol (60% solution in water, 1.5 ml) were combined and the mixture was stirred at 60° C. for 3 hours. After cooled to ambient temperature, the reaction mixture was concentrated in vacuo. The residue was dissolved in chloroform, washed with water and brine and dried over magnesium sulfate and evaporated in vacuo. The residue was purified by basic preparative thin-layer chromatography (chloroform:methanol=15:1) to give 4-(2-syn-hydroxyiminomethyl-1H-benzimidazol-4-yl)carbonylamino-3-methoxy-N-methyl-N-[4-methyl-2-[5-(4-methylpiperazin-1-yl)carbonylpent-1-yloxy]phenyl]benzamide (38 mg) and 4-(2-anti-hydroxyiminomethyl-1H-benzimidazol-4-yl)carbonylamino-3-methoxy-N-methyl-N-[4-methyl-2-[5-(4-methylpiperazin-1-yl)carbonylpent-1-yloxy]phenyl]benzamide (89 mg).

Syn isomer:

NMR (DMSO-d$_6$, δ): 1.37–1.49 (2H, m), 1.49–1.63 (2H, m), 1.67–1.80 (2H, m), 2.13 (3H, s), 2.15–2.35 (9H, m), 3.20 (3H, s), 3.35–3.44 (4H, m), 3.76–3.90 (4H, m), 3.90–4.01 (1H, m), 6.65 (1H, d, J=8 Hz), 6.82 (1H, s), 6.90–6.98 (2H, m), 7.05 (1H, d, J=8 Hz), 7.45 (1H, t, J=8 Hz), 7.82 (1H, s), 7.87 (1H, d, J=8 Hz), 8.00 (1H, d, J=8 Hz), 8.40 (1H, d, J=8 Hz)

Anti isomer:

NMR (DMSO-d$_6$, δ): 1.37–1.49 (2H, m), 1.49–1.62 (2H, m), 1.67–1.81 (2H, m), 2.12 (3H, s), 2.16–2.35 (9H, m), 3.19 (3H, s), 3.35–3.45 (4H, m), 3.73–3.90 (4H, m), 3.90–4.02 (1H, m), 6.64 (1H, d, J=8 Hz), 6.81 (1H, s), 6.89–6.98 (2H, m), 7.04 (1H, d, J=8 Hz), 7.43 (1H, t, J=8 Hz), 7.72 (1H, d, J=8 Hz), 7.96 (1H, d, J=8 Hz), 8.23 (1H, s), 8.40 (1H, d, J=8 Hz)

EXAMPLE 111

To a solution of 4-[[2-cyanomethyl-1H-benzimidazol-4-yl]carbonylamino]-3-methoxy-N-methyl-N-[4-methyl-2-[5-(4-methylpiperazin-1-yl)carbonylpent-1-yloxy]phenyl]benzamide (224 mg) in ethanol (4 ml) and water (2 ml) was added hydroxylamine hydrochloride (93.5 mg) and sodium hydrogen carbonate (113 mg). The solution was heated at 90° C. for 2 hours. After being concentrated in vacuo, aqueous sodium hydrogen carbonate was added to the residue and extracted with ethyl acetate. The extract was washed with brine and dried over sodium sulfate. After evaporation of the solvent, the residue was purified by silica gel column chromatography (10% methanol in chloroform) to give 4-[[2-[(2-amino-2-(hydroxyimino)ethyl]-1H-benzimidazol-4-yl]carbonylamino]-3-methoxy-N-methyl-N-[4-methyl-2-[5-(4-methylpiperazin-1-yl)carbonylpent-1-yloxy]phenyl]benzamide (200 mg).

NMR (CDCl$_3$, δ): 1.37–1.58 (2H, m), 1.60–1.87 (4H, m), 2.22–2.49 (12H, m), 3.34 (3H, s), 3.39–3.51 (2H, m), 3.52–4.00 (9H, m), 5.49 (2H, br, s), 6.51–6.66 (2H, m), 6.72 (1H, s), 6.81–7.01 (2H, m), 7.17 (1H, dd, J=8, 8 Hz), 7.41 (1H, d, J=8 Hz), 8.02 (1H, d, J=8 Hz), 8.45 (1H, d, J=8 Hz)

EXAMPLE 112

To a solution of 4-[(2-formylindol-4-yl)carbonyl]amino-3-methoxy-N-methyl-N-[4-methyl-2-[5-(4-methylpiperazin-1-yl)carbonylpent-1-yloxy]phenyl]benzamide (200 mg) in pyridine (4.0 ml) was added hydroxylamine hydrochloride (21.3 mg), and the solution was stirred at ambient temperature for 1 hour. The resulting solution was concentrated in vacuo and the residue was diluted with chloroform. The organic layer was washed successively with water and brine, dried over magnesium sulfate and concentrate in vacuo to give 4-[(2-hydroxyiminomethylindol-4-yl)carbonyl]amino-3-methoxy-N-methyl-N-[4-methyl-2-[5-(4-methylpiperazin-1-yl)carbonylpent-1-yloxy]phenyl]benzamide (203 mg).

NMR (CDCl$_3$, δ): 1.48–1.60 (2H, m), 1.67–1.88 (4H, m), 2.27 (3H, s), 2.29 (3H, s), 2.32–2.47 (6H, m), 3.34 (3H, s), 3.48–3.56 (2H, m), 3.61–3.68 (2H, m), 3.70 (3H, s), 3.82–3.99 (2H, m), 6.57–6.64 (2H, m), 6.88 (1H, d, J=8 Hz), 6.94 (1H, d, J=8 Hz), 7.00 (1H, s), 7.12 (1H, s), 7.22 (1H, t, J=8 Hz), 7.44 (1H, d, J=8 Hz), 7.50 (1H, d, J=8 Hz), 8.14 (1H, s), 8.32 (1H, d, J=8Hz), 8.58–8.67 (2H, m), 9.32–9.38 (1H, br s)

EXAMPLE 113

To a solution of 2methoxy-4-[N-methyl-N-[4-methyl-2-[5-(4-methylpiperazin-1-yl)carbonylpent-1-yloxy]phenyl]-carbamoyl]benzoic acid (200 mg) in N,N-dimethylformamide (3 ml) at 0° C. were added 1-ethyl-3-(3-dimethylaminopropyl)-carbodiimide hydrochloride (97 mg), N-hydroxybenzotrizole (79 mg) and 4-amino-2-[(4-methylpiperazin-1-yl)methyl]-1H-benzimidazole (105 mg) and the mixture was stirred at ambient temperature for 15 hours. The reaction mixture was poured into saturated sodium bicarbonate aqueous solution and extracted with chloroform. The organic layer was washed with saturated sodium bicarbonate aqueous solution and brine, dried over magnesium sulfate and evaporated in vacuo. The residue was purified by preparative thin-layer chromatography (chloroform:methanol=10:1) to give 3-methoxy-N-methyl-N-[4-methyl-2-[5-(4-methylpiperazin-1-yl) carbonylpent-1-yloxy]-phenyl]-4-[2-[(4-methylpiperazin-1-yl)methyl]-1H-benzimidazol-4-yl]carbamoylbenzamide (104 mg).

NMR (CDCl₃, δ): 1.45–1.63 (2H, m), 1.63–1.79 (2H, m), 1.79–1.92 (2H, m), 2.28 (3H, s), 2.30–2.60 (12H, m), 2.60–3.00 (8H, m), 3.35 (3H, s), 3.46–3.58 (2H, m), 3.58–3.74 (2H, m), 3.82–4.06 (7H, m), 6.55–6.69 (2H, m), 6.88 (1H, d, J=8 Hz, 7.00–7.13 (2H, m), 7.13–7.41 (2H, m), 8.06 (1H, d, J=8 Hz), 8.32 (1H, br peak)

EXAMPLE 114

The following compounds were obtained according to a similar manner to that of Example 113.

1) 4-(1H-Benzimidazol-4-yl)carbamoyl-3-methoxy-N-methyl-N-[4-methyl-2-[5-(4-methylpiperazin-1-yl)carbonylpent-1-yloxy]phenyl]benzamide NMR (CDCl₃, δ): 1.49–1.60 (2H, m), 1.67–1.90 (4H, m), 2.29 (3H, s), 2.36 (2H, t, J=8Hz), 2.38 (3H, s), 2.42–2.53 (4H, m), 3.36 (4H, m), 3.36 (3H, s), 3.52–3.58 (2H, m), 3.60 (3H, s), 3.65–3.73 (2H, m), 3.87–4.00 (2H, m), 4.30–4.39 (2H, m), 6.59–6.68 (3H, m), 6.88 (1H, d, J=8 Hz), 7.01–7.07 (2H, m), 7.16 (1H, t, J=8 Hz), 7.28 (1H, d, J=8 Hz), 7.38 (1H, d, J=8 Hz), 7.68 (1H, s)

2) 4-[(Naphthalen-1-yl)carbamoyl]-3-methoxy-N-methyl-N-[4-methyl-2-[5-(4-methylpiperazin-1-yl)carbonylpent-1-yloxy]phenyl]benzamide NMR (CDCl₃, δ): 1.50–1.90 (6H, m), 2.28 (3H, s), 2.30 (3H, s), 2.32–2.41 (6H, m), 3.37 (3H, s), 3.46–3.51 (2H, m), 3.59–3.67 (2H, m), 3.87–3.99 (2H, m), 4.02 (3H, s), 6.58–6.64 (2H, m), 6.88 (1H, d, J=8 Hz), 7.02 (1H, d, J=8 Hz), 7.16 (1H, s), 7.48–7.58 (3H, m), 7.68 (1H, d, J=8 Hz), 7.86–7.95 (2H, m), 8.10 (1H, d, J=8 Hz), 8.28 (1H, d, J=8 Hz)

3) 3-(2-Carbamoylphenylcarbamoyl)-3-methoxy-N-methyl-N-[4-methyl-2-[5-(4-methylpiperazin-1-yl)carbonylpent-1-yloxy]phenyl]benzamide NMR (CDCl₃, δ): 1.48–1.59 (2H, m), 1.67–1.89 (4H, m), 2.27 (3H, s), 2.30 (3H, s), 2.32–2.43 (6H, m), 3.34 (3H, s), 3.47–3.52 (2H, m), 3.60–3.67 (2H, m), 3.82–3.98 (2H, m), 3.89 (3H, s), 5.84–5.95 (1H, br), 6.56–6.62 (2H, m), 6.87 (1H, d, J=8 Hz), 6.95–7.08 (3H, m), 7.44 (1H, d, J=9 Hz), 7.50 (1H, d, J=9 Hz), 7.93 (1H, d, J=8 Hz), 8.63 (1H, d, J=8 Hz)

4) 4-(2-Methoxycarbonylphenylcarbamoyl)-3-methoxy-N-methyl-N-[4-methyl-2-[5-(4-methylpiperazin-1-yl)carbonylpent-1-yloxy]phenyl]benzamide NMR (CDCl₃, δ):1.49–1.58 (2H, m), 1.67–1.88 (4H, m), 2.27 (3H, s), 2.37 (2H, t, J=8 Hz), 2.55 (3H, s), 2.77–2.88 (4H, m), 3.33 (3H, s), 3.62–3.68 (2H, m), 3.74–3.80 (2H, m), 3.87–3.98 (2H, m), 3.90(3H, s), 3.92 (3H, s), 6.57–6.60 (2H, m), 6.86 (1H, d, J=8 Hz), 6.94 (1H, d, J=8 Hz), 7.02 (1H, s), 7.29–7.37 (1H, m), 7.60 (1H, d, J=8 Hz), 7.82 (1H, d, J=8 Hz), 7.90 (1H, d, J=8 Hz), 8.01 (1H, d, J=8 Hz), 8.82 (1H, d, J=8 Hz)

5) 4-(2-Sulfamoylphenylcarbamoyl)-3-methoxy-N-methyl-N-[4-methyl-2-[5-(4-methylpiperazin-1-yl) carbonylpent-1-xloxy]phenyl]benzamide NMR (CDCl₃, δ):1.47–1.54 (2H, m), 1.64–1.84 (4H, m), 2.28 (3H, s), 2.34 (2H, t, J=8 Hz), 2.50(3H, s), 2.68–2.79 (4H, m), 3.28–3.42 (2H, br), 3.32 (3H, s), 3.58–3.64 (2H, m), 3.72–3.78 (2H, m), 3.82–3.97 (2H, m), 3.88 (3H, s), 6.57–6.61 (2H, m), 6.87 (1H, d, J=8 Hz), 6.98 (1H, d, J=8 Hz), 7.04 (1H, s), 7.29–7.39 (2H, m), 7.62 (1H, dd, J=2, 8 Hz), 7.83 (2H, d, J=8 Hz)

6) 4-[(Indol-4-yl)carbamoyl]-3-methoxy-N-methyl-N-[4-methyl-2-[5-(4-methylpiperazin-1-yl)carbonylpent-1-ylcxy]phenyl]benzamide NMR (CDCl₃, δ):1.49–1.76 (4H, m), 1.80–1.90 (2H, m), 2.28 (3H, s), 2.30 (3H, s), 2.32–2.43 (6H, m), 3.38 (3H, s), 3.47–3.52 (2H, m), 3.60–3.68 (2H, m), 3.87–3.97 (2H, m), 4.00 (3H, s), 6.48 (1H, s), 6.58–6.64 (2H, m), 6.88 (1H, d, J=8 Hz), 7.01 (1H, d, J=8 Hz), 7.11 (1H, s), 7.18–7.22 (2H, m), 7.23–7.32 (1H, br), 8.06–8.11 (2H, m), 8.37–8.41 (1H, br s)

7) 3-Methoxy-N-methyl-4-(2-methyl-1H-benzimidazol-4-yl) carbamoyl-N-(4-methyl-2-nitrophenyl)benzamide NMR (CDCl₃, δ):2.39 (3H, s), 2.59 (3H, s), 3.44 (3H, s), 4.01 (3H, s), 6.87 (1H, d, J=8 Hz), 7.07 (1H, s), 7.11–7.23 (4H, m), 7.34 (1H, m), 7.62 (1H, s), 8.01 (1H, d, J=8 Hz)

8) 3-Methoxy-N-methyl-4-(2-methyl-1H-benzimidazol-4-yl) carbamoyl-N-[2-(4-tert-butoxycarbonylaminobut-1-yl)oxy-4-methyl]phenylbenzamide NMR (CDCl₃, δ):1.46 (9H, s), 1.61–1.74 (2H, m), 1.74–1.88 (2H, m), 2.25 (3H, s), 2.65 (3H, s), 3.13–3.22 (2H, m), 3.34 (3H, s), 3.82–3.97 (2H, m), 3.93 (3H, s), 4.67 (1H, br), 6.58–6.63 ; (2H, m), 6.90 (1H, d, J=8 Hz), 7.00–7.10 (2H, m), 7.17 (1H, t, J=8 Hz), 7.30 (1H, m), 7.41 (1H, d, J=8 Hz), 8.03 (1H, d, J=8 Hz)

9) 4-[N-[1-[(tert-Butyl)oxycarbonyl]benzamidazol-4-yl]-carbamoyl]-N-[2-[4,4-dimethyl (2,5-oxazolinyl)]phenyl]-3-methoxy-N-methylbenzamide NMR (CDCl₃, δ):1.37 (3H, s), 1.38 (3H, s), 1.70 (9H, s), 3.40 (3H, s), 3.90 (3H, s), 4.02–4.16 (2H, m), 7.02–7.41 (7H, m), 7.61 (1H, d, J=8 Hz), 7.78 (1H, d, J=8 Hz), 8.08 (1H, dd, J=8, 8 Hz), 8.44 (1H, d, J=8 Hz)

10) 4-[N-[2-[(Dimethylamino)methyl]-1H-benzimidazol-4-yl]-carbamoyl]-N-[2-[4,4-dimethyl (2,5-oxazolinyl)]phenyl]-3-methoxy-N-methylbenzamide NMR (CDCl₃, δ):1.38 (3H, s), 1.39 (3H, s), 2.39 (6H, s), 3.39 (3H, s), 3.81 (2H, s), 3.89 (3H, s), 4.07–4.17 (2H, m), 7.04–7.39 (8H, m), 7.80 (1H, d, J=8 Hz), 8.10 (1H, d, J=8 Hz)

11) 4-[N-[1[-(tert-Butyl)oxycarbonyl]benzimidazol-4-yl]-carbamoyl]-3-methoxy-N-methyl-N-[2-(morpholin-4-yl)-phenyl]benzamide NMR (CDCl₃, δ):1.72 (9H, s), 2.32–2.46 (2H, m), 2.80–2.92 (2H, m), 3.53 (3H, s), 3.63–3.84 (4H, m), 3.91 (3H, s), 6.88 (1H, d, J=8 Hz), 7.05 (1H, s), 7.09–7.25 (3H, m), 7.32 (1H, m), 7.38 (1H, dd, J=8, 8 Hz), 7.64 (1H, d, J=8 Hz), 8.10 (1H, d, J=8 Hz), 8.37 (1H, s), 8.47 (1H, d, J=8 Hz)

12) 4-[N-[1-[(tert-Butyl)oxycarbonyl]benzimidazol-4-yl]-carbamoyl]-3-methoxy-N-methyl-N-[2-(1-pyrrolyl)phenyl]-benzamide NMR (CDCl₃δ):1.72 (9H, s), 3.50 (3H, s), 3.96 (3H, s), 6.22–6.31 (2H, m), 6.40–6.49 (2H, m), 6.54–6.69 (2H, m), 7.06–8.05 (8H, m), 8.38 (1H, s), 8.46 (1H, d, J=8 Hz)

13) 3-Methoxy-N-methyl-4-[N-2-methyl-1H-benzimidazol-4-yl) carbamoyl]-N-(2-piperidinophenyl)benzamide NMR (CDCl₃, δ):1.41–1.78 (6H, m), 2.26–2.41 (2H, m), 2.60 (3H, s), 2.70–2.86 (2H, m), 3.53 (3H, s), 3.72–3.93 (3H, m), 6.66–7.57 (9H, m), 8.00–8.39 (1H, m)

14) 4-[N-[1-[(tert-Butyl)oxycarbonyl]-2-methylbenzimidazol-4-yl]carbamoyl]-3-methoxy-N-methyl-N-[2-(4-methyl-1-piperazinyl) phenyl]benzamide NMR (CDCl₃, δ):1.70 (9H, s), 2.38 (3H, s), 2.41–2.65 (6H, m), 2.81 (3H, s), 2.86–3.01 (2H, m), 3.52 (3H, s), 3.89 (3H, s), 6.89 (1H, d, J=8 Hz), 6.98 (1H, s), 7.06–7.34 (4H, m), 7.57 (1H, d, J=8 Hz), 8.13 (1H, d, J=8 Hz), 8.41 (1H, d, J=8 Hz)

15) 4-[N-[1-[(tert-Butyl)oxycarbonyl]-2-methylbenzimidazol-4-yl]carbamoyl]-3-methoxy-N-methyl-N-[2-(2,5-oxazolyl)-phenyl]benzamide NMR (CDCl₃, δ):1.71 (9H, s), 2.81 (3H, s), 3.49 (3H, s), 3.90 (3H, s), 6.79–6.87 (2H, m), 7.17–7.46 (6H, m), 7.56 (1H, d, J=8 Hz), 7.78 (1H, s), 7.88 (1H, m), 8.00 (1H, d, J=8 Hz), 8.37 (1H, d, J=8 Hz)

16) 3-Methoxy-N-methyl-4-[N-(2-methyl-1H-benzimidazol-4-yl) carbamoyl]-N-[2-(2,5-oxazolinyl) phenyl]benzamide NMR (CDCl$_3$, δ):2.60 (3H, br s), 3.44 (3H, s), 3.79–3.96 (3H, m), 4.02–4.16 (2H, m), 4.29–4.49 (2H, m), 6.72 (2H, m), 6.98–7.59 (8H, m), 7.78 (1H, d, J=8 Hz), 8.06 (1H, d, J=8 Hz)

17) 3-Methoxy-N-methyl-4-[N-(2-methyl-1H-benzimidazol-4-yl) carbamoyl]-N-[2-(3H, 4H, 5H, 2,6-oxazinyl)phenyl]-benzamide NMR (CDCl$_3$, δ):1.93–2.09 (2H, m), 2.52–2.65 (3H, m), 3.43 (3H, s), 3.52–3.65 (2H, m), 3.80 and 3.88 (Total 3H, s), 4.27–4.42 (2H, m), 6.73 (1H, d, J=8 Hz), 6.96–8.36 (10H, m)

18) N-[2-(1-Aza-3-oxaspiro[4.4]non-1-en-2-yl)phenyl]-3-methoxy-N-methyl-4-[N-(2-methyl-1H-benzimidazol-4-yl)-carbamoyl]benzamide NMR (CDCl$_3$, δ):1.62–1.78 (4H, m), 1.83–2.06 (4H, m), 2.60 (3H, s), 3.40 (3H, s), 3.86 (3H, br s), 4.18–4.29 (2H, m), 6.72 (1H, m), 7.02–7.20 (4H, m), 7.22–7.40 (2H, m), 7.50 (1H, m), 7.77 (1H, m), 8.07 (1H, d, J=8 Hz)

19) 3-Methoxy-N-methyl-N-[4-methyl-2-[5-(4-methylpiperazin-1-yl) carbonylpent-1-yloxy]phenyl]-4-(2--phthalimido-methyl-1H-benzimidazol-4-yl) carbamoylbenzamide NMR (CDCl$_3$, δ):1.47–1.67 (2H, m), 1.67–1.80 (2H, m), 1.80–1.94 (2H, m), 2.23–2.33 (6H, m), 2.33–2.45 (6H, m), 3.38 (3H, s), 3.45–3.55 (2H, m), 3.59–3.71 (2H, m), 3.81–4.09 (5H, m), 5.15 (2H, s), 6.54–6.68 (2H, m), 6.76–6.95 (1H, m), 6.98–7.17 (3H, m), 7.67–7.83 (2H, m), 7.83–7.95 (2H, m), 8.03–8.17 (1H, m), 8.33 (1H, d, J=8 Hz), 9.75–9.83 (1H, m)

20) 3-Methoxy-N-methyl-N-[4-methyl-2-[5-(4-methylpiperazin-1-yl) carbonylpent-1-yloxy]phenyl]-4-[2-(2-(2-phthalimido- ethyl)-1H-benzimidazol-4-yl] carbamoylbenzamide NMR (CDCl$_3$, δ):1.46–1.63 (2H, m), 1.63–1.78 (2H, m), 1.78–1.91 (2H, m), 2.20–2.49 (9H, m), 2.49–2.71 (3H, m), 3.28–3.43 (5H, m), 3.43–4.04 (9H, m), 4.23 (2H, t, J=7.5 Hz), 6.56–6.69 (2H, m) 6.81–7.11 (3H, m), 7.18 (1H, br peak), 7.24–7.33 (1H, m), 7.48 (1H, br peak), 7.60–7.73 (2H, m), 7.78–7.87 (2H, m), 8.03 (1H, br peak)

21) 4-(2-tert-Butyldiphenylsiloxymethyl-1H-benzimidazol-4-yl) carbamoyl-3-methoxy-N-methyl-N-[4-methyl-2-[5-(4-methylpiperazin-1-yl) carbonylpent-1-yloxy]phenyl]-benzamide NMR (CDCl$_3$δ):1.16 (9H, s), 1.44–1.64 (2H, m), 1.64–1.79 (2H, m), 1.79–1.94 (2H, m), 2.20–2.31 (6H, m), 2.31–2.43 (6H, m), 3.33 (3H ×½, s), 3.38 (3H×½, s), 3.44–3.54 (2H, m), 3.57–3.69 (2H, m), 3.77–4.01 (5H, m), 4.99–5.06 (2H, m), 6.54–6.68 (2H, m), 6.74–6.94 (2H, m), 6.94–7.32 (3H, m), 7.32–7.59 (6H, m), 7.65–7.77 (4H, m), 8.00–8.14 (1H, m), 8.35 (1H×½, d, J=8 Hz), 9.34 (1H×½, s)

22) 3-Methoxy-N-methyl-N-[4-methyl-2-[5-(4-methylpiperazin-1-yl) carbonylpent-1-yloxy]phenyl]-4-[2-[(tert-butoxy)-carbonylamino]-1H-benzimidazol-4-yl] carbamoylbenzamide NMR (DMSO-d$_6$, δ):1.36–1.50 (2H, m), 1.50–1.61 (2H, m), 1.66 (9H, s), 1.70–1.80 (2H, m), 2.14 (3H, s), 2.17–2.37 (9H, m), 3.21 (3H, s), 3.38–3.46 (4H, m), 3.79–4.04 (5H, m), 6.65 (1H, d, J=8 Hz), 6.80 (1H, s), 6.96 (1H, t, J=8 Hz), 7.02 (1H, d, J=8 Hz), 7.05–7.14 (2H, m), 7.30 (1H, d, J=8 Hz), 7.34 (2H, br peak), 7.90 (1H, d, J=9 Hz), 8.11 (1H, d, J=8 Hz)

23) 3-Methoxy-N-methyl-N-[4-methyl-2-[5-(4-methylpiperazin-1-yl) carbonylpent-1-yloxy]phenyl]-4-[2-[(methyl-sulfonyl)amino]-1H-benzimidazol-4-yl] carbamoylbenzamide NMR (DMSO-d$_6$, δ):1.36–1.50 (2H, m), 1.50–1.64 (2H, m), 1.64–1.82 (2H, m), 2.15 (3H, s), 2.18–2.36 (9H, m), 3.20 (3H, s), 3.37–3.46 (4H, m), 3.49 (3H, s), 3.77–4.03 (5H, m), 6.64 (1H, d, J=8 Hz), 6.81 (1H, s), 6.96–7.14 (6H, m), 7.23 (1H, d, J=8 Hz), 7.90 (1H, d, J=8 Hz), 8.13 (1H, d, J=8 Hz)

24) 3-Methoxy-4-[2-methoxymethyl-1H-benzimidazol-4-yl]-carbamoyl-N-methyl-N-[4-methyl-2-[5-(4-methylpiperazin-1-yl) carbonylpent-1-yloxy]pheny]benzamide NMR (DMSO-d$_6$, δ):1.38–1.50 (2H, m), 1.50–1.64 (2H, m), 1.64–1.83 (2H, m), 2.13 (3H, s), 2.16–2.38 (9H, m), 3.20 (3H, s), 3.35–3.47 (7H, m), 3.82–4.01 (5H, m), 4.68 (2H, s), 6.65 (1H, d, J=8 Hz), 6.81 (1H, s), 7.00–7.23 (5H, m), 7.91 (1H, d, J=8 Hz), 8.11 (1H, d, J=8 Hz)

25) 3-Methoxy-N-methyl-4-[2-methyl-1H-benzimidazol-4-yl]-carbamoyl-N-[4-methyl-2-[5-(4-methylpiperazin-1-yl)-carbonylpent-1-yloxy]phenyl]benzamide NMR (DMSO-d$_6$, δ):1.38–1.51 (2H, m), 1.51–1.66 (2H, m), 1.66–1.83 (2H, m), 2.15 (3H, s), 2.18–2.38 (9H, m), 2.52 (3H, s), 3.22 (3H, s), 3.36–3.48 (4H, m), 3.80–4.05 (5H, m), 6.64 (1H, d, J=8 Hz), 6.81 (1H, s), 6.98–7.18 (5H, m), 7.90 (1H, d, J=8 Hz), 8.06 (1H, d, J=8 Hz)

26) 4-[1,2-Dimethyl-1H-benzimidazol-4-yl]carbamoyl-3-methoxy-N-methyl-N-[4-methyl-2-[5-(4-methylpiperazin-1-yl) carbonylpent-1-yloxy]phenyl]benzamide NMR (DMSO-d$_6$, δ):1.38–1.51 (2H, m), 1.51–1.65 ( 2H, m), 1.70–1.82 (2H, m), 2.15 (3H, s), 2.18–2.39 (9H, m), 2.56 (3H, s), 3.21 (3H, s), 3.37–3.50 (4H, m), 3.73 (3H, s), 3.81–4.05 (5H, m), 6.63 (1H, d, J=8 Hz), 6.81 (1H, s), 6.99–7.25 (5H, m), 7.90 (1H, d, J=8 Hz), 8.10 (1H, d, J=8 Hz)

27) 4-[2-Ethyl-1H-benzimidazol-4-yl]carbamoyl-3-methoxy-N-methyl-N-[4-methyl-2-[5-(4-methylpiperazin-1-yl)-carbonylpent-1-yloxy]phenyl]benzamide NMR (DMSO-d$_6$, δ):1.33–1.50 (5H, m), 1.50–1.66 (2H, m), 1.66–1.83 (2H, m), 2.14 (3H, s), 2.16–2.28 (7H, m), 2.28–2.38 (2H, m), 2.87 (2H, q, J=7.5 Hz), 3.22 (3H, s), 3.37–3.46 (4H, m), 3.81–4.02 (5H, m), 6.64 (1H, d, J=8 Hz), 6.81 (1H, s), 7.00–7.17 (5H, m), 7.93 (1H, d, J=8 Hz), 8.09 (1H, d, J=8 Hz)

28) 3-Methoxy-N-methyl-N-[4-methyl-2-[5-(4-methylpiperazin-1-yl) carbonylpent-1-yloxy]phenyl]-4-[2-(n-propyl)-1H-benzimidazol-4-yl]carbamoylbenzamide NMR (DMSO-d$_6$, δ):1.0 (3H, t, J=7.5 Hz), 1.37–1.50 (2H, m), 1.50–1.65 (2H, m), 1.70–1.94 (4H, m), 2.15 (3H, s), 2.18–2.38 (9H, m), 2.83 (2H, t, J=7.5 Hz), 3.22 (3H, s), 3.36–3.45 (4H, m), 3.81–4.05 (5H, m), 6.63 (1H, d, J=8 Hz), 6.80 (1H, s), 6.99–7.18 (5H, m), 7.92 (1H, d, J=8 Hz), 8.08 (1H, d, J=8 Hz)

29) 4-[2-Isopropyl-1H-benzimidazol-4-yl]carbamoyl-3-methoxy-N-methyl-N-[4-methyl-2-[5-(4-methylpiperazin-1-yl)-carbonylpent-1-yloxy]phenyl]benzamide NMR (DMSO-d$_6$, δ):1.35–1.50 (8H, m), 1.50–1.63 (2H, m), 1.70–1.81 (2H, m), 2.13 (3H, s), 2.17–2.37 (9H, m), 3.10–3.25 (4H, m), 3.36–3.46 (4H, m), 3.80–4.03 (5H, m), 6.64 (1H, d, J=8 Hz), 6.80 (1H, s), 7.00–7.18 (5H, m), 7.93 (1H, d, J=8 Hz), 8.09 (1H, d, J=8 Hz)

30) 3-Methoxy-N-methyl-N-[4-methyl-2-[5-(4-methylpiperazin-1-yl) carbonylpent-1-yloxy]phenyl]-4-[2-trifluoromethyl-1H-benzimidazol-4-yl] carbamoylbenzamide NMR (DMSO-d$_6$, δ): 1.35–1.50 (2H, m), 1.50–1.64 (2H, m), 1.69–1.82 (2H, m), 2.14 (3H, s), 2.19–2.38 (9H, m), 3.21

(3H, s), 3.37–3.49 (4H, m), 3.82–4.05 (5H, m), 6.63 (1H, d, J=8 Hz), 6.81 (1H, s), 6.99–7.13 (3H, m), 7.32–7.42 (2H, m), 7.84–7.96 (1H, m), 8.20 (1H, br peak)

31) 3-Methoxy-N-methyl-N-[4-methyl-2-[5-(4-methylpiperazin-1-yl) carbonylpent-1-yloxy]phenyl]-4-[2-(3-pyridyl)-1H-benzimidazol-4-yl]carbamoylbenzamide NMR (DMSO-$d_6$, δ):1.39–1.50 (2H, m), 1.50–1.66 (2H, m), 1.66–184 (2H, m), 2.12 (3H, s), 2.16–2.29 (7H, m), 2.31 (2H, t, J=5 Hz), 3.23 (3H, s), 3.36–3.50 (4H, m), 3.82–4.02 (2H, m), 4.07 (3H, s), 6.65 (1H, d, J=8 Hz), 6.82 (1H, s), 7.03 (1H, d, J=8 Hz), 7.07–7.16 (2H, m), 7.23 (1H, t, J=8 Hz), 7.30 (1H, d, J=8 Hz), 7.64 (1H, dd, J=5, 8 Hz), 7.95 (1H, d, J=8 Hz), 8.20 (1H, d, J=8 Hz), 8.50 (1H, d, J=8 Hz), 8.70 (1H, d, J=5 Hz), 9.37 (1H, s)

32) 4-[2-(N,N-Dimethylcarbamoyl)-1H-benzimidazol-4-yl]-carbamoyl-3-methoxy-N-methyl-N-[4-methyl-2-[5-(4-methylpiperazin-1-yl) carbonylpent-1-yloxy]phenyl]-benzamide NMR (CDCl$_3$, δ):1.44–1.66 (2H, m), 1.66–1.79 (2H, m), 1.79–1.92 (2H, m), 2.26 (3H, s), 2.30 (3H, s), 2.32–2.45 (6H, m), 3.32 (3H, s), 3.36 (3H, s), 3.43–3.54 (2H, m), 3.59–3.69 (2H, m), 3.82–4.04 (8H, m), 6.54–6.67 (2H, m), 6.82–6.95 (2H, m), 6.95–7.06 (1H, m), 7.11 (1H, s), 7.19–7.41 (2H, m), 8.08 (1H, d, J=8 Hz), 8.48 (1H, d, J=8 Hz)

33) 3-Methoxy-4-[2-methoxy-1H-benzimidazol-4-yl]carbamoyl-N-methyl-N-[4-methyl-2-[5-(4-methylpiperazin-1-yl)-carbonylpent-1-yloxy]phenyl]benzamide NMR (DMSO-$d_6$, δ):1.35–1.50 (2H, m), 1.50–1.64 (2H, m), 1.68–1.83 (2H, m), 2.13 (3H, s), 2.17–2.36 (9H, m), 3.21 (3H, s), 3.36–3.45 (4H, m), 3.83–4.02 (5H, m), 4.13 (3H, s), 6.64 (1H, d, J=8 Hz), 6.81 (1H, s), 6.97–7.13 (5H, m), 7.93 (1H, br peak), 8.06 (1H, br peak)

34) 4-[2-(N,N-Dimethylaminomethyl)-1H-benzimidazol-4-yl]-carbamoyl-3-methoxy-N-methyl-N-[4-methyl-2-[5-(4-methyl-piperazin-1-yl) carbonylpent-1-yloxy]phenyl]benzamide NMR (DMSO-$d_6$, δ):1.35–1.50 (2H, m), 1.50–1.63 (2H, m), 1.68–1.82 (2H, m), 2.15(3H, s), 2.20–2.38 (15H, m), 3.20 (3H, s), 3.36–3.46 (4H, m), 3.70 (3H, s), 3.80–4.03 (5H, m), 6.63 (1H, d, J=8 Hz), 6.80 (1H, s), 6.99–7.19 (5H, m), 7.91 (1H, d, J=8 Hz), 8.08 (1H, d, J=8 Hz)

35) 3-Methoxy-N-methyl-N-[4-methyl-2-[5-(4-methylpiperazin-1-yl) carbonylpent-1-yloxy]pheny]-4-[2-(1-imidazolyl)-methyl-1H-benzimidazol-4-yl]carbamoylbenzamide NMR (CDCl$_3$, δ):1.45–1.62 (2H, m), 1.62–1.78 (2H, m), 1.78–1.90 (2H, m), 2.26 (3H, s), 2.35 (2H, t, J=7.5 Hz), 2.44 (3H, s), 2.54–2.72 (6H, m), 3.33 (3H, s), 3.57–3.69 (2H, m), 3.69–3.82 (2H, m), 3.82–4.03 (5H, m), 5.44 (2H, s), 6.53–6.63 (2H, m), 6.88 (1H, d, J=8 Hz), 6.95–7.40 (5H, m), 7.74 (1H, br peak), 8.80 (1H, d, J=8 Hz)

36) 3-Methoxy-N-methyl-N-[4-methyl-2-[5-(4-methylpiperazin-1-yl) carbonylpent-1-yloxy]phenyl]-4-[2-(morpholin-4-ylmethyl)-1H-benzimidazol-4-yl]carbamoylbenzamide NMR (DMSO-$d_6$, δ):1.40–1.52 (2H, m), 1.52–1.65 (2H, m), 1.69–1.82 (2H, m), 2.21 (3H, s), 2.31–2.53 (13H, m), 3.23 (3H, s), 3.27–3.36 (4H, m), 3.58–3.67 (4H, m), 3.78 (2H, s), 3.82–4.01 (5H, m), 6.65 (1H, d, J=8 Hz), 6.81 (1H, s), 7.00–7.23 (5H, m), 7.93 (1H, d, J=8 Hz), 8.09 (1H, d, J=8 Hz)

37) 3-Methoxy-N-methyl-N-[4-methyl-2-[5-(4-methylpiperazin-1-yl) carbonylpent-1-yloxy]phenyl]-4-[2-(pyrrolidin-1-ylmethyl)-1H-benzimidazol-4-yl]carbamoylbenzamide NMR (CDCl$_3$, δ):1.45–1.60 (2H, m), 1.65–1.78 (2H, m), 1.78–1.91 (2H, m), 1.91–2.10 (4H, m), 2.27 (3H, s), 2.30 (3H, s), 2.32–2.45 (6H, m), 2.95 (4H, br peak), 3.35 (3H, s), 3.45–3.53 (2H, m), 3.58–3.68 (2H, m), 3.79–4.01 (5H, m), 4.21 (2H, br s), 6.52–6.65 (2H, m), 6.86 (1H, d, J=8 Hz), 7.00 (1H, d, J=8 Hz), 7.09 (1H, s), 7.18–7.29 (3H, m), 8.04 (1H, d, J=8 Hz)

38) 3-Methoxy-N-methyl-N-[4-methyl-2-[5-(4-methylpiperazin-1-yl) carbonylpent-1-yloxy]phenyl]-4-[2-(piperidino-methyl)-1H-benzimidazol-4-yl]carbamoylbenzamide NMR (CDCl$_3$, δ):1.33–1.64 (10H, m), 1.69–1.83 (2H, m), 2.14 (3H, s), 2.16–2.36 (9H, m), 2.40–2.49 (4H, m), 3.21 (3H, s), 3.36–3.49 (4H, m), 3.71 (2H, s), 3.80–4.04 (4H, m), 6.65 (1H, d, J=8 Hz), 6.81 (1H, s), 6.99–7.21 (5H, m), 7.91 (1H, d, J=8 Hz), 8.09 (1H, d, J=8 Hz)

39) 4-[2-[2-(Dimethylamino)ethyl]-1H-benzimidazol-4-yl]-carbamoyl-3-methoxy-N-methyl-N-[4-methyl-2-[5-(4-methyl-piperazin-1-yl) carbonylpent-1-yloxy]phenyl]benzamide NMR (CDCl$_3$, δ):1.45–1.95 (8H, m), 2.26 (3H, s), 2.30 (3H, s), 2.32–2.45 (12H, m), 2.79 (2H, t, J=5 Hz), 3.11 (2H, t, J=5 Hz), 3.36 (3H, s), 3.45–3.55 (2H, m), 3.60–3.67 (2H, m), 3.80–4.02 (5H, m), 6.55–6.64 (2H, m), 6.88 (1H, d, J=8 Hz), 7.00–7.10 (2H, m), 7.13–7.26 (2H, m), 7.93 (1H, br peak), 8.08 (1H, d, J=8 Hz)

40) 3-Methoxy-N-methyl-N-[4-methyl-2-[5(4-methylpiperazin-1-yl) carbonylpent-1-yloxy]phenyl]-4-[2-[2-(4-methyl-piperazin-1-yl) ethyl[-1H-benzimidazol-4]-carbamoylbenzamide NMR (DMSO-$d_6$, δ):1.37–1.50 (2H, m), 1.50–1.64 (2H, m), 1.68–1.82 (2H, m), 2.13 (6H, s), 2.17–2.54 (17H, m), 2.81 (2H, t-like), 3.01 (2H, t-like), 3.21 (3H, s), 3.38–3.48 (4H, m), 3.81–4.02 (5H, m), 6.65 (1H, d, J=8 Hz), 6.81 (1H, s), 6.89–7.21 (5H, m), 7.91 (1H, br peak), 8.07 (1H, br peak)

41) 3-Methoxy-N-methyl-N-[4-methyl-2-[5-(4-methylpiperazin-1-yl) carbonylpent-1-yloxy]phenyl]-4-[2-(4-methyl-piperazin-1-yl)-1H-benzimidazol-4-yl]carbamoylbenzamide NMR (DMSO-$d_6$, δ):1.38–1.50 (2H, m), 1.50–1.64 (2H, m), 1.64–1.82 (2H, m), 2.15 (3H, s), 2.19–2.39 (12H, m), 2.39–2.53 (4H, m), 320 (3H, s), 3.36–3.47 (4H, m), 3.47–3.61 (4H, m), 3.82–4.03 (5H, m), 6.63 (1H, d, J=8 Hz), 6.80 (1H, s), 6.83–6.98 (2H, m), 7.00 (1H, d, J=8 Hz), 7.03–7.13 (2H, m), 7.91 (1H, d, J=8 Hz), 8.00 (1H, d, J=8 Hz)

42) 4-[2-Dimethylamino-1H-benzimidazol-4-yl]carbamoyl-3-methoxy-N-methyl-N-[4-methyl-2-[5-(4-methylpiperazin-1-yl) carbonylpent-1-yloxy]phenyl]benzamide NMR (DMSO-$d_6$, δ):1.38–1.50 (2H, m), 1.50–1.65 (2H, m), 1.65–1.82 (2H, m), 2.14 (3H, s), 2.18–2.38 (9H, m), 3.11 (6H, s), 3.21 (3H, s), 3.38–3.48 (4H, m), 3.82–4.01 (5H, m), 6.63 (1H, d, J=8 Hz), 6.78–6.87 (2H, m), 6.91 (1H, d, J=8 Hz), 7.01 (1H, d, J=8 Hz), 7.03–7.13 (2H, m), 7.91 (1H, d, J=8 Hz), 7.99 (1H, d, J=8 Hz)

43) 4-[1-(tert-Butoxycarbonyl)-2-[[2-[N-(tert-butoxy-carbonyl)-N-methylamino]ethyl]amino]-1H-benzimidazol-4-yl]-carbamoyl-3-methoxy-N-methyl-N-[4-methyl-2-[5-(4-methylpiperazin-1-yl) carbonylpent-1-yloxy]phenyl]benzamide NMR (CDCl$_3$, δ):1.42 (9H, br peak), 1.50–1.64 (2H, m), 1.64–1.78 (11H, m), 1.78–1.93 (2H, m), 2.25 (3H, s), 2.30

(3H, s), 2.32–2.43 (6H, m), 2.93 (3H, s), 3.35 (3H, s), 3.44–3.53 (2H, m), 3.58–3.68 (4H, m), 3.73 (2H, br peak), 3.80–4.01 (5H, m), 6.53 –6.63 (2H, m), 6.85 (1H, d, J=8 Hz), 6.96–7.09 (3H, m), 7.30 (1H, d, J=8 Hz), 7.44 (1H, br peak), 8.06 (1H, d, J=8 Hz), 8.38 (1H, d, J=8 Hz)

44) 4-[1-(tert-Butoxycarbonyl)-2-[[2-[(tert-butoxy) carbonyl-amino]ethyl]methylamino]-1H-benzimidazol-4-yl]carbamoyl-3-methoxy-N-methyl-N-[4-methyl-2-[5-(4-methylpiperazin-1-yl) carbonylpent-1-yloxy]phenyl] benzamide NMR (DMSO-$d_6$, δ):1.21 (9H, s), 1.38–1.50 (2H, m), 1.50–1.68 (11H, m), 1.68–1.81 (2H, m), 2.14 (3H, s), 2.18–2.38 (9H, m), 3.05 (3H, s), 3.15–3.28 (5H, m), 3.36–3.46 (4H, m), 3.46–3.56 (2H, m), 3.81–4.01 (5H, m), 6.63 (1H, d, J=8 Hz), 6.70–6.82 (2H, m), 7.00–7.13 (4H, m), 7.34 (1H, d, J=8 Hz), 7.92 (1H, d, J=8 Hz), 8.20 (1H, d, J=8 Hz)

45) 4-[2-(1-Imidazolyl)-1H-benzimidazol-4-yl]carbamoyl-3-methoxy-N-methyl-N-[4-methyl-2[5-(4-methylpiperazin-1- yl) carbonylpent-1-yloxy]phenyl]benzamide NMR (DMSO-$d_6$, δ):1.36–1.51 (2H, m), 1.51–1.64 (2H, m), 1.69–1.84 (2H, m), 2.13 (3H, s), 217–238 (9H, m), 3.23 (3H, s), 3.38–3.49 (4H, m), 3.82–4.08 (5H, m), 6.64 (1H, d, J=8 Hz), 6.81 (1H, s), 7.03 (1H, d, J=8 Hz), 7.08–7.14 (2H, m), 7.17–7.32 (3H, m), 7.92 (2H, br peak), 8.18 (1H, br peak), 8.49 (1H, s)

46) 4-[1-(tert-Butoxycarbonyl)-2-[[2-(dimethylamino) ethyl]-amino]-1H-benzimidazol-4-yl]carbamoyl-3-methoxy-N-methyl-N-[4-methyl-2-[5-(4-methylpiperazin-1-yl)- carbonylpent-1-yloxy]-phenyl]benzamide NMR (CDCl$_3$, δ):1.45–1.88 (13H, m), 1.88–1.91 (2H, m), 2.22–2.43 (18H, m), 2.64 (2H, t, J=5 Hz), 3.35 (3H, s), 3.45–3.53 (2H, m), 3.60–3.73 (4H, m), 3.80–4.02 (5H, m), 6.54–6.64 (2H, m), 6.86 (1H, d, J=8 Hz), 6.95–7.10 (3H, m), 7.34 (1H, d, J=8 Hz), 7.44 (1H, br peak), 8.07 (1H, d, J=8 Hz), 8.36 (1H, d, J=8 Hz)

47) 4-[2-(Dimethylamino)ethyl]methylamino]-1H-benzimidazol-4-yl]carbamoyl-3-methoxy-N-methyl-N-[4-methyl-2-[5-(4-methylpiperazin-1-yl)carbonylpent-1-yloxy]phenyl]benzamide NMR (DMSO-$d_6$, δ):1.35–1.50 (2H, m), 1.50–1.63 (2H, m), 1.68–1.82 (2H, m), 2.13 (3H, s), 2.17–2.37 (15H, m), 2.45–2.53 (2H, m), 3.11 (3H, s), 3.21 (3H, s), 3.37–3.48 (4H, m), 3.62 (3H, t, J=5 Hz), 3.79–4.02 (5H, m), 6.64 (1H, d, J=8 Hz), 6.76–6.86 (2H, m), 6.90 (1H, d, J=8 Hz), 6.99–7.13 (3H, m), 7.91 (1H, d, J=8 Hz), 7.99 (1H, d, J=8 Hz)

48) 3-Methoxy-N-methyl-N-[4-methyl-2-[5-(4-methylpiperazin-1-yl) carbonylpent-1-yloxy]phenyl]-4-[2-(1,2,4-triazol-1- yl)-1H-benzimidazol-4-yl] carbamoylbenzamide NMR (DMSO-$d_6$, δ): 1.38–1.50 (2H, m), 1.50–1.65 (2H, m), 1.69–1.82 (2H, m), 2.13 (3H, s), 2.17–2.37 (9H, m), 3.21 (3H, s), 3.36–3.45 (4H, m), 3.82–4.05 (5H, m), 6.64 (1H, d, J=8 Hz), 6.81 (1H, s), 7.03(1H, d, J=8 Hz), 7.07–7.15 (2H, m), 7.18–7.31 (2H, m), 7.89 (1H, br peak), 8.17 (1H, br peak), 8.46 (1H, s), 9.40 (1H, s)

49) 4-[2-[(2-Methoxymethyl)amino]-1H-benzimidazol-4-yl]-carbamoyl-3-methoxy-N-methyl-N-[4-methyl-2-[5-(4-methyl-piperazin-1-yl) carbonylpent-1-yloxy]phenyl] benzamide NMR (CDCl$_3$, δ):1.42–1.76 (4H, m), 1.76–1.91 (2H, m), 2.26 (3H, s), 2.30 (3H, s), 2.31–2.45 (6H, m), 3.34 (4H, s), 3.40 (3H, s), 3.45–3.55 (2H, m), 3.55–3.69 (6H, m), 3.79–4.02 (5H, m), 5.17 (1H, br peak), 6.56–6.65 (2H, m), 6.81 (1H, d, J=8 Hz), 6.95–7.10 (3H, m), 7.10–7.35 (2H, m), 8.03 (1H, d, J=8 Hz)

EXAMPLE 115

The following compounds were obtained according to a similar manner to that of Example 38.

1) 4-(Imidazo[1,5-a]pyridine-1-carbonyl)amino-3-methoxy-N-methyl-N-[4-methyl-2-[5-(4-methylpiperazin-1-yl)-carbonylpent-1-yloxy]phenyl]benzamide dihydrochloride NMR (DMSO-$d_6$, δ):1.39–1.63 (4H, m), 1.70–1.82 (2H, n), 2.22 (3H, s), 2.39 (2H, t, J=8 Hz), 2.75 (3H, s), 2.90–3.08 (3H, m), 3.19 (3H, s), 3.33–3.50 (3H, m), 3.75 (3H, s), 3.88–4.10 (3H, m), 4.40–4.48 (1H, m), 6.66 (1H, d, J=8 Hz), 6.80–6.87 (1H, m), 6.90–7.07 (3H, m), 7.25 (1H, t, J=8 Hz), 8.08 (1H, d, J=9 Hz), 8.27 (1H, d, J=8 Hz), 8.52–8.58 (2H, m), 9.52 (1H, s)

2) 4-[(2-Ethoxycarbonylindolin-4-yl)carbonyl]amino-3-methoxy-N-methyl-N-[4-methyl-2-[5- (4-methylpiperazin-1-yl) carbonylpent-1-yloxy]phenyl]benzamide dihydrochloride NMR (DMSO-$d_6$, δ):1.21 (3H, t, J=8 Hz), 1.41–1.63 (4H, m), 1.70–1.80 (2H, m), 2.23 (3H, s), 2.74 and 2.75 (Total 3H, s), 2.86–3.07 (3H, m), 3.19 (3H, s), 3.32–3.61 (6H, m), 3.65 (3H, s), 3.83–4.05 (3H, m), 4.11 (2H, q, J=8 Hz), 4.37–4.49 (2H, m), 6.66 (1H, d, J=8 Hz), 6.71 (1H, d, J=8 Hz), 6.82 (1H, s), 688–6.93 (2H, m), 6.96 (1H, d, J=8 Hz), 7.01–7.09 (2H, m), 7.77 (1H, d, J=8 Hz), 8.99 (1H, s)

3) 4-[(2-Carbamoylindolin-4-yl)carbonyl]amino-3-methoxy-N- methyl-N-[4-methyl-2-[5-(4-methylpiperazin-1-yl)- carbonylpent-1-yloxy]phenyl]benzamide dihydrochloride NMR (DMSO-$d_6$, δ):1.42–1.63 (4H, m), 1.70–1.80 )(2H, m), 2.22 (3H, s), 2.40 (2H, t, J=8 Hz), 2.74 (3H, s), 2.90–3.05 (3H, m), 3.19 (3H, s), 3.33–3.59 (6H, m), 3.65 (3H, s), 3.92–4.45 (6H, m), 6.67 (1H, d, J=8 Hz), 6.80–6.94 (3H, m), 7.01–7.13 (3H, m), 7.19 (1H, s), 7.48 (1H, s), 7.76 (1H, d, J=8 Hz), 9.03 (1H, s)

4) 4-[(2-Carbamoylindol-4-yl)carbonyl]amino-3-methoxy-N-methyl-N-[4-methyl-2-[5-(4-methylpiperazin-1-yl)-carbonylpent-1-yloxy]phenyl]benzamide hydrochloride NMR (DMSO-$d_6$, δ):1.42–1.63 (4H, m), 1.71–1.81 (2H, m), 2.26 (3H, s), 2.40 (2H, t, J=8 Hz), 2.74 (3H, s), 2.88–3.05 (3H, m), 3.20 (3H, s), 3.28–3.48 (4H, m), 3.68 (3H, s), 3.83–4.02 (3H, m), 6.68 (1H, d, J=8 Hz), 6.83 (1H, s), 6.91–6.98 (2H, m), 7.07 (1H, d, J=8 Hz), 7.29 (1H, t, J=8 Hz), 7.39–7.45 (1H, br s, 7.56 (1H, d, J=8 Hz), 7.57 (1H, s), 7.61 (1H, d, J=8 Hz), 7.91 (1H, d, J=8 Hz), 8.06–8.11 (1H, br s), 9.12 (1H, s)

5) 4-[[2- (N-Methylcarbamoyl)indol-4-yl]carbonyl]amino-3-methoxy-N-methyl-N-[4-methyl-2-[5-(4-methylpiperazin-1-yl)carbonylpent-1-yloxy]phenyl] benzamide hydrochloride NMR (CDCl$_3$, δ): 1.42–1.62 (4H, m) 1.71–1.80 (2H, m), 2.24 (3H, s), 2.40 (2H, t, J=8 Hz), 2.74 (3H, s), 2.79 and 2.81 (Total 3H, s), 2.88–3.02 (3H, m), 3.19 (3H, s), 3.27–3.42 (4H, m), 3.67 (3H, s), 3.86–4.10 (3H, m), 6.67 (1H, d, J=8 Hz), 6.83 (1H, s), 6.91–6.98 (2H, m), 7.06 (1H, d, J=8 Hz), 7.28 (1H, t, J=8 Hz), 7.52 (1H, s), 7.54 (1H, d, J=8 Hz), 7.62 (1H, d, J=8 Hz), 7.90 (1H, d, J=8 Hz), 8.57–8.62 (1H, m), 9.11 (1H, s)

6) 4-[(Indolin-4-yl)carbonyl]amino-3-methoxy-N-methyl-N-[4-methyl-2-[5-(4-methylpiperazin-1-yl)carbonylpent-1-yloxy]phenyl]benzamide dihydrochloride NMR (DMSO-$d_6$, δ): 1.40–1.62 (4H, m), 1.70–1.80 (2H, m), 2.23 (3H, s), 2.39 (2H, t, J=8 Hz), 2.74 (3H, s), 2.87–3.06 (3H, m), 3.19 (3H, s), 3.30–3.51 (5H, m), 3.63 (3H, s), 3.67 (2H, t, J=8 Hz), 3.81–4.10 (4H, m), 4.39–4.48 (1H, m), 6.64 (1H, d, J=8Hz), 6.82 (1H, s), 6.88–6.93 (2H, m), 7.04 (1H, d, J=8 Hz), 7.40–7.47 (2H, m), 7.61–7.72 (2H, m), 9.40 (1H, s)

7) 4-[(2-Hydroxymethylindolin-4-yl)carbonyl]amino-3-methoxy-N-methyl-N-[4-methyl-2-[5-(4-methylpiperazin-1-yl)carbonylpent-1-yloxy]phenyl]benzamide dihydrochloride NMR (DMSO-d$_6$, δ): 1.40–1.62 (4H, m), 1.69–1.80 (2H, m), 2.23 (3H, s), 2.39 (2H, t, J=8 Hz), 2.73 and 2.74 (Total 3H, s), 2.90–3.12 (4H, m), 3.19 (3H, s), 3.30–3.60 (6H, m), 3.64 (3H, s), 3.82–4.12 (5H, m), 4.39–4.49 (1H, m), 6.65 (1H, d, J=9 Hz), 6.82 (1H, s), 6.88–6.93 (2H, m), 7.03 (1H, d, J=9 Hz), 7.15 (1H, d, J=7 Hz), 7.30 (1H, t, J=9 Hz), 7.40 (1H, d, J=7 Hz), 7.72 (1H, d, J=9 Hz), 9.24 (1H, s)

8) 4-[2-Aminomethylindol-4-yl)carbonyl]amino-3-methoxy-N-methyl-N-[4-methyl-2-[5-(4-methylpiperazin-1-yl)-carbonylpent-1-yloxy]phenyl]benzamide dihydrochloride NMR (DMSO-d$_6$, δ): 1.42–1.63 (4H, m), 1.70–1.81 (2H, m), 2.24 (3H, s), 2.39 (2H, t, J=8 Hz), 2.70 (3H, s), 2.98–3.12 (3H, m), 3.19 (3H, s), 3.28–3.46 (4H, m), 3.69 (3H, s), 3.84–4.02 (3H, m), 4.23 (2H, s), 6.67 (1H, d, J=8 Hz), 6.84 (1H, s), 6.90–6.98 (3H, m), 7.05 (1H, d, J=8 Hz), 7.22 (1H, t, J=9 Hz), 7.56 (1H, d, J=9 Hz), 7.92 (1H, d, J=9 Hz), 7.93 (1H, d, J=8 Hz), 8.68–8.77 (2H, br), 9.08 (1H, s)

9) 4-[(2-Methylindol-4-yl)carbonyl]amino-3-methoxy-N-methyl-N-[4-methyl-2-[5-(4-methylpiperazin-1-yl)carbonylpent-1-yloxy]phenyl]benzamide hydrochloride NMR (DMSO-d$_6$, δ): 1.42–1.63 (4H, m), 1.70–1.80 (2H, m), 2.23 (3H, s), 2.39 (2H, t, J=8 Hz), 2.43 (3H, s), 2.76 (3H, s), 2.88–3.02 (3H, m), 3.19 (3H, s), 3.28–3.43 (4H, m), 3.70 (3H, s), 3.86–4.07 (3H, m), 6.53 (1H, s), 6.67 (1H, d, J=8 Hz), 6.83 (1H, s), 6.90–6.97 (2H, m), 7.06 (1H, d, J=9 Hz), 7.11 (1H, d, J=9 Hz), 7.49 (2H, d, J=9 Hz), 8.02 (1H, d, J=8 Hz), 8.98 (1H, s)

10) 4-[(Indolin-6-yl)carbonyl]amino-3-methoxy-N-methyl-N-[4-methyl-2-[5-(4-methylpiperazin-1-yl)carbonylpent-1-yloxy]phenyl]benzamide dihydrochloride NMR (DMSO-d$_6$, δ): 1.40–1.63 (4H, m), 1.69–1.80 (2H, m), 2.23 (3H, s), 2.39 (2H, t, J=8 Hz), 2.73 (3H, s), 2.90–3.07 (2H, m), 3.19 (3H, s), 3.20 (2H, t, J=8 Hz), 3.32–3.50 (3H, m), 3.63 (3H, s), 3.70 (2H, t, J=8 Hz), 3.82–4.12 (4H, m), 4.38–4.48 (1H, m), 6.65 (1H, d, J=8 Hz), 6.82 (1H, s), 6.88–6.95 (2H, m), 7.04 (1H, d, J=8 Hz), 7.48 (1H, d, J=8 Hz), 7.53 (1H, d, J=8 Hz), 7.62 (1H, d, J=8 Hz), 7.72 (1H, s), 7.78 (1H, d, J=8 Hz), 9.46 (1H, s)

11) 4-[(Indol-6yl)carbonyl]amino-3-methoxy-N-methyl-N-[4-methyl-2-[5-(4-methylpiperazin-1-yl)carbonylpent-1-yloxy]phenyl]benzamide hydrochloride NMR (DMSO-d$_6$, δ): 1.40–1.63 (4H, m), 1.70–181 (2H, m), 2.23 (3H, s), 2.40 (2H, t, J=8 Hz), 2.73 and 2.74 (Total 3H, s), 2.83–3.06 (3H, m), 3.18 (3H, s), 3.31–3.46 (3H, m), 3.67 (3H, s), 3.82–4.12 (3H, m), 4.39–4.49 (1H, m), 6.50 (1H, s), 6.67 (1H, d, J=8 Hz), 6.83 (1H, s), 6.89–6.96 (2H, m), 7.05 (1H, d, J=8 Hz), 7.51–7.58 (2H, m), 7.62 (1H, d, J=8 Hz), 7.81 (1H, d, J=8 Hz), 8.00 (1H, s), 9.18 (1H, s)

12) 4-(1H-Benzimidazol-4-yl)carbamoyl-3-methoxy-N-methyl-N-[4-methyl-2-[5-(4-methylpiperazin-1-yl)carbonylpent-1-yloxy]phenyl]benzamide dihydrochloride

ESI-MASS: 627.5 (M+H)

13) 4-[(Naphthalen-1-yl)carbamoyl]-3-methoxy-N-methyl-N-[4-methyl-2-[5-(4-methylpiperazin-1-yl)carbonylpent-1-yloxy]phenyl]benzamide hydrochloride NMR (DMSO-d$_6$, δ): 1.42–1.66 (4H, m), 1.73–1.83 (2H, m), 2.23 (3H, s), 2.40 (2H, t, J=8 Hz), 2.73 (3H, s), 2.86–3.08 (3H, m), 3.22 (3H, s), 3.31–3.48 (3H, m), 3.87 (3H, s), 3.90–4.02 (3H, m), 4.38–4.50 (1H, m), 6.68 (1H, d, J=8 Hz), 6.82 (1H, s), 6.99 (1H, d, J=8 Hz), 7.08 (1H, s), 7.12 (1H, d, J=8 Hz), 7.49–7.67 (4H, m), 7.77–7.86 (2H, m), 7.93–8.02 (2H, m)

14) 4-(2-Carbamoylphenylcarbamoyl)-3-methoxy-N-methyl-N-[4-methyl-2-[5-(4-methylpiperazin-1-yl)carbonylpent-1-yloxy]phenyl]benzamide hydrochloride NMR (DMSO-d$_6$, δ): 1.40–1.63 (4H, m), 1.70–1.81 (2H, m), 2.22 (3H, S), 2.39 (2H, t, J=8 Hz), 2.73 (3H, s), 2.88–3.05 (3H, m), 3.20 (3H, s), 3.30–3.50 (4H, m), 3.80 (3H, s), 3.83–4.00 (3H, m), 6.65 (1H, d, J=8 Hz), 6.80 (1H, s), 6.95–7.00 (2H, m), 7.08–7.18 (2H, m), 7.48 (1H, t, J=8 Hz), 7.64 (1H, s), 7.69 (1H, d, J=8 Hz), 7.77 (1H, d, J=8 Hz), 8.18 (1H, s), 8.53 (1H, d, J=8 Hz)

15) 4-(2-Methoxycarbonylphenylcarbamoyl)-3-methoxy-N-methyl-N-[4-methyl-2-[5-(4-methylpiperazin-1-yl)carbonylpent-1-yloxy]phenyl]benzamide hydrochloride NMR (DMSO-d$_6$, δ): 1.41–1.62 (4H, m), 1.71–1.80 (2H, m), 2.21 (3H, s), 2.40 (2H, t, J=8 Hz), 2.74–2.78 (3H, br s), 2.88–3.02 (3H, m), 3.20 (3H, s), 3.32–3.52 (3H, m), 3.85 (3H, s), 3.88 (3H, s), 3.90–4.12 (3H, m), 4.40–4.48 (1H, m), 6.66 (1H, d, J=8 Hz), 6.81 (1H, s), 6.98 (1H, d, J=8 Hz), 7.03 (1H, s), 7.09 (1H, d, J=8 Hz), 7.21 (1H, t, J=8 Hz), 7.63 (1H, t, J=8 Hz), 7.72 (1H, d, J=8 Hz), 7.79 (1H, d, J=8 Hz), 7.98 (1H, d, J=8 Hz), 8.67 (1H, d, J=8 Hz)

16) 4-[2-(N,N-Dimethylcarbamoyl)phenylcarbamoyl]-3-methoxy-N-methyl-N-[4-methyl-2-[5-(4-methylpiperazin-1-yl)-carbonylpent-1-yloxy]phenyl]benzamide hydrochloride NMR (DMSO-d$_6$, δ): 1.41–1.63 (4H, m), 1.72–1.81 (2H, m), 2.22 (3H, s), 2.40 (2H, t, J=8 Hz), 2.76 (3H, s), 2.83–3.08 (3H, m), 2.89 (3H, s), 3.05 (3H, s), 3.20 (3H, s), 3.25–3.45 (4H, m), 3.83 (3H, s), 3.86–4.00 (3H, m), 6.65 (1H, d, J=8 Hz), 6.81 (1H, s), 6.97–7.02 (2H, m), 7.09 (1H, d, J=8 Hz), 7.18 (1H, t, J=8 Hz), 7.35 (1H, d, J=8 Hz), 7.42 (1H, t, J=8 Hz), 7.82 (1H, d, J=8 Hz), 8.27 (1H, d, J=8 Hz)

17) 4-(2-Sulfamoylphenylcarbamoyl)-3-methoxy-N-methyl-N-[4-methyl-2-[5-(4-methylpiperazin-1-yl)carbonylpent-1-yloxy]phenyl]benzamide hydrochloride NMR (DMSO-d$_6$, δ): 1.39–1.62 (4H, m), 1.69–1.79 (2H, m), 2.22 (3H, s), 2.38 (2H, t, J=8 Hz), 2.77 (3H, s), 2.86–3.04 (3H, m), 3.19 (3H, s), 3.35–3.58 (5H, m), 3.61 (3H, s), 3.82–4.12 (3H, m), 4.39–4.49 (1H, m), 6.63 (1H, d, J=8 Hz), 6.80 (1H, s), 6.86–6.92 (2H, m), 7.06 (1H, d, J=8 Hz), 7.39–7.47 (2H, m), 7.55 (1H, t, J=8 Hz), 7.72 (1H, d, J=8 Hz), 7.98 (1H, d, J=8 Hz)

18) 4-[(Indol-4-yl)carbamoyl]-3-methoxy-N-methyl-N-[4-methyl-2-[5-(4-methylpiperazin-1-yl)carbonylpent-1-yloxy]phenyl]benzamide hydrochloride NMR (DMSO-d$_6$, δ): 1.42–1.63 (4H, m), 1.72–1.81 (2H, m), 2.22 (3H, s), 2.40 (2H, t, J=8 Hz), 2.75 (3H, s), 2.90–3.03 (3H, m), 3.21 (3H, s), 3.30–3.44 (4H, m), 3.88 (3H, s), 3.90–4.00 (3H, m), 6.50 (1H, s), 6.67 (1H, d, J=8 Hz), 6.82 (1H, s), 6.99 (1H, d, J=8 Hz), 7.04–7.08 (2H, m), 7.12 (1H, d, J=8 Hz), 7.18 (1H, d, J=8 Hz), 7.34 (1H, t, J=3 Hz), 7.69 (1H, d, J=8 Hz), 7.78 (1H, d, J=8 Hz)

19) 3-Methoxy-N-methyl-N-[4-methyl-2-[5-(4-methylpiperazin-1-yl)carbonylpent-1-yloxy]phenyl]-4-(quinolin-8-yl)-carbonylaminobenzamide dihydrochloride NMR (DMSO-d$_6$, δ): 1.40–1.51 (2H, m), 1.53–1.63 (2H, m), 1.70–1.81 (2H, m), 2.23 (3H, s), 2.34–2.42 (2H, m), 2.50 (3H, s), 2.80–3.07 (4H, m), 3.20 (3H, s), 3.31–3.55 (4H, m), 3.83 (3H, s), 4.08 (1H, m), 4.45 (1H, m), 6.65 (1H, d, J=8 Hz), 6.82 (1H, s), 6.90–6.99 (2H, m), 7.05 (1H, d, J=8 Hz), 7.71–7.85 (2H, m), 8.29 (1H, d, J=8 Hz), 8.42 (1H, d, J=8 Hz), 8.63 (1H, d, J=8 Hz), 8.72 (1H, d, J=8 Hz), 9.14 (1H, m)

20) 3-Methoxy-N-methyl-N-[4-methyl-2-[5-(4-methylpiperazin-1-yl)carbonylpent-1-yloxy]phenyl]-4-(1,2,3,4-tetrahydroquinolin-8-yl)carbonylaminobenzamide dihydrochloride NMR (DMSO-d$_6$, δ): 1.39–1.50 (2H, m), 1.52–1.61 (2H, m), 1.68–1.83 (4H, m), 2.23 (3H, s), 2.38 (2H, t, J=7.5 Hz), 2.49 (3H, s), 2.80–3.07 (4H, m), 3.18 (3H, s), 3.23–3.50 (6H, m), 3.60 (3H, s), 3.76–4.11 (3H, m), 4.42 (1H, m), 6.50 (1H, t, J=8 Hz), 6.64 (1H, d, J=8 Hz), 6.82 (1H, s), 6.86–6.92 (2H, m), 7.01–7.04 (2H, m), 7.43 (1H, d, J=8 Hz), 7.61 (1H, d, J=8 Hz), 9.08 (1H, s)

21) 3-Methoxy-N-methyl-N-[4-methyl-2-[5-(4-methylpiperazin-1-yl)carbonylpent-1-yloxy]phenyl]-4-(quinoxalin-5-yl)-carbonylaminobenzamide dihydrochloride NMR (DMSO-d$_6$, δ): 1.40–1.53 (2H, m), 1.53–1.64 (2H, m), 1.70–1.81 (2H, m), 2.22 (3H, s), 2.40 (2H, t, J=7.5 Hz), 2.73 (1H, s), 2.78–3.10 (3H, m), 3.20 (3H, s), 3.30–3.57 (3H, m), 3.65 (3H, s), 3.82–4.11 (3H, m), 4.41 (1H, m), 6.65 (1H, d, J=8 Hz), 6.83 (1H, s), 6.88–6.95 (2H, m), 7.04 (2H, d, J=8 Hz), 7.64 (1H, d, J=8 Hz), 8.20 (1H, d, J=8 Hz), 8.30 (1H, d, J=8 Hz), 8.60 (1H, s), 9.04 (2H, s), 9.84 (1H, s)

22) 4-2-Aminomethyl-1H-benzimidazol-4-yl)carbonylamino-3-methoxy-N-methyl-N-[4-methyl-2-[4-(4-methylpiperazin-1-yl)carbonylphenylmethoxy]phenyl]benzamide trihydrochoride 23) 4-(2-Aminomethyl-1H-benzimidazol-4-yl)carbonylamino-3-methoxy-N-methyl-N-[4-methyl-2-[3-(4-methylpiperazin-1-yl)carbonylprop-1-yloxy]phenyl]benzamide trihydrochloride 24) 4-(2-Aminomethyl-1H-benzimidazol-4-yl)carbonylamino-3-methoxy-N-methyl-N-[4-methyl-2-[5-(4-methylpiperazin-1-yl)carbonylbut-1-yloxy]phenyl]benzamide trihydrochloride NMR (DMSO-d$_6$, δ): 1.60–1.83 (4H, m), 2.22 (3H, s), 2.46 (2H, t, J=7.5 Hz), 2.72 (3×½H, s), 2.74 (3×½H, s), 2.81–3.09 (3H, m), 3.20 (3H, s), 3.32–3.56 (3H, m), 3.70–4.12 (3H, m), 3.77 (3H, s), 4.40–4.50 (3H, m), 6.67 (1H, d, J=8 Hz), 6.82 (1H, s), 6.94–6.99 (2H, m), 7.08 (1H, d, J=8 Hz), 7.43 (1H, t, J=8 Hz), 7.84 (1H, d, J=8 Hz), 7.98 (1H, d, J=8 Hz), 8.29 (1H, d, J=8 Hz), 8.88–9.00 (3H, br)

25) 4-(2-Aminomethyl-1H-benzimidazol-4-yl)carbonylamino-N-[2-[5-[N-(2-dimethylaminoeth-1yl)-N-methylamino-carbonyl]-pent-1-yloxy]-4-methylphenyl]-3-methoxy-N-methylbenzamide trihydrochloride NMR (DMSO-d$_6$, δ): 1.40–1.51 (2H, m), 1.51–1.63 (2H, m), 1.69–1.80 (2H, m), 2.22 (3H, s), 2.33 (2H, t, J=7.5 Hz), 2.74 (3H, s), 2.76 (3H, s), 2.99 (3H, s), 3.17 (2H, m), 3.19 (3H, s), 3.62 (2H, t, J=5.7 Hz), 3.77 (3H, s), 3.86 (1H, m), 3.97 (1H, m), 4.46 (2H, m), 6.66 (1H, d, J=8 Hz), 6.84 (1H, s), 6.91–6.97 (2H, m), 7.02 (1H, d, J=8 Hz), 7.43 (1H, t, J=8 Hz), 7.83 (1H, d, J=8 Hz), 7.97 (1H, d, J=8 Hz), 8.29 (1H, d, J=8 Hz), 8.94 (2H, br)

26) N-[2-(5-Carbamoylpent-1-yloxy)-4-methylphenyl]-4-(2-aminomethyl-1H-benzimidazol-4-yl)carbonylamino-3-methoxy-N-methylbenzamide dihydrochloride 27) 4-(2-Aminomethyl-1H-benzimidazol-4-yl)carbonylamino-N-[2-[5-(2,2-dimethylhydrazino)carbonylpent-1-yloxy]-4-methylphenyl]-3-methoxy-N-methylcarbonylaminobenzamide trihydrochloride NMR (DMSO-d$_6$, δ): 1.39–1.51 (2H, m), 1.58–1.69 (2H, m), 1.69–1.81 (2H, m), 2.21 (3H, s), 2.25 (2H, t, J=7.5 Hz), 3.02 (6H, sx2), 3.19 (3H, s), 3.76 (3H, s), 3.89 (1H, m), 3.99 (1H, m), 4.45 (2H, m), 6.67 (1H, d, J=8 Hz), 6.83 (1H, s), 6.91–6.96 (2H, m), 7.03 (1H, d, J=8 Hz), 7.42 (1H, t, J=8 Hz), 7.84 (1H, d, J=8 Hz), 7.97 (1H, d, J=8 Hz), 8.30 (1H, d, J=8 Hz), 8.82–8.98 (3H, br)

28) N-[2-(4-Aminobut-1-yloxy)-4-methylphenyl]-3-methoxy-N-methyl-4-(2-methyl-1H-benzimidazol-4-yl)-carbonylaminobenzamide dihydrochloride NMR (DMSO-D$_6$, δ): 1.69–1.86 (2H, m), 2.21 (3H, s), 2.76 (3H, s), 2.81–2.92 (2H, m), 3.21 (3H, s), 3.69 (3H, s), 3.89 (1H, m), 4.01 (1H, m), 6.64 (1H, d, J=8 Hz), 6.83 (1H, s), 6.90–6.98 (2H, m), 7.02 (1H, d, J=8 Hz), 7.51 (1H, t, J=8 Hz), 7.88 (1H, d, J=8 Hz), 8.01–8.18 (4H, m)

29) N-[2-(4-Dimethylaminobut-1-yloxy)-4-methylphenyl]-3-methoxy-N-methyl-4-(2-methyl-1H-benzimidazol-4-yl)carbonylaminobenzamide dihydrochloride NMR (DMS-d$_6$, δ): 1.73–1.89 (4H, m), 2.24 (3H, s), 2.69 (3H, s), 2.70 (3H, s), 2.73 (3H, s), 3.07–3.16 (2H, m), 3.23 (3H, s), 3.67 (3H, s), 3.88 (1H, m), 3.99 (1H, m), 6.68 (1H, d, J=8 Hz), 6.83 (1H, s), 6.93 (1H, s), 6.98 (1H, d, J=8 Hz), 7.09 (1H, d, J=8 Hz), 7.52 (1H, t, J=8 Hz), 7.83 (1H, br), 7.90 (1H, d, J=8 Hz), 8.08 (1H, d, J=8 Hz)

30) N-[2-(4-Aminobut-1-yl)oxy-4-methyl]phenyl-3-methoxy-N-methyl-4-(2-methyl-1H-benzimidazol-4-yl)-carbamoylbenzamide dihydrochloride NMR (DMSO-d$_6$, δ): 1.70–1.88 (4H, m), 2.23 (3H, s), 2.78 (3H, s), 2.82–2.92 (2H, m), 3.23 (3H, s), 3.73 (3H, s), 3.87–6.08 (2H, m), 6.67 (1H, d, J=8 Hz), 6.84 (1H, s), 6.97–7.02 (2H, m), 7.09 (1H, d, J=8 Hz), 7.45 (1H, t, J=8 Hz), 7.55 (1H, d, J=8 Hz), 7.59–7.68 (2H, m), 8.08 (2H, br)

31) N-[2-(5-Aminopent-1-yl)oxy-4-methyl]phenyl-3-methoxy-N-methyl-4-(2-methyl-1H-benzimidazol-4-yl)-carbonylaminobenzamide dihydrochloride NMR (DMSO-d$_6$, δ): 1.41–1.51 (2H, m), 1.58–1.69 (2H, m), 1.69–1.81 (2H, m), 2.3 (3H, s), 2.71 (3H, s), 2.71–2.82 (2H, m), 3.20 (3H, s), 3.70 (3H, s), 3.88 (1H, m), 3.98 (1H, m), 6.67 (1H, d, J=8 Hz), 6.82 (1H, s), 6.91 (1H, s), 6.93 (1H, d, J=8 Hz), 7.07 (1H, d, J=8 Hz), 7.49 (1H, m), 7.85 (1H, d, J=8 Hz), 7.92–8.10 (3H, m)

32) N-[2-(6-Aminohex-1-yl)oxy-4-methyl]phenyl-4-(2-aminomethyl-1H-benzimidazol-4-yl)carbonylamino-3-methoxy-N-methylbenzamide trihydrochloride NMR (DMSO-d$_6$, δ): 1.34–1.50 (4H, m), 1.52–1.65 (2H, m), 1.70–1.79 (2H, m), 2.21 (3H, s), 2.71–2.80 (2H, m), 3.17 (3H, s), 3.75 (3H, s), 3.80–4.20 (2H, m), 4.41 (2H, m), 6.67 (1H, d, J=8 Hz), 6.82 (1H, s), 6.90–6.98 (2H, m), 7.06 (1H, d, J=8 Hz), 7.40 (1H, t, J=8 Hz), 7.83 (1H, d, J=8 Hz), 7.90–8.03 (3H, m), 8.30 (1H, m), 8.82–8.97 (2H, br)

33) 3-Methoxy-N-methyl-N-[4-methyl-2-[5-(4-methylpiperazin-1-yl)carbonylpent-1-yloxy]phenyl]-4-[2-(4-methylpiperazin-1-yl)-1H-benzimidazol-4-yl]-carbonylaminobenzamide dihydrochloride NMR (DMSO-d$_6$, δ): 1.38–1.64 (4H, m), 1.65–1.82 (2H, m, 2.22 (3H, s), 2.39 (2H, t, J=8 Hz), 2.68–2.84 (6H, m), 2.85–4.72 (24H, m), 6.65 (1H, d, J=8 Hz), 6.82 (1H, s), 6.87–7.00 (2H, m), 7.03 (1H, d, J=8 Hz), 7.10 (1H, dd, J=8, 8 Hz), 7.45 (1H, d, J=8 Hz), 7.74 (1H, d, J=8Hz), 8.40 (1H, d, J=8 Hz)

34) 3-Methoxy-N-methyl-N-[4-methyl-2-[5-(4-methylpiperazin-1-yl)carbonylpent-1-yloxylpent-1-yloxy]phenyl]-4-[2-(morpholin-4-yl)-1H-benzimidazol-4-yl]carbonylaminobenzamide dihydrochloride NMR (DMSO-d$_6$, δ): 1.38–1.66 (4H, m), 1.68–1.83 (2H, m), 2.23 (3H, s), 2.40 (2H, t, J=7 Hz), 2.69–2.78 (3H, m), 2.80–3.11 (2H, m), 3.20 (3H, s), 3.28–3.59 (3H, m), 3.60–4.18 (15H, m), 4.42 (1H, m), 6.64 (1H, d, J=8 Hz), 6.82 (1H, s), 6.87–6.97 (2H, m), 7.02 (1H, d, J=8 Hz), 7.11 (1H, dd, J=8, 8 Hz), 7.44 (1H, d, J=8 Hz), 7.72 (1H, d, J=8 Hz), 8.26 (1H, m), 8.50 (1H, m)

35) 4-[(2-Dimethylamino-1H-benzimidazol-4-yl)carbonylamino]-3-methoxy-N-methyl-N-[4-methyl-2-[5-(4-methylpiperazin-1-yl)carbonylpent-1-yloxy]phenyl]benzamide dihydrochloride NMR (DMSO-$d_6$, $\delta$): 1.37–1.66 (4H, m), 1.68–1.82 (2H, m), 2.22 (3H, s), 2.39 (2H, t, J=7 Hz), 2.72 and 2.74 (Total 3H, s), 2.80–3.11 (3H, m), 3.18 (3H, s), 3.21 (6H, s), 3.30–4.18 (9H, m), 4.44 (1H, m), 6.65 (1H, d, J=8 Hz), 6.81 (1H, s), 6.87–6.97 (2H, m), 6.97–7.09 (2H, m), 7.35 (1H, d, J=8 Hz), 7.68 (1H, d, J=8 Hz), 8.37 (1H, m)

36) 4-[2-[4-(Dimethylamino)piperidino]-1H-benzimidazol-4-yl]carbonylamino-3-methoxy-N-methyl-N-[4-methyl-2-[5-(4-methylpiperazin-1-yl)carbonylpent-1-yloxy]phenyl]-benzamide dihydrochloride NMR (DMSO-$d_6$, $\delta$): 1.32–1.88 (10H, m), 1.99–4.60 (35H, m), 6.66 (1H, d, J=8 Hz), 6.83 (1H, s), 6.87–7.00 (2H, m), 7.01–7.12 (2H, m), 7.40 (1H, d, J=8 Hz), 7.71 (1H, d, J=8 Hz), 8.00 (1H, s), 8.41 (1H, m)

37) 4-[[2-(Dimethylamino)amino-1H-benzimidazol-4-yl]-carbonylamino]-3-methoxy-N-methyl-N-[4-methyl-2-[5-(4-methylpiperazin-1-yl)carbonylpent-1-yloxy]phenyl]-benzamide dihydrochloride NMR (DMSO-$d_6$, $\delta$): 1.37–1.66 (4H, m), 1.67–1.84 (2H, m), 2.22 (3H, s), 2.39 (2H, t, J=7 Hz), 2.73 (3H, s), 2.80–3.11 (3H, m), 3.19 (3H, s), 3.28–4.15 (15H, m), 4.43 (1H, m), 6.66 (1H, d, J=8 Hz), 6.83 (1H, s), 6.88–7.12 (3H, m), 7.59 (1H, dd, J=8, 8 Hz), 7.92 (1H, d, J=8 Hz), 8.10 (1H, d, J=8 Hz), 8.41 (1H, m)

38) 4-[[2-Cyanomethyl-1H-benzimidazol-4-yl]carbonylamino]-3-methoxy-N-methyl-N-[4-methyl-2-[5-(4-methylpiperazin-1-yl)carbonylpent-1-yloxy]phenyl]benzamide dihydrochloride NMR (DMSO-$d_6$, $\delta$): 1.36–1.66 (4H, m), 1.67–1.83 (2H, m), 2.22 (3H, s), 2.39 (2H, t, J=7 Hz), 2.72 and 2.73 (Total 3H, s), 2.80–3.11 (3H, m), 3.20 (3H, s), 3.28–3.58 (3H, m), 3.73–4.15 (6H, m), 4.43 (1H, m), 4.59 (2H, s), 6.66 (1H, d, J=8 Hz), 6.83 (1H, s), 6.88–7.00 (2H, m), 7.04 (1H, d, J=8 Hz), 7.41 (1H, dd, J=8, 8 Hz), 7.79 (1H, d, J=8 Hz), 7.97 (1H, d, J=8 Hz), 8.39 (1H, d, J=8 Hz)

39) 4-[[2-[(2-Amino-2-(hydroxyimino)ethyl]-1H-benzimidazol-4-yl]carbonylamino]-3-methoxy-N-methyl-N-[4-methyl-2-[5-(4-methylpiperazin-1-yl)carbonylpent-1-yloxy]phenyl]benzamide trihydrochloride NMR (DMSO-$d_6$, $\delta$): 1.37–1.65 (4H, m), 1.66–1.83 (2H, m), 2.22 (3H, s), 2.40 (2H, t, J=7 Hz), 2.72 and 2.73 (Total 3H, s), 2.78–3.15 (3H, m), 3.19 (3H, s), 3.24–3.59 (3H, m), 3.77 (3H, s), 3.81–4.17 (3H, m), 4.32 (2H, s), 4.43 (1H, m), 6.66 (1H, d, J=8 Hz), 6.83 (1H, s), 6.88–6.99 (2H, m), 7.05 (1H, d, J=8 Hz), 7.40 (1H, dd, J=8, 8 Hz), 7.80 (1H, d, J=8 Hz), 7.96 (1H, d, J=8 Hz), 8.29 (1H, d, J=8 Hz)

40) [[2-[2-Aminoethyl)methylamino]-1H-benzimidazol-4-yl]-carbonylamino]-3-methoxy-N-methyl-N-[4-methyl-2-[5-(4-methylpiperazin-1-yl)carbonylpent-1-yloxy]phenyl]-benzamide trihydrochloride NMR (DMSO-$d_6$, $\delta$): 1.37–1.65 (4H, m), 1.66–1.83 (2H, m), 2.22 (3H, s), 2.40 (2H, t, J=7 Hz), 2.70 and 2.72 (Total 3H, s), 2.80–3.58 (14H, m), 3.70 (3H, s), 3.77–4.15 (5H, m), 4.43 (1H, m), 6.66 (1H, d, J=8Hz), 6.83 (1H, s), 6.87–6.99 (2H, m), 7.04 (1H, d, J=8 Hz), 7.12 (1H, dd, J=8, 8 Hz), 7.44 (1H, d, J=8 Hz), 7.71 (1H, d, J=8 Hz), 8.18 (1H, br), 8.38 (2H, br)

41) 4-[[2-[[2-(Dimethylamino)ethyl]amino]-1H-benzimidazol-4-yl]carbonylamino]-3-methoxy-N-methyl-N-[4-methyl-2-[5-(4-methylpiperazin-1-yl)carbonylpent-1-yloxy]phenyl]-benzamide trihydrochloride NMR (DMSO-$d_6$, $\delta$): 1.38–1.65 (4H, m), 1.68–1.84 (2H, m), 2.23 (3H, s), 2.39 (2H, t, J=7 Hz), 2.65–4.27 (28H, m), 4.42 (1H, m), 6.66 (1H, d, J=8 Hz), 6.83 (1H, s), 6.88–6.99 (2H, m), 7.05 (1H, d, J=8 Hz), 7.27 (1H, m), 7.55 (1H, d, J=8 Hz), 7.83 (1H, d, J=8 Hz)

42) 3-Methoxy-4-(2-mercaptomethyl-1H-benzimidazol-4-yl)-carbonylamino-N-methyl-N-[4-methyl-2-[5-(4-methylpiperazin-1-yl)carbonylpent-1-yloxy]phenyl]-benzamide dihydrochloride NMR (DMSO-$d_6$, $\delta$): 1.38–1.66 (4H, m), 1.68–1.84 (2H, m), 2.22 (3H, s), 2.39 (2H, t, J=7 Hz), 2.70–2.77 (3H, m), 2.79–3.12 (3H, m), 3.20 (3H, s), 3.30–4.18 (11H, m), 4.36–4.51 (1H, m), 6.66 (1H, d, J=8 Hz), 6.82 (1H, s), 6.88–7.00 (2H, m), 7.05 (1H, d, J=8 Hz), 7.44 (1H, dd, J=8, 8 Hz), 7.81 (1H, d, J=8 Hz), 8.00 (1H, d, J=8 Hz), 8.17 (1H, m)

43) 4-[2-(3-Hydroxypropyl)-1H-benzimidazol-4-yl]-carbonylamino-3-methoxy-N-methyl-N-[4-methyl-2-[5-(4-methylpiperazin-1-yl)carbonylpent-1-yloxy]phenyl]-benzamide dihydrochloride NMR (DMSO-$d_6$, $\delta$): 1.38–1.64 (4H, m), 1.68–1.84 (2H, m), 1.94–2.10 (2H, m), 2.22 (3H, s), 2.39 (2H, t, J=7 Hz), 2.70–2.77 (3H, m), 2.78–3.16 (6H, m), 3.20 (3H, s), 3.26–3.57 (5H, m), 3.70 (3H, m), 3.79–4.14 (5H, m), 4.43 (1H, m), 6.66 (1H, d, J=8 Hz), 6.83 (1H, s), 6.88–7.00 (2H, m), 7.05 (1H, d, J=8 Hz), 7.46 (1H, m), 7.81 (1H, m), 7.93–8.10 (2H, m)

44) 4-[N-(1H-Benzimidazol-4-yl)carbamoyl]-N-[2-[4,4-dimethyl(2,5-oxazolinyl)]phenyl]-3-methoxy-N-methylbenzamide dihydrochloride NMR (DMSO-$d_6$, $\delta$): 1.30–1.55 (6H, m), 3.30 (3H, s), 3.67 (3H, s), 3.96–4.11 (1H, m), 4.22–4.38 (1H, m), 7.00–7.10 (1H, m), 7.17–8.04 (9H, m), 9.60 (1H, s)

45) 4-[N-[2-[(Dimethylamino)methyl]-1H-benzimidazol-4-yl]-carbamoyl]-N-[2-[4,4-dimethyl(2,5-oxazolinyl)]phenyl]-3-methoxy-N-methylbenzamide trihydrochloride NMR (DMSO-$d_6$, $\delta$): 1.30–1.56 (6H, m), 2.90 and 2.94 (Total 6H, s), 3.31 and 3.46 (Total 3H, s), 3.84 and 4.21 (Total 3H, s), 4.42–4.81 (4H, m), 7.06–8.32 (10H, m)

46) N-[2-[4,4-Dimethyl(2,5-oxazolinyl)]phenyl]-3-methoxy-N-methyl-4-(2-methyl-1H-benzimidazol-4-yl)-carbonylaminobenzamide dihydrochloride NMR (DMSO-$d_6$, $\delta$): 1.32–1.51 (6H, m), 2.78 (3H, s), 3.29 and 3.30 (Total 3H, s), 3.60 (3H, s), 3.92–4.16 (1H, m), 4.30–4.49 (1H, m), 6.90–8.36 (10H, m)

47) 4-[N-(1H-Benzimidazol-4-yl)carbamoyl]-3-methoxy-N-methyl-N-[2-(1-pyrrolyl)phenyl]benzamide hydrochloride NMR (DMSO-$d_6$, $\delta$): 3.40 (3H, s), 3.68 (3H, s), 6.23 (2H, s), 6.52 (2H, s), 6.60 (2H, s), 7.24 (1H, d, J=8 Hz), 7.30–7.58 (6H, m), 7.62 (1H, d, J=8 Hz), 7.71 (1H, d, J=8 Hz), 7.84 (1H, d, J=8 Hz), 9.46 (1H, s)

48) 3-Methoxy-N-methyl-4-[N-(2-methyl-1H-benzimidazol-4-yl)-carbamoyl]-N-(2-piperidinophenyl)benzamide hydrochloride NMR (DMSO-$d_6$, $\delta$): 1.38–1.70 (6H, m), 2.16–2.40 (2H, m), 2.65–2.89 (5H, m), 3.40 (3H, s), 3.63 (3H, br s), 6.83–7.03 (2H, m), 7.04–7.28 (3H, m), 7.40–7.72 (5H, m)

49) 3-Methoxy-N-methyl-4-(2-methyl-1H-benzimidazol-4-yl)-carbonylamino-N-(2-piperidinophenyl)benzamide dihydrochloride NMR (DMSO-$d_6$, $\delta$): 1.37–1.72 (6H, m), 2.14–2.43 (2H, m), 2.65–2.92 (5H, m), 3.39 (2H, s), 3.59 (3H, br s), 6.80–7.32 (5H, m), 7.47 (1H, m), 7.58 (1H, dd, J=8, 8 Hz), 7.70 (1H, m), 7.94 (1H, d, J=8 Hz), 8.14 (1H, d, J=8 Hz)

50) 3-Methoxy-N-methyl-4-[N-(2-methyl-1H-benzimidazol-4-yl)carbamoyl]-N-[2-(4-methyl-1-piperazinyl)phenyl]-benzamide dihydrochloride NMR (DMSO-$d_6$, $\delta$): 2.78 (3H, s), 2.80–3.26 (9H, m), 3.30–3.82 (8H, m), 6.90–7.10 (2H, m), 7.14–7.32 (3H, m), 7.40–7.63 (4H, m), 7.75 (1H, d, J=8 Hz)

51) 3-Methoxy-N-methyl-4-(2-methyl-1H-benzimidazol-4-yl)-carbonylamino-N-[2-(4-methyl-1-piperazinyl)phenyl]-benzamide dihydrochloride NMR (DMSO-d$_6$, δ): 2.30 (1H, br s), 2.74 (3H, s), 2.81 and 2.82 (Total 3H, s), 2.86–3.26 (6H, m), 3.29–3.49 (5H, m), 3.60 (3H, s), 6.90–7.02 (2H, m), 7.11–7.29 (3H, m), 7.42–7.58 (2H, m), 7.78–8.16 (3H, m)

52) 3Methoxy-N-methyl-4-[N-(2-methyl-1H-benzimidazol-4-yl)-carbamoyl]-N-[2-(2,5-oxazolyl)phenyl]benzamide hydrochloride NMR (DMSO-d$_6$, δ): 2.77 (3H, s), 3.36 (3H, s), 3.61 (3H, s), 6.70 (1H, d, J=8 Hz), 6.76 (1H, s), 7.37–7.69 (8H, m), 7.84 (1H, d, J=8 Hz), 8.32 (1H, s)

53) 3-Methoxy-N-methyl-4-[N-(2-methyl-1H-benzimidazol-4-yl)-carbamoyl]-N-[2-(2,5-oxazolinyl)phenyl]benzamide dihydrochloride NMR (DMSO-d$_6$, δ): 2.78 (3H, s), 3.28 (3H, s), 3.38–4.11 (7H, m), 7.08–8.80 (10H, m)

54) 3-Methoxy-N-methyl-4-[N-(2-methyl-1H-benzimidazol-4-yl)carbamoyl]-N-[2-(3H, 4H, 5H-2,6-oxazinyl)phenyl]-benzamide NMR (DMSO-d$_6$, δ): 1.90–2.06 (2H, m), 2.72–2.85 (3H, m), 3.12–4.08 (10H, m), 6.82–8.58 (10H, m)

55) N-[2-(1-Aza-3-oxaspiro[4.4]non-1-en-2-yl)phenyl]-3-methoxy-N-methyl-4-[N-(2-methyl-1H-benzimidazol-4-yl) carbamoyl]benzamide dihydrochloride NMR (DMSO-d$_6$, δ): 1.52–2.07 (8H, m), 2.79 (3H, s), 3.30 (3H, s), 3.66 (3H, s), 4.38–4.58 (2H, m), 6.97–7.10 (2H, m), 7.20–8.08 (8H, m)

56) 3-Methoxy-N-methyl-N-[4-methyl-2-[5-(4-methylpiperazin-1-yl)carbonylpent-1-yloxy]phenyl]-4-(2-sulfamoylamino-1H-benzimidazol-4-yl) carbonylaminobenzamide dihydrochloride NMR (DMSO-d$_6$, δ): 1.38–1.52 (2H, m), 1.52–1.65 (2H, m), 1.65–1.83 (2H, m), 2.3 (3H, s), 2.39 (2H, t, J=7.5 Hz), 2.75 (3H, d, J=4 Hz), 2.80–3.08 (3H, m), 3.20 (3H, s), 3.33–3.42 (3H, m), 3.80–3.91 (1H, m), 3.91–4.02 (1H, m), 4.02–4.13 (1H, m), 4.39–4.50 (1H, m), 6.65 (1H, d, J=8 Hz), 6.83 (1H, s), 6.89–6.98 (2H, m), 7.04 (1H, d, J=8 Hz), 7.21 (1H, t, J=8 Hz), 7.38–7.48 (1H, m), 7.54–7.67 (1H, m), 7.77 (1H, d, J=8 Hz), 9.61 (1H, br peak), 10.55 (1H, br peak)

57) 4-[2-Carbamoyl-1H-benzimidazol-4-yl]carbonylamino-3-methoxy-N-methyl-N-[4-methyl-2-[5-(4-methylpiperazin-1-yl)carbonylpent-1-yloxy]phenyl] benzamide dihydrochloride NMR (DMSO-d$_6$, δ): 1.39–1.52 (2H, m), 1.52–1.65 (2H, m), 1.65–1.81 (2H, m), 2.23 (3H, s), 2.39 (2H, t, J=7.5 Hz), 2.77 (3H, d, J=5 Hz), 2.83–3.10 (3H, m), 3.20 (3H, s), 3.31–3.48 (3H, m), 3.77 (3H, s), 3.81–3.92 (1H, m), 3.92–4.01 (1H, m), 4.10 (1H, br d, J=15 Hz), 4.45 (1H, br d, J=15 Hz), 6.66 (1H, d, J=8 Hz), 6.83 (1H, s), 6.91–7.03 (2H, m), 7.07 (1H, d, J=8 Hz), 7.51 (1H, t, J=8 Hz), 7.71 (1H, s), 7.80 (1H, d, J=8 Hz), 8.04 (1H, d, J=8 Hz), 8.30 (1H, s), 8.37 (1H, d, J=8 Hz), 10.46 (1H, br peak), 12.00 (1H, s)

58) 4-[2-(N,N-Dimethylcarbamoyl)-1H-benzimidazol-4-yl]-carbo nylamino-3-methoxy-N-methyl-N-[4-methyl-2-[5-(4-methylpiperazin-1-yl) carbonylpent-1-yloxy]phenyl]-benzamide dihydrochloride NMR (DMSO-d$_6$, δ) : 1.40–1.52 (2H, m), 1.52–1.66 (2H, m), 1.70–1.82 (2H, m), 2.22 (3H, s), 2.40 (2H, t, J=8 Hz), 2.77 (3H, s), 2.83–3.10 (3H, m), 3.15 (3H, s), 3.20 (3H, s), 3.33–3.60 (6H, m), 3.72 (3H, s), 3.80–3.93 (1H, m), 3.93–4.02 (1H, m), 4.02–4.15 (1H, m), 4.40–4.50 (1H, m), 6.65 (1H, d, J=8 Hz), 6.82 (1H, s), 6.88–6.98 (2H, m) 7.05 (1H, d, J=8 Hz), 7.49 (1H, t, J=8 Hz), 7.80 (1H, d, J=8 Hz), 8.03 (1H, d, J=8 Hz), 8.30 (1H, d, J=8 Hz)

59) 3-Methoxy-N-methyl-N-[4-methyl-2-[5-(4-methylpiperazin-1-yl) carbonylpent-1-yloxy]phenyl]-4-[2-(4-piperidyl)-1H-benzimidazol-4-yl] carbonylaminobenzamide trihydrochloride NMR (DMSO-d$_6$, δ): 1.40–1.53 (2H, m), 1.53–1.65 (2H, m), 1.70–1.84 (2H, m), 2.03–2.20 (2H, m), 2.23 (3H, s), 2.32–2.48 (4H, m), 2.75 (3H, d, J=5 Hz), 2.83–3.15 (4H, m), 3.19 (3H, s), 3.30–3.54 (7H, m), 3.77 (3H, s), 3.88 (1H, br peak), 3.97 (1H, br peak), 4.09 (1H, br d, J=15 Hz), 4.44 (1H, br d, J=15 Hz), 6.65 (1H, d, J=8 Hz), 6.83 (1H, s), 6.90–7.00 (2H, m), 7.05 (1H, d, J=8 Hz), 7.36 (1H, t, J=8 Hz), 7.74 (1H, d, J=8 Hz), 8.97 (1H, br peak), 9.27 (1H, br peak), 11.05 (1H, br peak)

60) 4(2-Aminomethyl-1-methyl-1H-benzimidazol-4-yl)-carbonylamino-3-methoxy-N-methyl-N-[4-methyl-2-[5-(4-methylpiperazin-1-yl) carbonylpent-1-yloxy]phenyl]-benzamide trihydrochloride NMR (DMSO-d$_6$, δ): 1.40–1.53 (2H, m), 1.53–1.67 (2H, m), 1.70–1.84 (2H, m), 2.23 (3H, s), 2.40 (2H, t, J=7.5 Hz), 2.74 (3H, d, J=5 Hz), 2.80–3.10 (3H, m), 3.20 (3H, s), 3.32–3.54 (3H, m), 3.68–4.03 (8H, m), 4.10 (1H, br d, J=15 Hz), 4.44 (1H, br d, J=15 Hz), 4.51–4.61 (2H, m), 6.66 (1H, d, J=8 Hz), 7.50 (1H, t, J=8 Hz), 7.93(1H, d, J=8 Hz), 8.03 (1H, d, J=8 Hz), 8.30 (1H, d, J=8 Hz), 8.83–8.96 (3H, m)

61) 4-(2Aminomethyl-3methyl-3H-benzimidazol-4-yl)-carbonylamino-3-methoxy-N-methyl-N-[4-methyl-2-[5-(4-methylpiperazin-1-yl) carbonylpent-1-yloxy]phenyl]-benzamide trihydrochloride NMR (DMSO-d$_6$-D$_2$O, δ): 1.41–1.53 (2H, m), 1.53–1.68 (2H, m), 1.68–1.85 (2H, m), 2.26 (3H, s), 2.41 (2H, t, J=7.5 Hz), 2.80 (3H, s), 2.86–3.14 ) (3H, m), 3.21 (3H, s), 3.35–3.52 (2H, m), 3.68 (1H, s), 3.75 (3H, s), 3.84–4.05 (2H, m), 4.05–4.19 (1H, m), 4.42–4.53 (3H, m), 6.70 (1H, d, J=8 Hz), 6.87 (1H, s), 6.91–7.01 (2H, m), 7.10 (1H, d, J=8 Hz), 7.33 (1H, t, J=8 Hz), 7.49 (1H, d, J=8 Hz), 7.78 (1H, d, J=8 Hz), 7.84 (1H, d, J=8 Hz)

62) 4-(2-Methylthio-1H-benzimidazol-4-yl)carbonylamino-3-methoxy-N-methyl-N-[4-methyl-2-]5-(4-methylpiperazin-1-yl) carbonylpent-1-yloxy]phenyl] benzamide dihydrochloride NMR (CDCl$_3$, δ): 1.40–1.52 (2H, m), 1.52–1.66 (2H, m), 1.66–1.82 (2H, m), 2.23 (3H, s), 2.40 (2H, t, J=7 Hz), 2.75 (3H, d, J=5 Hz), 2.80–3.08 (5H, m), 3.20 (3H, s), 3.33–3.49 (3H, m), 3.72 (3H, s), 3.87 (1H, br peak), 3.95 ) (1H, br peak), 4.10 (1H, br d, J=15 Hz), 4.44 (1H, br d, J=15 Hz), 6.65 (1H, d, J=8 Hz), 6.81 (1H, s), 6.89–6.99 (2H, m), 7.04 (1H, d, J=8 Hz), 7.30 (1H, t, J=8 Hz), 7.63 (1H, d, J=8 Hz), 7.88 (1H, d, J=8 Hz), 8.39 (1H, d, J=8 Hz)

63) 3- Methoxy-N-methyl-N-[4-methyl-2-[5-(4-methylpiperazin-1-yl) carbonylpent-1-yloxy]phenyl]-4-(2-methylsulfonyl-1H-benzimidazol-4yl) carbonylaminobenzamide dihydrochloride NMR (DMSO-d$_6$, δ): 1.36–1.51 (2H, m), 1.51–1.66 (2H m), 1.66–1.83 (2H, m), 2.21 (3H, s), 2.40 (2H, t, J=7.5 Hz), 2.76 (3H, d, J=5 Hz), 2.81–3.10 (3H, m), 3.19 (3H, s), 3.30–3.68 (6H, m), 3.80 (3H, s), 3.88 (1H, br peak), 3.96 (1H, br peak), 4.09 (1H, br d, J=15 Hz), 4.45 (1H, br d, J=15 Hz), 6.65 (1H, d, J=8 Hz), 6.81 (1H, s), 6.90–7.00 (2H, m), 7.04 (1H, d, J=8 Hz), 7.64 (1H, t, J=8 Hz), 7.90 (1H, d, J=8 Hz), 8.13 (1H, d, J=8 Hz), 8.40 (1H, d, J=8 Hz)

64) 3-Methoxy-N-methyl-N-[4-methyl-2-[5-(4-methylpiperazin-1-yl) carbonylpent-1-yloxy]phenyl]-4-(2-sulfamoyl-1H -benzimidazol-4-yl) carbonylaminobenzamide dihydrochloride NMR (DMSO-d$_6$, δ): 1.39–1.52 (2H, m), 1.52–1.67 (2H, m), 1.70–1.83 (2H, m), 2.22 (3H, s), 2.40 (2H, t, J=7.5 Hz, 2.76 (3H, d, J=5 Hz), 2.85–3.09 (3H, m), 3.20 (3H, s), 65) 4(2-Aminomethyl-1H-benzimidazol-4-yl) carbamoyl-3-methoxy-N-methyl-N-[4-methyl-2-[5-(4-methylpiperazin-1-yl) carbonylpent-1-yloxy]phenyl]benzamide trichrolochloride NMR (DMSO-$d_6$, δ): 1.40–1.52 (2H, m), 1.52–1.68 (2H, m), 1.68–1.84 (2H, m), 2.22 (3H, s), 2.41 (2H, t, J=6 Hz), 2.75 (3H, d, J=5 Hz), 2.81–3.10 (3H, m), 3.22 (3H, s), 3.32–3.52 (4H, m), 3.82–4.02 (4H, m), 4.09 (1H, br d, J=12 Hz), 4.30–4.50 (3H, m), 6.65 (1H, d, J=8Hz), 6.81 (1H, s), 7.02 (1H, d, J=8 Hz), 7.07–7.16 (2H, m), 7.21 (1H, t, J=8 Hz), b7.31 (1H, d, J=8 Hz), 7.88 (1H, d, J=8 Hz), 8.05 (1H, br peak), 8.64–8.75 (3H, m)

66) 4-[2-(2-Aminoethyl)-1H-benzimidazol-4-yl]carbamoyl-3-methoxy-N-methyl-N-[4-methyl-2-[5-(4-methylpiperazin-1-yl) carbonylpent-1-yloxy]phenyl]benzamide trichrolochloride NMR (DMSO-$d_6$, δ): 1.39–1.52 (2H, m), 1.52–1.67 (2H, m), 1.71–1.84 (2H, m), 2.22 (3H, s), 2.41 (2H, t, J=7.5 Hz), 2.80–3.09 (3H, m), 3.21 (3H, d, J=5 Hz), 3.27–3.74 (7H, m), 3.74–4.03 (5H, m), 4.09 (1H, br d, J=15 Hz), 4.44 (1H, br d, J=15 Hz), 6.65 (1H, d, J=8 Hz), 6.82 (1H, s), 6.99 (1H, d, J=8 Hz), 7.06 (1H, s), 7.11 (1H, d, J=8 Hz), 7.26–7.49 (2H, m), 7.65–7.80 (1H, m) 7.90–7.93 (1H, m), 8.26 (3H, br peak)

67) 4-(2-Hydroxymethyl-1H-benzimidazol-4-yl) carbamoyl-3-methoxy-N-methyl-N-[4-methyl-2-[5-(4-methylpiperazin-1-yl) carbonylpent-1-yloxy]phenyl] benzamide dihydrochloride NMR (DMSO-$d_6$, δ): 1.41–1.52 (2H, m), 1.52–1.66 (2H, m), 171.–1.85 (2H, m), 2.22 (3H, s), 2.40 (2H, t, J=7.5 Hz), 2.76 (3H, s), 2.82–3.09 (3H, m), 3.21 (3H, s), 3.79 (3H, s), 3.85–4.03 (2H, m), 4.03–4.15 (1H, m), 4.38–4.51 (1H, m), 4.91 (2H, s), 6.66 (1H, d, J=8 Hz), 6.84 (1H, s), 7.00 (1H, d, J=8 Hz), 7.04 (1H, s), 7.11 (1H, d, J=8 Hz), 7.36–7.52 (2H, m), 7.63–7.72 (1H, m) 7.72–7.84 (1H, m)

68) 4-[2-Amino-1H-benzimidazol-4-yl)]carbamoyl-3-methoxy-N-methyl-N-[4-methyl-2-[5-(4-methylpiperazin-1-yl)-carbonylpent-1-yloxy]phenyl]benzamide dihydrochloride NMR (DMSO-$d_6$, δ): 1.40–1.53 (2H, m), 1.53–1.68 (2H m), 1.70–1.85 (2H, m), 2.23 (3H, s), 2.40 (2H, t, J=7.5 Hz), 2.73 (3H, d, J=5 Hz), 2.80–3.09 (3H, m), 3.20 (3H, s), 3.30–3.60 (3H, m), 3.71 (3H, s), 3,84–4.02 (2H, m), 4.08 (1H, br d, J=15 Hz), 4.43 (1H, br d, J=15 Hz), 6.65 (1H, d, J=8 Hz), 6.83 (1H, s), 6.97 (1H, d, J=8 Hz), 7.01 (1H, s), 7.10 (1H, d, J=8 Hz), 7.16–7.23 (2H, m), 7.30–7.38 (1H, m) 7.54 (1H, d, J=8 Hz), 8.37 (2H, s)

69) 3-Methoxy-N-methyl-N-[4-methyl-2-[5-(4-methylpiperazin-1-yl) carbonylpent-1-yloxy]phenyl ]-4-[2-[(methylsulfonyl) amino]-1H-benzimidazol-4-yl]carbamouylbenzamide dihydrochloride NMR (DMSO-$d_6$, δ): 1.38–1.52 (2H, m), 1.52–1.67 (2H, m), 1.67–1.83 (2H, m) 2.22 (3H, s), 2.40 (2H, t, J=7.5 Hz), 2.76 (3H, d, J=5 Hz), 2.82–3.08 (3H, m), 3.23 (3H, s), 3.32–3.48 (3H, m), 3.51 (3H, s), 3.75–4.23 (6H, m), 4.45 (1H, br d, J=15 Hz), 6.65 (1H, d, J=8 Hz), 6.80 (1H, s) 6.97–7.15 (4H, m), 7.15–7.30 (2H, m), 7.88 (1H, d, J=8 Hz), 8.10 (1H, d, J=8 Hz)

70) 3-Methoxy-4-[2-methoxymethyl-1H-benzimidazol-4-yl]-carbamoyl-N-methyl-N-[4-methyl-2-[5-(4-methylpiperazin-1-yl) carbonylpent-1-yloxy]phenyl]benzamide dihydrochloride NMR (DMSO-$d_6$, δ): 1.39–1.52 (2H, m), 1.52–1.67 (2H, m), 1.67–1.85 (2H, m), 2.23 (3H, s), 2.40 (2H, t, J=7.5 Hz), 2.74 (3, d, J=5 Hz), 2.80–3.10 (3H, m), 3.21 (3H, s), 3.26–3.54 (6H, m), 3.77 (3H, s), 3.81–4.20 (3H, m), 4.43 (1H, br d, J=15 Hz), 4.90 (2H, s), 6.65 (1H, d, J=8 Hz), 6.83 (1H, s), 7.00 (1H, d, J=8 Hz), 7.03 (1H, s), 7.11 (1H, d, J=8 Hz), 7.40–7.58 (2H, m), 7.66 (1H, d, J=8 Hz), 7.79 (1H, d, J=8 Hz)

71) 3-Methoxy-N-methyl-4-[2-mehtyl-1H-benzimidazol-4-yl]carbamoyl-N-[4-methyl-2-[5-(4-methylpiperazin-1-yl)-carbonylpent-1-yloxy]phenyl ]benzamide dihydrochloride NMR (DMSO-$d_6$, δ): 1.41–1.53 (2H, m), 1.53–1.67 (2H, m), 1.72–1.85 (2H, m), 2.23 (3H, s), 2.40 (2H, t, J=7.5 Hz), 2.73 (3H, t, J=5 Hz), 2.78 (3H, s), 2.82–3.13 (3H, m), 3.21 (3H, s), 3.30–3.56 (3H, m), 3.75 (3H, s), 3.80–4.17 (3H, m), 4.43 (1H, br d, J=15 Hz), 6.65 (1H, d, J=8 Hz), 6.84 (1H, s), 6.98 (1H, d, J=8 Hz), 7.02 (1H, s), 7.10 (1H, d, J=8 Hz), 7.40–7.65 (4H, m)

72(4-[1,2-dimethyl-1H-benzimidazol-4-yl]carbamoyl-3-methoxy-N-methyl-N-[4-methyl-2-[5-(4-methylpiperazin-1-yl) carbonylpent-1-yloxy]phenyl]benzamide dihydrochloride NMR (DMSO-$d_6$, δ): 1.39–1.53 (2H, m), 1.53–1.65(2H, m), 1.71–1.85 (2H, m), 2.22 ) (3H, s), 2.40 (2H, t, J=7.5 Hz), 2.67–2.80 (6H, m), 2.80–3.10 (3H, m), 3.21 (3H, s), 3.25–3.64 (3H, m), 3.73–4.20 (9H, m), 4.38–4.50 (1H, m), 6.65 (1H, d, J=8 Hz), 6.81 (1H, s), 6.95–7.08 (2H, m) 7.11 (1H, d, J=8 Hz), 7.45 (1H, br peak), 7.54–7.82 (3H, s)

73) 4-[2-Ethyl-1H-benzimidazol-4-yl]carbamoyl-3-methoxy-N-methyl-N-[4-methyl-2-[5-(4-methylpiperazin-1-yl) carbonylpent-1-yloxy]phenyl]benzamide dihydrochloride NMR (DMSO-$d_6$, δ): 1.37–1.52 (5H, m), 1.52–1.68 (2H, m), 1.71–1.85 (2H, m), 2.23 (3H, s), 2.40 (2H, t, J=7.5 Hz), 2.75 (3H, s), 2.80–3.17 (5H, m), 3.21 (3H, s), 3.31–3.61 (3H, m), 3.77 (3H, s), 3.85–4.01 (2H, m), 4.09 (1H, br d, J=15 Hz), 4.44 (1H, br d, J=15 Hz, 6.66 (1H, d, J=8 Hz), 6.83 (1H, s), 6.99 (1H, d, J=8 Hz), 7.03 (1H, s), 7.11 ) 1H, d, J=8 Hz), 7.43 (1H, br peak), 7.53 (1H, br peak), 7.66 (2H, br peak)

74) 3-Methoxy-N-methyl-N-[4-methyl-2-[5-(4-methylpiperazin-1-yl) carbonylpent-1-yloxy]phenyl]-4-[2-(n-propyl)-1H-benzimidazol-4-yl]carbamoylbenzamide dihydrochloride NMR (DMSO-$d_6$, δ): 0.97 (3H, t, J=7.5 Hz), 1.40–1.53 (2H, s), 1.53–1.69 (2H, m), 1.69–1.84 (4H, m), 2.22 (3H, s), 2.39 (2H, t, J=7.5 Hz), 2.75 (3H, s), 2.80–3.14 (5H, m), 3.20 (3H, s), 3.30–3.60 (3H, m), 3.78 (3H, s), 3.83–4.16 (3H, m), 4.04 (1H, br peak), 6.65 (1H, d, J=8 Hz), 6.83 (1H, s), 7.00 (1H, d, J=8 Hz), 7.03 (1H, s), 7.10 (1H, d, J=8 Hz), 7.43 (1H, br peak), 7.52 (1H, br peak), 7.66 (2H, br peak)

75) 4-[2-Isopropyl-1H-benzimidazol-4-yl]carbamoyl-3-methoxy-N-methyl-N-[4-methyl-2-[5-(4-methylpiperazin-1-yl)-carbondylpent-1-yloxy ]phenyl]benzamide dihydrochloride NMR (DMSO-$d_6$, δ): 1.40–1.53 (8H, m), 1.53–1.69 (2H, m), 1.69–1.88 (2H, m), 2.23 (3H, s), 2.40 (2H, t, J=7.5 Hz), 2.73 (3H, d, J=5 Hz), 2.80–3.08 (3H, m), 3.21 (3H, s), 3.31–3.56 (4H, m), 3.76 (3H, s), 3.85–4.03 (2H, m), 4.09 (1H, br d, J=15 Hz), 4.43 (1H, d, J=15 Hz), 6.66 (1H, d, J=8 Hz), 6.83 (1H, s), 6.98 (1H, d, J=8 Hz), 7.02 (1H, s), 7.10 (1H, d, J=8 Hz), 7.39–7.69 (3H, m), 7.80 (1H, br peak)

76) 3-Methoxy-N-methyl-N-[4-methyl-2-[5-(4-methylpiperazin-1-yl) carbonylpent-1-yloxy]phenyl]-4-[2-trifluoromethyl-1H-benzimidazol-4-yl] carbamoylbenzamide dihydrochloride NMR (DMSO-$d_6$, δ): 1.40–1.52 (2H, m), 1.52–1.68 (2H, m), 1.68–1.83 (2H, m), 2.21 (3H, s), 2.40 (2H, t, J=7.5 Hz), 2.76 (3H, d, J=5 Hz), 2.83–3.13 (3H, m), 3.22 (3H, s), 3.33–3.63 (3H, m), 3.82–4.02 (4H, m), 4.09 (1H, br d, J=15 Hz), 4.45 (1H, br d, J=15 Hz), 6.64 (1H, d, J=8 Hz), 6.81 (1H, s), 7.00–7.16 (3H, m), 7.32–7.46 (2H, m), 7.90 (1H, br peak), 8.23 (1H, br peak)

77) 3-Methyoxy-N-methyl-N-[4-methyl-2-[5-(4-methylpiperazin-1-yl) carbonylpent-1-yloxy]phenyl]-4-[2-(3-pyridyl)-1H-benzimidazol-4-yl]carbamoylbenzamide trihydrochloride NMR (DMSO-$d_6$, δ): 1.41–1.53 (2H, m), 1.53–1.66 (2H, m), 1.73–1.85 (2H, m), 2.21 (3H, s), 2.41 (2H, t, J=7.5 Hz), 2.74 (3H, d, J=5 Hz), 2.81–3.08 (3H, m), 3.23 (3H, s), 3.31–3.51 (3H, m), 3.71–4.16 (6H, m), 4.40–4.52 (1H, m), 6.66 (1H, d, J=8 Hz), 6.81 (1H, s), 7.04 (1H, d, J=8 Hz), 7.08–7.16 (2H, m), 7.29 (1H, t, J=8 Hz), 7.38 (1H, d, J=8 Hz), 7.85 (1H, dd, J=5, 8 Hz), 7.90 (1H, d, J=8 Hz), 8.19 (1H, d, J=8 Hz), 8.77 (1H, d, J=8 Hz), 8.83 (1H, d, J =5 Hz), 9.48 (1H, s)

78) 4-[2-(N,N-Dimethylcarbamoyl)-1H-benzimidazol-4-yl)-carbamoyl-3-methoxy-N-methyl-N-[4-methyl-2-[5-(4-methyl-piperazin-1-yl)carbonylpent-1-yloxy]phenyl] benzamide dihydrochloride NMR (DMSO-$d_6$, δ): 1.38–1.52 (2H, m), 1.52–1.65 (2H, m), 1.65–1.83 (2H, m), 2.22 (3H, s), 2.40 (2H, t, J=5 Hz), 2.74 (3H, d, J5 Hz), 2.79–3.07 (3H, m), 3.11 (3H, s), 3.21 (3.21 (3H, s), 3.31–3.49 (3H, m), 3.71 (3H, s), 3.82–4.01 (4H, m), 4.01–4.38 (2H, m), 4.45 (1H, d, J=15 Hz), 6.65 (1H, d, J=8 Hz), 6.80 (1H, s), 7.02 (1H, d, J=8 Hz), 7.06–7.17 (2H, m), 7.24–7.31 (2H, m), 7.84–7.93 (1H, m), 8.19–8.29 (1H, m)

79) 4-[2-(N,N-Dimethylaminomethyl)-1H-benzimidazol-4-yl ]-carbamoyl-3-methoxy-N-methyl-N-[4-methyl-2-[5-(4-methylpiperazin-1-yl)carbonylpent-1-yloxy]phenyl]-benzamide trihydrochloride NMR (DMSO-$d_6$, δ): 1.38–1.53 (2H, m), 1.53–1.67 (2H, m), 1.67–1.84 (2H, m), 2.20 (3H, s), 2.40 (2H, t, J=7.57 Hz), 2.74 (3H, d, J=5Hz), 2.80–3.10 (9H, m), 3.21 (3H, s), 3.31–3.45 (3H, m), 3.81–4.01 (4H, m), 4.08 (1H, br d, J=15 Hz), 4.44 (1H, be d, J=15 Hz), 4.61 (2H, s), 6.65 (1H, d, J=8 Hz), 6.81 (1H, s), 7.02 (1H, d, J=8 Hz), 7.07–7.15 (2H, m), 7.24 (1H, t, J=8 Hz), 7.34 (1H, d, J=8 Hz), 7.88 (1H, d, J=8 Hz), 8.10 (1H, br peak)

80) 3-Methoxy-N-methyl-N-[4-methyl-2-[5-(4-methylpiperazin-1-yl)carbonylpent-1-yloxy]pheny]-4-[2-(2-imidazolyl)-methyl-1H-benzimidazol-4-yl] carbamoylbenzamide trihydrochloride NMR (DMSO-$d_6$, δ): 1.40–1.53 (2H, m), 1.53–1.68 (2H, m), 1.68–1.85 (2H, m), 2.22 (3H, s), 2.40 (2H, t, J=7.5 Hz), 2.74 (3H, s), 2.80–3.10 (3H, m), 3.23 (3H, s), 3.31–3.54 (3H, m), 3.70–4.20 (6H, m), 4.44 (1H, br peak), 5.84 (2H, s), 6.65 ((1H, d, J=8 Hz), 6.82 (1H, s), 7.01 (1H, d, J=8Hz), 7.04–7.15(2H, m), 7.21 (1H, t, J=8 Hz), 7.30 (1H, d, J=8 Hz), 7.78 (1H, s-like), 7.87 (1H, d, J=8 Hz), 7.92 (1H, s-like), 8.08 (1H, br peak), 9.40 (1H, s)

81) 3-Methoxy-N-methyl-N-[4-methyl-2-[5-(4-methylpiperazin-1-yl)carbonylpent-1-yloxy]phenyl]-4-[2-[(4-methyl-piperazin-1-yl)methyl]-1H-benzimidazol-4yl]-carbamoylbenzamide trihydrochloride NMR (DMSO-$d_6$, δ): 1.40–1.53 (2H, m), 1.53–1.64 (2H, m), 1.70–1.83 (2H, m), 2.23 (3H, s), 2.40 2.40 (2H, t, J=7.5 Hz), 2.70–3.18 (9H, m), 3.21 (3H, s), 3.32–4.20 (19H, m), 4.43 (1H, br d, J=15 Hz), 6.66 (1H, d, J=8 Hz), 6.84 (1H, s), 7.00 (1H, d, J=8 Hz), 7.05 (1H, s), 7.10 (1H, d, J=8 Hz), 7.37 (1H, br peak), 7.45 (1H, br peak), 7.70 (1H, br peak), 7.99 (1H, br peak)

82) 3-Methoxy-N-methyl-N-[4-methyl-2-5-(4-methylpiperazin-1-yl)carbonylpent-1-ylopxy]phenyl]-4-[2-(morpholin-4-ylmethyl)-1H-benzimidazol-4-yl] carbamoylbenzamide trihydrochloride NMR (DMSO-$d_6$, δ): 1.39–1.52 (2H, m), 1.52–1.66 (2H, m), 1.66–1.85 ( 2H, m), 2.21 (3H, s), 2.40 (2H, t, J=7.5 Hz), 2.74 (3H, d, J=5 Hz), 2.78–3.11 (3H, m), 3.21 (3H, s), 3.30–4.00 (16H, m), 4.09 (1H, d, J=15 Hz), 4.44 (1H, d, J=15 Hz), 4.64 (2H, s), 6.65 (1H, d, J=8 Hz), 6.82 (1H, s), 7.03 (1H, d, J=8 Hz), 7.06–7.15 (2H, m), 7.26 (1H, t, J=8 Hz), 7.36 (1H, d, J=8 Hz), 7.87 (1H, d, J=8 Hz), 8.08 (1H, br peak)

83) 3-Methoxy-N-methyl-N-[4-methyl-2-[5-(4-methylpiperazin-1-yl)carbonylpent-1-yloxy]phenyl]-4-[2-(prrolidin-1-ylmethyl)-1H-benzimidazol-4-yl] carbamoylbenzamide trihydrochloride NMR (DMSO-$d_6$, δ): 1.39–1.53 (2H, m), 1.53–1.68 (2H, m), 1.68–1.87 (2H, m), 1.87–2.11 (4H, m), 2.21 (3H, s), 2.40 (2H, t, J=7.5 Hz), 2.74 (3H, d, J=5 Hz), 2.80–3.11 (3H, m), 3.21 (3H, s), 3.25–3.79 (7H, m), 3.79–4.02 (5H, m), 4.09 (1H, br d, J=15 Hz), 4.44 (1H, br d, J=15 Hz), 4.70 (2H, s), 6.65 (1H, d, J=8 Hz), 6.81 (1H, s), 7.01 (1H, d, J=8 Hz), 7.04–7.15 (2H, m), 7.24 (1H, t, J=8 Hz), 7.32 (1H, d, J=8 Hz), 7.87 (1H, d, J=8 Hz), 8.03–8.13 (1H, m)

84) 3-Methoxy-N-methyl-N-[4-methyl-2-[5-(4-methylpiperazin-1-yl)carbonylpent-1-yloxy]phenyl]-4-[2-(piperidino-methyl)-1H-benzimidazol-4-yl] carbamoylbenzamide trihydrochloride NMR (DMSO-$d_6$, δ): 1.38–1.90 (12H, m), 2.21 (3H, s), 2.40 (2H, t, J=7.5 Hz), 2.75 (3H, d, J=5 Hz), 2.80–3.17 (3H, m), 3.23 (3H, s), 3.28–4.02 (15H, m), 4.09 (1H, br d, J=15 Hz), 4.44 (1H, br d, J=15 Hz), 4.59 (2H, s), 6.64 (1H, d, J=8 Hz), 6.81 (2H, s), 7.02 (1H, d, J=8 Hz), 7.06–7.15 (2H, m), 7.24 (1H, t, J=8 Hz), 7.34 (1H, d, J=8 Hz), 7.87 (1H, d, J=8 Hz), 8.09 (1H, br peak)

85) 4-[2-[2-(Dimethylamino)ethyl]-1H-benzimidazol-4-yl ]-carbamoyl-3-methoxy-N-methyl-N-[4-methyl-2-[5-(4-methylpiperazin-1-yl)carbonylpent-1-yloxy]phenyl]-benzamide trihydrochloride NMR (DMSO-$d_6$, δ): 1.39–1.52 (2H, m), 1.52–1.67 (2H, m), 1.70–1.86 (2H, m), 2.22 (3H, s), 2.40 (2H, t, J=7.5 Hz), 2.75 (3H, d, J=5 Hz), 2.81–3.08 (9H, m), 3.22 (3H, s), 3.28–3.72 (7H, m), 3.82–4.02 (5H, m), 4.09 (1H, br d, J=15 Hz), 4.43 (1H, br d, J=15 Hz), 6.65 (1H, d, J=8 Hz), 6.81 (1H, s). 7.01 (1H, d, J=8 Hz), 7.05–7.17 (2H, m), 7.20–7.40 (2H, m), 7.80 (1H, d, J=8 Hz), 7.93 (1H, br peak)

86) 3-Methoxy-N-methyl-N-[4-methyl-2-[5-(4-methylpiperazin-1-yl)carbonylpent-1-yloxy]phenyl]-4-[2-[2-(4-methylpiperazion-1yl) ethyl]-1H-benzimidazol-4yl]-carbampylbenzamide trihydrochloride NMR (DMSO-$d_6$, δ): 1.40–1.53 (2H, m), 1.53–1.66 (2H, m), 1.71–1.86 (2H, m), 2.22 (3H, s), 2.40 (2H, t, J=5 Hz), 2.70–2.79 (6H, m), 2.79–3.65 (21H, m), 3.78–4.01 (5H, m), 4.09 (1H, br d, J=15 Hz), 4.44 (1H, br d, J=15 Hz), 6.65 (1H, d, J=8 Hz), 6.82 (1H, s), 7.00 (1H, d, J=8 Hz), 7.05 (1H, s), 7.10 (1H, d, J=8 Hz), 7.35 (1H, t, J=8 Hz), 7.46 (1H, d, J=8 Hz), 7.66–7.80 (2H, m)

87) 3-Methoxy-N-methyl-N-[4-methyl-2-[5-(4-methylpiperazin-1-yl)carbonylpent-1-yloxy]phenyl]-4-[2-(4-methyl-piperazin-1-yl)-1H-benzimidazol-4-yl] carbamoylbenzamide trihydrochloride NMR (DMSO-$d_6$, δ): 1.48–1.53 (2H, m), 1.53–1.65 (2H, m), 1.70–1.85 (2H, m), 2.21 (3H, s), 2.40 (2H, t, J=7.5 Hz), 2.74 (3H, d, J=5 Hz), 2.80 (3H, s), 2.83–3.10 (3H, m), 3.16–3.83 (13H, m), 3.83–4.15 (2H, m), 4.33 (1H, br d, J=15 Hz), 4.43 (1H, br, d J=15 Hz), 6.65 (1H, d, J=8 Hz), 6.81 (1H, s), 6.96 (1H, d, J=8 Hz), 7.01 (1H, s), 7.09 (1H, d, J=8 Hz), 7.13–7.24 (2H, m), 7.61 (1H, br peak), 7.79 (1H, br peak)

88) 4-[2-Dimethylamino-1H-benzimidazol-4-yl]carbamoyl-3-methoxy-N-methyl-N-[4-methyl-2-[5-(4-methylpiperazin-1-yl)carbonylpent-1-yloxy]phenyl] benzamide hydrochloride NMR (DMSO-d$_6$, δ): 1.41–1.52 (2H, m), 1.52–1.67 (2H, m), 1.71–1.83 (2H, m), 2.22 (3H, s), 2.40 (2H, t, J=7.5 Hz), 2.75 (3H, s), 2.80–3.10 (3H, m), 3.15 (6H, s), 3.21 (3H, s), 3.70–4.50 (6H, m), 4.50 (1H, br peak), 6.65 (1H, d, J=8 Hz), 6.82 (1H, s), 6.95–7.06 (2H, m), 7.11 (1H, d, J=8 Hz), 7.50–8.10 (4H, m)

89) 3-Methoxy-N-methyl-4-[2-[[2-(methylamino)ethyl]amino]-1H-benzimidazol-4-yl]carbamoyl-N-[4-methyl-2-[5-(4-methylpiperazin-1-yl)carbonylpent-1-yloxy]phenyl]-benzamide trihydrochloride NMR (DMSO-d$_6$, δ): 1.40–1.53 (2H, m), 1.53–1.65 (2H, m) 1.65–1.84 (2H, m), 2.22 (3H, s), 2.40 (2H, t, J=7.5 Hz), 2.61 (2H, t-like, J=5 Hz), 2.74 (3H, d, J=5 Hz), 2.78–3.11 (3H, m), 3.11–3.29 (5H, m), 3.29–3.55 (3H, m), 3.72 (3H, s), 3.73–4.01 (2H, m), 4.09 (1H, br d, J=15 Hz), 4.43 (1H, br d, J=15 Hz), 6.65 (1H, d, J=8 Hz), 6.83 (1H, s), 6.95 (1H, d, J=8 Hz), 7.00 (1H, s), 7.10 (1H, d, J=8 Hz), 7.18–7.27 (2H, m), 7.47–7.61 (2H, m), 9.10 (3H, br peak)

90) 4-[2-[(2-Aminoethyl)methylamino]-1H-benzimidazol-4-yl]-carbamoyl-3-methoxy-N-methyl-N-[4-methyl-2-[5-(4-methylpiperazin-1-yl)carbonylpent-1-yloxy]phenyl]-benzamide trihydrochloride NMR (DMSO-d$_6$, δ): 1.40–1.53 (2H, m), 1.53–1.67 (2H, m), 1.70–1.83 (2H, m), 2.23 (3H, s), 2.40 (2H, t, J=7.5 HZ), 2.74 (32H, d, J=5 Hz), 2.79–3.11 (3H, m), 3.11–3.23 (5H, m), 3.26 (3H, s), 3.33–3.56 (5H, m), 3.71 (3H, s), 3.84–4.02 (5H, m), 4.09 (1H, br d, J=15 Hz), 4.43 (1H, br d, J=15 Hz), 6.65 (1H, d, J=8 Hz), 6.82 (1H, s), 6.93 (1H, d, J=8 Hz), 6.99 (1H, s), 7.09 (1H, d, J=8 Hz), 7.18–7.28 (2H, m), 7.50 (1H, br peak), 7.80 (1H, br peak) 8.29 (3H, br peak)

91) 4-[2-(1-Imidazolyl)-1H-benzimidazol-4-yl)]carbamoyl-3-methoxy-N-methyl-N-[4-methyl-2-[5-(4-methylpiperazin-1-yl)carbonylpent-1-yloxy]phenyl] benzamide trihydrochloride NMR (DMSO-d$_6$, δ): 1.41–1.52 (2H, m), 1.52–1.67 (2H, m), 1.67–1.84 (2H, m), 2.20 (3H, s), 2.40 (2H, t, J=7.5 Hz), 2.74 (3H, s-like), 2.81–3.10 (3H, m), 3.22 (3H, s), 3.30–3.53 (3H, m), 3.78–4.22 (6H, m), 4.39–4.51 (1H, m), 6.66 (1H, d, J=8 Hz), 6.81 (3H, s), 7.04 (1H, d, J=8 Hz), 7.09–7.19 (2H, m), 7.23–7.40 (2H, m), 7.65 (1H, s), 7.91 (1H, d, J=8 Hz), 8.15–8.29 (2H, m), 9.28 (1H, s)

92) 4-[2-[[2-(Dimethylamino)ethyl]amino]-1H-benzimidazol-4-yl]carbamoyl-3-methoxy-N-methyl-N-[4-methyl-2-[5-(4-methylpiperazin-1-yl)carbonylpent-1-yloxy]phenyl]-benzamide trihydrochloride NMR (DMSO-d$_6$, δ): 1.39–1.52 (2H, m), 1.52–1.66 (2H, m), 1.70–1.85 (2H, m), 2.22 (3H, s), 2.40 (2H, t, J=7.5 Hz), 2.73 (3H, d, J=5 Hz), 2.84 (6H, s), 2.88–3.10 (3H, m), 3.20 (3H, s), 3.28–3.53 (7H, m), 3.84–4.02 (5H, m), 4.08 (1H, br d, J=15 Hz), 4.43 (1H, br d, J=15 Hz), 6.66 (1H, d, J=8 Hz), 6.83 (1H, s), 6.92–7.02 (2H, m), 7.10 (1H, d, J=8 Hz), 7.19–7.27 (2H, m), 7.50 (1H, d, J=8 Hz), 7.58 (1H, br peak), 9.14 (1H, br peak)

93) 4-[2-[[2-(Dimethylamino)ethyl]methylamino]-1H-benzimidazol-4-yl]carbamoyl-3-methyoxy-N-methyl-N-[4-methyl-2-[5-(4-methylpiperazion-1-yl)carbonylpent-1-yloxy]phenyl]benzamide trihydrochloride NMR (DMSO-d$_6$, δ ): 1.41–1.53 (2H, m), 1.53–1.66 (2H, m), 1.70–1.85 (2H, m), 2.22 (3H, s), 2.40 (2H, d, J=7.5 Hz), 2.74 (3H, d, J=5 Hz), 2.81–3.09 (9H, m), 3.21 (3H, s), 3.26 (3H, s), 3.32–3.55 (7H, m), 3.71 (3H, br s), 3.81–4.14 (3H, m), 4.44 (1H, br d, J=15 Hz), 6.65 (1H, d, J=8 Hz), 6.82 (1H, s), 6.92 (1H, d, J=8 Hz), 6.98 (1H, s), 7.09 (1H, d, J=8 Hz), 7.15–7.25 (2H, m), 7.49 (1H, br peak), 7.85 (1H, br peak)

94) 3-Methoxy-N-methyl-N-[4-methyl-2-[5-(4-methylpiperazin-1-yl)carbonylpent-1-yloxy]phenyl]-4-[2-(1,2,4-triazol-1-yl)-1H-benzimidazol-4-yl]carbamoylbenzamide trihydrochloride NMR (DMSO-d$_6$, δ): 1.40–1.53 (2H, m), 1.53–1.67 (2H, m), 1.72–1.85 (2H, m), 2.22 (3H, s), 2.41 (2H, t, J=7.5 Hz), 2.76 (3H, d, J=5Hz), 2.80–310 (3H, m), 3.21 (3H, S), 3.28–3.64 (3H, m), 3.83–4.03 (5H, m), 4.10 (1H, br d, J=15 Hz), 4.55 (1H, br d, J=15 Hz), 6.66 (1H, d, J=8 Hz), 6.83 (1H, s), 7.05 (1H, d, J=8 Hz), 7.08–7.17 (2H, m), 7.21–7.32 (2H, m), 7.90 (1H, br peak), 8.19 (1H, br peak), 8.50 (1H, s), 9.41 (1H, s)

95) 4-[2-[(2-Methoxyethyl)amino]-1H-benzimidazol-4-yl]-carbamoyl-3-methoxy-N-methyl-N-[4-methyl-2-[5-(4-methylpiperazin-1-yl)carbonylpent-1-yloxy]phenyl]-benzamide dihydrochloride NMR (DMSO-d$_6$, δ): 1.39–1.52 (2H, m), 1.52–1.67 (2H, m), 1.70–1.85 (2H, m), 2.22 (3H, s), 2.40 (2H, t, J=7.5 Hz), 2.73 (3H, s), 2.80–3.10 (3H, m), 3.21 (3H, s), 3.27–3.49 (6H, m), 3.53–3.64 (4H, m), 3.73 (3H, s), 3.84–4.16 (3H, m), 4.43 (1H, br peak), 6.65 (1H, d, J=8 Hz), 6.84 (1H, s), 6.97 (1H, d, J=8 Hz), 7.00 (1H, s), 7.10 (1H, d, J=8 HZ), 7.16–7.26 (2H, m), 7.40 (1H, br peak), 7.55 (1H, br peak), 8.80 (1H, br peak)

96) 4-(2-Dimethylaminomethyl-1H-benzimidazol-4-yl)-carbonylamino-3-methoxy-N-methyl-N-[4-methyl-2-[5-(4-methylpiperazin-1-yl)carbonylpent-1-yloxy]phenyl]-benzamide trihydrochloride NMR (DMSO-d$_6$, δ): 1.40–1.52 (2H, m), 1.52–1.63 (2H, m), 1.72–1.82 (2H, m), 2.22 (3H, s), 2.40 (2H, t, J=7 Hz), 2.73 (3H, s), 2.90–3.05 (10H, m), 3.20 (3H, s), 3.35–3.50 (3H, m), 3.78 (3H, s), 3.95–4.13 (2H, m), 4.40–4.45 (1H, m), 4.68 (2H, s), 6.64 (1H, d, J=8 Hz), 6.82 (1H, s), 6.90–6.95 (2H, m), 7.04 (1H, d, J=8 Hz), 7.46 (1H, t, J=8 Hz), 7.89 (1H, d, J=8 Hz), 8.01 (1H, d, J=8 Hz), 8.30 (1H, d, J=8 Hz)

97) 3-Methoxy-N-methyl-N-[4-methyl-2-[5-(4-methylpiperazin-1-yl)carbonylpent-1-yloxy]phenyl]-4-[2-(4-methyl-piperazin-1-yl)methyl-1H-benzimidazol-4-yl]-carbonylaminobenzamide trihydrochoride NMR (DMSO-d$_6$, δ): 1.42–1.52 (2H, m), 1.52–1.64 (2H, m), 1.73–1.82 (2H, m), 2.22 (3H, s), 2.40 (2H, t, J=7 Hz), 2.72 (3H, s), 2.77 (3H, s), 2.85–3.10 (4H, m), 3.20 (3H, s), 3.20–3.40 (7H, m), 3.45–3.56 (4H, m), 3.78 (3H, s), 3.83–4.10 (2H, m), 4.37–4.43 (3H, m), 6.65 (1H, d, J=8Hz), 6.82 (1H, s), 6.90–6.93 (2H, m), 7.03 (1H, d, J=8 Hz), 7.47 (1H, t, J=8 Hz), 7.87 (1H, d, J=8 Hz), 8.03 (1H, d, J=8 Hz), 8.20–8.23 (1H, m)

98) 4-[2-(4-Dimethylaminopiperidion)methyl-1H-benzimidazol-4-yl]carbonylamino-3-methoxy-N-methyl-N-[4-methyl-2-[5-(4-methylpiperazin-1-yl)carbonylpent-1-yloxy]phenyl]- benzamide trihydrochloride NMR (DMSO-d$_6$, δ): 1.40–1.53 (2H, m), 1.53–1.66 (2H, m), 1.70–1.82 (2H, m), 2.10–2.35 (7H, m), 2.42 (2H, t, J=7 Hz), 2.64–2.73 (7H, m), 2.85–3.08 (4H, m), 3.18 (3H, s), 3.3.–3.53 (3H, m), 3.73–4.30 (9H, m), 4.40–4.47 (1H, m), 4.69 (2H, s), 6.63 (1H, d, J=8 Hz), 6.83 (1H, s), 6.92–6.97 (2H, m), 7.04 (1H, d, J=8 Hz), 7.47 (1H, t, J=8 Hz), 7.91 (1H, d, J=8 Hz), 8.02 (1H, d, J=8 Hz), 8.30–8.35 (1H, m)

99) 3-Methoxy-N-methyl-N-[4-methyl-2-[5-(4-methylpiperazin-1-yl)carbonylpent-1-yloxy]phenyl]-4-(2-morpholinomethyl-1H-benzimidazole-4-yl)carbonylaminobenzamide trihydrochloride NMR (DMSO-d$_6$, δ): 1.41 –1.52 (2H, m), 1.52–1.64 (2H, m), 1.72–1.80 (2H, m), 2.22 (3H, s), 2.40 (2H, t, J=8 Hz), 2.73 (3H, s), 2.80–3.10 (4H, m), 3.18 (3H, s), 3.34–3.55 (7H, m), 3.80 (3H, s), 3.82–4.10 (6H, m), 4.37–4.45 (1H, m), 4.72 (2H, s), 6.64 (1H, d, J=8 Hz), 6.82 (1H, s), 6.92–6.94 (2H, m), 7.03 (1H, d, J=8 Hz), 7.46 (1H, t, J=8 Hz), 7.90 (1H, d, J=8 Hz), 8.03 (1H, d, J=8 Hz), 8.30 (1H, d, J=8 Hz)

What is claimed is:

1. A compound of the formula:

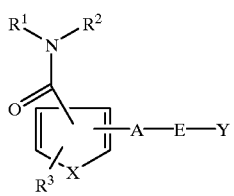

(I)

wherein:

R$^1$ is aryl, cyclo(lower)alkyl or a heterocyclic group, each of which may be substituted with substituent(s) selected from the group consisting of halogen; hydroxy; nitro; protected amino; amino; acyl; substituted acyl; acyl(lower)alkylsulfinyl; acyl(lower)alkylsulfonyl; acyloxy; lower alkylamino(lower)alkylcarbamoyloxy; aryl; cyano; a heterocyclic group; lower alkenyl optionally substituted with acyl, substituted acyl, aryl or acyl-substituted aryl; lower alkynyl optionally substituted with amino, acylamino or substituted acylamino; lower alkyl optionally substituted with halogen, amino, lower alkylamino, acylamino, substituted acylamino, hydroxy, acyloxy, acyl(lower)alkanoyloxy, acyl, substituted acyl, aryl(lower)alkoxyimino, aryl or acyl-substituted aryl; lower alkylthio optionally substituted with acyl or substituted acyl; alkoxy optionally substituted with aryl, substituted aryl, hydroxy, acyloxy, amino, lower alkylamino, protected amino, a heterocyclic group, acyl-substituted pyridyl, substituted acyl-substituted pyridyl, halogen, acyl(lower)alkylamino, N-protected-acyl(lower)-alkylamino, N-acyl(lower)alkyl-N-lower alkylamino, acyl substituted acyl, acylamino, substituted acylamino, lower alkylhydrazinocarbonylamino, hydroxyimino, acyl(lower)alkoxyimino, substituted acyl(lower)alkoxyimino, acyl(lower)alkoxy, guanidino or N-protected guanidino; and lower alkenyloxy optionally substituted with acyl or substituted acyl;

R$^2$ is hydrogen; lower alkyl optionally substituted with hydroxy, aryl or acyl; or cyclo(lower)alkyl;

R$^3$ is hydrogen; halogen; hydroxy; acyloxy; substituted acyloxy; lower alkyl optionally substituted with hydroxy or lower alkoxy, lower alkoxy optionally substituted with aryl, amino, protected amino, acyl, hydroxy, cyano or lower alkylthio; nitro; amino; acyl; substituted acyl; or cyclo(lower)alkyloxy;

A is a single bond, O or NH;

E is lower alkylene, lower alkenylene,

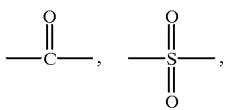

or a group of the formula:

in which G is lower alkylene or

and

J is O or

wherein R$^4$ is hydrogen or N-protective group;

X is —CH═CH—, —CH═N— or S; and

Y is aryl which may be substituted with acyl, protected amino(lower)alkanoyl, protected amino and nitro, amino and nitro or diamino; or a condensed heterocyclic group which may be substituted with substituent(s) selected from the group consisting of halogen, acyl, lower alkoxy, hydroxy, guanidino, mercapto, acylamino, amino, a heterocyclic group, cyanoamino, amino(lower)alkyl(lower)alkylamino, lower alkylamino, lower alkylamino(lower)alkylamino, substituted-heterocyclic group, lower alkylhydrazino, aryloxy, lower alkylthio, aryl, protected amino, N-protected lower alkylamino(lower)alkylamino, N-protected amino(lower)alkyl(N'-lower alkyl)amino, amino(lower)alkyl (N-lower alkyl)amino, lower alkylamino(lower)alkyl(N-lower alkyl)amino, lower alkoxy(lower)alkylamino and lower alkyl optionally substituted with aryl, ar(lower)alkoxy, cyano, hydroxyimino, mercapto, lower alkylamino, acyloxy, halogen, lower alkoxy, protected hydroxy, hydroxy, lower alkoxyaryl, protected amino, amino, a heterocyclic group or substituted heterocyclic group;

provided that when Y is phenyl which may be substituted with lower alkyl or acyl, then A is a single bond and E is

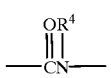

wherein R$^4$ is as defined above;

and a pharmaceutically acceptable salt thereof.

2. A new compound according to claim 1, wherein

R$^1$ is aryl, cyclo(lower)alkyl or a heterocyclic group, each of which may be substituted with substituent(s) selected from the group consisting of halogen; hydroxy; nitro; amino; acyl; substituted acyl; acyl(lower)alkylsulfinyl; acyl(lower)alkylsulfonyl; acyloxy; lower alkylamino(lower)alkylcarbamoyloxy; aryl; cyano; a heterocyclic group; lower alkenyl optionally substituted with acyl, substituted acyl, aryl or acyl-substituted aryl; lower alkynyl optionally substituted with amino, acylamino or substituted acylamino; lower alkyl optionally substituted with halogen, amino, lower alkylamino, acylamino, substituted acylamino, hydroxy, acyloxy, acyl(lower)alkanoyloxy, acyl, substituted acyl, aryl(lower)alkoxyimino, aryl or acyl-substituted aryl; lower alkylthio optionally substituted with acyl or substituted acyl; alkoxy optionally substituted with aryl, substituted aryl, hydroxy, acyloxy, amino, lower alkylamino, protected amino, a heterocyclic group, acyl-substituted pyridyl, substituted acyl-substituted pyridyl, halogen, acyl(lower)alkylamino, N-protected-acyl(lower)-alkylamino, N-acyl(lower)alkyl-N-lower alkylamino, acyl, substituted acyl, acylamino, substituted acylamino, lower alkylhydrazinocarbonylamino, hydroxyimino, acyl(lower)alkoxyimino, substituted acyl(lower)alkoxyimino, acyl(lower)alkoxy, guanidino or N-protected guanidino; and lower alkenyloxy optionally substituted with acyl or substituted acyl;

$R^2$ is hydrogen; lower alkyl optionally substituted with hydroxy, aryl or acyl; or cyclo(lower)alkyl;

$R^3$ is hydrogen; halogen; hydroxy; acyloxy; substituted acyloxy; lower alkyl optionally substituted with hydroxy or lower alkoxy, lower alkoxy optionally substituted with aryl, amino, protected amino, acyl, hydroxy, cyano or lower alkylthio; nitro; amino; acyl; substituted acyl; or cyclo(lower)alkyloxy;

A is a single bond, O or NH;

E is lower alkylene, lower alkenylene,

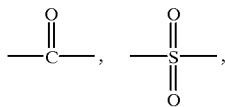

or a group of the formula:

in which G is lower alkylene or

and
J is O or

wherein $R^4$ is hydrogen or N-protective group;
X is —CH=CH—, —CH=N— or S; and
Y is aryl which is substituted with protected amino and nitro, amino and nitro or diamino; or a condensed heterocyclic group which may be substituted with substituent(s) selected from the group consisting of halogen, acyl, lower alkoxy, hydroxy, guanidino, mercapto, acylamino, amino and lower alkyl optionally substituted with lower alkylamino, acyloxy, halogen, lower alkoxy, protected hydroxy, hydroxy, lower alkoxyaryl, protected amino, amino or a heterocyclic group.

3. A compound according to claim 2, wherein
$R^1$ is aryl which may be substituted with lower alkoxy substituted with acyl or acylamino,
$R^2$ is lower alkyl,
$R^3$ is hydrogen, lower alkyl or lower alkoxy,
A is a single bond or NH,

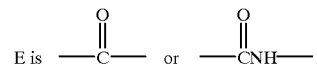

X is —CH=CH—, and
Y is a condensed heterocyclic group which is substituted with lower alkyl optionally substituted with lower alkylamino, acyloxy, halogen, lower alkoxy, protected hydroxy, hydroxy, lower alkoxyaryl, protected amino, amino or a heterocyclic group.

4. A compound according to claim 3, wherein
$R^1$ is phenyl or tolyl, each of which is substituted with lower alkoxy substituted with N-lower alkylpiperazinylcarbonyl,
$R^3$ is lower alkoxy,
A is a single bond,

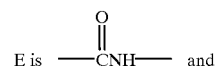

Y is benzimidazol which is substituted with lower alkyl optionally substituted with amino, hydroxy or N-lower alkylpiperazinyl.

5. A compound according to claim 3, wherein
$R^1$ is phenyl of tolyl, each or which is substituted with lower alkoxy substituted with N-lower alkylpiperazinylcarbonyl,
$R^3$ is lower alkoxy,
A is NH,

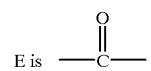

Y is benzimidazolyl which is substituted with lower alkyl optionally substituted with amino, hydroxy or N-lower alkylpiperazinyl.

6. A process for preparing the formula:

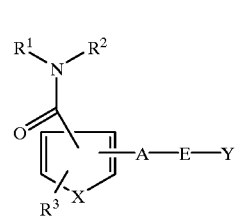

(I)

wherein
$R^1$ is aryl, cyclo(lower)alkyl or a heterocyclic group, each of which may be substituted with substituent(s)

selected from the group consisting of halogen; hydroxy; nitro; protected amino; amino; acyl; substituted acyl; acyl(lower)alkylsulfinyl; acyl(lower)alkylsulfonyl; acyloxy; lower alkylamino(lower)alkylcarbamoyloxy; aryl; cyano; a heterocyclic group; lower alkenyl optionally substituted with acyl, substituted acyl, aryl or acyl-substituted aryl; lower alkynyl optionally substituted with amino, acylamino or substituted acylamino; lower alkyl optionally substituted with halogen, amino, lower alkylamino, acylamino, substituted acylamino, hydroxy, acyloxy, acyl(lower)alkanoyloxy, acyl, substituted acyl, aryl(lower)alkoxyimino, aryl or acyl-substituted aryl; lower alkylthio optionally substituted with acyl or substituted acyl; alkoxy optionally substituted with aryl, substituted aryl, hydroxy, acyloxy, amino, lower alkylamino, protected amino, a heterocyclic group, acyl-substituted pyridyl, substituted acyl-substituted pyridyl, halogen, acyl(lower)alkylamino, N-protected-acyl(lower)alkylamino, N-acyl(lower)alkyl-N-lower alkylamino, acyl substituted acyl, acylamino, substituted acylamino, lower alkylhydrazinocarbonylamino, hydroxyimino, acyl(lower)alkoxyimino, substituted acyl(lower)alkoxyimino, acyl(lower)alkoxy, guanidino or N-protected guanidino; and lower alkenyloxy optionally substituted with acyl or substituted acyl;

R² is hydrogen; lower alkyl optionally substituted with hydroxy, aryl or acyl; or cyclo(lower) alkyl;

R³ is hydrogen; halogen; hydroxy; acyloxy; substituted acyloxy; lower alkyl optionally substituted with hydroxy or lower alkoxy; lower alkoxy optionally substituted with aryl, amino, protected amino, acyl, hydroxy, cyano or lower alkylthio; nitro; amino; acyl; substituted acyl; or cyclo(lower)alkyloxy;

A is a single bond, O or NH;

E is lower alkylene, lower alkenylene,

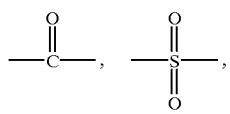

or a group of the formula:

—G—J— in which G is lower alkylene or

and

J is O or

wherein R⁴ is hydrogen or N-protective group;
X is —CH=CH—, —CH=N— or S; and
Y is aryl which may be substituted with acyl, protected amino(lower)alkanoyl, protected amino and nitro, amino and nitro or diamino; or a condensed heterocyclic group which may be substituted with substituent(s) selected from the group consisting of halogen, acyl, lower alkoxy, hydroxy, guanidino, mercapto, acylamino, amino, a heterocyclic group, cyanoamino, amino(lower)alkyl(lower)alkylamino, lower alkylamino, lower alkylamino(lower)alkylamino, substituted-heterocyclic group, lower alkylhydrazino, aryloxy, lower alkylthio, aryl, protected amino, N-protected lower alkylamino(lower)alkylamino, N-protected amino(lower)alkyl(N'-lower alkyl)amino, amino(lower)alkyl(N-lower alkyl)amino, lower alkylamino(lower)alkyl(N-lower alkyl)amino, lower alkoxy(lower)alkylamino and lower alkyl optionally substituted with aryl, ar(lower)alkoxy, cyano, hydroxyimino, mercapto, lower alkylamino, acyloxy, halogen, lower alkoxy, protected hydroxy, hydroxy, lower alkoxyaryl, protected amino, amino, a heterocyclic group or substituted heterocyclic group;

provided that when Y is phenyl which may be substituted with lower alkyl or acyl, then A is a single bond and

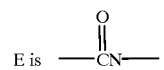

wherein R⁴ is as defined above;

or a pharmaceutically acceptable salt thereof, which comprises:

1) reacting a compound of the formula:

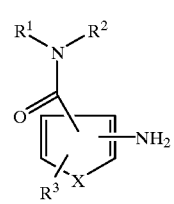

(II)

or its salt with a compound of the formula:

HO—Ea—Y          (III)

or its reactive derivative at the carboxy group or the sulfo group, or a salt thereof to provide a compound of the formula:

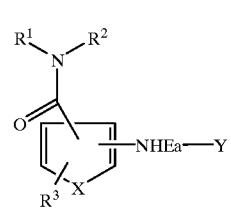

(Ia)

or its salt, in the above formulas, $R^1$, $R^2$, $R^3$, X and Y are each as defined above, and E is 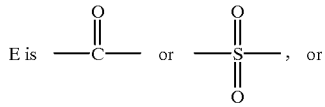, or 2) reacting a compound of the formula:

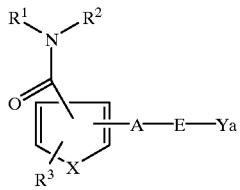 (Ib)

or its salt with a compound of the formula:

 $R^5-Z^1$ (IV)

in the presence of a base to provide a compound to the formula:

(Ic)

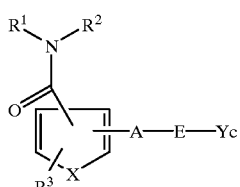

or its salt, in the above formulas,
$R^1$, $R^2$, $R^3$, A, E and X are each as defined above,
Ya is indolyl,
$R^5$ is lower alkyl,
$Z^1$ is an acid residue, and
Yb is N-(lower alkyl)indolyl, or 3) reducing a compound of the formula:

(Id)

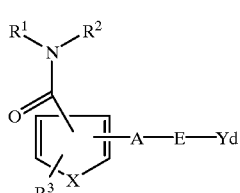

or its salt to provide a compound of the formula:

(Ie)

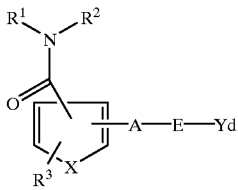

or its salt, in the above formulas,
$R^1$, $R^2$, $R^3$, A, E and X are each as defined above,
Yc is phenyl substituted with amino and nitro, and
Yd is phenyl substituted with diamino, or 4) reacting a compound of the formula:

(Ie)

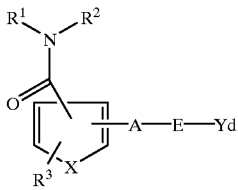

or its salt with aroyl halide, cyano(lower)alkylcarboxylic acid, mercapto(lower)alkylcarboxylic acid, lower alkyllactone, 1,1-dihalo-1,1-diphenoxymethane, diphenyl N-sulfamoylcarbonimidate, diphenyl N-cyanocarbonimidate, dicyandiamide, 1,1'-thiocarbonylimidazole, cyanogen bromide, lower alkoxycarbonyl isothiocyanate, tri(lower)alkyl orthoformate, tetra(lower)alkyl orthoformate, lower alkylcarboxylic acid, halo(lower)alkylcarboxylic acid, protected amino(lower)alkylcarbonyl halide or a heterocyclic(lower)alkylcarbonyl halide to provide a compound of the formula:

(If)

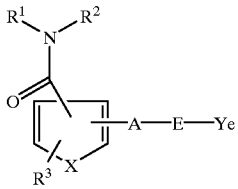

or its salt, in the above formulas,
$R^1$, $R^2$, $R^3$, A, E, X and Yd are each as defined above; and
Ye is benzimidazolyl optionally 2-position substituted with aryl, phenoxy, sulfamoylamino, cyanoamino, guanidino, mercapto, amino, lower alkoxycarbonylamino, lower alkoxy or lower alkyl optionally substituted with cyano, mercapto, hydroxy, halogen, protected amino or a heterocyclic group, or 5) reacting a compound of the formula:

(Ie)

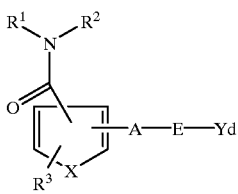

or its salt with glyoxal and sodium hydrogen sulfite, or sodium nitrite to provide a compound of the formula:

(Ig)

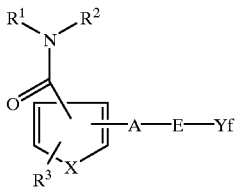

or its salt, in the above formulas,
$R^1$, $R^2$, $R^3$, A, E, X and Yd are each as defined above; and
Yf is quinoxalinyl or benzotriazolyl, or 6) reacting a compound of the formula

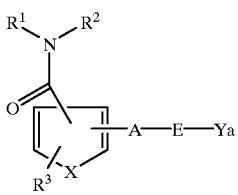

(Ib)

or its salt with an acylating agent to provide a compound of the formula:

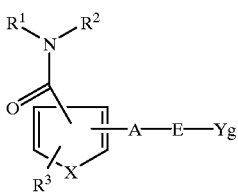

(Ih)

or its salt, in the above formulas,
$R^1$, $R^2$, $R^3$, A, E, X and Ya are each as defined above, and Yg is N-acylindolyl, or 7) reacting a compound of the formula:

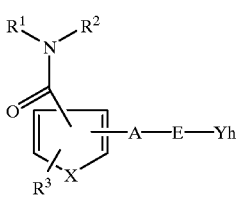

(Ii)

or its salt in an elimination reaction of the N-substituted group to provide a compound of the formula:

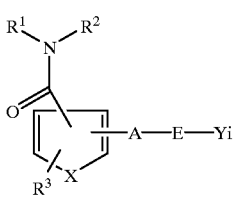

(Ij)

or its salt, in the above formulas,
$R^1$, $R^2$, $R^3$, A, E and X are each as defined above,
Yh is (N-acyl)acylindolinyl, N-acylindolinyl, (N-acyl) hydroxy(lower)alkylindolinyl, lower alkylamino (lower)alkylamino(N-acyl)indolinyl, (N-lower alkoxyarylmethyl)acylbenzimidazolyl, (N-lower alkoxycarbonyl)phthalimido(lower)alkylindolyl, N-protected lower alkylamino(lower)alkylamino(N-acyl)benzimidazolyl, (N-acyl)benzimidazolyl, (N-acyl) (lower)alkylbenzimidazolyl, N-protected amino(lower) alkyl(N-lower alkyl) amino(N-acyl)benzimidazolyl, N-acylindolyl, (N-acyloxymethyl)indolyl, (N-acyl) acylindolyl, (N-arylmethyl)lower alkoxy(lower) alkylbenzimidazolyl or (N-lower alkoxyarylmethyl) acylbenzimidazolyl; and
Yi is acylindolinyl, indolinyl, hydroxy(lower) alkylindolinyl, lower alkylamino(lower) alkylaminoindolinyl, acylbenzimidazolyl, phthalimido (lower)alkylindolyl, amino(lower)alkylindolyl, lower alkylamino(lower)alkylaminobenzimidazolyl, benzimidazolyl, lower alkylbenzimidazolyl, amino (lower)alkyl(N-lower alkyl) aminobenzimidazolyl, indolyl, acylindolyl, lower alkoxy(lower) alkylbenzimidazolyl or acylbenzimidazolyl; or 8) reacting a compound of the formula

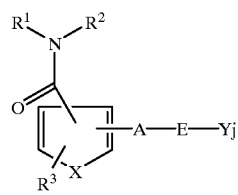

(Ik)

or its salt in an elimination reaction of the N-protective group to provide a compound of the formula:

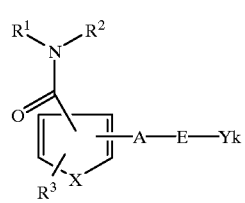

(Il)

or its salt, in the above formulas,
$R^1$, $R^2$, $R^3$, A, E and X are each as defined above,
Yj is aryl which is substituted with protected amino and nitro; or a condensed heterocyclic group which is substituted with protected amino or lower alkyl substituted with protected amino; and
Yk is aryl which is substituted with amino and nitro; or a condensed heterocyclic group which is substituted with amino or lower alkyl substituted with amino; or 9) deesterifying a compound of the formula:

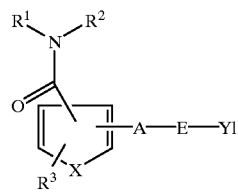

(Im)

or its salt to provide a compound of the formula:

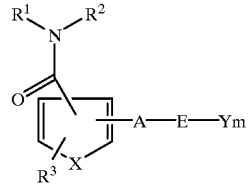

(In)

or its salt, in the above formulas,
$R^1$, $R^2$, $R^3$, A, E and X are each as defined above,
Yl is aryl substituted with esterified carboxy, or a condensed heterocyclic group substituted with esterified carboxy, and
Ym is aryl substituted with carboxy, or a condensed heterocyclic group substituted with carboxy, or 10) reacting a compound of the formula:

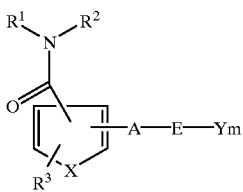
(In)

or its reactive derivative at the hydrogen group or a salt thereof with an amine or its salt to provide a compound of the formula:

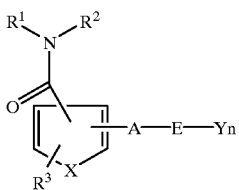
(Io)

or its salt, in the above formulas, $R^1$, $R^2$, $R^3$, A, E, X and Ym are each as defined above, and Yn is aryl or a condensed heterocyclic group, each of which is substituted with substituted or unsubstituted N-containing heterocyclic carbonyl, carbamoyl, heterocyclic carbamoyl, or substituted or unsubstituted lower alkylcarbamoyl; or 11) reacting a compound of the formula:

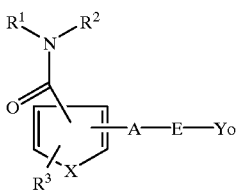
(Ip)

or its salt in an elimination reaction of methyl or the hydroxy-protective group to provide a compound of the formula:

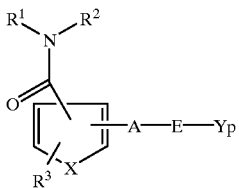
(Iq)

or its salt, in the above formulas, $R^1$, $R^2$, $R^3$, A, E and X are each as defined above, Yo is a condensed (N-acyl)N-containing heterocyclic group or a condensed heterocyclic group, each of which is substituted with methoxy or lower alkyl substituted with protected hydroxy; and Yp is a condensed (N-acyl)N-containing heterocyclic group, or a condensed heterocyclic group, each of which is substituted with hydroxy or lower alkyl substituted with hydroxy; or 12) reacting a compound of the formula:

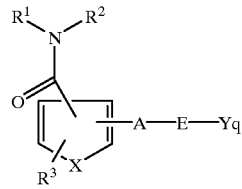
(Ir)

or its salt with an acylating agent to provide a compound of the formula:

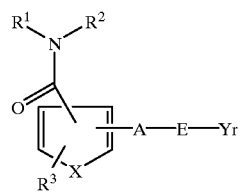
(Is)

or its salt, in the above formulas, $R^1$, $R^2$, $R^3$, A, E and X are each as defined above, Yq is a condensed heterocyclic group which is substituted with amino or amino(lower)alkyl, and Yr is a condensed heterocyclic group which is substituted with acylamino or acylamino(lower)alkyl, or 13) reacting a compound of the formula:

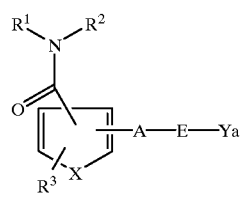
(Ib)

or its salt with N-lower alkylmethylene ammonium halide to provide a compound of the formula:

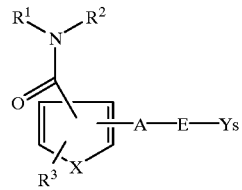
(It)

or its salt, in the above formulas, $R^1$, $R^2$, $R^3$, A, E, X and Ya are each as defined above, and Ys is indolyl which is substituted with methyl substituted with lower alkylamino, or 14) reacting a compound of the formula:

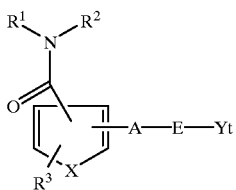

(Iu)

or its salt in an oxidation reaction to provide a compound of the formula:

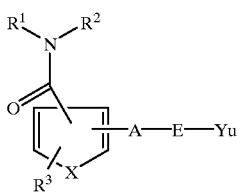

(Iv)

or its salt, in the above formulas,
$R^1$, $R^2$, $R^3$, A, E and X are each as defined above,
Yt is a condensed heterocyclic group which is substituted with lower alkyl substituted with hydroxy, and
Yu is a condensed heterocyclic group which is substituted with lower alkyl substituted with formyl, or 15) reacting a compound of the formula:

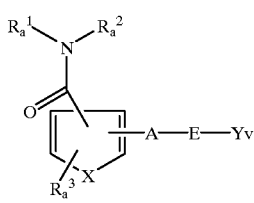

(Iw)

or its salt in a deesterification reaction to provide a compound of the formula:

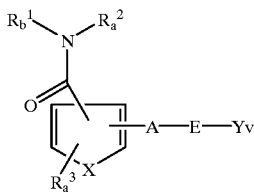

(Ix)

or its salt, in the above formulas,
A, E and X are each as defined above,
$R_a^1$ is aryl substituted with esterified carboxyl or lower alkoxy substituted with esterified carboxy,
$R_b^1$ is aryl substituted with carboxy or lowers alkoxy substituted with carboxy,
$R_a^2$ is lower alkyl,
$R_a^3$ is hydrogen or lower alkoxy, and
Yv is benzimidazolyl optionally substituted with lower alkyl or protected amino (lower)alkyl, or 16) reacting a compound of the formula:

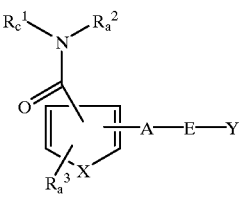

(Iy)

or its salt in an elimination reaction of methyl substituted with aryl or substituted aryl to provide a compound of the formula:

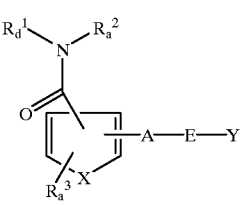

(Iz)

or its salt, in the above formulas,
$R_a^2$, $R_a^3$, A, E, X and Y are each as defined above,
$R_c^1$ is aryl substituted with methoxy which is substituted with substituted or unsubstituted aryl, and
$R_d^1$ is aryl substituted with hydroxy, or 17) reacting a compound of the formula:

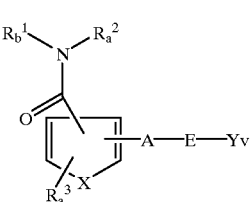

(Ix)

or its reactive derivative at the carboxy group or a salt thereof with an amine or its salt to provide a compound of the formula:

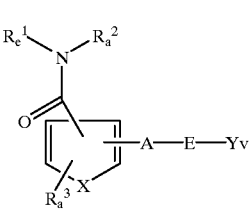

(I-1)

or its salt, in the above formulas,
$R_b^1$, $R_a^2$, $R_a^3$, A, E, X and Yv are each as defined above, and
$R_e^1$ is aryl substituted with N-protected piperazinylcarbonyl, oxopiperidinylcarbonyl, carbamoyl, lower alkylcarbamoyl, lower alkylaminocarbamoyl or lower alkylamino(lower)alkyl(N-lower)alkylcarbamoyl, or aryl which is substituted with lower alkoxy substituted with N-protected piperazinylcarbonyl, oxopiperidinylcarbonyl, carbamoyl, lower alkylcarbamoyl, lower alkylaminocarbamoyl or lower alkylamino(lower)alkyl(N-lower)alkylcarbamoyl, or 18) reacting a compound of the formula:

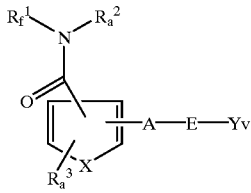

(I-2)

or its salt with a reducing agent to provide a compound of the formula:

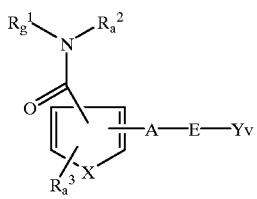

(I-3)

or its salt, in the above formulas, $R_a^2$, $R_a^3$, A, E, X and Yv are each as defined above, $R_f^1$ is aryl which is substituted with lower alkoxy substituted with oxopiperidinylcarbonyl, and $R_g^1$ is aryl which is substituted with lower alkoxy substituted with hydroxypiperidinylcarbonyl, or 19) reacting a compound of the formula:

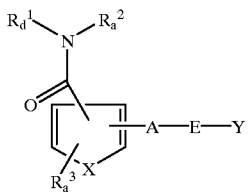

(Iz)

or its salt with an acylating agent to provide a compound of the formula:

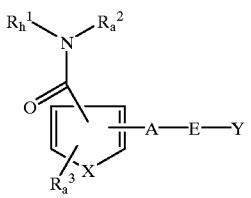

(I-4)

or its salt, in the above formulas, $R_d^1$, $R_a^2$, $R_a^3$, A, E, X and Y are each as defined above; and $R_h^1$ is aryl substituted with acyloxy, or 20) reacting a compound of the formula:

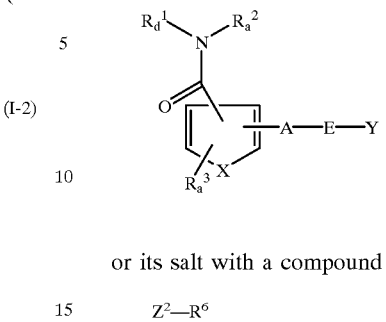

(Iz)

or its salt with a compound of the formula:

$$Z^2-R^6 \quad (V)$$

to provide a compound of the formula:

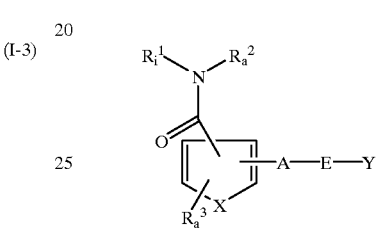

(I-5)

or its said in the above formulas, $R_d^1$, $R_a^2$, $R_a^3$, A, E, X and Y are each as defined above, $R_i^1$ is aryl which is substituted with lower alkoxy substituted with protected amino, $R^6$ is lower alkyl substituted with protected amino, and $Z^2$ is an acid residue, or 21) reacting a compound of the formula:

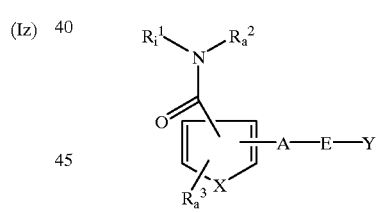

(I-5)

or its salt in an elimination reaction of N-protective group to provide a compound of the formula:

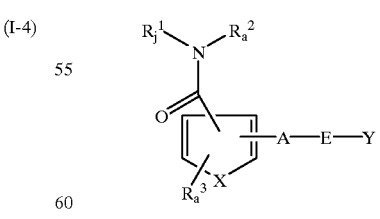

(I-6)

or its salt, in the above formulas, $R_i^1$, $R_a^2$, $R_a^3$, A, E, X and Y are each as defined above, and $R_j^1$ is aryl which is substituted with lower alkoxy substituted with amino, or 22) reacting a compound of the formula:

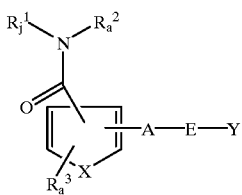

(I-6)

or its salt with an acylating agent to provide a compound of the formula:

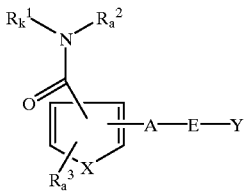

(I-7)

or its salt, in the above formulas, $R_j^1$, $R_a^2$, $R_a^3$, A, E, X and Y are each as defined above, and $R_k^1$ is aryl which is substituted with acylamino, or 23) reacting a compound of the formula:

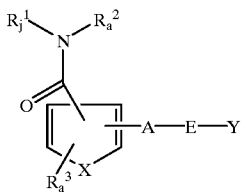

(I-6)

or its salt with lower alkanal in the presence of a reducing agent to provide a compound of the formula:

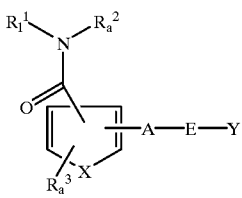

(I-8)

or its salt, in the above formulas, $R_j^1$, $R_a^2$, $R_a^3$, A, E, X and Y are each as defined above, and $R_l^1$ is aryl which is substituted with lower alkylamino, or 24) reducing a compound of the formula:

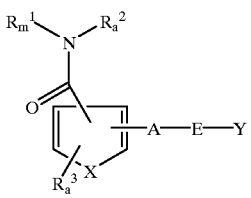

(I-9)

or its salt to provide a compound of the formula:

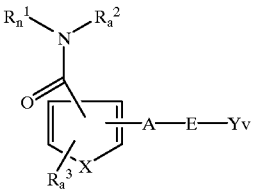

(I-10)

or its salt, in the above formulas, $R_a^2$, $R_a^3$ A, E, X and Y are each as defined above, $R_m^1$ is aryl substituted with nitro, and $R_n^1$ is aryl substituted with amino, or 25) reacting a compound of the formula:

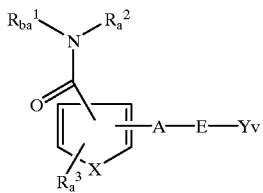

(I-11)

or its salt with an azide compound to provide a compound of the formula:

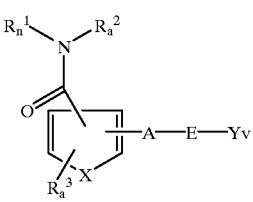

(I-10)

or its salt, in the above formulas, $R_n^1$, $R_a^2$, $R_a^3$, A, E, X and Yv are each as defined above, and $R_{ba}^1$ is aryl substituted with carboxy, or 26) reacting a compound of the formula:

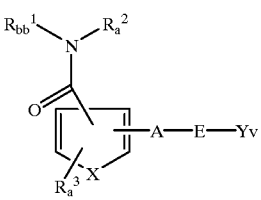

(I-12)

or its reactive derivative at the carboxy group or a salt thereof with a reducing agent to provide a compound of the formula:

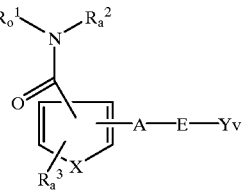

(I-13)

or its salt, in the above formulas, $R_a^2$, $R_a^3$, A, E, X and Yv are each as defined above, $R_{bb}^1$ is aryl which is substituted with lower alkoxy substituted with carboxy, and $R_o^1$ is aryl which is substituted with lower alkoxy substituted with hydroxymethyl, or 27) reacting a compound of the formula:

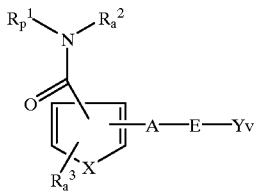

(I-14)

or its salt with an acylating agent to provide a compound of the formula:

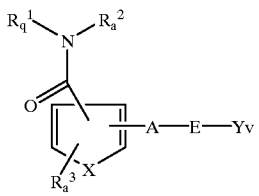

(I-15)

or its salt, in the above formulas, $R_a^2$, $R_a^3$, A, E, X and Yv are each as defined above, $R_p^1$ is aryl which is substituted with lower alkoxy substituted with hydroxy, and $R_q^1$ is aryl which is substituted with lower alkoxy substituted with acyloxy, or 28) reacting a compound of the formula:

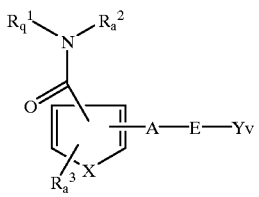

(I-15)

or its salt with an alkali metal salt of phthalimide to provide a compound of the formula:

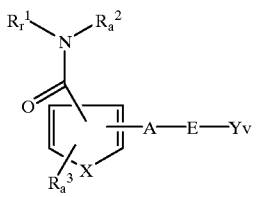

(I-16)

or its salt, in the above formulas, $R_q^1$, $R_a^2$, $R_a^3$, A, E, X and Yv are each as defined above, $R_r^1$ is aryl which is substituted with lower alkoxy substituted with phthalimido, or 29) reacting a compound of the formula:

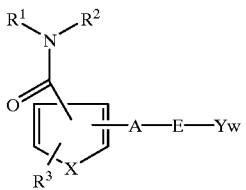

(I-17)

or its salt with an amine to provide a compound of the formula:

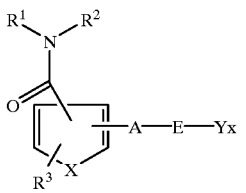

(I-18)

or its salt, in the above formulas, $R^1$, $R^2$, $R^3$, A, E and X are each as defined above, Yw is benzimidazolyl substituted with halogen, and Yx is benzimidazolyl substituted with N-lower alkylpiperidyl, morpholino, lower alkylamino, di(lower)alkylaminopiperidino, di(lower)alkylhydrazino, amino(lower)alkyl (N-lower alkyl)amino or di(lower)alkylamino(lower)alkylamino, or 30) reacting a compound of the formula:

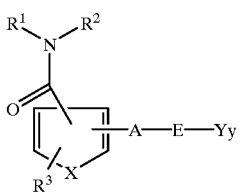

(I-19)

or its salt in an elimination reaction of N-protective group to provide a compound of the formula:

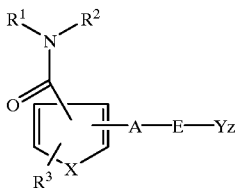

(I-20)

or its salt, in the above formulas, $R^1$, $R^2$, $R^3$, A, E and X are each as defined above, Yy is benzimidazolyl substituted with N-protected piperidyl, and Yz is benzimidazolyl substituted with piperidyl, or 31) reacting a compound of the formula:

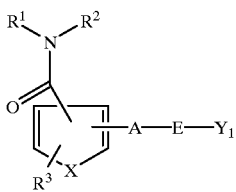

(I-21)

or its salt with hydroxylamine or its salt to provide a compound of the formula:

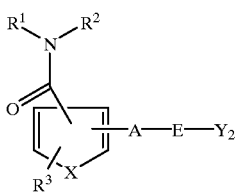

(I-22)

or its salt, in the above formulas,
$R^1$, $R^2$, $R^3$, A, E and X are each as defined above,
$Y_1$ is benzimidazolyl or indolyl, each of which is substituted with formyl or cyano(lower)alkyl, and
$Y_2$ is benzimidzolyl or indolyl, each of which is substituted with hydroxyiminomethyl or amino (hydroxyimino)(lower)alkyl, or
32) reacting a compound of the formula:

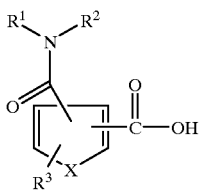

(V1)

or its reactive derivative at the carboxy group
or a salt thereof with a compound of the formula:

 (VII)

or its salt to provide a compound of the formula:

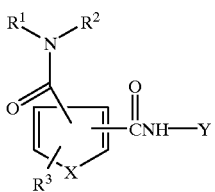

(I-23)

or its salt, in the above formulas,
$R^1$, $R^2$, $R^3$, X and Y are each as defined above.

7. A pharmaceutical composition, comprising:
a compound of claim 1, as an active ingredient, in association with a pharmaceutically acceptable, substantially non-toxic carrier or excipient.

8. A medicament, comprising:
the compound of claim 1, and
a physiologically acceptable carrier.

9. A method of vasopressin receptor binding, comprising:
administering an effective amount of the compound of claim 1 to a subject in need thereof.

10. A method of manufacturing a medicament for inducing vasopressin receptor binding, comprising:
mixing the compound of claim 1 with a physiologically acceptable carrier.

11. A compound of the formula:

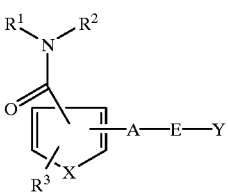

(I)

wherein:

$R^1$ is aryl, cyclo(lower)alkyl or a heterocyclic group, each of which may be substituted with substituent(s) selected from the group consisting of halogen; hydroxy; nitro; protected amino; amino; acyl; substituted acyl; acyl(lower)alkylsulfinyl; acyl(lower)alkylsulfonyl; acyloxy; lower alkylamino(lower)alkylcarbamoyloxy; aryl; cyano; a heterocyclic group; lower alkenyl optionally substituted with acyl, substituted acyl, aryl or acyl-substituted aryl; lower alkynyl optionally substituted with amino, acylamino or substituted acylamino; lower alkyl optionally substituted with halogen, amino, lower alkylamino, acylamino, substituted acylamino, hydroxy, acyloxy, acyl(lower)alkanoyloxy, acyl, substituted acyl, acryl(lower)alkoxyimino, aryl or acyl-substituted aryl; lower alkylthio optionally substituted with acyl or substituted acyl; alkoxy optionally substituted with aryl, substituted aryl, hydroxy, acyloxy, amino, lower alkylamino, protected amino, a heterocyclic group, acyl-substituted pyridyl, substituted acyl-substituted pyridyl, halogen, acyl(lower)alkylamino, N-protected-acyl(lower)-alkylamino, N-acyl(lower)alkyl-N-lower alkylamino, acyl, substituted acyl, acylamino, substituted acylamino, lower alkylhydrazinocarbonylamino, hydroxyimino, acyl(lower)alkoxyimino, substituted acyl(lower)alkoxyimino, acyl(lower)alkoxy, guanidino or N-protected guanidino; and lower alkenyloxy optionally substituted with acyl or substituted acyl;

$R^2$ is hydrogen; lower alkyl optionally substituted with hydroxy, aryl or acyl; or cyclo(lower)alkyl;

$R^3$ is hydrogen; halogen; hydroxy; acyloxy; substituted acyloxy; lower alkyl optionally substituted with hydroxy or lower alkoxy, lower alkoxy optionally substituted with aryl, amino, protected amino, acyl, hydroxy, cyano or lower alkylthio; nitro; amino; acyl; substituted acyl; or cyclo(lower)alkyloxy;

A is a single bond, O or NH;

E is lower alkylene, lower alkenylene,

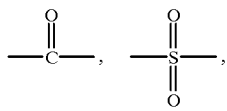

a group of the formula:

—G—J— in which G is lower alkylene or

and
J is O or

wherein $R^4$ is hydrogen or N-protective group;
X is —CH=CH—, —CH=N— or S; and
Y is benzimidazolyl optionally substituted by substituent(s) selected from the group consisting of halogen, acyl, lower alkoxy, hydroxy, guanidino, mercapto, acylamino, amino, a heterocyclic group, cyanoamino, amino(lower)alkyl(lower)alkylamino, lower alkylamino, lower alkylamino(lower)alkylamino, substituted-heterocyclic group, lower alkylhydrazino, aryloxy, lower alkylthio, aryl, protected amino, N-protected lower alkylamino(lower)alkylamino, N-protected amino(lower)alkyl(N'-lower alkyl)amino, amino(lower)alkyl(N-lower alkyl)amino, lower alkylamino(lower)alkyl(N-lower alkyl)amino, lower alkoxy(lower)alkylamino and lower alkyl optionally substituted with aryl, ar(lower)alkoxy, cyano, hydroxyimino, mercapto, lower alkylamino, acyloxy, halogen, lower alkoxy, protected hydroxy, hydroxy, lower alkoxyaryl, protected amino, amino, a heterocyclic group or substituted heterocyclic group; and E is

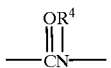

wherein $R^4$ is as defined above;
and a pharmaceutically acceptable salt thereof.

12. The process of claim 6, wherein said reactive derivative of the compound of formula (III) is selected from the group consisting of an acid halide, an acid anhydride, an amide, an ester and an acid azide.

13. The process of claim 6, wherein said reactive derivative of the compound in formula (In) is selected from the group consisting of an acid halide, an acid anhydride, an amide, an ester and an acid azide.

14. The process of claim 6, wherein said reactive derivative of the compound of formula (Ix) is selected from the group consisting of an acid halide, an acid anhydride, an amide, an ester and an acid azide.

15. The process of claim 6, wherein said reactive derivative of the compound of formula (I-12) is selected from the group consisting of an imide, an amide and an ester.

16. The process of claim 6, wherein said reactive derivative of the compound of formula (VI) is selected from the group consisting of an acid halide, an acid anhydride, an amide, an ester and an acid azide.

* * * * *